US010766921B2

(12) United States Patent
Weymouth-Wilson et al.

(10) Patent No.: US 10,766,921 B2
(45) Date of Patent: Sep. 8, 2020

(54) PROCESS AND INTERMEDIATES FOR THE 6,7-ALPHA-EPOXIDATION OF STEROID 4,6-DIENES

(71) Applicant: NZP UK Limited, Bristol (GB)

(72) Inventors: Alexander Weymouth-Wilson, Reading (GB); Zofia Komsta, Reading (GB); Laura Wallis, Reading (GB); Timothy Evans, Reading (GB)

(73) Assignee: NZP UK Limited, Bristol (GB)

( * ) Notice: Subject to any disclaimer, the term of this patent is extended or adjusted under 35 U.S.C. 154(b) by 0 days.

(21) Appl. No.: 16/302,057

(22) PCT Filed: May 18, 2017

(86) PCT No.: PCT/GB2017/051389
§ 371 (c)(1),
(2) Date: Nov. 15, 2018

(87) PCT Pub. No.: WO2017/199036
PCT Pub. Date: Nov. 23, 2017

(65) Prior Publication Data
US 2019/0309012 A1    Oct. 10, 2019

(30) Foreign Application Priority Data

May 18, 2016 (GB) .................................. 1608776.9

(51) Int. Cl.
| | | |
|---|---|---|
| *C07J 71/00* | (2006.01) | |
| *C07J 9/00* | (2006.01) | |
| *C07J 41/00* | (2006.01) | |
| *C07J 43/00* | (2006.01) | |
| *C07J 31/00* | (2006.01) | |
| *C07J 17/00* | (2006.01) | |
| *C07J 13/00* | (2006.01) | |
| *C07J 51/00* | (2006.01) | |

(52) U.S. Cl.
CPC ............. *C07J 71/001* (2013.01); *C07J 9/005* (2013.01); *C07J 41/0088* (2013.01); *C07J 41/0094* (2013.01); *C07J 43/003* (2013.01); *C07J 9/00* (2013.01); *C07J 13/007* (2013.01); *C07J 17/00* (2013.01); *C07J 31/006* (2013.01); *C07J 41/0055* (2013.01); *C07J 41/0061* (2013.01); *C07J 51/00* (2013.01)

(58) Field of Classification Search
CPC ...................................................... C07J 71/001
USPC ........................................................ 549/543
See application file for complete search history.

(56) References Cited

U.S. PATENT DOCUMENTS

| | | |
|---|---|---|
| 2,624,748 A | 1/1953 | Levin et al. |
| 4,289,872 A | 9/1981 | Denkewalter et al. |
| 5,155,247 A | 10/1992 | Herrmann et al. |
| 5,166,372 A | 11/1992 | Crocco et al. |
| 5,229,490 A | 7/1993 | Tam |
| 5,643,575 A | 7/1997 | Martinez et al. |
| 5,723,636 A | 3/1998 | Fenelli et al. |
| 5,932,462 A | 8/1999 | Harris et al. |
| 2003/0143596 A1 | 7/2003 | Bentley et al. |
| 2006/0252948 A1 | 11/2006 | Takehara et al. |
| 2009/0062256 A1 | 3/2009 | Olson |
| 2014/0148428 A1 | 5/2014 | Pruzanski et al. |
| 2014/0206657 A1 | 7/2014 | Yu et al. |
| 2016/0145295 A1 | 5/2016 | Or et al. |

FOREIGN PATENT DOCUMENTS

| | | |
|---|---|---|
| CN | 105348365 A | 2/2016 |
| EP | 1568706 A1 | 8/2005 |
| EP | 1985621 A1 | 10/2008 |
| GB | 1568734 | 6/1980 |
| WO | WO 93/21259 A1 | 10/1993 |
| WO | WO 96/21469 A1 | 7/1996 |
| WO | WO 2011/014661 A2 | 2/2001 |
| WO | WO 02/072598 A1 | 9/2002 |
| WO | WO 2004/076469 A1 | 9/2004 |
| WO | 2006/122977 A2 | 11/2006 |
| WO | WO 2007/080951 A1 | 7/2007 |
| WO | WO 2008/002573 A2 | 1/2008 |
| WO | WO 2010/014836 A2 | 2/2010 |
| WO | WO 2010/059859 A1 | 5/2010 |
| WO | WO 2013/192097 A1 | 12/2013 |
| WO | WO 2014/066819 A1 | 5/2014 |
| WO | WO 2015/183794 A1 | 12/2015 |
| WO | 2016/079517 A1 | 5/2016 |
| WO | WO 2016/079518 A1 | 5/2016 |
| WO | WO 2016/079519 A1 | 5/2016 |
| WO | WO 2016/079520 A1 | 5/2016 |

(Continued)

OTHER PUBLICATIONS

International Search Report issued in corresponding International Patent Application No. PCT/GB2017/051389 dated Sep. 7, 2017.
Tochtrop et al., "Synthesis of [3,4-13C2]-Enriched Bile Salts as NMR Probes of Protein-Ligand Interactions," Journal of Organic Chemistry, 67: 6764-6771 (2002).
De et al., "Regio- and Stereoselective Monoepoxidation of Dienes using Methylthoxorhenium: Synthesis of Allylic Epoxides," Journal of Organic Chemistry, 79: 10323-10333 (2014).
Written Opinion issued in corresponding International Patent Application No. PCT/GB2017/051389 dated Sep. 7, 2017.
Amato, et al., "Selective Oxidation Reactions of Natural Compounds with Hydrogen Peroxide Mediated by Methyltrioxorhenium" Molecules, 2013, 18, pp. 13754-13768.

(Continued)

*Primary Examiner* — Taofiq A Solola
(74) *Attorney, Agent, or Firm* — Morgan, Lewis & Bockius LLP

(57) ABSTRACT

The invention relates to a process for preparing a compound of general formula (Ia): wherein $R^2$, Y, $R^4$ and $R^5$ are as defined herein, wherein the epoxidation is conducted using an oxidant and methyltrioxorhenium as a catalyst (MeReO3). The invention also relates to certain compounds per se. The compounds are intermediates in the synthesis of synthetic bile acids.

25 Claims, 6 Drawing Sheets

(56) References Cited

FOREIGN PATENT DOCUMENTS

Figure 1:
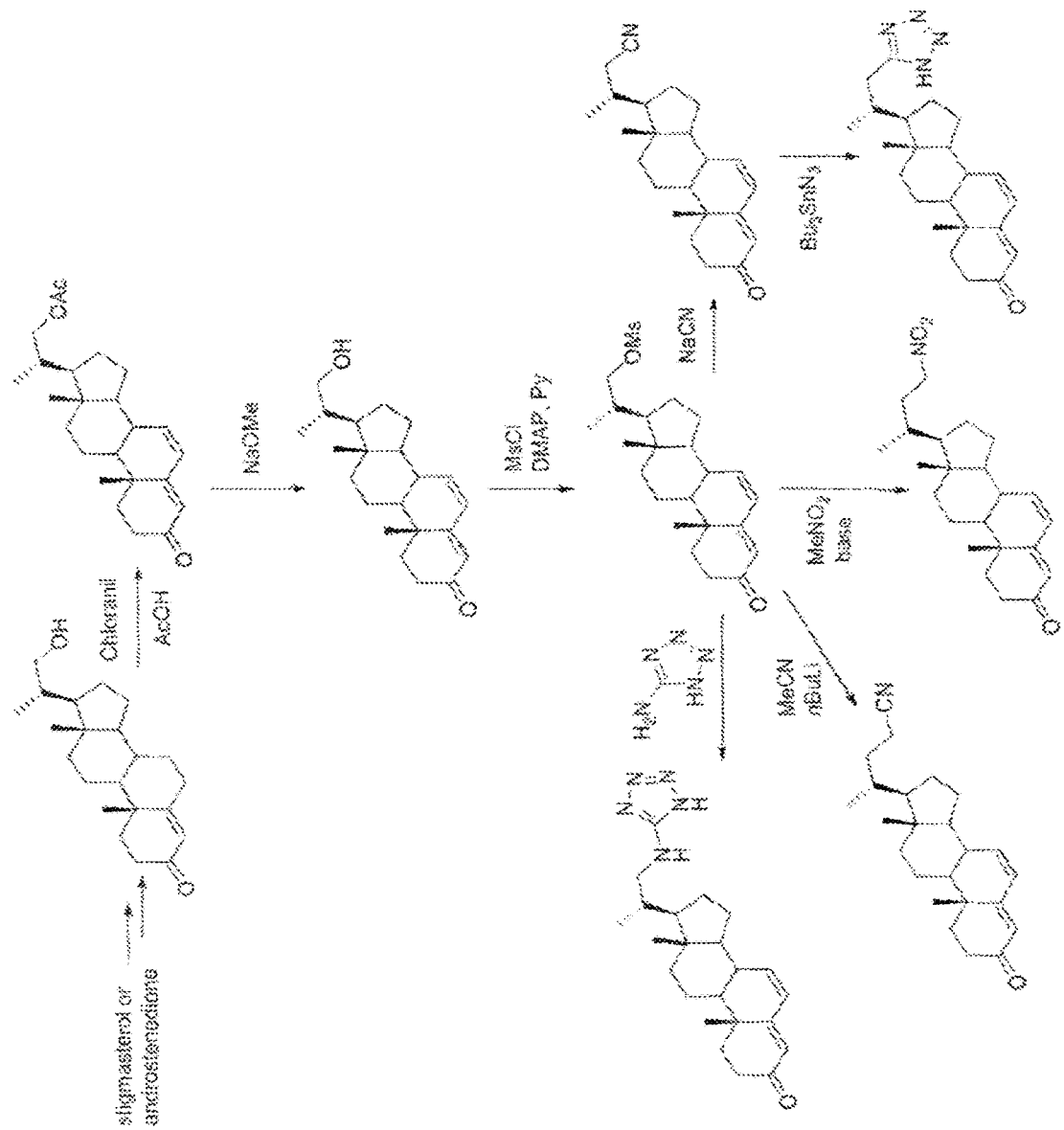
Figure 1:
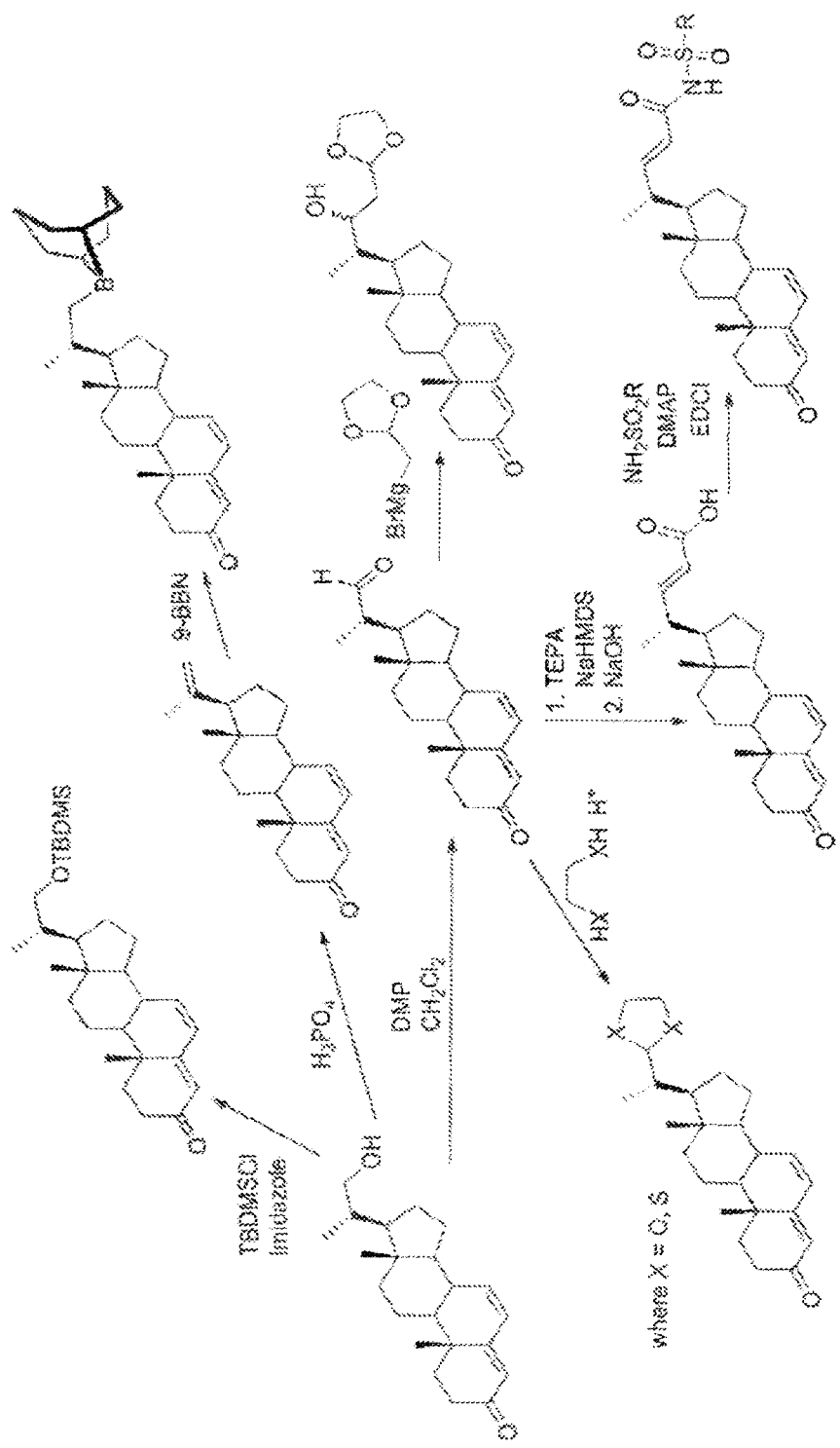
Figure 1:
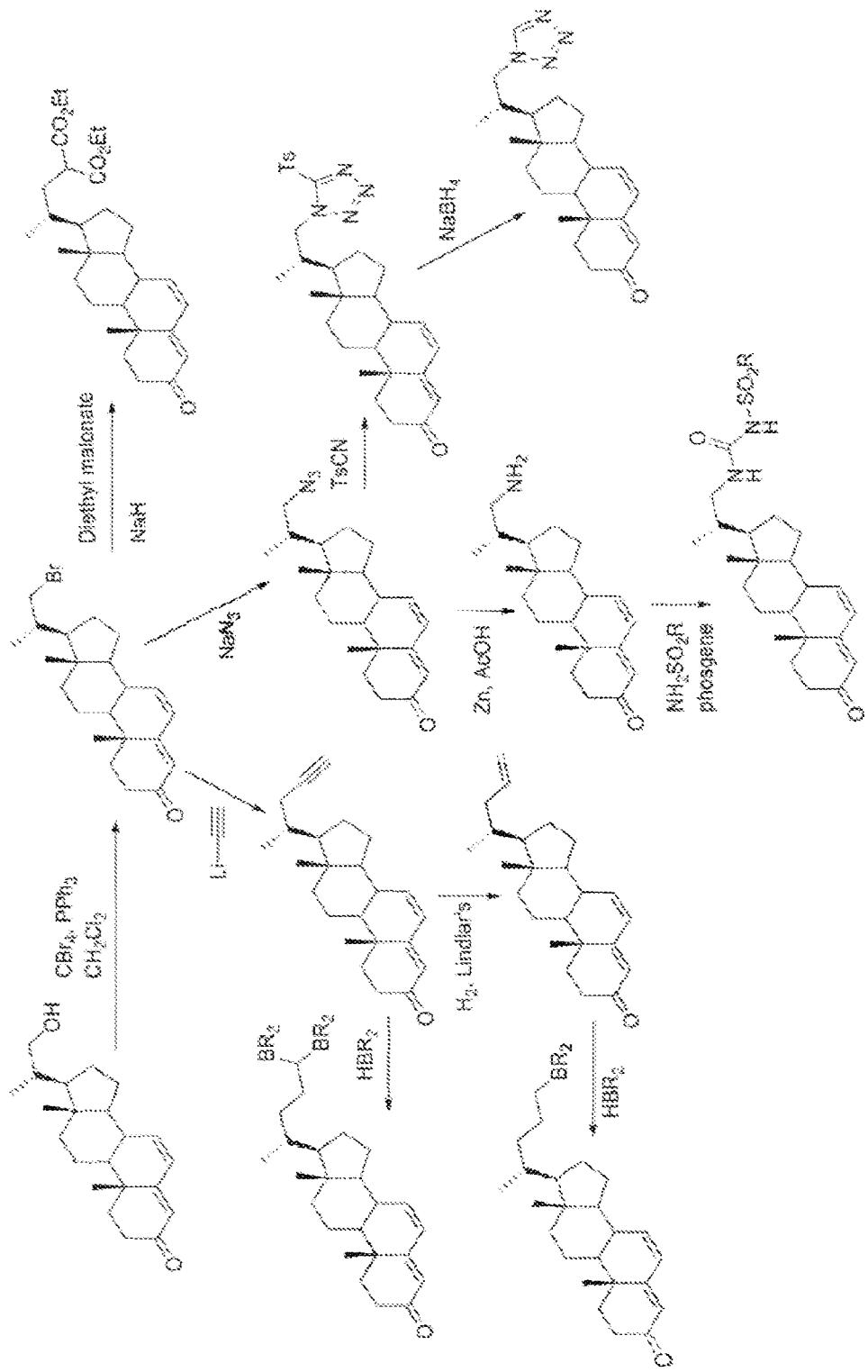

WO    WO 2017/199033 A1    11/2017
WO    WO 2017/199036 A1    11/2017

OTHER PUBLICATIONS

Bortolini, et al., "Improved Enantioselectivity in the Epoxidation of Cinnamic Acid Derivatives with Dioxiranes from Keto Bile Acids", J. Org. Chem, 2002, 67(16), pp. 5802-5806.
Brown, et al., "The antimicrobial natural product chuangxinmycin and Some synthetic analogues are potent and selective inhibitors of bacterial tryptophanyl tRNA synthetase", Bioorganic & Medicinal Chemistry Letters, 2002, 12, 21, pp. 3171-3174.
Carnell, et al., "Design, Synthesis, and in Vitro Testing of α-Methylacyl-CoA Racemase Inhibitors", J. Med. Chem., 2007, 50(11), pp. 2700-2707.
Classon, et al., "New halogenation reagent systems useful for the mild one-step conversion of alcohols into iodides or bromides", J. Org. Chem, 1988, (53)26, pp. 6126-6130.
Dauben, et al., "Stereocontrolled Synthesis of Steroidal Side Chains", J. Am. Chem. Soc., 1981, 103(1), pp. 237-238.
Edelsztein, et al., "Synthesis of C—C bonded dimeric steroids by olefin metathesis" Tetrahedron, 2009, vol. 65, 18, pp. 3615-3623.
Festa, et al., "Exploitation of Cholane Scaffold for the Discovery of Potent and Selective Farnesoid X Receptor (FXR) and G-Protein Coupled Bile Acid Receptor 1 (GP-BAR1) Ligands", J Med. Chem., 2014, 57(20), pp. 8477-8495.

PROCESS AND INTERMEDIATES FOR THE 6,7-ALPHA-EPOXIDATION OF STEROID 4,6-DIENES

CROSS-REFERENCE TO RELATED APPLICATIONS

This application claims the benefit of International Application No. PCT/GB2017/051389, filed May 18, 2017, which claims the benefit of GB Patent Application No. 1608776.9 filed May 18, 2016, the entire contents of which are hereby incorporated by reference herein in their entireties.

FIELD OF THE INVENTION

The present invention relates to methods of preparing compounds which are intermediates in the synthesis of bile acid derivatives with pharmacological activity. In particular, the invention relates to methods of preparing intermediates in the synthesis of obeticholic acid and its analogues. The invention further relates to novel intermediates per se.

BACKGROUND OF THE INVENTION

Bile acids are steroid acids which are found in the bile of mammals and include compounds such as cholic acid, chenodeoxycholic acid, lithocholic acid and deoxycholic acid, all of which are found in humans. Many bile acids are natural ligands of the farnesoid X receptor (FXR) which is expressed in the liver and intestine of mammals, including humans.

Bile acids are derivatives of steroids and are numbered in the same way. The following shows the general numbering system for steroids and the numbering of the carbon atoms in chenodeoxycholic acid.

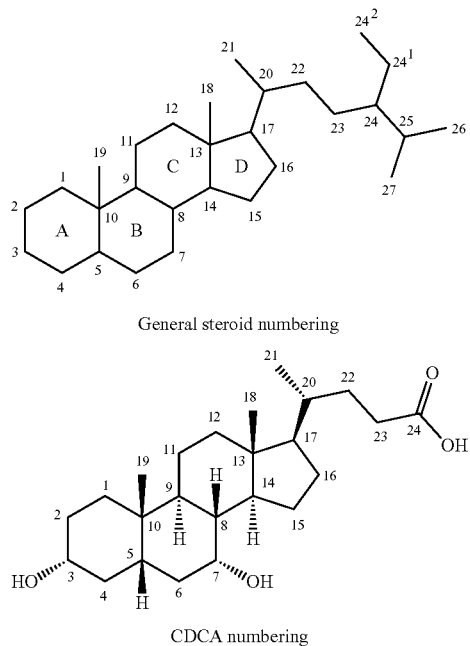

General steroid numbering

CDCA numbering

Agonists of FXR have been found to be of use in the treatment of cholestatic liver disorders including primary biliary cholangitis and non-alcoholic steatohepatitis (see review by Jonker et al., in *Journal of Steroid Biochemistry & Molecular Biology*, 2012, 130, 147-158; incorporated herein by reference).

Ursodeoxycholic acid (UDCA), a bile acid originally isolated from the gall bladder of bears, is currently used in the treatment of cholestatic liver disorders, although it appears to be inactive at the FXR.

As well as their action at the FXR, bile acids and their derivatives are also modulators of the G protein-coupled receptor TGR5. This is a member of the rhodopsin-like superfamily of G-protein coupled receptors and has an important role in the bile acid signalling network, which complements the role of the FXR.

Because of the importance of FXR and TGR5 agonists in the treatment of cholestatic liver disorders, efforts have been made to develop new compounds which have agonist activity at these receptors. One particularly active compound is obeticholic acid, which is a potent agonist of both FXR and TGR5. Obeticholic acid is described in WO02/072598 and EP1568706 (both incorporated herein by reference), both of which describe a process for the preparation of obeticholic acid from 7-keto lithocholic acid, which is derived from cholic acid. Further processes for the production of obeticholic acid and its derivatives are described in WO2006/122977, US2009/0062256 and WO2013/192097 (all incorporated herein by reference) and all of these processes also start from 7-keto lithocholic acid.

It is clear from the number of patent publications directed to processes for the production of obeticholic acid that it is by no means simple to synthesise this compound and indeed the process which is currently used starts from cholic acid, has 12 steps and a low overall yield.

In addition to the inefficiency and high cost of this process, there are also problems with the cost and availability of the starting materials. Cholic acid, the current starting material for the production of obeticholic acid, is a natural bile acid which is usually obtained from the slaughter of cows and other animals. This means that the availability of cholic acid and other bile acids is limited by the number of cattle available for slaughter. Since the incidence of cholestatic liver disease is increasing worldwide, the demand for synthetic bile acids such as obeticholic acid is also likely to increase and it is doubtful whether the supply of naturally derived bile acids will continue to be sufficient to meet demand.

Furthermore, the use of a starting material derived from animals means that there is the possibility of the contamination of the material with infectious agents such as viruses or prions, which can not only be hazardous to workers but could potentially contaminate the end products if steps are not taken to prevent this.

Although some patients with cholestatic liver disease can be treated with ursodeoxycholic acid, this is also a natural bile acid and faces the same problems of limited availability and high cost.

In an attempt to solve the problems associated with the use of bile acids as starting materials, the present inventors have devised a process for the synthesis of synthetic bile acid derivatives, such as obeticholic acid (OCA, referred to herein as compound (XVIIIA)), which uses plant sterols as starting materials.

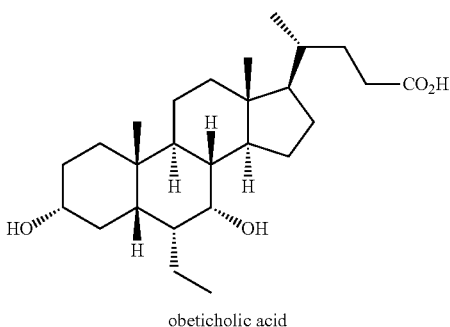

(XVIIIA)

obeticholic acid

The inventors have developed a process for the production of synthetic bile acids which proceeds via novel intermediates and which provides the final product in significantly higher yield than current processes. The process is flexible and can use a variety of different starting materials including animal, fungal and plant sterols.

Suitable animal sterols which can be used as starting materials include deoxycholic acid, cholic acid, while fungal sterols include ergosterol.

Plant sterols are widely available at significantly lower cost than bile acids and, indeed, are often waste products of other processes. Suitable plant sterol and plant sterol derivatives which can be used as starting materials include 3-keto-bis-norcholenol (also known as 20-hydroxymethylpregn-4-en-3-one), androstenedione, androstadienedione, dehydroepiandrosterone, stigmasterol, brassicasterol, campesterol and R-sitosterol.

Our patent applications Nos. PCT/GB2015/053516 (WO2016/079517), PCT/GB2015/053517 (WO2016/079518), PCT/GB2015/053518 (WO2016/079519) and PCT/GB2015/053519 (WO2016/079520) (all incorporated herein by reference) relate to intermediates in the process of synthesizing obeticholic acid (and analogues) as well as to processes for preparing the intermediates and processes for converting them to the desired products.

SUMMARY OF THE INVENTION

In a first aspect, the present invention provides a process for preparing a compound of general formula (Ia):

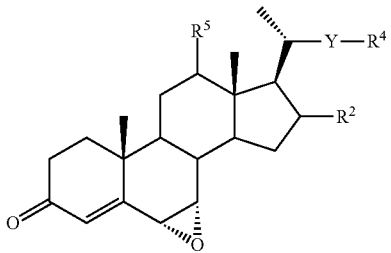

(Ia)

or a salt or isotopic variant thereof
wherein:

$R^2$ is H, halo, OH or a protected OH group;

Y is a bond, or a $C_{1-20}$ alkylene, $C_{2-20}$ alkenylene or $C_{2-20}$ alkynylene linker group any of which is optionally substituted with one or more $R^3$;

wherein each $R^3$ is independently H, halo, OH, a protected OH group or $NR^8R^9$; wherein each of $R^8$ and $R^9$ is independently H, $C_{1-6}$ alkyl, C(O)Ph, benzyl, phthalimide, tert-butyloxycarbonyl or carboxybenzyl;

$R^4$ is $C(O)OR^{10}$, $OC(O)R^{10}$, $C(O)NR^{10}R^{11}$, $OR^{10}$, $OSi(R^{13})_3$, $S(O)R^{10}$, $SO_2R^{10}$, $OSO_2R^{10}$, $SO_3R^{10}$, $OSO_3R^{10}$, halo, CN, $C(O)R^{10}$, $NR^{10}R^{11}$, $BR^{10}R^{11}$, $C(O)CH_2N_2$, $-CH=CH_2$, $-C\equiv CH$, $CH[C(O)OR^{10}]_2$, $CH(BR^{10}R^{11})_2$, azide, $NO_2$, $NR^{10}C(O)NR^{10}SO_2R^{11}$, $NR^{10}C(O)NR^{10}SO_2NR^{10}R^{11}$, $NR^{10}SO_2R^{11}$, $C(O)NR^{10}SO_2R^{11}$, $CH(XR^{10})(XR^{11})$, $CH(R^{10})(XR^{11})$, phthalimide or a carboxylic acid mimetic group such as tetrazole;

wherein each X is independently O, S or $NR^8$;

wherein each $R^{10}$ and $R^{11}$ is independently:

a. hydrogen; or b. $C_{1-20}$ alkyl, $C_{3-7}$ cycloalkyl, $C_{2-20}$ alkenyl or $C_{2-20}$ alkynyl, any of which is optionally substituted with one or more substituents selected from:

$C_{1-4}$ alkyl, $C_{1-4}$ haloalkyl, halo, $NO_2$, CN, $OR^{19}$, $SR^{19}$, $C(O)OR^{19}$, $C(O)N(R^{19})_2$, $SO_2R^{19}$, $OSO_2R^{19}$, $SO_3R^{19}$, $OSO_3R^{19}$, $N(R^{19})_2$ and a 6- to 14-membered aryl or 5- to 14-membered heteroaryl group, either of which is optionally substituted with one or more substituents selected from $C_{1-6}$ alkyl, $C_{1-6}$ haloalkyl, halo, $NO_2$, CN, $OR^{19}$, $SR^{19}$, $C(O)OR^{19}$, $C(O)N(R^{19})_2$, $SO_2R^{19}$, $SO_3R^{19}$ and $N(R^{19})_2$; or c. a 6- to 14-membered aryl, 5- to 14-membered heteroaryl group or 3- to 10-membered heterocyclic ring, any of which is optionally substituted with one or more substituents selected from:

$C_{1-6}$ alkyl, $C_{3-7}$ cycloalkyl, $C_{1-6}$ haloalkyl, halo, $NO_2$, CN, $OR^{19}$, C=O, $C(O)C_{1-4}$alkyl, $SR^{19}$, $C(O)OR^{19}$, $C(O)N(R^{19})_2$, $SO_2R^{19}$, $SO_3R^{19}$, $N(R^{19})_2$, phenyl, 5- to 14-membered heteroaryl, 3- to 10-membered heterocyclic ring, methylenedioxy and ethylenedioxy; or d. a polyethylene glycol residue; or e. when $R^4$ is $C(O)NR^{10}R^{11}$, $CH(XR^{10})(XR^{11})$, $CH(R^{10})(XR^{11})$, $NR^{10}R^{11}$, $BR^{10}R^{11}$, $CH[C(O)OR^{10}]_2$ or $CH(BR^{10}R^{11})_2$ an $R^{10}$ and an $R^{11}$ group, together with the atom or atoms to which they are attached, may combine to form a 3 to 10-membered heterocyclic ring;

wherein each $R^{19}$ is independently:

H, $C_{1-6}$ alkyl, $C_{1-6}$ haloalkyl, or a 6- to 14-membered aryl or 5- to 14-membered heteroaryl group either of which is optionally substituted with one or more substituents selected from halo, $C_{1-6}$ alkyl and $C_{1-6}$ haloalkyl;

and wherein each $R^{13}$ is independently:

a. $C_{1-20}$ alkyl, $C_{2-20}$ alkenyl or $C_{2-20}$ alkynyl, any of which is optionally substituted with one or more substituents selected from:

halo, $NO_2$, CN, $OR^{19}$, $SR^{19}$, $C(O)OR^{19}$, $C(O)N(R^{19})_2$, $SO_2R^{19}$, $SO_3R^{19}$, $OSO_3R^{19}$, $N(R^{19})_2$ and a 6- to 14-membered aryl or 5- to 14-membered heteroaryl group, either of which is optionally substituted with one or more substituents selected from $C_{1-6}$ alkyl, $C_{1-6}$ haloalkyl, halo, $NO_2$, CN, $OR^{19}$, $SO_2R^{19}$, $SO_3R^{19}$ and $N(R^{19})_2$; or b. a 6- to 14-membered aryl or 5- to 14-membered heteroaryl group either of which is optionally substituted with one or more substituents selected from:

$C_{1-6}$ alkyl, $C_{1-6}$ haloalkyl, halo, $NO_2$, CN, $OR^{19}$, $SR^{19}$, $C(O)OR^{19}$, $C(O)N(R^{19})_2$, $SO_2R^{19}$, $SO_3R^{19}$ and $N(R^{19})_2$;

wherein each $R^{19}$ is independently:
H, $C_{1-6}$ alkyl or $C_{1-6}$ haloalkyl; or
Y and $R^4$ together form a $=CH_2$ group; and
$R^5$ is H, OH or a protected OH group;
the process comprising:
oxidation of a compound of general formula (IIa) using an oxidant and methyltrioxorhenium as catalyst:

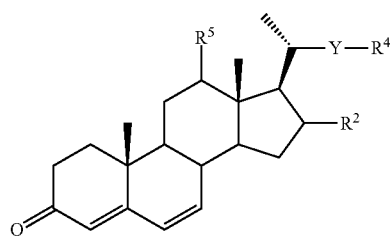

(IIa)

or a salt or isotopic variant thereof
wherein $R^2$, $R^4$, $R^5$ and Y are as defined for compounds of general formula (Ia).

In a second aspect, the present invention provides a process for preparing a compound of general formula (I):

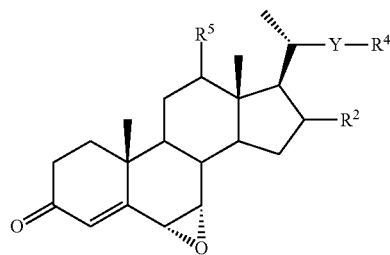

(I)

or a salt or isotopic variant thereof
wherein:
$R^2$ is H, halo, OH or a protected OH group;
Y is a bond, or a $C_{1-20}$ alkylene, $C_{2-20}$ alkenylene or $C_{2-20}$ alkynylene linker group any of which is optionally substituted with one or more $R^3$;
wherein each $R^3$ is independently halo, $OR^8$ or $NR^8R^9$;
wherein each of $R^8$ and $R^9$ is independently H or $C_{1-4}$ alkyl;
$R^4$ is $C(O)OR^{10}$, $OC(O)R^{10}$, $C(O)NR^{10}R^{11}$, $OR^{10}$, $OSi(R^{13})_3$, $S(O)R^{10}$, $SO_2R^{10}$, $OSO_2R^{10}$, $SO_3R^{10}$, $OSO_3R^{10}$, halo, CN, $C(O)R^{10}$, $CH(OR^{10})(OR^{11})$, $CH(R^{10})(OR^{11})$, $CH(SR^{10})(SR^{11})$, $NR^{10}R^{11}$, $BR^{10}R^{11}$, $C(O)CH_2N_2$, $-CH=CH_2$, $-C\equiv CH$, $CH[C(O)OR^{10}]_2$, $CH(BR^{10}R^{11})_2$, azide or a carboxylic acid mimetic group such as tetrazole;
wherein each $R^{10}$ and $R^{11}$ is independently:
b. hydrogen; or
b. $C_{1-20}$ alkyl, $C_{2-20}$ alkenyl or $C_{2-20}$ alkynyl, any of which is optionally substituted with one or more substituents selected from:
halo, $NO_2$, CN, $OR^{19}$, $SR^{19}$, $C(O)OR^{19}$, $C(O)N(R^{19})_2$, $SO_2R^{19}$, $SO_3R^{19}$, $OSO_3R^{19}$, $N(R^{19})_2$ and a 6- to 14-membered aryl or 5- to 14-membered heteroaryl group, either of which is optionally substituted with one or more substituents selected from $C_{1-6}$ alkyl, $C_{1-6}$ haloalkyl, halo, $NO_2$, CN, $OR^{19}$, $SR^{19}$, $C(O)OR^{19}$, $C(O)N(R^{19})_2$, $SO_2R^{19}$, $SO_3R^{19}$ and $N(R^{19})_2$; or c. a 6- to 14-membered aryl or 5- to 14-membered heteroaryl group either of which is optionally substituted with one or more substituents selected from: $C_{1-6}$ alkyl, $C_{1-6}$ haloalkyl, halo, $NO_2$, CN, $OR^{19}$, $SR^{19}$, $C(O)OR^{19}$, $C(O)N(R^{19})_2$, $SO_2R^{19}$, $SO_3R^{19}$ and $N(R^{19})_2$; or
d. a polyethylene glycol residue; or
e. when $R^4$ is $C(O)NR^{10}R^{11}$, $CH(OR^{10})(OR^{11})$, $CH(R^{10})(OR^{11})$, $CH(SR^{10})(SR^{11})$, $NR^{10}R^{11}$, $BR^{10}R^{11}$, $CH[C(O)OR^{10}]_2$ or $CH(BR^{10}R^{11})_2$ an $R^{10}$ and an $R^{11}$ group, together with the atom or atoms to which they are attached, may combine to form a 3- to 10-membered heterocyclic ring;
wherein each $R^{19}$ is independently:
H, $C_{1-6}$ alkyl, $C_{1-6}$ haloalkyl, or a 6- to 14-membered aryl or 5- to 14-membered heteroaryl group either of which is optionally substituted with one or more substituents selected from halo, $C_{1-6}$ alkyl and $C_{1-6}$ haloalkyl;
and wherein each $R^{13}$ is independently:
a. $C_{1-20}$ alkyl, $C_{2-20}$ alkenyl or $C_{2-20}$ alkynyl, any of which is optionally substituted with one or more substituents selected from:
halo, $NO_2$, CN, $OR^{19}$, $SR^{19}$, $C(O)OR^{19}$, $C(O)N(R^{19})_2$, $SO_2R^{19}$, $SO_3R^{19}$, $OSO_3R^{19}$, $N(R^{19})_2$ and a 6- to 14-membered aryl or 5- to 14-membered heteroaryl group, either of which is optionally substituted with one or more substituents selected from $C_{1-6}$ alkyl, $C_{1-6}$ haloalkyl, halo, $NO_2$, CN, $OR^{19}$, $SO_2R^{19}$, $SO_3R^{19}$ and $N(R^{19})_2$; or
b. a 6- to 14-membered aryl or 5- to 14-membered heteroaryl group either of which is optionally substituted with one or more substituents selected from:
$C_{1-6}$ alkyl, $C_{1-6}$ haloalkyl, halo, $NO_2$, CN, $OR^{19}$, $SR^{19}$, $C(O)OR^{19}$, $C(O)N(R^{19})_2$, $SO_2R^{19}$, $SO_3R^{19}$ and $N(R^{19})_2$;
wherein each $R^{19}$ is independently:
H, $C_{1-6}$ alkyl or $C_{1-6}$ haloalkyl; or
Y and $R^4$ together form a $=CH_2$ group; and
$R^5$ is H, OH or a protected OH group;
the process comprising:
oxidation of a compound of general formula (II) using an oxidant and methyltrioxorhenium as catalyst:

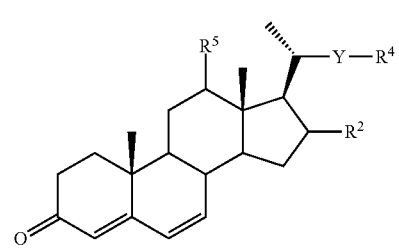

(II)

or a salt or isotopic variant thereof
wherein $R^2$, $R^4$, $R^5$ and Y are as defined for compounds of general formula (I).

Compounds of general formulae (Ia), (I), (IIa) and (II) are intermediates in the synthesis of pharmaceutically active compounds such as obeticholic acid and its derivatives.

In a third aspect, the present invention provides a process for the preparation of a compound of general formula (XVIIIa):

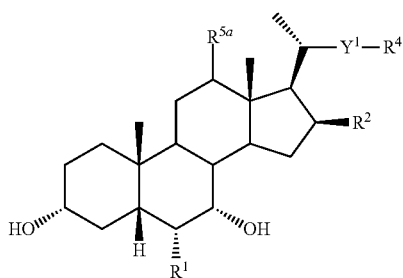

(XVIIIa)

wherein $R^1$ is $C_{1-4}$ alkyl, $C_{2-4}$ alkenyl or $C_{2-4}$ alkynyl optionally substituted with one or more substituents selected from halo, $OR^6$ and $NR^6R^7$;

wherein each of $R^6$ and $R^7$ is independently H or $C_{1-4}$ alkyl;

$R^2$ is H, halo or OH;

$R^{5a}$ is H or OH; and $Y^1$ is a bond, or a $C_{1-20}$ alkylene linker group which is optionally substituted with one or more $R^3$;

or $Y^1$ and $R^4$ together form a $=CH_2$ group;

wherein $R^3$ and $R^4$ are as defined for compounds of general formula (Ia);

the process comprising:

i. preparing a compound of general formula (Ia):

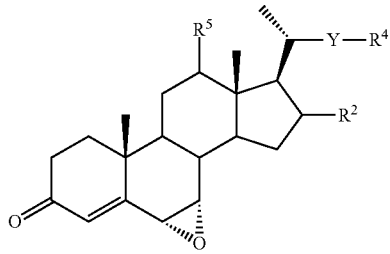

(Ia)

wherein Y, $R^2$, $R^4$ and $R^5$ are as defined in the first aspect of the invention; by oxidation of a compound of general formula (IIa) using an oxidant and methyltrioxorhenium as catalyst:

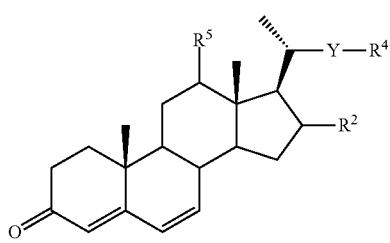

(IIa)

wherein Y, $R^2$, $R^4$ and $R^5$ are as defined for compounds of general formula (Ia);

ii. selective alkylation of a compound of general formula (Ia) with an organometallic reagent to give a compound of general formula (XIXa):

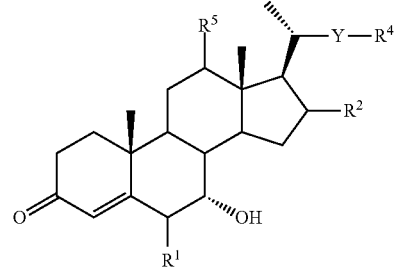

(XIXa)

wherein $R^1$ is as defined for compounds of general formula (XVIIIa) and Y, $R^2$, $R^4$ and $R^5$ are as defined for compounds of general formula (Ia);

iii. reducing a compound of formula (XIXa) using a suitable reducing agent to give a compound of general formula (XXa):

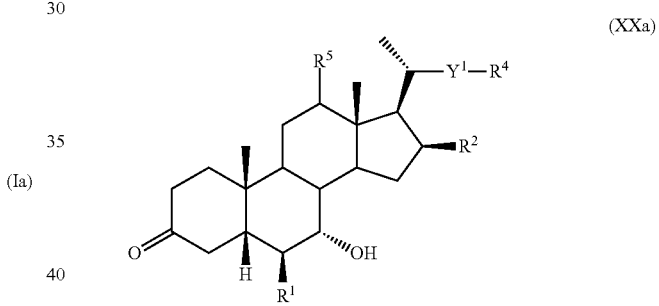

(XXa)

wherein $R^1$ and $Y^1$ are as defined for compounds of general formula (XVIIIa) and $R^2$, $R^4$ and $R^5$ are as defined for compounds of general formula (Ia);

iv. oxidising the compound of general formula (XXa) using a suitable oxidizing agent to give a compound of general formula (XXIa):

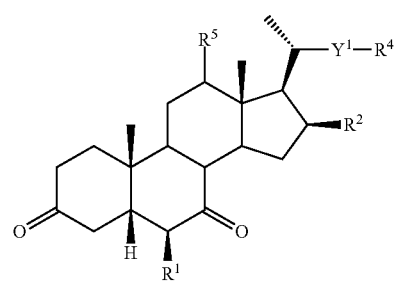

(XXIa)

wherein $R^1$ and $Y^1$ are as defined for compounds of general formula (XVIIIa) and $R^2$, $R^4$ and $R^5$ are as defined for compounds of general formula (Ia);

v. epimerisation of the compound of general formula (XXIa) to give a compound of general formula (XXIIa):

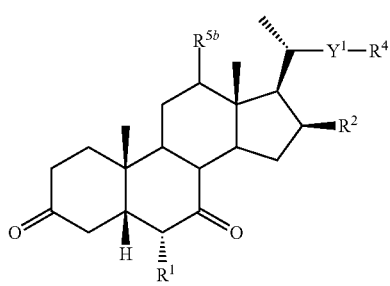

(XXIIa)

wherein $R^1$ and $Y^1$ are as defined for compounds of general formula (XVIIIa) and $R^4$ is as defined for compounds of general formula (Ia);
$R^2$ is H or OH or a protected OH group which is stable under basic conditions; and
$R^{5b}$ is H or OH or a protected OH group which is stable under basic conditions; and (vi) reduction of the compound of general formula (XXIIa) using a suitable reducing agent and, where $R^2$ and/or $R^{5b}$ is a protected OH, removal of the protecting group(s), to give a compound of general formula (XVIIIa) as defined above, wherein removal of the protecting group can take place before or after the reduction;
wherein the process further includes one or more optional steps of converting compounds of general formulae (Ia), (XIXa), (XXa), (XXIa), (XXIIa) and (XVIIIa) to other compounds of general formulae (Ia), (XIXa), (XXa), (XXIa), (XXIIa) and (XVIIIa).

The optional steps consist of reacting the side chains of the compounds of general formulae (Ia), (XIXa), (XXa), (XXIa), (XXIIa) and (XVIIIa) as described below to arrive at compounds with alternative Y and/or $R^4$ moieties.

In a fourth aspect, the present invention provides a process for the preparation of a compound of general formula (XVIII):

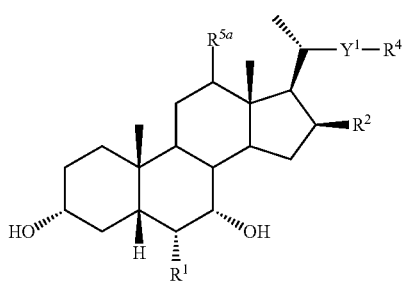

(XVIII)

wherein $R^1$ is $C_{1-4}$ alkyl optionally substituted with one or more substituents selected from halo, $OR^6$ and $NR^6R^7$;
 wherein each of $R^6$ and $R^7$ is independently H or $C_{1-4}$ alkyl;
$R^2$ is H, halo or OH;
 $R^{5a}$ is H or OH; and
 $Y^1$ is a bond, or a $C_{1-20}$ alkylene linker group which is optionally substituted with one or more $R^3$;
 or $Y^1$ and $R^4$ together form a $=CH_2$ group;
wherein $R^3$ and $R^4$ are as defined for compounds of general formula (I);

the process comprising:
i. preparing a compound of general formula (I):

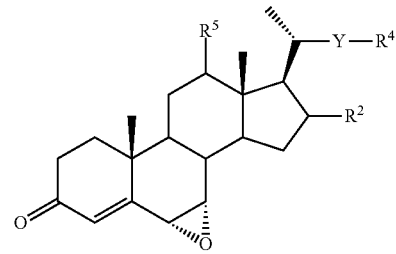

(I)

wherein Y, $R^2$, $R^4$ and $R^5$ are as defined in the first aspect of the invention;
 by oxidation of a compound of general formula (II) using an oxidant and methyltrioxorhenium as catalyst:

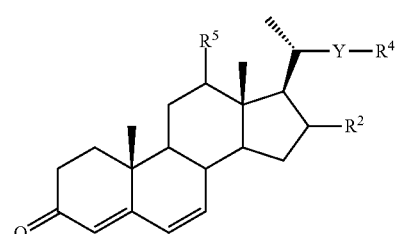

(II)

wherein Y, $R^2$, $R^4$ and $R^5$ are as defined for compounds of general formula (I);

ii. selective alkylation of a compound of general formula (I) with an organometallic reagent to give a compound of general formula (XIX):

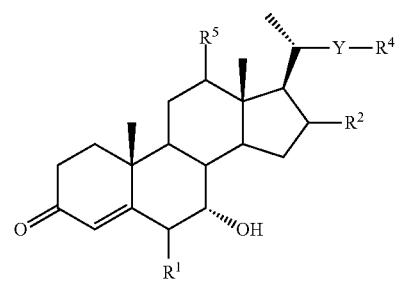

(XIX)

wherein $R^1$ is as defined for compounds of general formula (XVIII) and Y, $R^2$, $R^4$ and $R^5$ are as defined for compounds of general formula (I);

iii. reducing a compound of formula (XIX) using a suitable reducing agent to give a compound of general formula (XX):

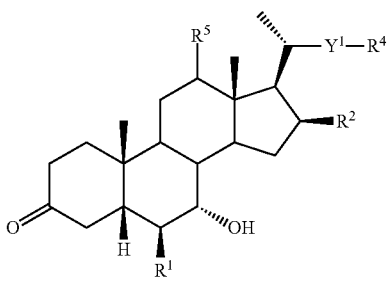

(XX)

wherein $R^1$ and $Y^1$ are as defined for compounds of general formula (XVIII) and $R^2$, $R^4$ and $R^5$ are as defined for compounds of general formula (I);

iv. oxidising the compound of general formula (XX) using a suitable oxidizing agent to give a compound of general formula (XXI):

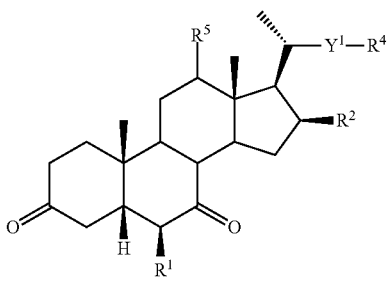

(XXI)

wherein $R^1$ and $Y^1$ are as defined for compounds of general formula (XVIII) and $R^2$, $R^4$ and $R^5$ are as defined for compounds of general formula (I);

v. epimerisation of the compound of general formula (XXI) to give a compound of general formula (XXII):

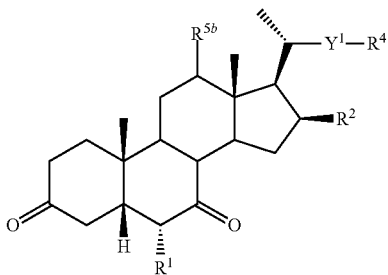

(XXII)

wherein $R^1$ and $Y^1$ are as defined for compounds of general formula (XVIII) and $R^4$ is as defined for compounds of general formula (I);

$R^2$ is H or OH or a protected OH group which is stable under basic conditions; and $R^{5b}$ is H or OH or a protected OH group which is stable under basic conditions; and (vi) reduction of the compound of general formula (XXII) using a suitable reducing agent and, where $R^2$ and/or $R^{5b}$ is a protected OH, removal of the protecting group(s), to give a compound of general formula (XVIII) as defined above, wherein removal of the protecting group can take place before or after the reduction;

wherein the process further includes one or more optional steps of converting compounds of general formulae (I), (XIX), (XX), (XXI), (XXII) and (XVIII) to other compounds of general formulae (I), (XIX), (XX), (XXI), (XXII) and (XVIII).

The optional steps consist of reacting the side chains of the compounds of general formulae (I), (XIX), (XX), (XXI), (XXII) and (XVIII) as described below to arrive at compounds with alternative Y and/or $R^4$ moieties.

FIGURES

FIG. 1: shows the conversion of a compound of general formula (IIa) or of general formula (II) in which the side chain is —$CH_2OH$ to other compounds of general formula (IIa) or of general formula (II), respectively, with different side chains.

Figure 2:
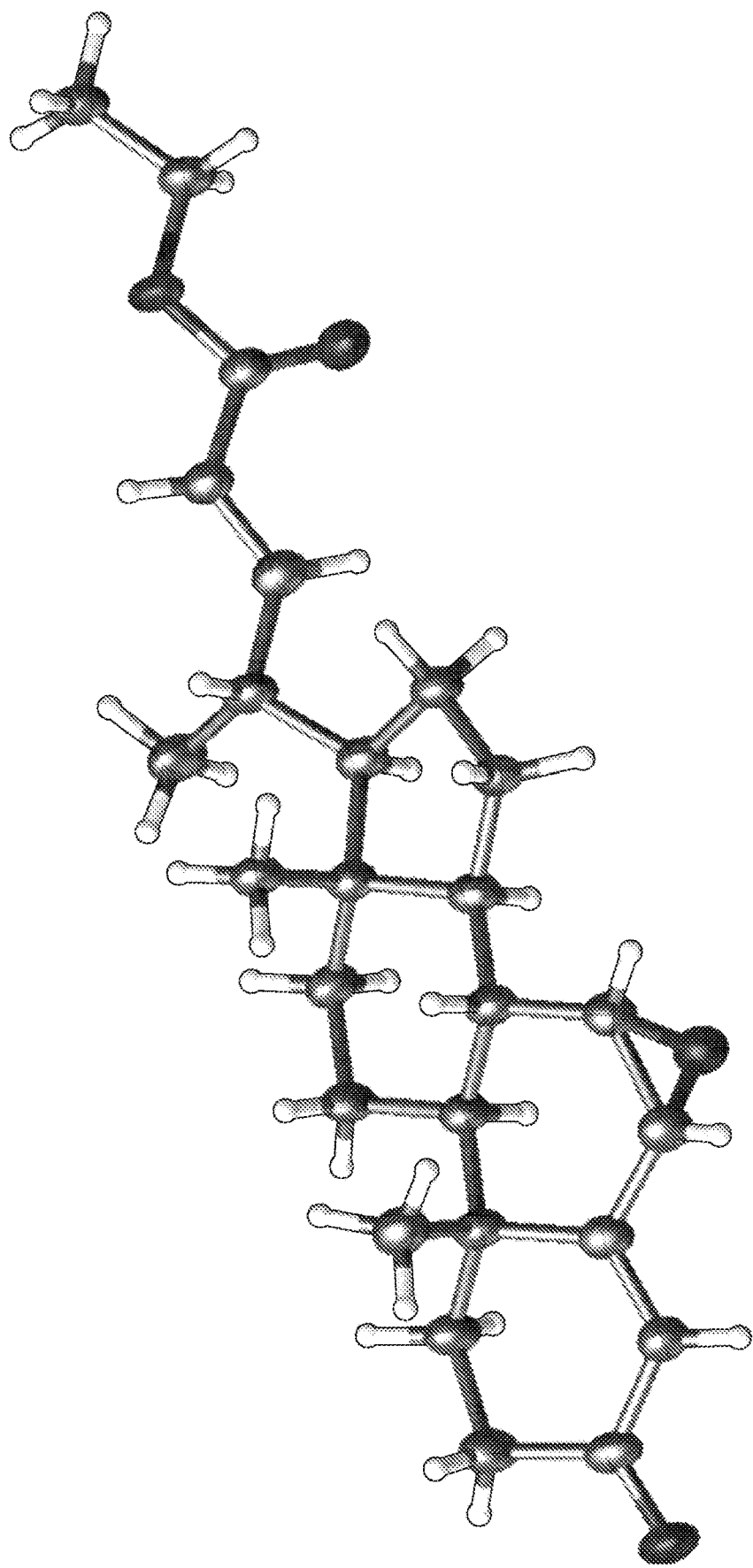

FIG. 2: shows the single crystal structure of (6α, 7α, 22E)-6,7-epoxy-3-oxo-4,22-choladien-24-oic acid ethyl ester (IA) (Thermal ellipsoids drawn at the 50% probability level, see Example 10).

Figure 3:
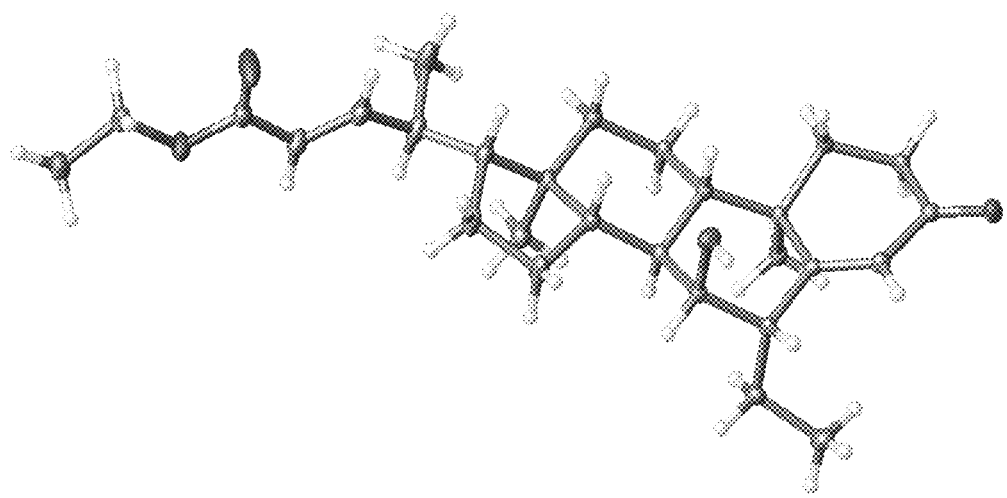

FIG. 3 shows an image showing the chemical structure of (6β, 7α, 22E)-6-ethyl-7-hydroxy-3-oxo-4,22-choladien-24-oic acid ethyl ester.

Figure 4:
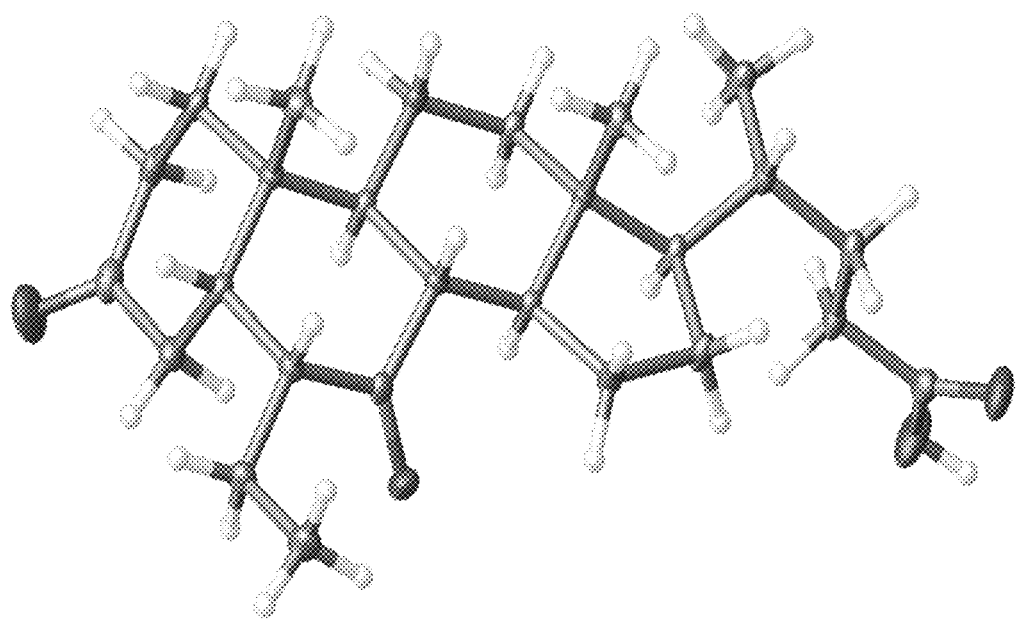

FIG. 4: shows an image showing the chemical structure of (5β, 6α)-3,7-dioxo-6-ethyl-cholan-24-oic acid.

DETAILED DESCRIPTION OF THE INVENTION

In the present specification, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments of the invention.

All publications, including but not limited to patents and patent applications, cited in this specification are herein incorporated by reference as if each individual publication were specifically and individually indicated to be incorporated by reference herein as though fully set forth.

In the present application the term "$C_{1-20}$" alkyl refers to a straight or branched fully saturated hydrocarbon group having from 1 to 20 carbon atoms. The term encompasses methyl, ethyl, n-propyl, isopropyl, n-butyl, isobutyl, s-butyl and t-butyl. Other alkyl groups, for example $C_{1-12}$ alkyl, $C_{1-10}$ alkyl, $C_{1-8}$ alkyl, $C_{1-6}$ alkyl, $C_{1-5}$ alkyl, $C_{1-4}$ alkyl, $C_{1-3}$ alkyl, or $C_{1-2}$ alkyl are as defined above but contain different numbers of carbon atoms.

The terms "heterocyclic" and "heterocyclyl" refer to a non-aromatic cyclic group having 3 to 10 ring atoms and at least one heteroatom selected from N, O, S and B and optionally substituted with one or more =O moieties. Examples of heterocyclic groups include pyrrolidine, piperidine, morpholine, piperazine, tetrahydrofuran, dioxolane (e.g. 1,3-dioxolane), dioxane (e.g. 1,3-dioxane) and cyclic thioethers. The term also includes bicyclic and bridged groups such as 9-borabicyclo(3.3.1)nonane (9-BBN).

The term "halogen" refers to fluorine, chlorine, bromine or iodine and the term "halo" to fluoro, chloro, bromo or iodo groups.

The term "$C_{1-6}$ haloalkyl" refers to a straight or branched alkyl group as defined above having from 1 to 6 carbon atoms and substituted with one or more halo atoms, up to perhalo substitution. Examples include trifluoromethyl, chloroethyl and 1,1-difluoroethyl.

Other haloalkyl groups, for example $C_{1-5}$ haloalkyl, $C_{1-4}$ haloalkyl, $C_{1-3}$ haloalkyl or $C_{1-2}$ haloalkyl are as defined above but contain different numbers of carbon atoms.

The term "$C_{2-20}$ alkenyl" refers to a straight or branched hydrocarbon group having from 2 to 20 carbon atoms and at least one carbon-carbon double bond. Examples include ethenyl (vinyl), prop-1-enyl, prop-2-enyl (allyl), hex-2-enyl etc. Other alkenyl groups, for example $C_{2-12}$ alkenyl, $C_{2-10}$ alkenyl, $C_{2-8}$ alkenyl, $C_{2-6}$ alkenyl, $C_{2-5}$ alkenyl, $C_{2-4}$ alkenyl or $C_{2-3}$ alkenyl are as defined above but contain different numbers of carbon atoms.

The term "$C_{2-20}$ alkynyl" refers to a straight or branched hydrocarbon group having from 2 to 20 carbon atoms and at least one carbon-carbon triple bond. Examples include ethynyl, prop-1-ynyl, hex-2-ynyl etc. Other alkynyl groups, for example $C_{2-12}$ alkynyl, $C_{2-10}$ alkynyl, $C_{2-8}$ alkynyl, $C_{2-6}$ alkynyl, $C_{2-5}$ alkynyl, $C_{2-4}$ alkynyl or $C_{2-3}$ alkynyl are as defined above but contain different numbers of carbon atoms.

The term "alkylene" refers to a straight or branched fully saturated hydrocarbon chain. Suitably alkylene is $C_{1-20}$ alkylene, $C_{1-12}$ alkylene, $C_{1-10}$ alkylene, $C_{1-8}$ alkylene, $C_{1-6}$ alkylene, $C_{1-5}$ alkylene, $C_{1-4}$ alkylene, $C_{1-3}$ alkylene, or $C_{1-2}$ alkylene. Examples of alkylene groups include —$CH_2$—, —$CH_2CH_2$—, —$CH(CH_3)$—$CH_2$—, —$CH_2CH(CH_3)$—, —$CH_2CH_2CH_2$—, —$CH_2CH(CH_2CH_3)$— and —$CH_2CH(CH_2CH_3)CH_2$—.

The term "alkenylene" refers to a straight or branched hydrocarbon chain containing at least one carbon-carbon double bond. Suitably alkenylene is $C_{2-20}$ alkenylene, $C_{2-12}$ alkenylene, $C_{2-10}$ alkenylene, $C_{2-8}$ alkenylene, $C_{2-6}$ alkenylene, $C_{2-5}$ alkenylene, $C_{2-4}$ alkenylene, or $C_{2-3}$ alkenylene. Examples of alkenylene groups include —CH=CH—, —CH=C($CH_3$)—, —$CH_2$CH=CH—, —CH=CH$CH_2$—, —$CH_2CH_2$CH=CH—, —$CH_2$CH=C($CH_3$)— and —$CH_2$CH=C($CH_2CH_3$)—.

The term "$C_{2-20}$ alkynyl" refers to a straight or branched hydrocarbon group having from 2 to 20 carbon atoms and at least one carbon-carbon triple bond. Examples include ethynyl, prop-1-ynyl, hex-2-ynyl etc. Other alkynyl groups, for example $C_{2-12}$ alkynyl, $C_{2-10}$ alkynyl, $C_{2-8}$ alkynyl, $C_{2-6}$ alkynyl, $C_{2-5}$ alkynyl, $C_{2-4}$ alkynyl or $C_{2-3}$ alkynyl are as defined above but contain different numbers of carbon atoms.

The term "alkyl" refers to a straight or branched fully saturated hydrocarbon chain. Suitably alkylene is $C_{1-20}$ alkyl, $C_{1-12}$ alkyl, $C_{1-10}$ alkyl, $C_{1-8}$ alkyl, $C_{1-6}$ alkyl, $C_{1-5}$ alkyl, $C_{1-4}$ alkyl, $C_{1-3}$ alkyl, or $C_{1-2}$ alkyl. Examples of alkyl groups include —$CH_3$, —$CH_2CH_3$, —CH($CH_3$)—$CH_3$, —$CH_2CH_2CH_3$, —C($CH_3$)$_3$ and —$CH_2CH_2CH_2CH_3$.

The term "alkenyl" refers to a straight or branched hydrocarbon chain containing at least one carbon-carbon double bond. Suitably alkenyl is $C_{2-20}$ alkenyl, $C_{2-12}$ alkenyl, $C_{2-10}$ alkenyl, $C_{2-8}$ alkenyl, $C_{2-6}$ alkenyl, $C_{2-5}$ alkenyl, $C_{2-4}$ alkenyl, or $C_{2-3}$ alkenyl. Examples of alkenyl groups include —CH=$CH_2$, —CH=CH($CH_3$), —$CH_2$CH=$CH_2$, —CH=CH$CH_3$, —$CH_2CH_2$CH=$CH_2$, —$CH_2$CH=CH($CH_3$)— and —$CH_2$CH=CH($CH_2CH_3$).

The term "alkynylene" refers to a straight or branched hydrocarbon chain containing at least one carbon-carbon triple bond. Suitably alkynylene is $C_{2-20}$ alkynylene, $C_{2-12}$ alkynylene, $C_{2-10}$ alkynylene, $C_{2-8}$ alkynylene, $C_{2-6}$ alkynylene, $C_{2-5}$ alkynylene, $C_{2-4}$ alkynylene, or $C_{2-3}$ alkynylene. Examples of alkynylene groups include —C≡C—, —$CH_2$C≡C—, —C≡C—$CH_2$—, —$CH_2CH_2$C≡C—, —$CH_2$C≡C$CH_2$— and —$CH_2$C≡C—$CH_2CH_2$—.

The terms "aryl" and "aromatic" refer to a cyclic group with aromatic character having from 6 to 14 ring carbon atoms (unless otherwise specified, for example 6 to 10 ring carbon atoms) and containing up to three rings. Where an aryl group contains more than one ring, not all rings must be aromatic in character. Examples include phenyl, naphthyl and anthracenyl as well as partially saturated systems such as tetrahydronaphthyl, indanyl and indenyl. A further example of an aryl group is 1,2,3,4-tetrahydronaphthalene.

The terms "heteroaryl" and "heteroaromatic" refer to a cyclic group with aromatic character having from 5 to 14 ring atoms (unless otherwise specified, for example 5 to 10 ring atoms), at least one of which is a heteroatom selected from N, O and S, and containing up to three rings. Where a heteroaryl group contains more than one ring, not all rings must be aromatic in character. Examples of heteroaryl groups include pyridine, pyrimidine, indole, benzofuran, benzimidazole and indolene. Further examples of heteroaryl groups include quinoline and isoquinoline.

The term "isotopic variant" refers to isotopically-labelled compounds which are identical to those recited in formula (Ia) or formula (I) but for the fact that one or more atoms are replaced by an atom having an atomic mass or mass number different from the atomic mass or mass number most commonly found in nature, or in which the proportion of an atom having an atomic mass or mass number found less commonly in nature has been increased (the latter concept being referred to as "isotopic enrichment"). Examples of isotopes that can be incorporated into compounds of the invention include isotopes of hydrogen, carbon, nitrogen, oxygen, fluorine, iodine and chlorine such as $^2H$ (deuterium), $^3H$, $^{11}C$, $^{13}C$, $^{14}C$, $^{18}F$, $^{123}I$ or $^{125}I$ (e.g. $^3H$, $^{11}C$, $^{14}C$, $^{18}F$, $^{123}I$ or $^{125}I$), which may be naturally occurring or non-naturally occurring isotopes.

Polyethylene glycol (PEG) is a polyether compound, which in linear form has general formula H—[O—$CH_2$—$CH_2$]$_n$—OH. A polyethylene glycol residue is a PEG in which the terminal H is replaced by a bond linking it to the remainder of the molecule.

Branched versions, including hyperbranched and dendritic versions are also contemplated and are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, glycerol oligomers, pentaerythritol and sorbitol. The central branch moiety can also be derived from several amino acids, such as lysine. The branched poly (ethylene glycol) can be represented in general form as R(-PEG-OH)$_m$ in which R is derived from a core moiety, such as glycerol, glycerol oligomers, or pentaerythritol, and m represents the number of arms. Multi-armed PEG molecules, such as those described in U.S. Pat. Nos. 5,932,462; 5,643,575; 5,229,490; 4,289,872; US2003/0143596; WO96/21469; and WO93/21259 (all incorporated herein by reference) may also be used.

The PEG polymers may have an average molecular weight of, for example, 600-2,000,000 Da, 60,000-2,000, 000 Da, 40,000-2,000,000 Da, 400,000-1,600,000 Da, 800-1,200,000 Da, 600-40,000 Da, 600-20,000 Da, 4,000-16,000 Da, or 8,000-12,000 Da.

The term "protected OH" relates to an OH group protected with any suitable protecting group. For example, the protected OH may be a group $R^4$ as defined above.

Suitable protecting groups include esters such that, for example when $R^2$ and/or $R^5$ and/or $R^3$ is a protected OH group, $R^2$ and/or $R^5$ and/or $R^3$ may independently be a group $OC(O)R^{14}$, where $R^{14}$ is a group $R^{10}$ as defined above. Silyl ethers are also suitable, and in this case, $R^2$ and/or $R^5$ and/or $R^3$ may independently be a group $OSi(R^{16})_3$, where each $R^{16}$ is independently a group $R^{13}$ as defined above.

Other suitable protecting groups for OH are well known to those of skill in the art (see Wuts, P G M and Greene, T W (2006) "Greene's Protective Groups in Organic Synthesis", $4^{th}$ Edition, John Wiley & Sons, Inc., Hoboken, N.J., USA, incorporated herein by reference).

Salts of the compounds of general formula (XVIIIa) and (XVIII) are suitably pharmaceutically or veterinarily acceptable salts. Salts which are not pharmaceutically or veterinarily acceptable may still be valuable as intermediates.

References to a protecting group which is stable in basic conditions mean that the protecting group cannot be removed by treatment with a base.

Appropriate salts of the compounds described herein include basic addition salts such as sodium, potassium, calcium, aluminium, zinc, magnesium and other metal salts as well as choline, diethanolamine, ethanolamine, ethyl diamine, meglumine and other well-known basic addition salts as summarised in Paulekuhn et al., *J. Med. Chem.* 2007, 50, 6665-6672 (incorporated herein by reference) and/or known to those skilled in the art.

The term "carboxylic acid mimetic group" relates to known carboxylic acid isosteres including tetrazole, substituted tetrazole, $—SO_2—NHR^{10}$, $C(O)NH—SO_2R^{10}$ and $NHC(O)NH—SO_2R^{10}$;

wherein $R^{10}$ is as above defined for a compound of general formulae (Ia) or (I) and is suitably H, $C_{1-6}$ alkyl, $C_{3-7}$ cycloalkyl or 6- to 14-membered aryl (e.g. phenyl).

Tetrazole groups include tetrazole-5-yl and tetrazole-1-yl. Substituted tetrazole includes tetrazole substituted with $C_{1-4}$ alkyl, halo, OH, $O(C_{1-4}$ alkyl), $SO_2R^{10}$ (e.g. $SO_2(C_{1-4}$ alkyl), $SO_2$-phenyl or $SO_2$-tolyl).

Such carboxylic acid mimetic groups are well known in the art and are discussed, for example in "On Medicinal Chemistry"; M Stocks, L Alcaraz, E Griffen; Pub: Sci-ink Ltd (April 2007).

Particularly suitable carboxylic acid mimetic groups include tetrazole, $C(O)NH—SO_2R^{10}$ and $NHC(O)NH—SO_2R^{10}$, with tetrazole being particularly suitable.

The epoxidation of (22E)-3-oxo-4,6,22-cholatrien-24-oic acid ethyl ester (referred to herein as compound (IIA)) to form (6α,7β,22E)-6,7-epoxy-3-oxo-4,22-choladien-24-oic acid ethyl ester (referred to herein as compound (IA)) is described by Uekawa et al. in *Biosci. Biotechnol. Biochem.*, 2004, 68, 1332-1337 (incorporated herein by reference) using either magnesium monoperoxyphthalate hydrate (MMPP) in $Et_2O$ and $CHCl_3$ at ambient temperature, or meta-chloroperoxybenzoic acid (mCPBA) in $CHCl_3$ at reflux (Scheme 1). The reactions were performed on 19.8 mg and 200 mg scale and yields of 59.6% and 55.0% respectively were reported.

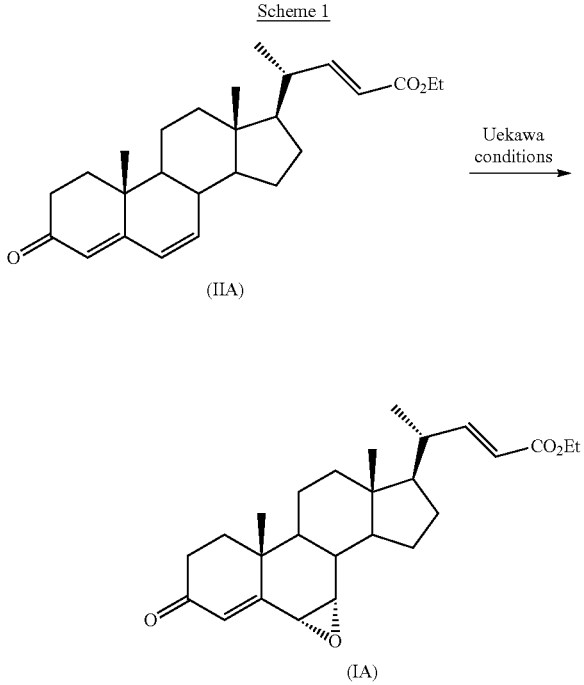

When both sets of epoxidation conditions were repeated by the present inventors, conversions of 50-60% were observed. Purified compound (IA) was isolated in yields of up to around 50%. For both sets of conditions degradation and the formation of side products was observed during the reaction process. This was attributed to opening of the epoxide, and complex over-oxidation side reactions and/or a competing Baeyer Villager oxidation. As such, neither of the methods proposed by Uekawa et al. are suitable for large scale synthesis of compound (IA).

Furthermore, the reaction conditions described by Uekawa et al. require purification by preparative thin layer chromatography and column chromatography, and utilise chloroform and diethyl ether as solvent, again rendering the processes unsuitable for large scale synthesis and manufacture.

Regarding the observed degradation and formation of side products, the formation of compounds other than compound (IA) are not unexpected. Epoxidation at the 6,7-position of compound (IIA) must occur to form compound (IA). However, compound (IA) contains two additional double bonds at the 4,5- and 22,23-positions which are also susceptible to oxidation. Furthermore, each double bond has the potential to be oxidised on the alpha- or beta-face of the molecule, and a single molecule may be oxidised at multiple sites. The isolated products and possible epoxides are shown in Scheme 2.

Scheme 2

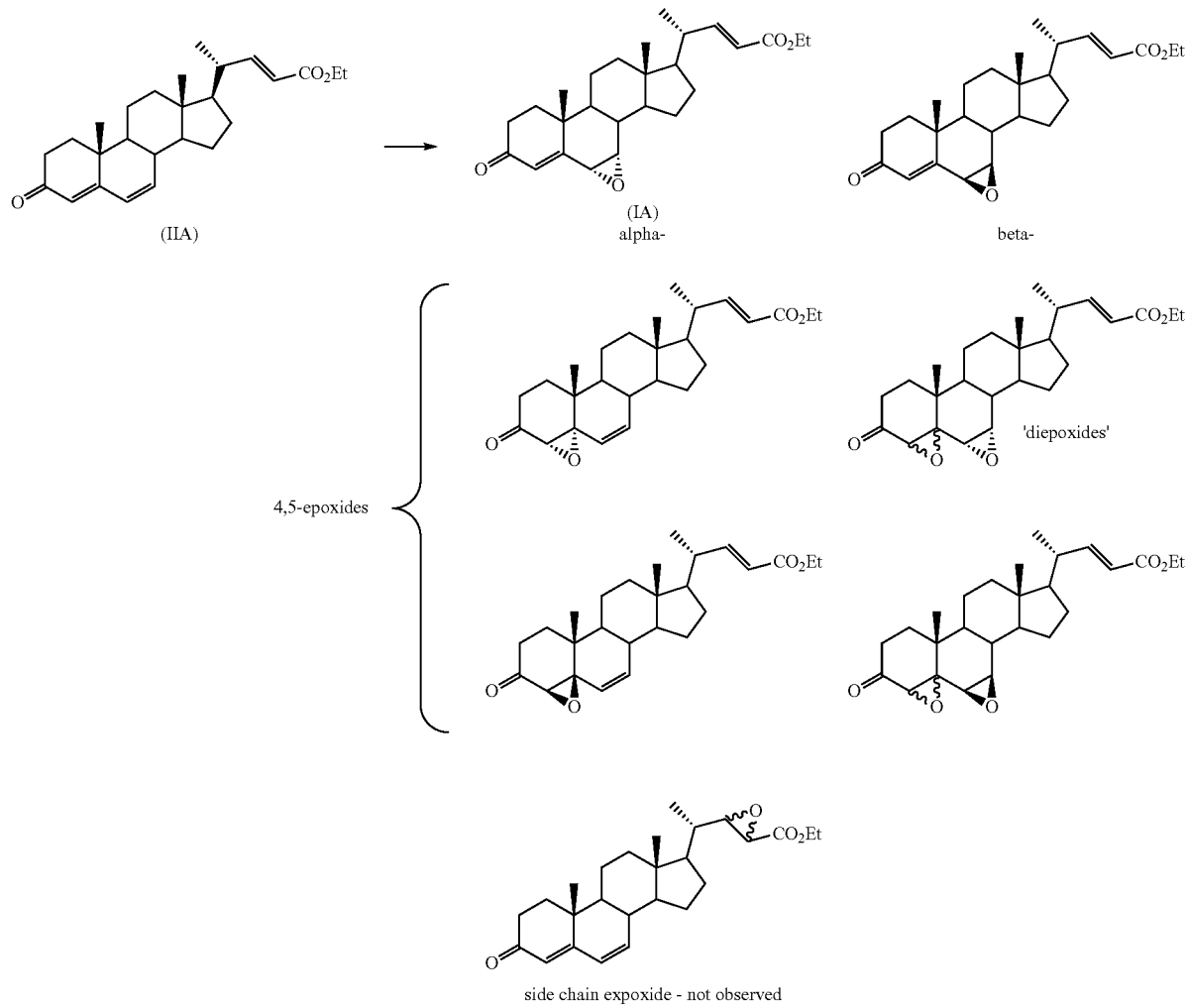

A similar issue arises with the epoxidation of 3-oxo-4,6-choladien-24-oic acid ethyl ester (referred to herein as compound (IIB)) to form (6α, 7α)-6,7-epoxy-3-oxo-4-choladien-24-oic acid ethyl ester (referred to herein as compound (IB)).

Another consideration to be taken into account for both (IA) and (IB) is that under certain conditions e.g. acidic conditions, the epoxide product can undergo further reactions such as ring-opening and possibly polymerization, once formed.

Thus, it is an object of the present invention to provide an improved process for the epoxidation of compounds of general formula (IIa) and of compounds of general formula (II), in particular an improved process for the epoxidation of a compound of formula (IIA) or formula (IIB) to form a compound of general formula (IA) or (IB), respectively. Suitably the process is regioselective and stereoselective, thereby providing higher yields of the desired epoxide. In addition, the process is suitably scalable, meaning that it is suitable for use on a large scale, e.g. on an industrial scale.

As described in Example 9, the present inventors evaluated a number of alternative epoxidation conditions and found that, surprisingly, the use of an oxidant in the presence of methyltrioxorhenium (MTO) as catalyst provided improved yields of the desired alpha epoxide compared with the Uekawa et al. conditions of MMPP and mCPBA and alternative conditions including dimethyldioxirane (DMDO). The improvement was consistently observed for various oxidants and solvents. A representative epoxidation procedure using MTO is set out in Example 10.

Moreover, as shown in Example 10a, the process using MTO is also suitable for large scale synthesis, with the compound of formula (IA) being isolated in 72% yield on a scale of 4.9 kg (based on starting compound (IIA)). Such high yields could not be achieved on such a large scale using the conditions described by Uekawa et al.

Thus, the present invention provides an improved process for the epoxidation of compounds of general formula (IIa) to form compounds of general formula (Ia) and for for the epoxidation of compounds of general formula (II) to form compounds of general formula (I). In particular, the process is scalable, has improved regioselectivity, stereoselectivity, and also reduced degradation.

In a first aspect is provided a process for preparing a compound of general formula (Ia):

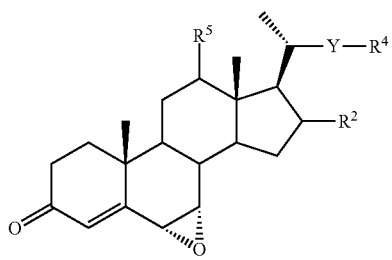

(Ia)

or a salt or isotopic variant thereof, wherein Y, $R^2$, $R^4$ and $R^5$ are as defined above, the process comprising:
oxidation of a compound of general formula (IIa) using an oxidant and methyltrioxorhenium as catalyst:

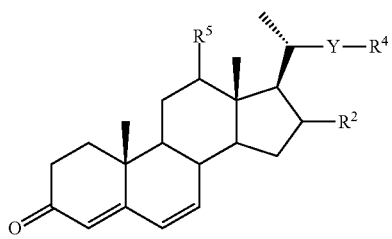

(IIa)

or a salt or isotopic variant thereof,
wherein Y, $R^2$, $R^4$ and $R^5$ and are as defined for compounds of general formula (Ia).

In a second aspect is provided a process for preparing a compound of general formula (I):

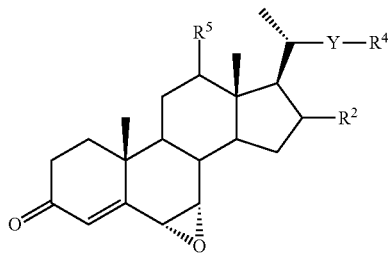

(I)

or a salt or isotopic variant thereof, wherein Y, $R^2$, $R^4$ and $R^5$ are as defined above, the process comprising:
oxidation of a compound of general formula (II) using an oxidant and methyltrioxorhenium as catalyst:

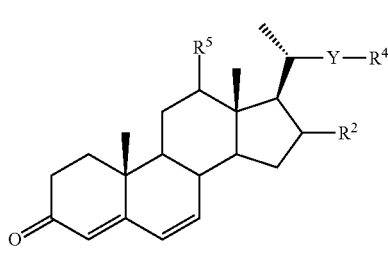

(II)

or a salt or isotopic variant thereof,
wherein Y, $R^2$, $R^4$ and $R^5$ and are as defined for compounds of general formula (I).

The oxidation is catalysed by methyltrioxorhenium (MTO, also known as methyltrioxyrhenium and methylrhenium trioxide) which is a commercially available organometallic compound of formula $CH_3ReO_3$ (Scheme 3).

Scheme 3

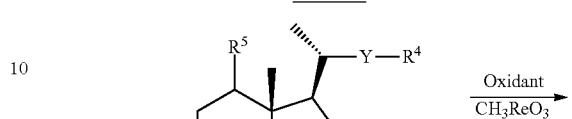

(II)

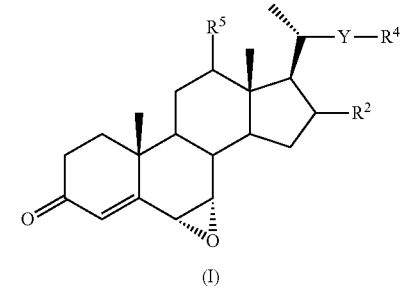

(I)

The methyltrioxorhenium is typically present in the reaction at 0.1-10 mol %, such as 0.1-5 mol %, 0.2-3 mol %, 0.5-2 mol %, 0.5-1.5 mol %, about 1-2 mol % or about 1 mol %.

The reaction is carried out in the presence of an oxidant such as hydrogen peroxide (for example 30% hydrogen peroxide), a hydrogen peroxide adduct such as urea-hydrogen peroxide (a solid adduct of hydrogen peroxide and urea), or sodium percarbonate. In one embodiment, the oxidant is hydrogen peroxide or a hydrogen peroxide adduct. Suitably the oxidant is urea-hydrogen peroxide.

Up to 3 equivalents (per mole of compound of general formula (II)) of oxidant are typically used, for example up to 2 equivalents such as up to 1.8 equivalents, up to 1.5 equivalents or up to 1.2 equivalents. At least 1 equivalent of oxidant is required.

A representation of two possible complexes formed between methyltrioxorhenium and hydrogen peroxide (possible active epoxidation complexes) is shown below in Scheme 4:

Scheme 4

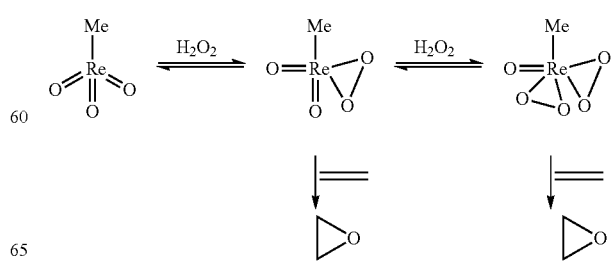

The reaction is suitably carried out in the presence of a ligand which will coordinate with the active epoxidation complexes. Such ligands are well known to the skilled person (see Rudolph et al., *J. Am. Chem. Soc.*, 1997, 119(26), 6189-6190, incorporated herein by reference) and are typically Lewis bases such as N-donor ligands (including N-oxides), aromatic Schiff bases or aliphatic amines.

In one embodiment, the ligand is a moiety which is bound to the rhenium via 1 to 3 atoms of at least one element selected from oxygen and nitrogen, such that the 5- to 7-valency of rhenium is fulfilled. In one embodiment, the ligand is an amine e.g. a primary, secondary or tertiary aliphatic or aromatic amine, such as aniline, aminoacetone, aminoacetonitrile, or ephidrine; a nitrogen-containing aliphatic heterocycle e.g. pyrrolidine, piperidine, piperazine, morpholine or quinuclidine; or a nitrogen-containing aromatic heterocycle e.g. pyridine, pyrimidine, pyrazine, imidazaole, pyrazole, indole, quinoline, quinolone or isoquinoline; any of which may be optionally substituted, e.g. by $C_{1-4}$alkyl, or by —O— (i.e. forming an N-oxide).

In one embodiment, the ligand is a substituted pyridine or pyrazole. Suitably the ligand is pyridine, 3-cyanopyridine, 4-cycanopyridine, 2-hydroxypyridine, 3-methyl pyridine, 1-methyl pyrazole or 3-methyl pyrazole; in particular 3-cyanopyridine, 4-cycanopyridine, 2-hydroxypyridine, 3-methyl pyridine or 3-methyl pyrazole; for example 3-methyl pyrazole.

If used, the ligand is typically present at 5-40 mol %, such as 5-30 mol %, 5-15 mol %, 8-15 mol % or about 12 mol %.

The presence of a ligand in the reaction mixture may provide a number of benefits including the acceleration of the reaction, the suppression of hydrolytic pathway of MTO to perrhenic acid, and buffering the reaction thereby avoiding acid catalysed opening of epoxide reaction product.

The reaction is carried out in an organic solvent. Suitable organic solvents include $CH_2Cl_2$, $CHCl_3$, toluene, $CH_3CN$, EtOAc, IPA, MIBK, nBuOAc and fluorinated solvents, and mixtures thereof. In one embodiment, the organic solvent is selected from $CH_2Cl_2$, $CH_3CN$, EtOAc, IPA, MIBK, nBuOAc, fluorinated solvents, and mixtures thereof. Suitable fluorinated solvents include HFIP (hexafluoroisoproanol), TFE (2,2,2-trifluoroethanol), hexafluorobutanol, trifluorotoluene, hexafluorobenzene and the solvents sold under the trade mark Vertrel®. In one embodiment, fluorinated solvents are selected from HFIP, TFE and the solvents sold under the trade mark Vertrel®.

In one embodiment, the reaction solvent comprises fluorinated solvent. In one embodiment, the reaction solvent comprises HFIP. In one embodiment the reaction solvent is a fluorinated solvent or a mixture of a fluorinated and non-fluorinated solvent. In one embodiment, the reaction solvent is a mixture of two or more different fluorinated solvents. In one embodiment, the reaction solvent is a fluorinated solvent such as HFIP. In one embodiment, the reaction solvent is a mixture of a fluorinated solvent and ethyl acetate. In one embodiment, the reaction solvent is a mixture of HFIP and ethyl acetate. In one embodiment, the reaction solvent is a mixture of HFIP and toluene.

Suitably the reaction solvent comprises fluorinated solvent. In certain embodiments, the use of a reaction solvent comprising fluorinated solvent may be expected to lead to an improved conversion of starting material to desired epoxide product compared to the use of reaction solvent not comprising a fluorinated solvent. In certain embodiments, the use of a reaction solvent comprising fluorinated solvent may be expected to lead to higher α:β epoxide ratio compared to the use of reaction solvent not comprising a fluorinated solvent. In certain embodiments, the use of a reaction solvent comprising fluorinated solvent may be expected to lead to improved selectivity for epoxidation of the 6,7 double bond in preference to the 4,5 double bond. Without wishing to be bound by theory, the present inventors believe that fluorinated solvents such as HFIP are involved in activating the oxidant e.g. the peroxide, leading to improved conversion. Fluorinated solvents may also enhance solubility of the oxidant, e.g. UHP.

In one embodiment, the reaction is carried out in the temperature range of about −10° C. to about 50° C., such as about −5° C. to about 25° C., about 0° C. to about 10° C., about 0° C. to about 5° C., about 0° C. to about 4° C., about 0° C. to about 3° C., about 0° C. to about 2° C., about 0° C. to about 1° C., or about 0° C. Another temperature range of interest is about 0° C. to about 15° C. e.g. about 0° C. to about 10° C., about 2° C. to about 8° C. e.g. about 5° C.

Once the epoxidation reaction is complete (as determined by, for example by TLC or HPLC), the extent of conversion can be determined using HPLC analysis to quantitatively determine the proportion of each component in the reaction mixture. A representative set of HPLC conditions are set out in General Procedures and utilised in Example 10 to determine the relative amounts of desired alpha-epoxide, undesired beta-epoxide and unreacted starting material. Suitably the extent of conversion is such that no starting material is observed once the reaction is complete. In one embodiment, the ratio of alpha-epoxide:beta-epoxide:starting material observed following completion of the reaction using the HPLC conditions described in General Procedures is between about 20:1:0 and about 10:1:0 e.g. between about 15:1:0 and 10:1:0, e.g. around 13:1:0. In one embodiment, the ratio of alpha-epoxide:beta-epoxide observed following completion of the reaction using the HPLC conditions described in General Procedures is between about 20:1 and about 8:1 e.g. between about 18:1 and 8:1. In one embodiment, the ratio of alpha-epoxide:beta-epoxide observed at a given time point e.g. 1 hour, 2 hours, 3 hours, 4 hours, 5 hours, 10 hours, 20 hours, or 24 hours, using the HPLC conditions described in General Procedures is between about 25:1 and about 5:1 e.g. between about 20:1 and 8:1 e.g. between about 18:1 and 8:1. In one embodiment, the ratio of alpha-epoxide:beta-epoxide observed at a given time point e.g. 1 hour, 2 hours, 3 hours, 4 hours, 5 hours, 10 hours, 20 hours, or 24 hours, using the HPLC conditions described in General Procedures is at least 5:1 e.g. at least 8:1, at least 10:1, at least 12:1, at least 15:1 or at least 20:1.

Suitably, the MTO process of the invention is a batch process using a minimum quantity of starting compound of general formula (IIa) or (II) of at least 1 g, at least 5 g, at least 100 g, at least 1 kg, at least 4 kg or at least 5 kg.

The process according to the invention, in at least some embodiments, is expected to have one or more advantages of:
- improved yield, in particular for large-scale synthesis;
- being scalable i.e. consistent yields for both small and large-scale synthesis;
- reduced degradation and side product formation;
- improved regioselectivity, i.e. selectivity for the 6,7-position of compound (IIA);
- improved stereoselectivity, i.e. selectivity for the alpha-epoxide;
- improved conversion;
- simplified purification process;
- suitability for large-scale synthesis compared with known processes.

Compounds of General Formulae (Ia), (I), (IIa) and (II)

In a further aspect is provided a novel compound of general formula (IIa):

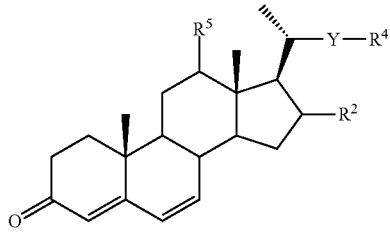

(IIa)

or a salt or isotopic variant thereof,
wherein, Y, $R^2$, $R^4$ and $R^5$ are as described above for compounds of general formula (IIa).

In a further aspect is provided a novel compound of general formula (II):

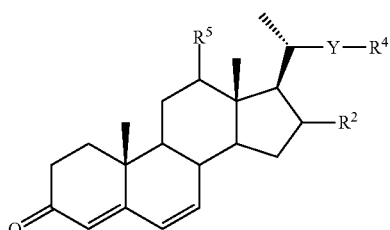

(II)

or a salt or isotopic variant thereof,
wherein, Y, $R^2$, $R^4$ and $R^5$ are as described above for compounds of general formula (II).

In a still further aspect is provided a novel compound of general formula (Ia):

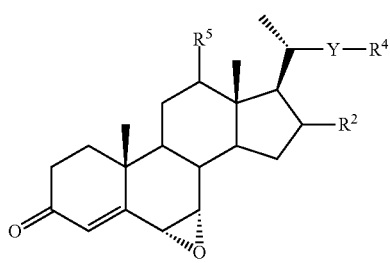

(Ia)

or a salt or isotopic variant thereof
wherein, Y, $R^2$, $R^4$ and $R^5$ are as described above for compounds of general formula (Ia).

In a still further aspect is provided a novel compound of general formula (I):

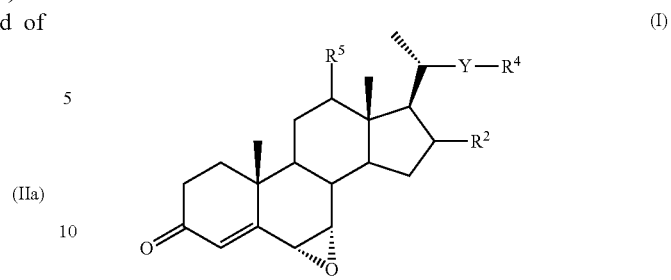

(I)

or a salt or isotopic variant thereof
wherein, Y, $R^2$, $R^4$ and $R^5$ are as described above for compounds of general formula (I).

The following embodiments relate to compounds of general formulae (Ia), (I), (IIa) and (II) where applicable, and to methods for their preparation as described herein, unless otherwise stated. The embodiments also relate to compounds of general formulae (XVIIIa), (XVIII), (XIXa), (XIX), (XXa), (XX), (XXIa), (XXI), (XXIIa) and (XXII) where appropriate (i.e. as far as chemically sensible).

Embodiments relating to individual R groups, Y groups and X groups are envisaged as being fully combinable with one or more other R groups to form further embodiments of the invention.

In one embodiment, $R^2$ is H. In one embodiment, $R^2$ is halo. In one embodiment, $R^2$ is OH.

In one embodiment, $R^2$ is a protected OH group. In one embodiment, $R^2$ is a protected OH group which is not stable in a basic environment such that treatment with a base converts the protected OH group to OH. Examples of such groups are well known in the art and include a group $OC(O)R^{14}$, wherein $R^{14}$ is a group $R^{10}$ as defined above for general formula (Ia) or (I), and is suitably $C_{1-6}$ alkyl or benzyl, or $C_{1-6}$ alkyl or phenyl. In another embodiment, $R^2$ is a protected OH group which is stable in a basic environment. Examples of such groups include $OSi(R^{16})_3$, where each $R^{16}$ is independently a group $R^{13}$ as defined above for general formula (Ia) or (I), and is suitably $C_{1-6}$ alkyl or phenyl. In one embodiment, $Si(R^{16})_3$ is selected from the group consisting of trimethylsilyl (TMS), triethylsilyl (TES), triphenylsilyl (TPS), tri-isopropylsilyl (TIPS), thexyldimethylsilyl (TDS), tert-butyldiphenylsilyl (TBDPS), tert-butyldimethylsilyl (TBDMS or TBS), di-tert-butylmethylsilyl (DTBMS), diethylisopropylsilyl (DEIPS) and dimethylisopropylsilyl (DMIPS), in particular TMS, TES, TIPS, TBDMS and TBDPS.

In one embodiment, $R^2$ is in the "up" position i.e. is in the beta-configuration.

In one embodiment, Y is a bond. In one embodiment, Y is a $C_{1-20}$, $C_{1-12}$, $C_{1-10}$, $C_{1-8}$, $C_{1-6}$, $C_{1-5}$, $C_{1-4}$, $C_{1-3}$ or $C_{1-2}$ alkylene or a $C_{2-12}$, $C_{2-10}$, $C_{2-8}$, $C_{2-6}$, $C_{2-5}$, $C_{2-4}$, $C_{2-3}$ or $C_2$ alkenylene linker group either of which is optionally substituted with one or more groups $R^3$ as defined above.

In one embodiment, Y is bond, or a $C_{1-3}$ alkylene or $C_{2-3}$ alkenylene linker group either of which is optionally substituted with one or more groups $R^3$ as defined above. Suitably Y is a $C_{1-3}$ alkylene or $C_{2-3}$ alkenylene linker group either of which is optionally substituted with one or more groups $R^3$ as defined above.

In one embodiment, Y is a bond, —$CH_2$—, —$CH_2CH_2$—, —CH=CH— or —CH=C($CH_3$)—; suitably —$CH_2$—, —$CH_2CH_2$—, —CH=CH— or —CH=C($CH_3$)—, in particular —$CH_2CH_2$— or —CH=CH—.

In one embodiment, Y is a bond, an unsubstituted $C_{1-3}$ alkylene group, a $C_{1-3}$ alkylene group substituted with OH, or a $C_{1-3}$ alkenylene group. For example, Y may be a bond, —$CH_2$—, —$CH_2CH_2$—, —CH(OH)—$CH_2$—, —CH=CH— or —CH=C($CH_3$)—, in particular a bond, —$CH_2$—, —$CH_2$—$CH_2$—, —CH=CH— or —CH=C ($CH_3$)—, especially —$CH_2$—, —$CH_2$—$CH_2$—, —CH=CH— or —CH=C($CH_3$)—.

In one embodiment, Y is an $C_{1-15}$ alkylene linker, more suitably $C_{1-12}$, $C_{1-10}$ or $C_{1-8}$ alkylene linker and is substituted with an OH group. In this case, the OH group may be separated from the $R^4$ moiety by a single $CH_2$ group such that the linker Y is a group $Y^4$—CH(OH)—$CH_2$, where $Y^4$ is as defined for Y, but is shorter by two carbon atoms. For example, Y may be —CH(OH)—$CH_2$—.

This Y linker is particularly suitable when $R^4$ is CN or $R^4$ is CH($XR^{10}$)($XR^1$) e.g. CH($OR^{10}$)($OR^{11}$) wherein $R^{10}$ and $R^{11}$ are as defined above, but particularly wherein the $XR^{10}$ and $XR^{11}$ e.g $OR^{10}$ and $OR^{11}$ groups together with the carbon atom to which they are attached form a cyclic group, e.g. a cyclic acetal group such as a 1,3-dioxane or 1,3-dioxolane ring.

In one embodiment, $R^3$ is H. In one embodiment, $R^3$ is halo. In one embodiment, $R^3$ is OH. In one embodiment, $R^3$ is $NR^8R^9$, wherein each of $R^8$ and $R^9$ are suitably independently selected from H, methyl, ethyl, benzyl and tert-butyoxycarbonyl. In one embodiment, $R^3$ is a protected OH group. In one embodiment, $R^3$ is a protected OH group which is not stable in a basic environment such that treatment with a base converts the protected OH group to OH. Examples of such groups are well known in the art and include a group $OC(O)R^{14}$, wherein $R^{14}$ is a group $R^{10}$ as defined above for general formula (Ia) or (I), and is suitably $C_{1-6}$ alkyl or benzyl, or $C_{1-6}$ alkyl or phenyl. In another embodiment, $R^3$ is a protected OH group which is stable in a basic environment. Examples of such groups include $OSi(R^{16})_3$, where each $R^{16}$ is independently a group $R^{13}$ as defined above for general formula (Ia) or (I), and is suitably $C_{1-6}$ alkyl or phenyl. In one embodiment, $Si(R^{16})_3$ is selected from the group consisting of trimethylsilyl (TMS), triethylsilyl (TES), triphenylsilyl (TPS), tri-isopropylsilyl (TIPS), thexyldimethylsilyl (TDS), tert-butyldiphenylsilyl (TBDPS), terf-butyldimethylsilyl (TBDMS or TBS), di-tert-butyImethylsilyl (DTBMS), diethylisopropylsilyl (DEIPS) and dimethylisopropylsilyl (DMIPS), in particular TMS, TES, TIPS, TBDMS and TBDPS.

In one embodiment $R^3$ is H, halo, OH, $OC(O)R^{14}$, $OSi(R^{16})_3$, or $NR^8R^9$;

wherein $R^{14}$ is $C_{1-6}$ alkyl or phenyl;
each $R^{16}$ is independently $C_{1-6}$ alkyl or phenyl; and
each $R^8$ and $R^9$ is independently H, methyl, ethyl or tert-butoxycarbonyl.

In one embodiment, each $R^3$ is independently halo, $OR^8$ or $NR^8R^9$; wherein each of $R^8$ and $R^9$ is independently H or $C_{1-4}$ alkyl.

In one embodiment, each $R^3$ is independently halo, $OR^8$ or $NR^8R^9$; wherein each of $R^8$ and $R^9$ is independently selected from H, methyl or ethyl, especially H or methyl.

In one embodiment, Y and $R^4$ together form a =$CH_2$ group.

In one embodiment, when present in the $R_4$ moiety, each $R^{10}$ and $R^{11}$ is independently:
a. hydrogen; or
b. $C_{1-10}$ alkyl, $C_{2-10}$ alkenyl or $C_{2-10}$ alkynyl, any of which is optionally substituted with one or more substituents as described above; or c. a 6- to 10-membered aryl or 5- to 10-membered heteroaryl group either of which is optionally substituted with one or more substituents as described above; or
d. a polyethylene glycol residue; or
e. when $R^4$ is CH($XR^{10}$)($XR^{11}$), CH($R^{10}$)($XR^{11}$), $NR^{10}R^{11}$, $BR^{10}R^{11}$, CH[C(O)$OR^{10}$]$_2$ or CH($BR^{10}R^{11}$)$_2$, an $R^{10}$ and an $R^{11}$ group, together with the atom or atoms to which they are attached, may combine to form a 3- to 10-membered heterocylic ring, more suitably a 5- to 6-membered heterocyclic ring.

In one embodiment, each $R^{10}$ and $R^{11}$ is independently:
a. hydrogen; or
b. $C_{1-10}$ alkyl, $C_{2-10}$ alkenyl or $C_{2-10}$ alkynyl, any of which is optionally substituted with one or more substituents as described above; or
c. a 6- to 10-membered aryl or 5- to 10-membered heteroaryl group either of which is optionally substituted with one or more substituents as described above; or
d. a polyethylene glycol residue; or
e. when $R^4$ is CH($OR^{10}$)($OR^{11}$), CH($R^{10}$)($OR^{11}$), CH($SR^{10}$)($SR^{11}$), $NR^{10}R^{11}$, $BR^{10}R^{11}$, CH[C(O)$OR^{10}$]$_2$ or CH($BR^{10}R^{11}$)$_2$, an $R^{10}$ and an $R^{11}$ group, together with the atom or atoms to which they are attached, may combine to form a 3- to 10-membered heterocylic ring.

Suitably, each $R^{10}$ and $R^{11}$ is independently
a. hydrogen; or
b. $C_{1-10}$ alkyl, $C_{2-10}$ alkenyl or $C_{2-10}$ alkynyl optionally substituted with one or more substituents as described above, or
c. a 6- to 10-membered aryl group or a 5- to 6-membered heteroaryl group optionally substituted with one or more substituents as described above; or
e. when $R^4$ is C(O)$NR^{10}R^{11}$ or $NR^{10}R^{11}$, an $R^{10}$ and an $R^{11}$ group, together with the nitrogen to which they are attached, combine to form a pyrrolidine or piperidine ring or when $R^4$ is CH($XR^{10}$)($XR^{11}$), for example CH($OR^{10}$)($OR^{11}$), the $XR^{10}$ and $XR^{11}$ group, together with the carbon atom to which they are attached, combine to form a ring; suitably X is 0 and the ring is a 1,3-dioxane or 1,3-dioxolane ring; or when $R^4$ is $BR^{10}R^{11}$, the $R^{10}$ and $R^{11}$ groups, together with the boron atom to which they are attached combine to form a bridged boron-containing ring, such as 9-BBN.

Suitably, each $R^{10}$ and $R^{11}$ is independently:
a. hydrogen or
b. $C_{1-10}$ alkyl, $C_{2-10}$ alkenyl or $C_{2-10}$ alkynyl optionally substituted with one or more substituents as described above or
c. a 6- to 10-membered aryl group optionally substituted with one or more substituents as described above; or
e. when $R^4$ is C(O)$NR^{10}R^{11}$ or $NR^{10}R^{11}$, an $R^{10}$ and an $R^{11}$ group, together with the nitrogen to which they are attached, combine to form a pyrrolidine or piperidine ring or when $R^4$ is CH($OR^{10}$)($OR^{11}$), the $OR^{10}$ and $OR^{11}$ group, together with the carbon atom to which they are attached, combine to form a 1,3-dioxane or 1,3-dioxolane ring; or when $R^4$ is $BR^{10}R^{11}$, the $R^{10}$ and $R^{11}$ groups, together with the boron atom to which they are attached combine to form a bridged boron-containing ring such as 9-BBN.

In one embodiment, when $R^4$ is $NR^{10}R^{11}$, $R^{10}$ is H or $C_{1-4}$ alkyl and $R^{11}$ is a 5-10 membered heteroaryl group such as tetrazole.

When $R^4$ is $OSi(R^{13})_3$, suitably each $R^{13}$ is independently selected from:
a. $C_{1-10}$ alkyl, $C_{2-10}$ alkenyl or $C_{2-10}$ alkynyl optionally substituted with one or more substituents as described above; or b. a 6- to 10-membered aryl or 5- to 10-membered heteroaryl group optionally substituted with one or more substituents as described above.

More suitably, each $R^{13}$ is independently selected from:

a. $C_{1-10}$ alkyl, $C_{2-10}$ alkenyl or $C_{2-10}$ alkynyl optionally substituted with one or more substituents as described above; or b. a 6- to 10-membered aryl group optionally substituted with one or more substituents as described above.

Still more suitably, each $R^{13}$ is independently selected from $C_{1-10}$ alkyl or phenyl, either of which is optionally substituted as described above.

In one embodiment, each $R^{13}$ is independently selected from $C_{1-6}$ alkyl (in particular methyl, ethyl, isopropyl, tert-butyl, hexyl) and phenyl.

In one embodiment, $Si(R^{13})_3$ is selected from the group consisting of trimethylsilyl (TMS), triethylsilyl (TES), triphenylsilyl (TPS), tri-isopropylsilyl (TIPS), thexyldimethylsilyl (TDS), tert-butyldiphenylsilyl (TBDPS), tert-butyldimethylsilyl (TBDMS or TBS), di-tert-butylmethylsilyl (DTBMS), diethylisopropylsilyl (DEIPS) and dimethylisopropylsilyl (DMIPS), in particular TMS, TES, TIPS, TBDMS and TBDPS.

Suitable substituents for alkyl, alkenyl and alkynyl $R^{10}$ and $R^{11}$ groups include halo, $NO_2$, CN, $OR^{19}$, $SR^{19}$, $C(O)OR^{19}$, $SO_2R^{19}$, $SO_3R^{19}$, $OSO_3R^{19}$, $N(R^{19})_2$ and a 6- to 10-membered aryl or 5- to 14-membered heteroaryl group, either of which is optionally substituted with $C_{1-6}$ alkyl, $C_{1-6}$ haloalkyl, halo, $NO_2$, CN, $OR^{19}$, $SO_2R^{19}$, $SO_3R^{19}$ or $N(R^{19})_2$; where $R^{19}$ is as defined above.

Similarly, suitable substituents for alkyl, alkenyl and alkynyl $R^{13}$ groups include halo, $NO_2$, CN, $OR^{19}$, $SR^{19}$, $C(O)OR^{19}$, $SO_2R^{19}$, $SO_3R^{19}$, $OSO_3R^{19}$, $N(R^{19})_2$ and a 6- to 10-membered aryl or 5- to 14-membered heteroaryl group, either of which is optionally substituted with $C_{1-6}$ alkyl, $C_{1-6}$ haloalkyl, halo, $NO_2$, CN, $OR^{19}$, $SO_2R^{19}$, $SO_3R^{19}$ or $N(R^{19})_2$; where $R^{19}$ is as defined above.

More suitable substituents for these $R^{10}$ and $R^{11}$ groups include halo, $OR^{19}$, $C(O)OR^{19}$, $N(R^{19})_2$, $SO_3R^{19}$, $OSO_3R^{19}$ or a 6- to 10-membered aryl group optionally substituted as described above, and more suitable substituents for these $R^{13}$ groups include halo, $OR^{19}$, $C(O)OR^{19}$, $N(R^{19})_2$, $SO_3R^{19}$, $OSO_3R^{19}$ or a 6- to 10-membered aryl group optionally substituted as described above.

More suitable substituents for these $R^{10}$, $R^{11}$ and $R^{13}$ groups include halo, $C_{1-4}$ alkyl, $C_{1-4}$ haloalkyl, —O—$C_{1-4}$ alkyl, —O—$C_{1-4}$ haloalkyl, C(O)OH, $SO_2$OH, —NH($C_{1-4}$ alkyl) or —N($C_{1-4}$ alkyl)$_2$; for example fluoro, chloro, methyl, ethyl, trifluoromethyl, methoxy, ethoxy, trifluoromethoxy, C(O)OH, $SO_2$OH, amino, methyl amino and dimethylamino.

More suitable substituents for these $R^{10}$, $R^{11}$ and $R^{13}$ groups include halo, $C_{1-4}$ alkyl, $C_{1-4}$ haloalkyl, —O—$C_{1-4}$ alkyl, —O—$C_{1-4}$ haloalkyl, C(O)OH, $SO_2$OH, —$NH_2$, —NH($C_{1-4}$ alkyl) or —N($C_{1-4}$ alkyl)$_2$; for example fluoro, chloro, methyl, ethyl, trifluoromethyl, methoxy, ethoxy, trifluoromethoxy, C(O)OH, $SO_2$OH, amino, methyl amino and dimethylamino.

Suitable substituents for aryl and heteroaryl $R^{10}$ and $R^{11}$ groups include $C_{1-6}$ alkyl, $C_{1-6}$ haloalkyl, halo, $NO_2$, CN, $OR^{19}$, $SR^{19}$ or $N(R^{19})_2$.

Similarly, suitable substituents for aryl and heteroaryl $R^{13}$ groups include $C_{1-6}$ alkyl, $C_{1-6}$ haloalkyl, halo, $NO_2$, CN, $OR^{19}$, $SR^{19}$ or $N(R^{19})_2$.

More suitable substituents for aryl and heteoaryl $R^{10}$ and $R^{11}$ groups include $C_{1-4}$ alkyl, $C_{1-4}$ haloalkyl, halo, $OR^{19}$ or $N(R^{19})_2$; and similarly, more suitable substituents for aryl and heteroaryl $R^{13}$ groups include $C_{1-4}$ alkyl, $C_{1-4}$ haloalkyl, halo, $OR^{19}$ or $N(R^{19})_2$.

Particularly suitable substituents for aryl and heteroaryl $R^{10}$, $R^{11}$ and $R^{13}$ groups include halo, $C_{1-4}$ alkyl, $C_{1-4}$ haloalkyl, —O—$C_{1-4}$ alkyl, —O—$C_{1-4}$ haloalkyl, —NH($C_{1-4}$ alkyl) or —N($C_{1-4}$ alkyl)$_2$.

Specific examples of substituents for aryl and heteroaryl $R^{10}$, $R^{11}$ and $R^{13}$ groups include fluoro, chloro, methyl, ethyl, trifluoromethyl, methoxy, ethoxy, trifluoromethoxy, amino, methyl amino and dimethylamino.

As set out above, with respect to groups $R^{10}$ and $R^{11}$, each $R^{19}$ is independently H, $C_{1-6}$ alkyl, $C_{1-6}$ haloalkyl, or a 6- to 14-membered aryl or 5- to 14-membered heteroaryl group either of which is optionally substituted with one or more halo substituents selected from, $C_{1-6}$ alkyl and $C_{1-6}$ haloalkyl.

Suitably, $R^{19}$ is H, $C_{1-6}$ alkyl, $C_{1-6}$ haloalkyl, or a 6- to 10-membered aryl or 5 to 10-membered heteroaryl group optionally substituted with one or more substituents selected from halo, $C_{1-4}$ alkyl and $C_{1-4}$ haloalkyl.

More suitably, $R^{19}$ is hydrogen, $C_{1-6}$ alkyl, $C_{1-6}$ haloalkyl or phenyl optionally substituted with one or more substituents selected from halo, $C_{1-4}$ alkyl and $C_{1-4}$ haloalkyl.

Specific examples of $R^{19}$ include H, methyl, ethyl, trifluoromethyl or phenyl optionally substituted with one or more substituents selected from fluoro, chloro, methyl, ethyl and trifluoromethyl.

As set out above, with respect to group $R^{13}$, each $R^{19}$ is independently H, $C_{1-6}$ alkyl or $C_{1-6}$ haloalkyl. In one embodiment, $R^{19}$ is H or $C_{1-6}$ alkyl such as $C_{1-4}$ alkyl, for example, methyl or ethyl. Specific examples of $R^{19}$ include H, methyl, ethyl or trifluoromethyl.

In some particularly suitable compounds of general formula (Ia), $R^4$ is $C(O)OR^{10}$, $OR^{10}$, $SO_3R^{10}$, $OSO_3R^{10}$, halo, CN, azide, $OSi(R^{13})_3$, $C(O)R^{10}$, $NR^{10}C(O)NR^{10}SO_2R^{11}$, $NR^{10}C(O)NR^{10}SO_2N$ $R^{10}R^{11}$, $NR^{10}SO_2R^{11}$, $CH(XR^{10})(XR^{11})$, $CH[C(O)OR^{10}]_2$, $BR^{10}R^{11}$ or phthalimide.

In some particularly suitable compounds of general formula (Ia), $R^4$ is $C(O)OR^{10}$, $OR^{10}$, $SO_3R^{10}$, $OSO_3R^{10}$, halo, CN, $C(O)R^{10}$, $CH(XR^{10})(XR^{11})$, $CH[C(O)OR^{10}]_2$ or $BR^{10}R^{11}$; and each $R^{10}$ and $R^{11}$ is independently H, $C_{1-6}$ alkyl or benzyl; or, when $R^4$ is $CH(XR^{10})(XR^{11})$ or $BR^{10}R^{11}$, $R^{10}$ and $R^{11}$ together with the atom or atoms to which they are attached, may combine to form a 3- to 10-membered heterocyclic ring; or $R^4$ is $C(O)NR^{10}R^{11}$ wherein each $R^{10}$ and $R^{11}$ is independently substituted with $C(O)OR^{19}$, $OR^{19}$, $SO_3R^{19}$, or $OSO_3R^{19}$ and $R^{19}$ is H.

In some particularly suitable compounds of general formula (I), $R^4$ is $C(O)OR^{10}$, $OR^{10}$, $SO_3R^{10}$, $OSO_3R^{10}$, halo, CN, $C(O)R^{10}$, $CH(OR^{10})(OR^{11})$, $CH[C(O)OR^{10}]_2$ or $BR^{10}R^{11}$; and each $R^{10}$ and $R^{11}$ is independently H, $C_{1-6}$ alkyl or benzyl; or, when $R^4$ is $CH(OR^{10})(OR^{11})$ or $BR^{10}R^{11}$, $R^{10}$ and $R^{11}$ together with the atom or atoms to which they are attached, may combine to form a 3- to 10-membered heterocyclic ring; or $R^4$ is $C(O)NR^{10}R^{11}$ wherein each $R^{10}$ and $R^{11}$ is independently substituted with $C(O)OR^{19}$, $OR^{19}$, $SO_3R^{19}$, or $OSO_3R^{19}$ and $R^{19}$ is H.

In some particularly suitable compounds of general formula (I), $R^4$ is $C(O)OR^{10}$, $OR^{10}$, $SO_3R^{10}$, or $OSO_3R^{10}$, halo, CN, $C(O)R^{10}$, $CH(OR^{10})(OR^{11})$, $CH[C(O)OR^{10}]_2$ or $BR^{10}R^{11}$; and each $R^{10}$ and $R^{11}$ is independently H, $C_{1-6}$ alkyl or benzyl; or, when $R^4$ is $CH(OR^{10})(OR^{11})$ or $BR^{10}R^{11}$, $R^{10}$ and $R^{11}$ together with the atom or atoms to which they are attached, may combine to form a 3- to 10-membered heterocyclic ring.

When $R^4$ is $CH(XR^{10})(XR^{11})$ and $R^{10}$ and $R^{11}$ together with the atom or atoms to which they are attached combine to form a 3 to 10-membered heterocyclic ring, suitably $R^4$ is a 3-5 membered heterocyclic ring, in particular a 5-membered heterocyclic ring e.g. $R^4$ is selected from:

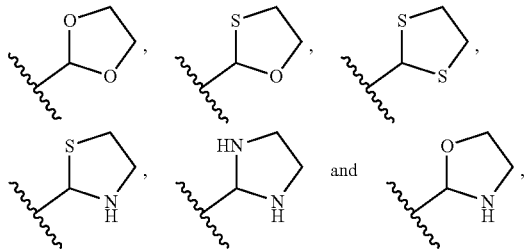

and in particular is

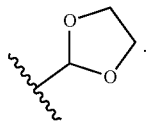

When $R^4$ is $CH(R^{10})(XR^{11})$ and $R^{10}$ and $R^{11}$ together with the atom or atoms to which they are attached combine to form a 3 to 10-membered heterocyclic ring, suitably $R^3$ is a 3-membered heterocyclic ring e.g. $R^4$ is selected from:

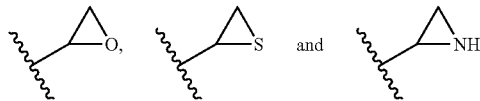

and in particular is

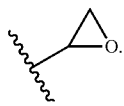

Alternatively, the compound may be in the form of a salt such that:

$R^4$ is $C(O)O^-$, $O^-$, $SO_3^-$, or $OSO_3^-$; or $R^4$ is $C(O)NR^{10}R^{11}$ wherein $R^{10}$ and $R^{11}$ are independently substituted with $C(O)O^-$, $O^-$, $SO_3^-$, or $OSO_3^-$;

and a counter ion is present as described above for basic addition salts.

In one embodiment, $R^4$ is $C(O)OR^{10}$, $OR^{10}$, $C(O)NR^{10}R^{11}$, $SO_3R^{10}$, or $OSO_3R^{10}$.

In one embodiment, $R^4$ is $OSi(R^{13})_3$.

In one embodiment, $R^4$ is halo, CN, $C(O)R^{10}$, $CH(XR^{10})(XR^{11})$, $NR^{10}R^{11}$, $BR^{10}R^{11}$, $-CH=CH_2$, $-C\equiv CH$, $CH[C(O)OR^{10}]_2$ or $CH(BR^{10}R^{11})_2$ or Y and $R^4$ together form a $=CH_2$ group.

In one embodiment, $R^4$ is halo, CN, $C(O)R^{10}$, $CH(OR^{10})(OR^{11})$, $NR^{10}R^{11}$, $BR^{10}R^{11}$, $-CH=CH_2$, $-C\equiv CH$, $CH[C(O)OR^{10}]_2$ or $CH(BR^{10}R^{11})_2$ or Y and $R^4$ together form a $=CH_2$ group.

In one embodiment, $R^4$ is halo, CN, $C(O)R^1$, $NR^{10}R^{11}$, $BR^{10}R^{11}$, $C(O)CH_2N_2$, $-CH=CH_2$, $-C\equiv CH$, $CH[C(O)OR^{10}]_2$, $CH(BR^{10}R^{11})_2$, azide, $NO_2$, $NR^{10}C(O)NR^{10}SO_2R^{11}$, $C(O)NR^{10}SO_2R^{11}$, $CH(XR^{10})(XR^{11})$, $CH(R^{10})(XR^{11})$ wherein each X is independently O, S or $NR^8$.

When $R^4$ is $CH(XR^{10})(XR^{11})$, X is suitably O or S, e.g. O. In such compounds, when $R^{10}$ and $R^{11}$ combine to form a ring, it is suitably a 5- or 6-membered ring. More suitably, both X moieties are O and $R^{10}$ and $R^{11}$ form a 1,3-dioxane or 1,3-dioxolane ring.

When $R^4$ is $CH(R^{10})(XR^{11})$, X is suitably O or S, e.g. O.

In one embodiment, $R^4$ is a carboxylic acid mimetic group.

In one embodiment, $R^4$ is a carboxylic acid mimetic group selected from tetrazole, substituted tetrazole, $-SO_2-NHR^{10}$, $C(O)NH-SO_2R^{10}$ and $NHC(O)NH-SO_2R^{10}$; wherein $R^{10}$ is as above defined for a compound of general formulae (Ia) or (I) and is suitably H, $C_{1-6}$ alkyl, $C_{3-7}$ cycloalkyl or 6- to 14-membered aryl, (e.g. phenyl). Suitably, substituted tetrazole is tetrazole substituted with $C_{1-4}$ alkyl, halo, OH, $O(C_{1-4}$ alkyl) or $SO_2R^{10}$ (e.g. $SO_2(C_{1-4}$ alkyl), $SO_2$-phenyl or $SO_2$-tolyl).

When $R^4$ is a carboxylic acid mimetic group, it is suitably a tetrazolyl group, for example tetrazol-1-yl or tetrazol-5-yl.

In one embodiment, $R^4$ is halo, CN, $C(O)R^{10}$, $CH(XR^{10})(XR^{11})$, $CH=CH_2$, $-C\equiv CH$, $CH[C(O)OR^{10}]_2$, $BR^{10}R^{11}$ or Y and $R^4$ together form a $=CH_2$ group.

In one embodiment, $R^4$ is halo, CN, $C(O)R^{10}$, $CH(OR^{10})(OR^{11})$, $CH=CH_2$, $-C\equiv CH$, $CH[C(O)OR^{10}]_2$, $BR^{10}R^{11}$ or Y and $R^4$ together form a $=CH_2$ group.

Suitably, $R^4$ is $C(O)OR^{10}$, $C(O)NR^{10}R^{11}$, $SO_3R^{10}$, or $OSO_3R^{10}$.

More suitably, $R^4$ is $C(O)OR^{10}$, $SO_3R^{10}$, or $OSO_3R^{10}$ and $R^{10}$ is H; or $R^4$ is $C(O)NR^{10}R^{11}$ substituted with $C(O)OR^{19}$, $SO_3R^{19}$, or $OSO_3R^{19}$ and $R^{19}$ is H.

In other particularly suitable compounds $R^4$ is halo, CN, $C(O)R^{10}$, $CH(OR^{10})(OR^{11})$, $NR^{10}R^{11}$, $CH[C(O)OR^{10}]_2$ or azide;

where $R^{10}$ and $R^{11}$ are as described above but are suitably each independently H or $C_{1-10}$ alkyl, $C_{2-10}$ alkenyl or $C_{2-10}$ alkynyl optionally substituted as described above or, when $R^4$ is $NR^{10}R^{11}$, $R^{11}$ may also suitably be a heteroaryl group such as tetrazole; or when $R^4$ is $CH(OR^{10})(OR^{11})$, the $OR^{10}$ and $OR^{11}$ groups together with the carbon atom to which they are attached may form a cyclic acetal group, particularly a 1,3-dioxane or 1,3-dioxolane group.

In still other particularly suitable compounds $R^4$ is $NR^{10}C(O)NR^{10}SO_2R^{11}$ or $C(O)NR^{10}SO_2R^{11}$, where $R^{10}$ and $R^{11}$ are as described above but are suitably each independently H or $C_{1-10}$ alkyl, $C_{2-10}$ alkenyl or $C_{2-10}$ alkynyl optionally substituted as described above.

In one embodiment, $R^4$ is $C(O)OR^{10}$, $OC(O)R^{10}$, $OR^{10}$, $OSi(R^{13})_3$, $OSO_2R^{10}$, halo, CN, $C(O)R^{10}$, $NR^{10}R^{11}$, $CH[C(O)OR^{10}]_2$, azide, $C(O)NR^{10}SO_2R^{11}$ $CH(XR^{10})(XR^{11})$; phthalimide, tetrazole or substituted tetrazole.

Other examples of $R^4$ groups include azide and tetrazole.

In one embodiment, $R^5$ is H. In one embodiment, $R^5$ is OH. In one embodiment, $R^5$ is a protected OH group. In one embodiment, $R^5$ is a protected OH group which is not stable in a basic environment such that treatment with a base converts the protected OH group to OH. Examples of such groups are well known in the art and include a group $OC(O)R^{14}$ wherein $R^{14}$ is a group $R^{10}$ as defined above for general formula (Ia) or formula (I). Particularly suitable $R^{14}$ groups are as defined for $R^{10}$ above and include $C_{1-6}$ alkyl such as methyl, or benzyl; or $C_{01}$ alkyl such as methyl, or phenyl. In another embodiment, $R^5$ is a protected OH group which is stable in a basic environment. Examples of such groups are well known in the art and include $OSi(R^{16})_3$, where each $R^{16}$ is independently a group $R^{13}$ as defined above for general formulae (Ia) and (I), and is suitably $C_{1-6}$ alkyl or phenyl. In one embodiment, $Si(R^{16})_3$ is selected from the group consisting of trimethylsilyl (TMS), triethylsilyl (TES), triphenylsilyl (TPS), tri-isopropylsilyl (TIPS), thexyldimethylsilyl (TDS), tert-butyldiphenylsilyl (TBDPS), tert-butyldimethylsilyl (TBDMS or TBS), di-tert-butylmethylsilyl (DTBMS), diethylisopropylsilyl (DEIPS) and dimethylisopropylsilyl (DMIPS), in particular TMS, TES, TIPS, TBDMS and TBDPS.

In one embodiment, the compound of general formula (Ia) or formula (I) is compound (IA): (6α, 7α, 22E)-6,7-epoxy-3-oxo-4,22-choladien-24-oic acid ethyl ester and the compound of general formula (II) is compound (IIA): (22E)-3-oxo-4,6,22-cholatrien-24-oic acid ethyl ester, or the compound of general formula (I) is compound (IB): (6α, 7α)-6,7-epoxy-3-oxo-4-chola-ene-24-oic acid ethyl ester and the compound of general formula (II) is compound (IIB): 3-oxo-4,6-choladien-24-oic acid ethyl ester.

In one aspect of the invention is provided a compound of general formula (IIa) or formula (II) selected from:
(20S)-20-acetoxymethyl-pregna-4,6-dien-3-one (Example 20);
(20S)-20-hydroxymethyl-pregna-4,6-dien-3-one (Example 21)
(20S)-20-tertbutyldimethylsilyloxymethyl-pregna-4,6-dien-3-one (Example 22)
(20S)-20-formyl-pregna-4,6-dien-3-one (Example 23)
(20S)-20-(ethylenedioxymethyl)-pregna-4,6-dien-3-one (Example 24)
(20S)-20-(1-mesyloxymethyl)-pregna-4,6-dien-3-one (Example 25)
(20S)-20-(1-bromomethyl)-pregna-4,6-dien-3-one (Example 26)
23-carboxy-3-oxo-4,6-choladien-24-oic acid diethyl ester (Example 27)
3-oxo-4,6-choladieno-24-nitrile (Example 28);
(20S)-20-(1-aminomethyl)-pregna-4,6-dien-3-one (Example 29);
(20R)-20-(1-cyanomethyl)-pregna-4,6-dien-3-one (Example 30);
23-carboxy-3-oxo-4,6-choladien-24-oic acid dimethyl ester (Example 31);
(22E)-3-oxo-4,6,22-cholatrien-24-oic acid (Example 32);
N-((22E)-3,24-dioxo-4,6,22-cholatrien-24-yl)cyclopropylsulfonamide (Example 33);
N-((22E)-3,24-dioxo-4,6,22-cholatrien-24-yl)-4-(trifluoromethoxy)benzenesulfonamide (Example 34);
(20S)-20-(5-tosyltetrazol-1-yl)methyl-pregna-4,6-dien-3-one (Example 35); and
(20S)—(N-phthalimidomethyl)-pregna-4,6-dien-3-one (Example 36);
or a salt or isotopic variant thereof.

In one aspect of the invention is provided a compound of general formula (Ia) or formula (I) selected from:
(6α, 7α, 20S)-6,7-epoxy-20-hydroxymethyl-pregn-4-en-3-one (Example 37)
(6α, 7α, 20S)-20-(1-bromomethyl)-6,7-epoxy-pregn-4-en-3-one (Example 38)
(6α, 7α, 20S)-20-(1-mesyloxymethyl)-6,7-epoxy-pregn-4-en-3-one (Example 39)
(6α, 7α, 20S)-20-(1-tertbutyldimethylsilyloxymethyl)-6,7-epoxy-pregn-4-en-3-one (Example 40);
(6α, 7α, 20S)-20-acetoxymethyl-6,7-epoxy-pregn-4-en-3-one (Example 41);
(6α, 7α, 20S)-6,7-epoxy-20-(ethylenedioxymethyl)-pregn-4-en-3-one (Example 42);
(6α, 7α)-23-carboxy-6,7-epoxy-3-oxo-4-cholen-24-oic acid dimethyl ester (Example 43);
(6α,7α)-6,7-epoxy-3-oxo-4-choleno-24-nitrile (Example 44);
(6α, 7α, 20R)-20-(1-cyanomethyl)-6,7-epoxy-pregn-4-en-3-one (Example 45);
(6α, 7α, 20S)-6,7-epoxy-20-azidomethyl-pregna-4-en-3-one (Example 46);
N-((6α, 7α, 22E)-3,24-dioxo-6,7-epoxy-4,22-choladien-24-yl)cyclopropylsulfonamide (Example 47);
N-((6α, 7α, 22E)-3,24-dioxo-6,7-epoxy-4,22-choladien-24-yl)-4-(trifluoromethoxy)benzenesulfonamide (Example 48);
(6α,7α,20S)-6,7-epoxy-20-(N-phthalimidomethyl)-pregna-4,6-dien-3-one (Example 49); and
(6α, 7α, 20S)-20-(5-tosyltetrazol-1-yl)methyl-6,7-epoxy-pregna-4-en-3-one (Example 50);
or a salt or isotopic variant thereof.

Preparation of Compounds of General Formula (IIa) and (II)

Compounds of general formula (IIa) or compounds of general formula (II) may be prepared from compounds of general formula (IIIa) or from compounds of general formula (III), respectively:

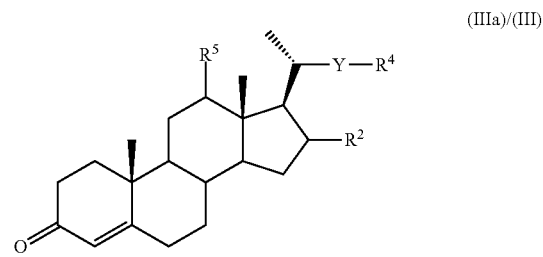

(IIIa)/(III)

wherein Y, $R^2$, $R^4$ and $R^5$ and are as defined above for general formula (Ia) (for formula (IIIa)) or are as above defined for general formula (I) (for formula (III)); by reaction with an oxidizing agent such as chloranil.

The reaction may be carried out under acidic conditions, for example in the presence of acetic acid, and in an organic solvent such as toluene. Such a reaction is described in Example 8.

Some compounds of general formulae (IIa), (II), (IIIa) and (III) are known. For example Uekawa et al. in *Biosci. Biotechnol. Biochem.*, 2004, 68, 1332-1337 describe the synthesis of (22E)-3-oxo-4,22-choladien-24-oic acid ethyl ester (compound (IIIA)) from stigmasterol followed by its conversion to (22E)-3-oxo-4,6,22-cholatrien-24-oic acid ethyl ester (referred to herein as compound (IIA)), which has the formula:

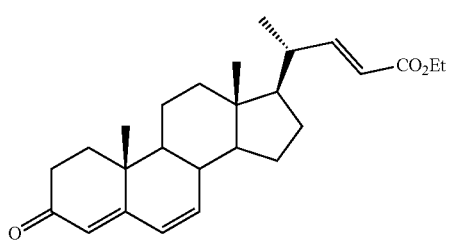
(IIA)

This reaction is described in Example 1.

Other compounds of general formulae (IIa), (II), (IIIa) and (III) may be prepared by analogous methods from phytosterols similar to stigmasterol. Stigmasterol and other phytosterols are plant sterols and are readily available or may be prepared by known routes.

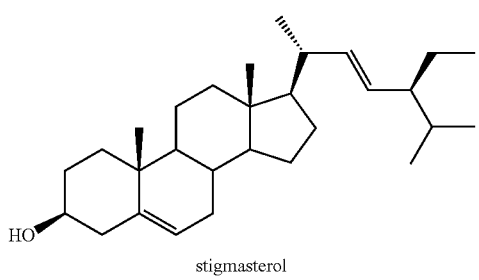
stigmasterol

Compounds of general formula (IIIa) or compounds of general formula (III) may also be prepared from compounds of general formula (IVa) or from compounds of general formula (IV), respectively:

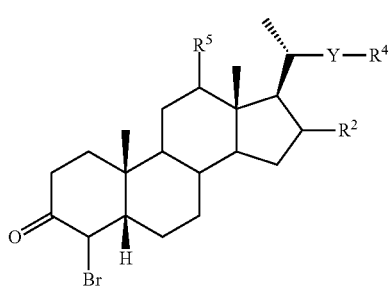
(IVa)/(IV)

wherein Y, $R^2$, $R^4$ and $R^5$ are as defined in general formula (Ia) (for formula (IVa)) or are as defined in general formula (I) (for formula (IV));

by reaction with lithium bromide and a base such as lithium carbonate. The reaction may be carried out in a solvent such as N,N-dimethylformamide (DMF) and at a temperature of about 120 to 180° C. Such a reaction is described in Example 7.

Compounds of general formula (IVa) or compounds of general formula (IV) may be obtained by bromination of a compound of general formula (Va), or by bromination of a compound of general formula (V), respectively:

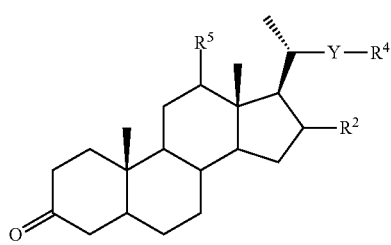
(Va)/(V)

wherein Y, $R^2$, $R^4$ and $R^5$ are as defined in general formula (Ia) (for formula (Va)) or are as defined in general formula (I) (for formula (V));

using, for example bromine in acetic acid. Such a reaction is described in Example 6.

Compounds of general formula (Va) or compounds of general formula (V) may be prepared from compounds of general formula (VIa) or from compounds of general formula (VI), respectively:

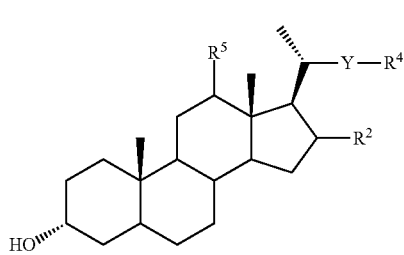
(VIa)/(VI)

wherein Y, $R^2$, $R^4$ and $R^5$ are as defined in general formula (Ia) (for formula (VIa)) or are as defined in general formula (I) (for formula (VI));

by oxidation, typically with a chromium-based oxidizing agent or with sodium hypochlorite. Such a reaction is described in Example 5.

Compounds of general formula (VIa) and compounds of general formula (VI) in which $R^4$ is $C(O)OR^{10}$, where $R^{10}$ is $C_{1-6}$ alkyl or benzyl, or $C_{1-6}$ alkyl or phenyl, may be prepared from compounds of general formula (VIa) and from compounds of general formula (VI), respectively, in which $R^4$ is C(O)OH by esterification, typically by reaction with an appropriate alcohol under acidic conditions.

Compounds of general formula (VIa) and compounds of general formula (VI) in which $R^4$ is C(O)OH and $R^5$ is H may be prepared from compounds of general formula (VIIa) and from compounds of general formula (VII), respectively:

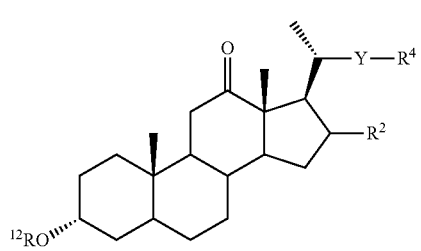
(VIIa)(VII)

wherein $R^2$ and Y are as defined in general formula (Ia) (for formula (VIIa)) or are as defined in general formula (I) (for formula (VII));

$R^4$ is $C(O)OR^{10}$, where $R^{10}$ is $C_{1-6}$ alkyl or benzyl; and $OR^{12}$ is a protected OH;

by reaction with a reducing agent, typically hydrazine, under basic conditions and in an alcoholic or glycolic solvent, for example diethylene glycol.

Where $OR^{12}$ is a protected OH group which is stable under basic conditions, the reaction may be followed by a reaction to remove the protecting group $R^{12}$ to leave an OH group.

Protecting groups for OH are discussed above and, for example, $R^{12}$ may be a group $C(O)R^{14}$, where $R^{14}$ is as defined above, in particular, $C_{1-6}$ alkyl or benzyl; or $C_{1-6}$ alkyl or phenyl. Silyl ethers are also suitable, and in this case, $R^{12}$ may be a group $Si(R^{16})_3$, where each $R^{16}$ is independently a group $R^{13}$ as defined above but is especially $C_{1-6}$ alkyl or phenyl. Other suitable protecting groups for OH are well known to those of skill in the art (see Wuts, P G M and Greene, T W (2006) "Greene's Protective Groups in Organic Synthesis", 4$^{th}$ Edition, John Wiley & Sons, Inc., Hoboken, N.J., USA).

Particularly suitable $R^{12}$ groups include groups which are not stable in the presence of a base since this removes the need for the additional step of removing the protecting group. An example of a group $R^{12}$ which is not stable in basic conditions is a group $C(O)R^{14}$, where $R^{14}$ is as defined above, and is particularly $C_{1-6}$ alkyl or benzyl; or $C_{1-6}$ alkyl or phenyl.

Alternatively, the reaction may be carried out in 2 steps such that the compound of general formula (VIIa) or a compound of general formula (VII) is reacted with a compound of general formula (XXXII):

$R^{20}$—NH—NH$_2$ (XXXII)

wherein $R^{20}$ is a leaving group such as toluene sulfonyl or methane sulfonyl; to give a compound of general formula (XXXIIIa) or a compound of general formula (XXXIII), respectively:

(XXXIIIa)/(XXXIII)

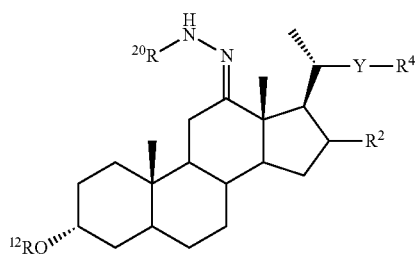

wherein $R^2$ and Y are as defined in general formula (Ia);
$R^4$ and $R^{12}$ are as defined for general formula (VIIa); and
$R^{20}$ is as defined for general formula (XXXIIa) (all for formula (XXXIIIa)); or
wherein $R^2$ and Y are as defined in general formula (I);
$R^4$ and $R^{12}$ are as defined for general formula (VII); and
$R^{20}$ is as defined for general formula (XXXII) (all for formula (XXXIII)); followed by reduction with a suitable reducing agent. Examples of reducing agents which can be used in this reaction include hydrides such as sodium borohydride, sodium cyanoborohydride, lithium aluminum hydride etc. In general formula (XXXIIIa) and in general formula (XXXIII) $R^{20}$ is as defined above for compounds of general formula (XXXIIa) and for compounds of general formula (XXXIII), respectively, and Y, $R^2$, $R^4$ and $R^{12}$ are as defined above for compounds of general formula (VIIa) and for compounds of general formula (VII), respectively.

Compounds of general formula (VIIa) or compounds of general formula (VII) may be prepared from compounds of general formula (VIIIa) or from compounds of general formula (VIII), respectively:

(VIIIa)/(VIII)

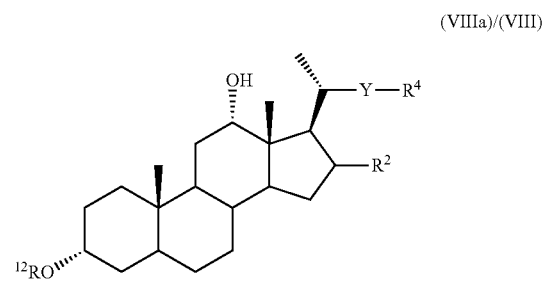

wherein $R^2$ and Y are as defined in general formula (Ia) (for formula (VIIIa)) or are as defined in general formula (I) (for formula (VIII));
$R^4$ is $C(O)OR^{10}$, where $R^{10}$ is $C_{1-6}$ alkyl or benzyl; and
$R^{12}$ is as defined above for general formula (VIIa) (for formula (VIIIa)) or is as defined above for general formula (VII) (for formula VIII)); and is suitably —$C(O)C_{1-6}$ alkyl; by reaction with an oxidizing agent, for example sodium hypochlorite. Such a reaction is described in Example 2.

The reaction may be carried out under acidic conditions, for example in the presence of acetic acid, and in an organic solvent such as ethyl acetate.

Compounds of general formula (VIIIa) or compounds of general formula (VIII) may be prepared from compounds of general formula (IXa) or from compounds of general formula (IX), respectively:

(IXa)/(IX)

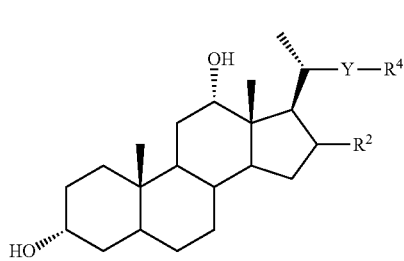

wherein $R^2$ and Y are as defined in general formula (Ia) (for formula (IXa)) or are as defined in general formula (I) (for formula (IX));
$R^4$ is $C(O)OR^{10}$, where $R^{10}$ is $C_{1-6}$ alkyl or benzyl;
by reaction with an agent suitable to introduce the protecting group $R^{12}$. For example, when $R^{12}$ is $C(O)R^{14}$, the compound of general formula (IXa) or a compound of general formula (IX) may be reacted with a carboxylic acid anhydride or an acid chloride in the presence of a weak base such as pyridine, suitably catalysed by 4-dimethylaminopyridine (DMAP). The reaction may be conducted in a solvent such as ethyl acetate. Such a reaction is described in Example 2.

Compounds of general formula (IXa) or compounds of general formula (IX) may be prepared by the esterification of compounds of general formula (Xa) or of compounds of general formula (X), respectively:

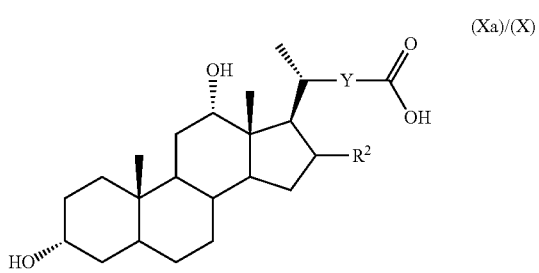

(Xa)/(X)

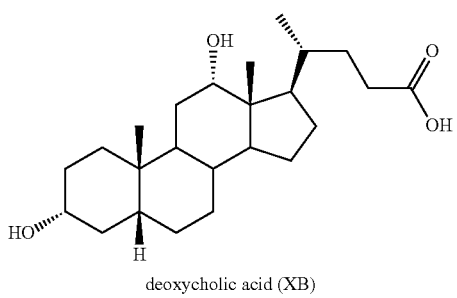 [SMILES: C[C@H](CCC(=O)O)[C@H]1CCC2C3CC[C@@H]4C[C@H](O)CC[C@]4(C)C3C[C@H](O)[C@@]21C]

deoxycholic acid (XB)

wherein $R^2$ and Y are as defined in general formula (Ia) and for general formula (I).

The esterification reaction may be carried out by reacting the acid of general formula (Xa) or of general formula (X) with a suitable alcohol under acidic conditions. Such a reaction is described in Example 2.

Compounds of general formula (Xa) and of general formula (X) are known. For example, the compound of general formula (Xa) or of general formula (X) in which Y is —$CH_2CH_2$— and $R^2$ is H is deoxycholic acid (referred to herein as compound (XB)), which is readily available from a number of sources.

An alternative route to compounds of general formula (IIIa) and to compounds of general formula (III) in which the group at the $R^4$ position is an ester is as shown in Scheme 5 in which 4-androstenedione is converted to a compound of general formula (IIIa) or of general formula (III), in which $R^2$ and $R^5$ are H; $R^4$ is —C(O)O$CH_3$ and Y is either —$CH_2CH_2$— or —CH=CH—.

Scheme 5

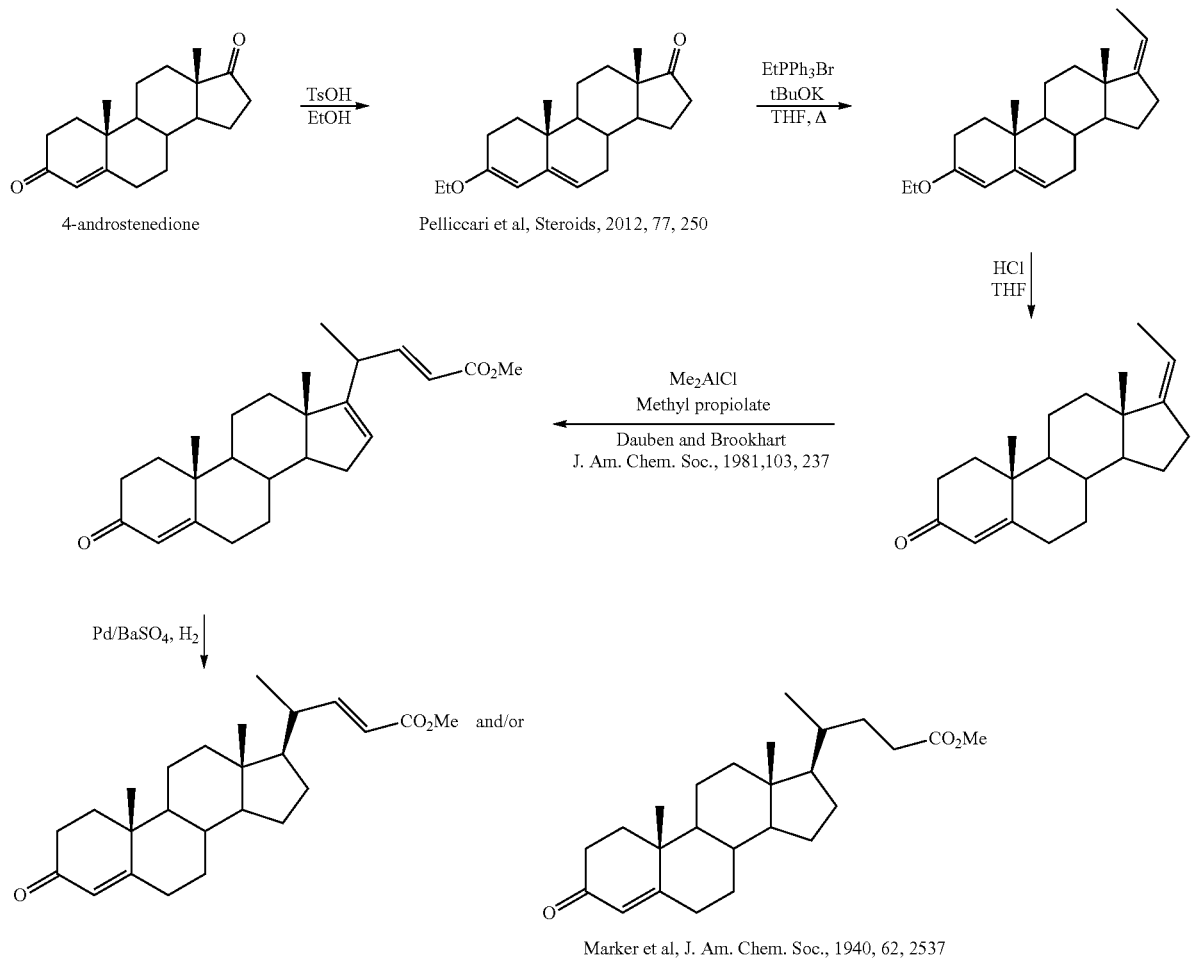

Other compounds with different values for Y and $R^2$ can be used as alternative starting materials.

An alternative route to compounds of general formula (IIa) and to compounds of general formula (II) in which Y is an alkenylene group is by use of an olefination reaction, for example a Horner-Wadsworth-Emmons (HWE) olefination of a compound of general formula (XIa) or of a compound of general formula (XI), respectively:

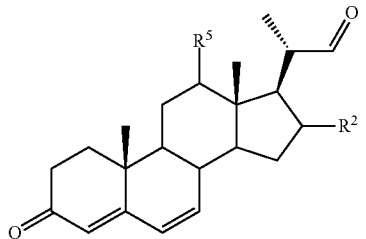
(XIa)(XI)

wherein $R^2$ and $R^5$ are as defined for general formula (Ia) and for general formula (I); using a compound of general formula (XII):

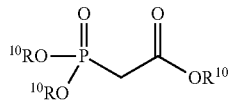
(XII)

wherein $R^{10}$ is as defined for general formula (Ia) and general formula (I).

The reaction may be carried out under standard HWE conditions, for example using a base such as sodium hydride.

Compounds of general formula (XII) are readily available or may be prepared by methods known to those of skill in the art.

Other olefination reactions, such as Tebbe olefination, Wittig type olefination or a Julia-Kocienski olefination, would also give rise to compounds of general formula (IIa) and to compounds of general formula (II) in which Y is an alkenylene group. These olefination reactions are familiar to a chemist of skill in the art.

Compounds of general formula (XIa) or compounds of general formula (XI) may be prepared by reaction of a compound of general formula (XIIIa) or a compound of formula (XIII), respectively, with ozone

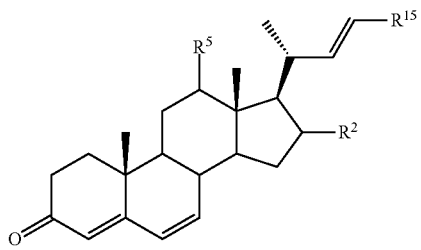
(XIIIa)/(XIII)

wherein $R^2$ and $R^5$ are as defined for general formula (Ia) and for general formula (I) and $R^{15}$ is $C_{1-6}$ alkyl.

An example of a reaction of this type is given in U.S. Pat. No. 2,624,748A (Levin et al. incorporated herein by reference).

Compounds of general formula (XIIIa) or compounds of general formula (XIII) may be prepared by reaction of a compound of general formula (XIVa) or a compound of general formula (XIV), respectively:

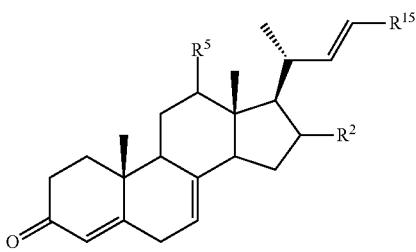
(XIVa)/(XIV)

wherein $R^2$ and $R^5$ are as defined for general formula (Ia) and for general formula (I), and $R^{15}$ is $C_{1-6}$ alkyl, with an acid in a solvent such as methanol.

Compounds of general formula (XIVa) and compounds of general formula (XIV) may be prepared by oxidation of a compound of general formula (XVIa) or a compound of general formula (XVI), respectively:

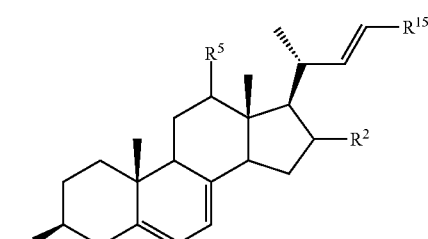
(XVIa)/(XVI)

wherein $R^2$ and $R^5$ are as defined for general formula (Ia) and for general formula (I), and $R^{15}$ is $C_{1-6}$ alkyl, using an Oppenauer oxidation.

Examples of the conversion of compounds of general formula (XVIa) to compounds of general formula (XIIIa) and of the conversion of compounds of general formula (XVI) to compounds of general formula (XIII) are taught by Shepherd et al, *J. Am. Chem. Soc.* 1955, 77, 1212-1215 and Goldstein, *J. Med. Chem.* 1996, 39, 5092-5099 (both incorporated herein by reference).

One example of a compound of general formula (XVIa) and of general formula (XVI) is ergosterol (referred to herein as (XVIA)), which is a fungal sterol and Scheme 6 below shows the conversion of ergosterol to a compound of general formula (II) in which both $R^2$ and $R^5$ are H, Y is CH=CH$_2$ and $R^4$ is C(O)OR$^{10}$, where $R^{10}$ is ethyl.

Scheme 6

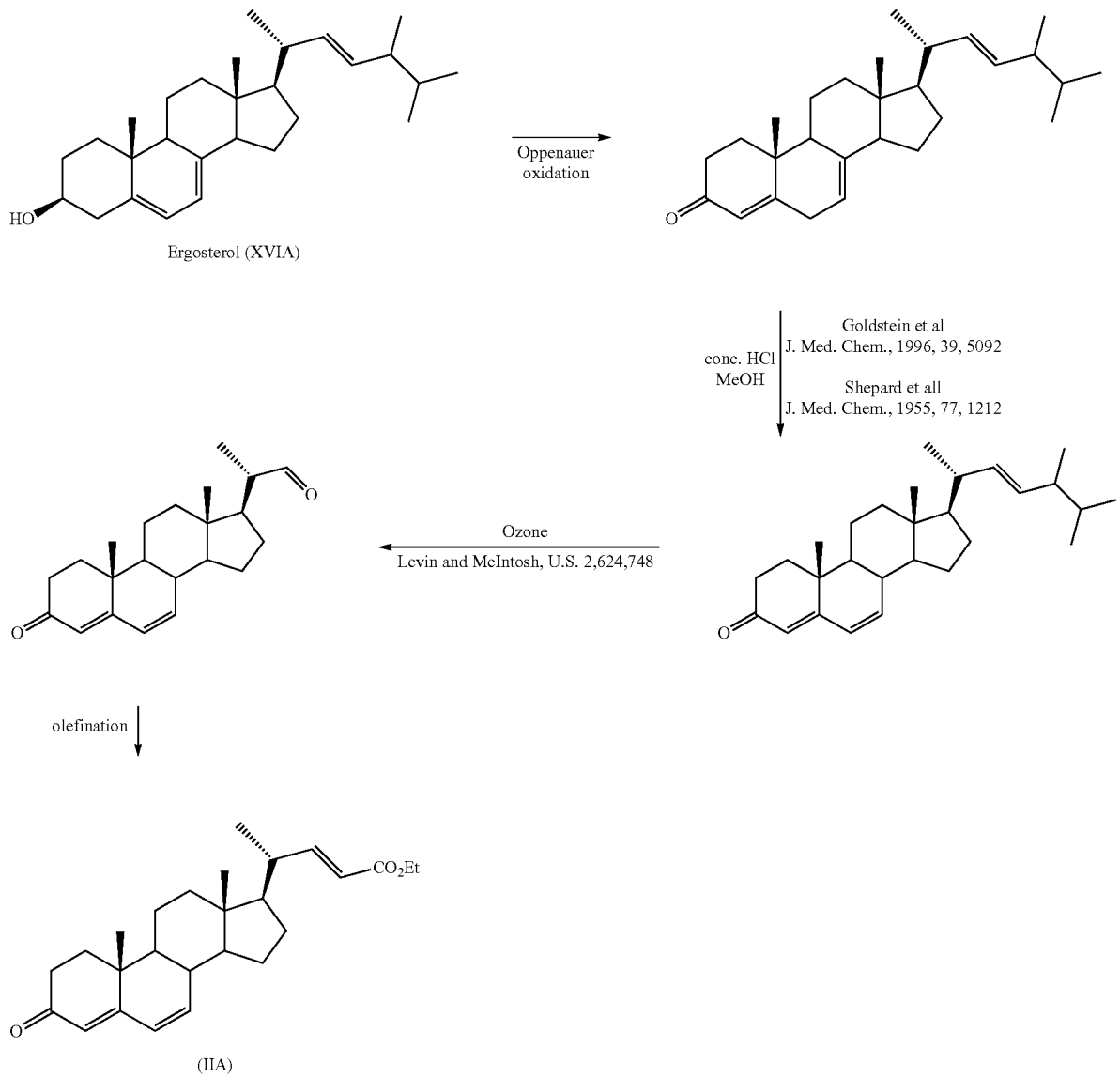

Compounds of general formula (Ia) and (IIa) and of general formula (I) and (II) in which $R^4$ is $C(O)R^{10}$, $C(O)NR^{10}R^{11}$, $S(O)R^{10}$, $SO_3R^{10}$, or $OSO_3R^{10}$ may be prepared from the corresponding compounds in which $R^4$ is $C(O)OR^{10}$ by reaction with an appropriate reagents using methods well known to those of skill in the art. For example, the methods described in WO2008/002573 and WO2010/014836 or methods similar to those described by Classon et al, *J. Org. Chem.*, 1988, 53, 6126-6130 and Festa et al, *J. Med. Chem.*, 2014, 57, 8477-8495 (all incorporated herein by reference).

Subsequent reactions of compounds of general formula (Ia) and general formula (I) Compounds of general formulae (Ia) and (IIa), or of general formulae (I) and (II) are intermediates in the synthesis of compounds of general formula (XVIIIa) or of formula (XVIII), respectively:

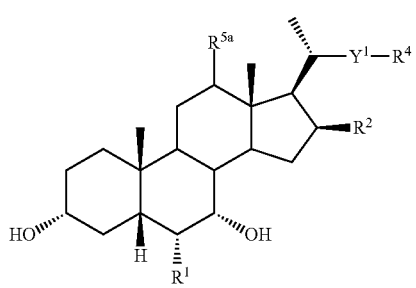

(XVIIIa)/(XVIII)

or a salt or an isotopic variant thereof;

wherein, $R^1$ is $C_{1-4}$ alkyl, $C_{2-4}$ alkenyl or $C_{2-4}$ alkynyl optionally substituted with one or more substituents selected from halo, $OR^6$ and $NR^6R^7$;

wherein each of $R^6$ and $R^7$ is independently H or $C_{1-4}$ alkyl;

$R^2$ is H, halo or OH;

$R^{5a}$ is H or OH; and $Y^1$ is a bond or a $C_{1-20}$ alkylene linker group and is optionally substituted with one or more $R^3$; or $Y^1$ and $R^4$ together form a $=CH_2$ group;

wherein $R^3$ and $R^4$ are as defined for a compound of general formula (Ia) (for formula (XVIIIa)) or are as defined for a compound of general formula (I) (for formula (XVIII)).

The compounds of general formula (IIa) or of general formula (II) may be converted to the compounds of general formula (XVIIIa) or of general formula (XVIII), respectively, in a 6 step process via intermediates of general formula (Ia), (I), (XIXa)-(XXIIa) and (XIX)-(XXII), as described above.

Compounds of general formula (XVIIIa) and of general formula (XVIII) are potent agonists of FXR and TGR5 and include, in particular, compounds in which $R^1$ is ethyl. Also included are the following.

Compounds in which $R^4$ is C(O)OH, for example:
  obeticholic acid, which is a compound of formula (XVIIIa)/(XVIII) in which $R^1$ is ethyl, $R^2$ and $R^{5a}$ are both H, $Y^1$ is —$CH_2CH_2$—, and $R^4$ is C(O)OH; and
  the compound of formula (XVIIIa)/(XVIII) in which $R^1$ is ethyl, $R^2$ and $R^{5a}$ are both H, $Y^1$ is —$CH_2CH(CH_3)$—, and $R^4$ is C(O)OH; and
  the compound of formula (XVIIIa)/(XVIII) in which $R^1$ is ethyl, $R^2$ is H, $R^{5a}$ is OH, $Y^1$ is —$CH_2CH(CH_3)$—, and $R^4$ is C(O)OH.

Compounds in which $R^4$ is $OSO_3H$ or a salt thereof, for example:
  the compound of formula (XVIIIa)/(XVIII) in which $R^1$ is ethyl, $R^2$ and $R^{5a}$ are both H, $Y^1$ is —$CH_2CH_2$—, and $R^4$ is $OSO_3H$ or a salt thereof; and
  the compound of formula (XVIIIa)/(XVIII) in which $R^1$ is ethyl, $R^2$ is H, $R^{5a}$ is OH, $Y^1$ is —$CH_2CH_2CH_2$—, and $R^4$ is $OSO_3H$ or a salt thereof; and
  the compound of formula (XVIIIa)/(XVIII) in which $R^1$ is ethyl, $R^2$ is OH, $R^{5a}$ is H, $Y^1$ is —$CH_2CH_2$—, and $R_4$ is $OSO_3H$ or a salt thereof.

In the compounds of general formulae (XVIIIa) to (XXIIa) and of general formula (XVIII) to (XXII), more suitable values for $R^4$ are as defined for general formula (Ia) and general formula (I), respectively.

In some compounds of general formulae (XVIIIa) to (XXIIa) or of general formulae (XVIII) to (XXII), $Y^1$ is a bond.

In other compounds of general formulae (XVIIIa) to (XXIIa) or of general formulae (XVIII) to (XXII), $Y^1$ is a $C_{1-15}$ alkylene linker group, more suitably $C_{1-12}$, $C_{1-10}$ or $C_{1-8}$ alkylene linker group and optionally substituted with one or more $R^3$ as defined above. Typically each $R^3$ is independently halo, $OR^8$ or $NR^8R^9$; where each of $R^8$ and $R^9$ is independently selected from H, methyl or ethyl, especially H or methyl.

In some suitable compounds of general formulae (XVIIIa) to (XXIIa) or of general formulae (XVIII) to (XXII), $Y^1$ is an unsubstituted $C_{1-15}$ alkylene or $C_{2-15}$ alkenylene linker, more suitably $C_{1-12}$ alkylene, $C_{1-10}$ alkylene or $C_{1-8}$ alkylene, or $C_{2-12}$ alkenylene, $C_{1-10}$ alkenylnene or $C_{1-8}$ alkenylene.

In suitable compounds of general formulae (XVIIIa) to (XXIIa) or of general formulae (XVIII) to (XXII), $R^1$ may be $C_{1-4}$ alkyl optionally substituted with one or more substituents selected from halo, $OR^6$ or $NR^6R^7$, where $R^6$ and $R^7$ are each independently H, methyl or ethyl, especially H or methyl. More suitably, $R^1$ is unsubstituted $C_{1-4}$ alkyl.

Step (i)

Step (i) is described in detail above in the section describing the methyltrioxorhenium epoxidation. Such reactions are described in Examples 10 and 10a, and Examples 35-50.

Suitably, a compound of general formula (Ia):

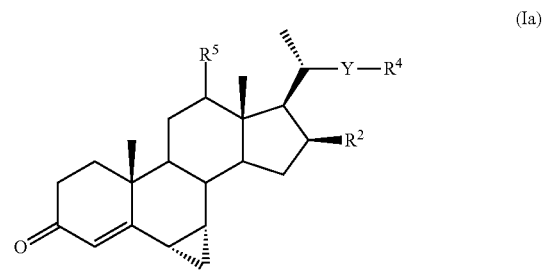
(Ia)

wherein Y, $R^2$, $R^4$ and $R^5$ are as defined above; is prepared as described above by oxidation of a compound of general formula (IIa):

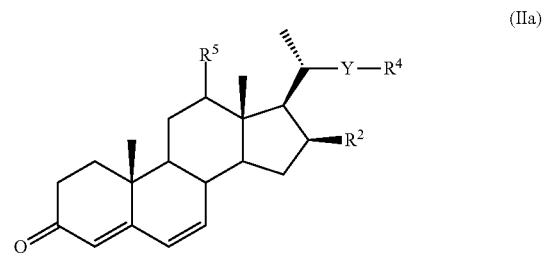
(IIa)

wherein Y, $R^2$, $R^4$ and $R^5$ are as defined for compounds of general formula (Ia).

Suitably, a compound of general formula (I):

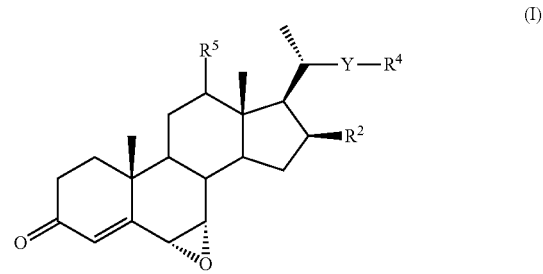
(I)

wherein Y, $R^2$, $R^4$ and $R^5$ are as defined above; is prepared as described above by oxidation of a compound of general formula (II):

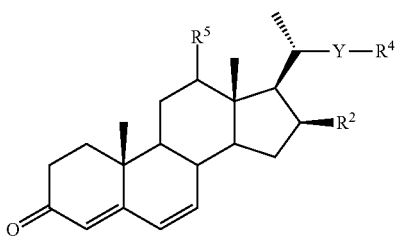

(II)

wherein Y, R², R⁴ and R⁵ are as defined for compounds of general formula (I).

Suitable embodiments of the reaction are described above.

Step (ii)

Compounds of general formula (XIXa) may be prepared from compounds of general formula (Ia):

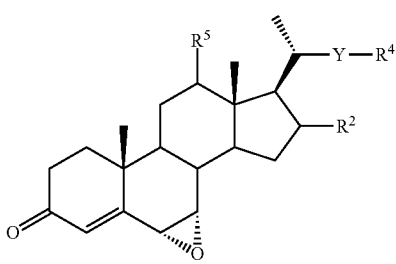

(Ia)

wherein R², R⁴, R⁵ and Y are as defined above;
by selective alkylation with an organometallic reagent, to give a compound of general formula (XIXa):

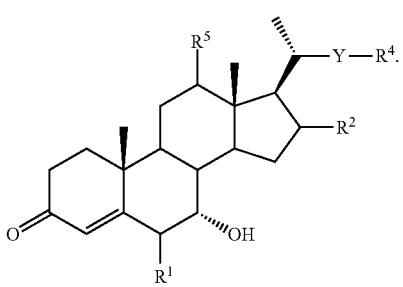

(XIXa)

wherein R², R⁴, R⁵ and Y are as defined for compounds of general formula (Ia).

Suitably, the compound of general formula (Ia) is

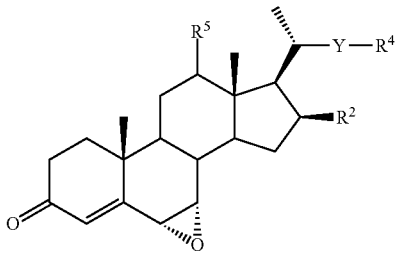

(Ia)

wherein R², R⁴, R⁵ and Y are as defined above.

Compounds of general formula (XIX) may be prepared from compounds of general formula

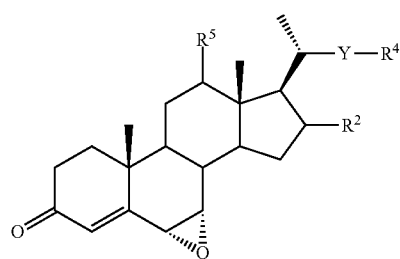

(I)

wherein R², R⁴, R⁵ and Y are as defined above;
by selective alkylation with an organometallic reagent, to give a compound of general formula (XIX):

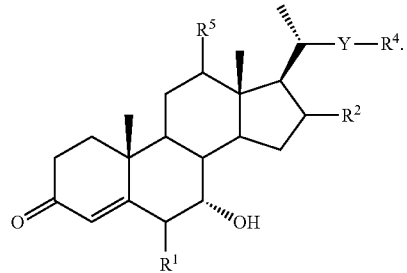

(XIX)

wherein R², R⁴, R⁵ and Y are as defined for compounds of general formula (I).

Suitably, the compound of general formula (I) is

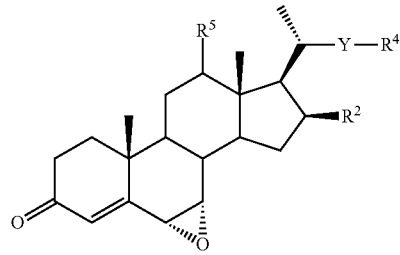

(I)

wherein R², R⁴, R⁵ and Y are as defined above.

Suitable organometallic reagents include Gilman reagents formed by reaction of an alkyl lithium compound of formula (XXIV):

R¹—Li        (XXIV)

wherein R¹ is as defined for general formula (XVIIIa) or (XVIII);
and a copper (I) salt, particularly a copper (I) halide such as copper (I) iodide.

The reaction may be conducted in an organic solvent such as tetrahydrofuran, other ethers such as diethylether or a mixture thereof.

Alternatively, the addition can be carried out using Grignard reagents R¹MgX, where R¹ is as defined for general formula (XVIIIa) or (XVIII), and X is a halide, for example ethylmagnesium bromide and the reaction is suitably conducted in the presence of a zinc (II) salt such as zinc chloride and a catalytic amount of a copper (I) or copper(II) salt or complex, for example copper (I) chloride, copper (II) chloride or a copper(I) or copper (II) acetylacetonate (acac) complex.

The reaction may be carried out in an organic solvent, for example an ether such as THF, 2-methyl THF, methyl tert-butyl ether (TBME) or diethyl ether. Surprisingly, the reaction temperature is not particularly significant and while in some cases the reaction may be carried out at reduced temperature, for example at about −25 to 0° C., it has also been successfully conducted at higher temperatures of up to about 55° C.

The method is particularly suitable for the preparation of compounds of general formula (XIXa) or compounds of general formula (XIX) in which $R^4$ is $C(O)OR^{10}$ from compounds of general formula (Ia) or from compounds of general formula (I), respectively, where $R^4$ is also $C(O)OR^{10}$, where $R^{10}$ is as defined above but is especially H, $C_{1-6}$ alkyl or benzyl.

Compounds of general formula (XIXa) or of general formula (XIX) with other $R^4$ groups may be prepared from the above compounds of general formula (XIXa) or compounds of general formula (XIX), respectively, by methods which are familiar to those of skill in the art, and described below.

Representative methods of forming a compound of formula (XIXa) or a compound of formula (XIX) are described in Example 12.

In one embodiment, the compound of formula (XIXa) is:

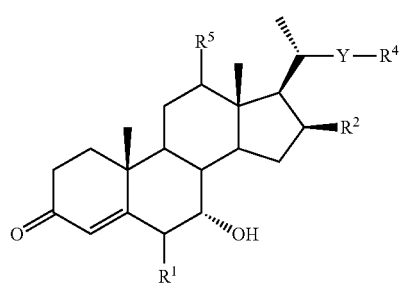

wherein $R^1$ is as defined above for compounds of general formula (XVIIIa) and Y, $R^2$, $R^4$ and $R^5$ are as defined above for compounds of general formula (Ia).

In one embodiment, the compound of formula (XIXa) is:

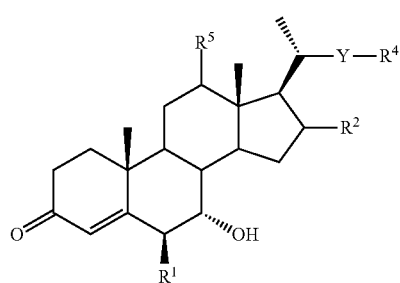

wherein $R^1$ is as defined above for compounds of general formula (XVIIIa) and Y, $R^2$, $R^4$ and $R^5$ are as defined above for compounds of general formula (Ia).

In one embodiment, the compound of formula (XIXa) is:

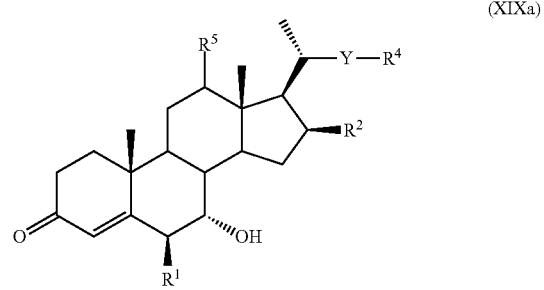

wherein $R^1$ is as defined above for compounds of general formula (XVIIIa) and Y, $R^2$, $R^4$ and $R^5$ are as defined above for compounds of general formula (Ia).

In one embodiment, the compound of formula (XIX) is:

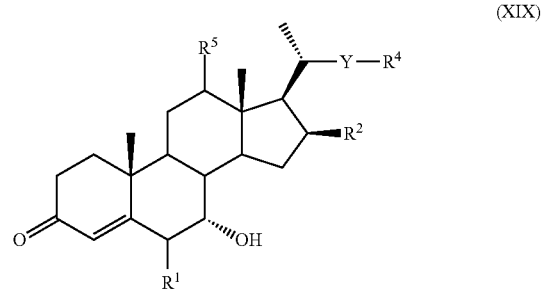

wherein $R^1$ is as defined above for compounds of general formula (XVIII) and Y, $R^2$, $R^4$ and $R^5$ are as defined above for compounds of general formula (I).

In one embodiment, the compound of formula (XIX) is:

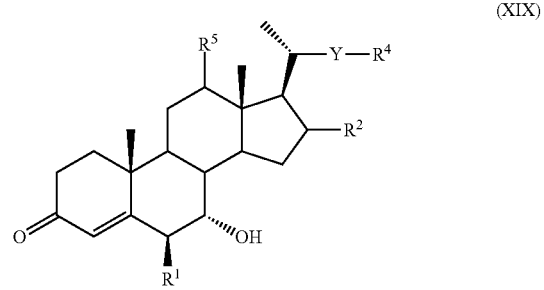

wherein $R^1$ is as defined above for compounds of general formula (XVIII) and Y, $R^2$, $R^4$ and $R^5$ are as defined above for compounds of general formula (I).

In one embodiment, the compound of formula (XIX) is:

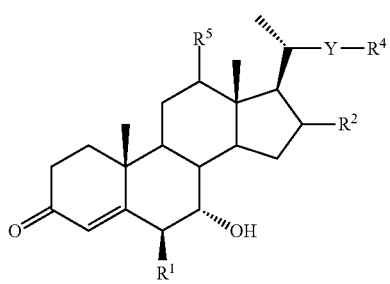

(XIX)

wherein $R^1$ is as defined above for compounds of general formula (XVIII) and Y, $R^2$, $R^4$ and $R^5$ are as defined above for compounds of general formula (I).

Step (iii)

The conversion of the compound of general formula (XIXa) or the compound of general formula (XIX) to the compound of general formula (XXa) or to the compound of general formula (XX), respectively, may be carried out by hydrogenation, usually catalytic hydrogenation. Suitable catalysts for the catalytic hydrogenation include a palladium/carbon, palladium/calcium carbonate, palladium/aluminium oxide, platinum/palladium or Raney nickel catalyst. The reaction may be carried out in an organic solvent, which may be an alcoholic solvent such as methanol, ethanol or isopropanol; ethyl acetate; pyridine; acetic acid; cyclopentyl methyl ether (CPME), acetonitrile (MeCN) or N,N-dimethylformamide (DMF). The organic solvent may optionally be mixed with a co-solvent such as acetone or water and/or a base such as triethylamine may also be added.

The choice of catalyst and solvent affects the ratio of the required product of general formula (XXa) or general formula (XX):

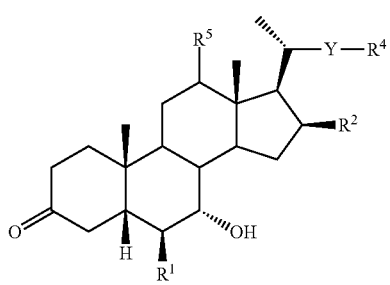

(XXa)(XX)

to its isomer of general formula (XXXa) or general formula (XXX):

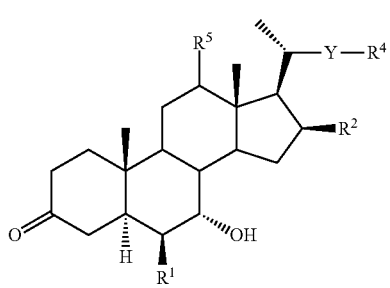

(XXXa)/(XXX)

More suitably, a palladium/carbon or palladium/calcium carbonate catalyst is used. Typically, in the catalyst the palladium is present in an amount of 5-10% by weight with respect to the weight of the matrix (where the matrix is the carbon, calcium carbonate etc.).

Particularly suitable solvents and catalysts used for the reaction included a mixture of DMF and MeCN with a palladium/calcium carbonate catalyst and DMF with a palladium/carbon catalyst.

Hydrogenation of a compound of formula (XIXa) or a compound of formula (XIX) will also reduce any alkene bonds, if present, in the linker Y.

Representative methods of forming a compound of general formula (XXa) or a compound of general formula (XX) are described in Examples 13 and 15.

Step (iv)

The oxidation reaction of a compound of general formula (XXa) to a compound of general formula (XXIa), or of a compound of general formula (XX) to a compound of general formula (XXI) may be carried out using any suitable method. One suitable method is a Dess-Martin periodinane (1,1,1-triacetoxy-1,1-dihydro-1,2-benziodoxol-3-(1H)-one) oxidation, which may be carried out in a chlorinated solvent such as chloroform or dichloromethane at a temperature of about 15 to 25° C., suitably at room temperature.

An alternative oxidation method is oxidation using a hypochlorite, for example sodium hypochlorite, under acidic conditions, for example provided by acetic acid. The reaction may be carried out in an aqueous solvent and at a temperature of 0 to 15° C., more usually at about 0 to 10° C.

Other oxidation methods include a Jones reaction using sodium dichromate or, more usually, chromic trioxide in dilute sulfuric acid. This process is known to be reliable for the clean conversion of bile acid hydroxyl groups to the corresponding keto derivatives (Bortolini et al, *J. Org. Chem.*, 2002, 67, 5802, incorporated herein by reference). Alternatively oxidation may be carried out using TEMPO ((2,2,6,6-tetramethyl-piperidin-1-yl)oxy) or a derivative thereof.

Representative examples of such a process are described in Example 16.

Step (v)

The epimerisation reaction of step (v) suitably comprises treating the compound of general formula (XXIa) or of general formula (XXI) with a base. The compound of general formula (XXIa) or compound of general formula (XXI) may be dissolved in an alcoholic solvent, optionally mixed with water and contacted with a base, for example sodium or potassium hydroxide or a sodium or potassium alkoxide, typically an ethoxide.

In the case of compounds of general formula (XXIa) or compounds of general formula (XXI) in which $R^4$ is C(O)OR$^{10}$, where $R^{10}$ is $C_{1-6}$ alkyl or benzyl and where a strong base such as sodium or potassium hydroxide is used, the epimerization reaction of step (v) may be accompanied by hydrolysis to give a compound of general formula (XXIIa) or a compound of general formula (XXII), respectively, in which $R^4$ is C(O)OH.

If, in the compound of general formula (XXIa) or compound of general formula (XXI), $R^2$ and/or $R^5$ is a protected OH, for example a group OC(O)$R^{14}$, where $R^{14}$ is as defined above but is especially $C_{1-6}$ alkyl or benzyl, or $C_{1-6}$ alkyl or phenyl, this will be removed during the epimerisation step to give a compound of general formula (XXIIa) or a compound of general formula (XXII), respectively, in which $R^2$ and/or $R^{5b}$ is OH. Other protected OH groups which are stable in basic conditions (for example a group OSi(R$^{16}$)$_3$ where each R$^{16}$ is independently as defined above but is especially C$_{1-6}$ alkyl or phenyl) may be removed before or after step (v).

Such a reaction is described in Example 17.

Step (vi)

The reduction of a compound of general formula (XXIIa) or a compound of general formula (XXII) to form a compound of general formula (XVIIIa) or compound of general formula (XVIII), respectively, utilises a reducing agent which is typically a hydride, such as sodium borohydride which may be used in a solvent such as a mixture of tetrahydrofuran and water. Typically, this reaction is carried out under basic conditions, for example in the presence of a strong base such as sodium or potassium hydroxide and at a temperature of about 0 to 110° C., more usually 60 to 100° C. A compound of general formula (XVIIIa) or a compound of general formula (XVIII) in which R$^4$ is C(O)OH may be produced by the reduction of a compound in which R$^4$ is C(O)OH. Such a reaction is described in Example 18.

The process optionally further includes one or more steps of converting compounds of general formulae (Ia), (XIXa), (XXa), (XXIa), (XXIIa) or (XVIIIa) to other compounds of general formulae (Ia), (XIXa), (XXa), (XXIa), (XXIIa) or (XVIIIa), or one or more steps of converting compounds of general formulae (I), (XIX), (XX), (XXI), (XXII) or (XVIII) to other compounds of general formulae (I), (XIX), (XX), (XXI), (XXII) or (XVIII).

The optional steps consist of reacting the side chains of the compounds of general formulae (Ia), (XIXa), (XXa), (XXIa), (XXIIa) and (XVIIIa) or of the compounds of general formulae (I), (XIX), (XX), (XXI), (XXII) and (XVIII) as described below to arrive at compounds with alternative Y and/or R$^4$ moieties.

It should be noted that embodiments described above with respect to different Y and R groups apply equally to the process embodiments just described.

Side Chain Conversions

The various side chain Y—R$^4$ and Y$^1$—R$^4$ groups of compounds of formulae (Ia)-(VIa) and (XVIIIa)-(XXIIa) and of compounds of formulae (I)-(VI) and (XVIII)-(XXII) may be prepared using conversion steps which are well known to the skilled person e.g. by reactions involving a side chain carboxylic acid, ester, OH or protected OH group. Analogues of the compounds of formulae (XVIII), (XVIIIa), (XXI), (XXIa), (XXII), (XXIIa), (XXIII), (XXIIIa) in which a saturated side chain Y$^1$—R$^4$ is converted to an unsaturated side chain Y—R$^4$ may also be prepared by these methods and are described in more detail below.

FIG. 1 shows the conversion of a compound of general formula (IIa) or of general formula (II) in which the side chain is —CH$_2$OH to other compounds of general formula (IIa) or of general formula (II), respectively, with different side chains.

Such reactions are equally applicable to compounds of general formulae (Ia), (I), (IIIa)-(VIa), (III)-(VI), (XVIIIa)-(XXIIa) and (XVIII)-(XXII), wherein appropriate (i.e. where chemically sensible).

As shown in FIG. 1, a compound of general formula (IIa) or a compound of general formula (II) wherein Y—R$^4$ is CH$_2$—OH may be prepared from a plant sterol such as stigmasterol (as described in Example 1).

As shown in FIG. 1, a compound of general formula (IIa) or a compound of general formula (IIa) with the —CH$_2$OH side chain can be converted to compounds of general formula (IIa) or of general formula (II) with side chains including —CH$_2$-9-borabicyclo(3.3.1) nonyl, —CH$_2$CH$_2$CH[B(alkyl)$_2$]2, —CH$_2$CN, —CH$_2$CH$_2$CN, —CH$_2$Br, —CH$_2$CH[C(O)OEt]$_2$, —CH$_2$—C≡CH, —CH$_2$—CH=CH$_2$, =CH$_2$, —C(O)H, —CH$_2$NH$_2$, CH$_2$OTBDMS, CH$_2$N$_3$, CH$_2$OMs,

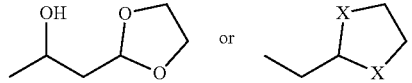

where X is O or S alkyl may be C$_{1-6}$ alkyl and Et is ethyl, and also carboxylic acid mimetic groups including —C(O)NHSO$_2$R$^{10}$ and —NHC(O)NH—SO$_2$R$^{10}$ Compounds of general formulae (Ia)-(VIa), and (XVIIIa)-(XXIIa) and compounds of general formulae (I)-(VI), (XVIII)-(XXII) with a side chain Y—OH (wherein Y is Y$^2$—CH$_2$, and Y$^2$ is as defined above for Y except it is shorter in length by at least one carbon) can be converted to compounds in which the side chain is —Y$^2$—C(O)H by oxidation, for example using oxalyl chloride suitably in the presence of dimethyl sulfoxide and a base such as trimethylamine. Alternatively, the oxidation may be carried out using Dess-Martin periodinane as shown in Example 23.

In compounds of general formulae (Ia)-(VIa), and (XVIIIa)-(XXIIa) and compounds of general formulae (I)-(VI), and (XVIII)-(XXII) in which the side chain is —Y$^2$—C(O)H, the side chain can be extended, for example using an olefination reaction with a compound of general formula (XXIII):

$$Ph_3P=CH—Y^3—C(O)OR^{27} \quad (XXIII)$$

where Y$^3$ is as defined for Y in general formula (Ia) and general formula (IIa) or Y in general formula (I) and general formula (II) except that it may have a shorter carbon chain such that the linker Y of general formula (Ia) and general formula (IIa) or of general formula (I) and general formula (II) can be a moiety —Y$^2$—CH$_2$CH$_2$—Y$^3$—, wherein Y$^2$ and Y$^3$ are as defined for Y except that they are shorter in length, wherein R$^{27}$ is suitably C$_{1-6}$ alkyl or benzyl, to give a compound in which the side chain is Y$^2$—CH=CH—Y$^3$—C(O)OR$^{27}$. An olefination reaction using (EtO)$_2$P(O)CH$_2$Y$^3$—C(O)OR$^{27}$ may also be used.

The olefination may be carried out at about 15 to 25° C., suitably room temperature, in a solvent such as dichloromethane.

These compounds can, in turn, be converted to compounds in which R$^4$ is the carboxylic acid mimetic group C(O)NHSO$_2$R$^{10}$, wherein R$^{10}$ is as defined above, by reaction with:

Wherein R$^{10}$ is as defined above, in the presence of a coupling agent such as 1-ethyl-3(3-dimethylaminopropyl) carbodiimide (EDCI).

Compounds of general formula formulae (Ia)-(VIa), and (XVIIIa)-(XXIIa) and compounds of general formula formulae (I)-(VI), and (XVIII)-(XXII) in which the group at the R$^4$ position is OH can be protected with a silyl protecting group. This may be achieved by reaction with (XV) as described below, typically in an organic solvent and in the presence of a base, for example imidazole, or triethylamine. Such a reaction is shown in Example 22.

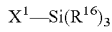

wherein, R$^{16}$ is as defined above and X$^1$ is a leaving group, for example a halide such as chloride or a sulfonate leaving group such as trifluoromethanesulfonate (triflate), methanesulfonate (mesylate) or toluene sulfate (tosylate).

Compounds of general formulae (Ia)-(VIa), and (XVIIIa)-(XXIIa) and compounds of general formulae (I)-(VI), and (XVII)-(XXII) in which $R^4$ is OH may also be converted to compounds in which $R^4$ is a sulfonate, for example methane sulfonate or toluene sulfonate, by reaction with a sulfonyl halide such as methane sulfonyl chloride, in the presence of a catalyst such as 4-dimethylaminopyridine (DMAP). Such a reaction is shown in Example 25. Alternatively, they may be converted to compounds of general formulae (Ia)-(VIa), and (XVIIIa)-(XXIIa) or compounds of general formulae (I)-(VI), and (XVIII)-(XXII) in which $R^4$ is halo, for example bromo, by reaction with a halogenating agent, e.g. a brominating agent such as carbon tetrabromide as illustrated in Example 26 or N-bromosuccinimide, as illustrated in Example 30.

Such sulfonate or halide compounds can then be converted to compounds of general formulae (Ia)-(VIa) and (XVIIIa)-(XXIIa) or compounds of general formulae (I)-(VI) and (XVIII)-(XXII) in which $R^4$ is cyano by reaction with a cyanide salt, for example sodium or potassium cyanide (see Example 30). Alternatively, reaction with acetonitrile in the presence of a base such as n-butyllithium leads to a chain lengthening reaction so that, for example, a side chain —$CH_2$—O-methanesulfonyl or —$CH_2$—Br is converted to a side chain —$CH_2CH_2$—CN. Such a reaction is shown in Example 28.

Compounds with a sulfonate side chain can also be converted to compounds in which $R^4$ is nitro by reaction with nitromethane in the presence of a base such as sodium or potassium carbonate.

Compounds of formulae (Ia)-(VIa), and (XVIIIa)-(XXIIa) and compounds of general formulae (I)-(VI), and (XVIII)-(XXII) in which the side chain is $Y^2$—C(O)OH or an ester thereof may be converted to compounds in which the side chain is $Y^2$—CH=$CH_2$ by reaction with PhI(OAc)$_2$ in the presence of copper (II) acetate using a process similar to Hunsdiecker reaction (see *J. Org. Chem.*, 1986, 51, 404-407 and V. C. Edelsztein et al. *Tetrahedron*, 2009, 65 (2009), 3615-3623, both incorporated herein by reference). Such compounds with side chain —$Y^2$—CH=$CH_2$ may in turn be oxidised using, for example, osmium tetroxide as described in *J. Org. Chem.*, 1986, 51, 404-407 (incorporated herein by reference) to give a compound in which the side chain is —$Y^2$—CH(OH)—$CH_2$—OH. Such compounds may be oxidised to compounds in which the side chain is $Y^2$—CH(OH)—C(O)H, which may then be protected as a 1,3-dioxane or 1,3-dioxolane by reaction with 1,3-propane diol or 1,2-ethandiol in the presence of an acid catalyst such as toluene sulfonic acid. Similar reactions can be used to prepare the equivalent cyclic dithioacetals, and cyclic aminals.

Compounds of general formulae (Ia)-(VIa), and (XVIIIa)-(XXIIa) and compounds of general formulae (I)-(VI), and (XVIII)-(XXII) with side chain —Y—CH=$CH_2$ may also be prepared by reduction of a compound with side chain —Y—C≡CH, typically by hydrogenation over a palladium catalyst, suitably Lindlar catalyst, as shown in FIG. 1.

Compounds of formulae (Ia)-(VIa), and (XVIIIa)-(XXIIa) and compounds of general formulae (I)-(VI), and (XVIII)-(XXII) with side chain —Y—C≡CH may be prepared from compounds with side chain Y—X, where X is a halo group, particularly bromo, by reaction with an organometallic reagent, for example:

Li—C≡CH.

Compounds of general formulae (Ia)-(VIa), and (XVIIIa)-(XXIIa) and compounds of general formulae (I)-(VI), and (XVIII)-(XXII) in which the side chain —Y—$R^4$ is —$CH_2$—OH may also be converted to compounds in which the side chain is =$CH_2$. This can be achieved by an elimination reaction in which the compound having side chain —Y—$R^4$ is —$CH_2$—OH is reacted with an acid such as phosphoric acid, sulphuric acid or toluene sulphonic acid as shown in FIG. 1. A similar reaction can be used to convert a compound with side chain —$Y^2$—$CH_2$—OH to a compound with side chain —C≡$CH_2$. Alternatively, compounds in which the side chain is $Y^2$—CH=$CH_2$ can be prepared by oxidising —$Y^2$—$CH_2$—OH to $Y^2$—CH(O) and then converting this to an alkene using an olefination reaction.

Compounds of general formulae (Ia)-(VIa), and (XVIIIa)-(XXIIa) or compounds of general formulae (I)-(VI), and (XVIII)-(XXII) with side chain Y—C≡CH, =$CH_2$ or —$Y^2$—C≡$CH_2$ may be reacted with a borane of formula:

H—$BR^{10}R^{11}$ to give compounds in which the side chain is —Y—$CH_2$—C($BR^{10}R^{11}$)$_2$, —$CH_2$—$BR^{10}R^{11}$ or —$Y^2$—$CH_2$—$BR^{10}R^{11}$ respectively. An example of this reaction is shown in FIG. 1.

Compounds of formulae (Ia)-(VIa), and (XVIIIa)-(XXIIa) and compounds of general formulae (I)-(VI), and (XVIII)-(XXII) in which the side chain is —$CH_2$—$BR^{10}R^{11}$ or —$Y^2$—$CH_2$—$BR^{10}R^{11}$ may be reacted with, for example phenoxyacetic acid to give a corresponding compound in which the side chain is —$CH_2$—C(O)OH or —$Y^2$—$CH_2$—C(O)OH.

Compounds of general formulae (Ia)-(VIa), and (XVIIIa)-(XXIIa) and compounds of general formulae (I)-(VI), and (XVIII)-(XXII) in which $R^4$ is —CH[C(O)$OR^{10}$]$_2$ may be prepared from compounds in which $R^4$ is halo, for example bromo, by reaction with a malonate ester in the presence of a base such as sodium hydride, as shown in FIG. 1. A reaction of this type is illustrated in Example 27 and Example 31.

Compounds of general formulae (Ia)-(VIa), and (XVIIIa)-(XXIIa) and compounds of general formulae (I)-(VI), and (XVIII)-(XXII) in which $R^4$ is a malonate ester —CH[C(O)$OR^{10}$]$_2$ may be heated under basic or acidic conditions to give compounds in which $R^4$ is $CH_2C(O)OH$ or, when basic conditions are used, a salt thereof.

Compounds of general formulae (Ia)-(VIa), and (XVIIIa)-(XXIIa) and compounds of general formulae (I)-(VI), and (XVIII)-(XXII) in which the side chain is —Y—C(O)OH may also be converted to compounds in which the side chain is —Y—C(O)—$CH_2$—$N_2$ by reaction with phosgene to form the acid chloride, followed by reaction with diazomethane.

The diazomethane may be formed in situ using conventional methods, e.g. the treatment of N-nitroso-N-methylurea with aqueous sodium or potassium hydroxide in diethyl ether. Suitably the diazomethane is used in excess, typically in an amount of greater than 2 equivalents compared with the acid chloride. The reaction is typically conducted in an organic solvent such as diethyl ether, toluene or a mixture thereof. The reaction is carried out at a temperature of about −5 to 15° C., typically 0-10° C.

The compound with side chain —Y—C(O)—$CH_2$—$N_2$ may be treated with an aqueous silver compound, for example silver nitrate, at an elevated temperature and in the presence of an alcohol of formula:

$R^{10a}$—OH wherein $R^{10a}$ is as defined for $R^{10}$ in general formula (Ia) or in general formula (I) except that it is not H. Most suitably, $R^{10a}$ is $C_{1-6}$ alkyl or benzyl. Under these conditions, the compound undergoes a Wolff rearrangement to give a compound in which the side chain is —Y—$CH_2$—C(O)$OR^{10a}$ and thus this sequence can be used to lengthen the side chain.

Compounds of general formulae (Ia)-(VIa), and (XVIIIa)-(XXIIa) or compounds of general formulae (I)-(VI), and (XVIII)-(XXII) in which the side chain is Y—C(O)OH may be converted to compounds in which the side chain is —$Y^2$—$CH_2$—CN by reaction with sodium nitrite under acidic conditions, for example in the presence of trifluoroacetic acid and trifluoroacetic anhydride (C. D. Schteingart and A. T. Hofmann, *Journal of Lipid Research*, 1988, 29, 1387-1395; Valentina Sepe et al, *Eur. J. Org. Chem.* 2012, 5187-5194, both incorporated herein by reference).

Compounds of general formulae (Ia)-(VIa), and (XVIIIa)-(XXIIa) or compounds of general formulae (I)-(VI), and (XVIII)-(XXII) in which the side chain is Y—C(O)H may be converted to compounds in which the side chain is —Y—CH($XR^{10}$)($XR^{11}$), for example —Y—CH($OR^{10}$)($OR^{11}$) or —Y—CH($SR^{10}$)($SR^{11}$) where $R^{10}$ and $R^{11}$ together with the atoms to which they are attached join to form a cyclic group. This can be achieved by reacting the compound in which the side chain is Y—C(O)H with a compound of formula:

$$HX^3\text{—}(CH_2)_p\text{—}X^3H$$

where $X^3$ is O, S or NH and p is 1 to 4 but usually is 2 or 3, or with a protected version of such a compound, for example in which OH or SH groups are protected with trimethylsilyl as shown in Example 24.

Compounds of general formulae (Ia)-(VIa), and (XVIIIa)-(XXIIa) or compounds of general formulae (I)-(VI), and (XVIII)-(XXII) in which the side chain is $Y^2$—C(O)H may also be converted to compounds with side chain —$Y^2$—CH(OH)—$CH_2$—CH($OR^{10}$)($OR^{11}$), —$Y^2$—CH(OH)—$CH_2$—CH($R^{10}$)($OR^{11}$) or —$Y^2$—CH(OH)—$CH_2$—CH($SR^{10}$)($SR^{11}$) by reaction with an appropriate organometallic reagent, typically a Grignard reagent of formula:

$$XMg\text{—}CH_2\text{—}R^{4c};$$

where X is halo, typically bromo, and $R^{4c}$ —CH($OR^{10}$)($OR^{11}$), —CH($R^{10}$)($OR^{11}$) or CH($SR^{10}$)($SR^{11}$).

Compounds of general formulae (Ia)-(VIa), and (XVIIIa)-(XXIIa) or compounds of general formulae (I)-(VI), and (XVIII)-(XXII) in which the side chain is —$Y^2$—CH(OH)—$CH_2$—CH($OR^{10}$)($OR^{11}$) can be converted to compounds in which the side chain is —$Y^2$—CH=CH—C(O)H by reaction with an acid. Following this, the aldehyde can be oxidised to give a carboxylic acid and/or the alkylene bond can be reduced by hydrogenation to give a saturated side chain in which Y is —$Y^2$—$CH_2CH_2$—.

Compounds of general formulae (Ia)-(VIa), and (XVIIIa)-(XXIIa) or compounds of general formulae (I)-(VI), and (XVIII)-(XXII) in which $R^4$ is —$N_3$ may be prepared from compounds in which $R^4$ is a leaving group such as toluene sulfonate, methane sulfonate or compounds of general formulae (Ia)-(IVa), and (XVIIIa)-(XXIIa) or compounds of general formulae (I)-(VI), and (XVIII)-(XXII), respectively, in which $R^4$ is halo (for example bromo) or a sulfonyl leaving group such as toluene sulfonate or methane sulfonate, by reaction with sodium azide. This is illustrated in Example 29.

Compounds of general formulae (Ia)-(VIa), and (XVIIIa)-(XXIIa) or compounds of general formulae (I)-(VI), and (XVIII)-(XXII) in which $R^4$ is $NH_2$ may be obtained by reduction of compounds of general formulae (Ia)-(VIa), and (XVIIIa)-(XXIIa) or compounds of general formulae (I)-(VI), and (XVIII)-(XXII), respectively, in which $R^4$ is azide as illustrated in Example 29.

Compounds of general formulae (Ia)-(VIa), and (XVIIIa)-(XXIIa) or of general formulae (I)-(VI), and (XVIII)-(XXII) in which $R^4$ is —NHC(O)$NHSO_2R^{10}$ may be prepared from compounds in which $R^4$ is $NH_2$ using a coupling reaction with a compound of formula:

$$NH_2SO_2R^{10}$$

wherein $R^{10}$ is as defined above;
in the presence of a reagent such as N,N'-carbonyldiimidazole (CDI).

Compounds of general formulae (Ia)-(VIa), and (XVIIIa)-(XXIIa) or compounds of general formulae (I)-(VI), and (XVIII)-(XXII) in which $R^4$ is tetrazole-5-yl may be prepared from compounds of general formulae (Ia)-(VIa), and (XVIIIa)-(XXIIa) or compounds of general formulae (I)-(VI), and (XVIII)-(XXII), respectively, in which $R^4$ is CN by reaction with azidotrimethylsilane/dibutylstannanone or $Bu_3SnN_3$ as described in US 2016/0145295. Alternatively, the compound in which $R^4$ is CN may be reacted with sodium azide in the presence of acid. For example, $NaN_3$/$NH_4Cl$ in toluene/DMF (*Organic and Biomolecular Chemistry*, 2008, 6, 4108) or $NaN_3$/$NEt_3$.HCl in DMF (Brown et al; *Bioorg Med Chem Lett*, 2002, 12, 3171). Alternatively, a compound in which $R^4$ is azide may be reacted with a suitable cyanide compound, for example tosyl cyanide, under reducing conditions to give a compound in which $R^4$ is tetrazol-1-yl.

Compounds of general formulae (Ia)-(VIa), and (XVIIIa)-(XXIIa) or compounds of general formulae (I)-(VI), and (XVIII)-(XXII) in which $R^4$ is amino tetrazole can be prepared from a compound in which the group at the $R^4$ position is mesyl by reaction with 5-amino tetrazole. Compounds of general formulae (Ia)-(VIa), and (XVIIIa)-(XXIIa) and compounds of general formulae (I)-(VI), and (XVIII)-(XXII) in which the side chain is —$Y^2$—C(O)H may also be converted to compounds —$Y^2$—$CH_2$—$NR^{10}R^{11}$ by reductive amination, using a reducing agent such as a hydride, borohydride or cyanoborohydride (for example sodium borohydride or sodium cyanoborohydride) and an amine of formula:

$$H\text{—}NR^{10}R^{11}$$

where $R^{10}$ and $R^{11}$ are as defined above.

Compounds of general formulae (Ia)-(VIa), and (XVIIIa)-(XXIIa) or compounds of general formulae (I)-(VI), and (XVII)-(XXII) in which $R^4$ is C(O)$OR^{10}$ may be converted to a compound of the same general formula, in which $R^4$ is OC(O)$R^{10}$, C(O)$NR^{10}R^{11}$, $OR^{10}$, OSi($R^{13}$)$_3$, S(O)$R^{10}$, $SO_2R^{10}$, $OSO_2R^{10}$, $SO_3R^{10}$, $OSO_3R^{10}$, halo, CN, C(O)$R^{10}$, CH($OR^{10}$)($OR^{11}$), CH($R^{10}$)($OR^{11}$), CH($SR^{10}$)($SR^{11}$), $NR^{10}R^{11}$, $BR^{10}R^{11}$, C(O)$CH_2N_2$, —CH=$CH_2$, —C≡CH, CH[C(O)$OR^{10}$]$_2$ or CH(BR$^{10}R^{11}$)$_2$, azide or a carboxylic acid mimetic group such as tetrazole.

Compounds of general formulae (Ia)-(VIa), and (XVIIIa)-(XXIIa) or compounds of general formulae (I)-(VI), and (XVIII)-(XXII) in which $R^4$ is $SO_3R^{10}$ may be synthesised from compounds in which $R^4$ is C(O)OH by the methods taught in WO2008/002573, WO2010/014836 and WO2014/066819 (all incorporated herein by reference).

Thus, a compound of general formulae (Ia)-(VIa) and (XVIIIa)-(XXIIa) or compounds of general formulae (I)-(VI) and (XVIII)-(XXII) in which $R^4$ is C(O)OH may first be reacted with a $C_{1-6}$ alkanoyl or benzoyl chloride or with a $C_{1-6}$ alkanoic anhydride to protect any OH groups. The protected compound may then be reacted with a reducing agent such as a hydride, suitably lithium aluminium hydride or sodium borohydride in order to reduce the carboxylic acid group to OH. The alcohol group may be replaced by a halogen, for example bromine or iodine, using the triphenyl phosphine/imidazole/halogen method described by Classon et al, *J. Org. Chem.*, 1988, 53, 6126-6130 (incorporated herein by reference). The halogenated compound may then be reacted with sodium sulphite in an alcoholic solvent to give a compound with a $SO_3^-Na^+$ substituent.

A compound of general formulae (Ia)-(VIa), and (XVIIIa)-(XXIIa) or a compound of general formulae (I)-(VI), and (XVIII)-(XXII) in which $R^4$ is $OSO_3R^{10}$ can be obtained by reacting the alcohol obtained from reducing the protected carboxylic acid as described above with chlorosulfonic acid in the presence of a base such as triethylamine to yield the protected triethylamine salt. Protecting groups can be removed using base hydrolysis as described above. Reduction of the carboxylic acid followed by reaction of the resultant alcohol with a sulfonyl chloride yields a compound of general formulae (Ia)-(VIa), and (XVIIIa)-(XXIIa) or a compound of general formula (I)-(VI), and (XVII)-(XXII) in which $R^4$ is $OSO_2R^{10}$.

Compounds of general formulae (Ia)-(VIa), and (XVIIIa)-(XXIIa) or of general formulae (I)-(VI), and (XVIII)-(XXII) in which $R^4$ is $C(O)NR^{10}R^{11}$ may be prepared from the carboxylic acid by reaction with an amine of formula H—$NR^{10}R^{11}$ in a suitable solvent with heating. Compounds of general formulae (Ia)-(VIa), and (XVIIIa)-(XXIIa) or of general formulae (I)-(VI), and (XVIII)-(XXII) in which $R^4$ is $C(O)NR^{10}R^{11}$ or $OSO_3R^{10}$ may also be prepared by methods similar to those described by Festa et al., *J. Med. Chem.*, 2014, 57, 8477-8495 (incorporated herein by reference).

An example of this is the synthesis of compounds of general formulae (Ia)-(VIa), and (XVIIIa)-(XXIIa) or compounds of general formulae (I)-(VI), and (XVII)-(XXII) in which $R^4$ is $C(O)NH(CH_2)_2SO_3H$ or $C(O)NHCH_2CO_2H$ or salts thereof from compounds of the same general formula in which $R^4$ is $C(O)OH$ by reaction with taurine or glycine respectively in the presence of a coupling reagent such as iso-butylchloroformate and a base such as diethylamine.

A compound of general formulae (Ia)-(VIa) and (XVIIIa) to (XXIIa) or a compound of general formulae (I)-(VI) and (XVIII) to (XXII) in which $R^4$ is $C(O)R^{10}$ can be obtained by reduction of a compound in which $R^4$ is $C(O)OR^{10}$ using one equivalent of diisobutyl aluminium hydride (DIBAL-H) to obtain an aldehyde in which $R^4$ is $C(O)H$ (see, for example, WO2011/014661, incorporated herein by reference).

Alternatively, the aldehyde may be prepared by oxidation of a protected compound in which $R^4$ is OH prepared as described above. The oxidation may be Swern oxidation carried out using oxalyl chloride and dimethyl sulfoxide followed by triethylamine (see, for example Xiang-Dong Zhou et al., *Tetrahedron*, 2002, 58, 10293-10299, incorporated herein by reference). Alternatively, the oxidation may be carried out using an oxidising agent such as pyridinium chlorochromate (PCC) as described by Carnell et al. (*J. Med. Chem.*, 2007, 50, 2700-2707, incorporated herein by reference.

A compound of general formulae (Ia)-(VIa) and (XVIIIa)-(XXIIa) or a compound of general formulae (I)-(VI) and (XVIII) to (XXII) in which $R^4$ is $C(O)R^{10}$ where $R^{10}$ is other than hydrogen can be obtained by known methods, for example by the reaction of the aldehyde in which $R^4$ is $C(O)H$ with a suitable Grignard reagent, followed by oxidation. Such methods are well known to those of skill in the art.

Compounds of general formulae (Ia)-(VIa), and (XVIIIa)-(XXIIa) or compounds of general formulae (I)-(VI) and (XVIII) to (XXII) with other $R^4$ groups may be prepared from the above compounds of the same general formula, by methods which are familiar to those of skill in the art.

General Information

The invention will now be described in greater detail with reference to the examples.

Abbreviations

Ac acetyl
AcOH acetic acid
nBuOAc n-butyl acetate
9-BBN 9-borabicyclo[3.3.1]nonane
nBuLi n-butyllithium
CDCA chenodeoxycholic acid
CDI N,N'-carbonyldiimidazole
CPME cyclopentyl methyl ether
DCM dichloromethane
DEIPS diethylisopropylsilyl
DIBAL-H diisobutyl aluminium hydride
DMAP 4-dimethylaminopyridine
DMDO dimethyldioxirane
DMF N,N-dimethylformamide
DMIPS dimethylisopropylsilyl
DMP Dess-Martin periodinane
DTBMS di-tert-butylmethylsilyl
EDCI 1-ethyl-3(3-dimethylaminopropyl)carbodiimide
EtOAc ethyl acetate
EtOH ethanol
$Et_2O$ diethyl ether
FXR farnesoid X receptor
HFIP 1,1,1,3,3,3-hexafluoro-2-propanol/hexafluoroisopropanol
HMPO (20S)-20-hydroxymethyl-pregna-4-en-3-one also known as 20-hydroxymethylpregn-4-en-3-one and 3-keto-bis-norcholenol
HPLC high performance liquid chromatography
HWE Horner-Wadsworth-Emmons
IPC in process control
IPA isopropyl alcohol
mCPBA meta-chloroperoxybenzoic acid
MeCN acetonitrile
MeOH methanol
MIBK methyl isobutyl ketone
MMPP magnesium bis(monoperoxyphthalate)
Ms methanesulfonyl
MsCl methanesulfonyl chloride
MTO methyltrioxorhenium (VII)
$NEt_3$ triethylamine
OCA obeticholic acid
PCC pyridinium chlorochromate
PEG polyethylene glycol
PhMe toluene
RRT relative retention time
pTSA.$H_2O$ p-toluenesulfonic acid monohydrate
TBDMS tert-butyldimethylsilyl
TBDPS tert-butyldiphenylsilyl
TBME tert-butyl methyl ether
TDS thexyldimethylsilyl
TEMPO (2,2,6,6-tetramethyl-piperidin-1-yl)oxy
TEPA triethyl phosphonoacetate TES triethylsilyl
TFE 2,2,2-trifluoroethanol
THF tetrahydrofuran
TIPS tri-isopropylsilyl
TLC thin layer chromatography
TMS trimethylsilyl
TMSOTf trimethylsilyl trifluoromethanesulfonate
TPS triphenylsilyl
Ts toluenesulfonlyl/tosyl
UDCA ursodeoxycholic acid
UHP urea hydrogen peroxide

EXAMPLES

General Procedures

HPLC conditions for monitoring the reaction and assessing conversion, for example, conversion of (22E)-3-oxo-4,6,22-cholatrien-24-oic acid ethyl ester to (6α, 7α) and (6β, 7β) isomers of (22E)-6,7-epoxy-3-oxo-4,22-choladien-24-oic acid ethyl ester.

Chromatographic Conditions

| Instrument | Agilent 1200 series HPLC fitted with RI detector |
|---|---|
| Column | ACE, C18, 250 mm × 4.6 mm, 5 μm |
| Column Temperature | 40° C. |
| Eluent | 30:70, 25 mM Ammonium acetate pH6:Acetonitrile |
| Flow Rate | 1.25 mL/min |
| Injection Volume | 10 μL |
| RID Conditions | 40° C. |
| Run Time | 60 minutes |

Example 1—Synthesis of (22E)-3-oxo-4,6,22-cholatrien-24-oic acid ethyl ester (IIA) from stigmasterol

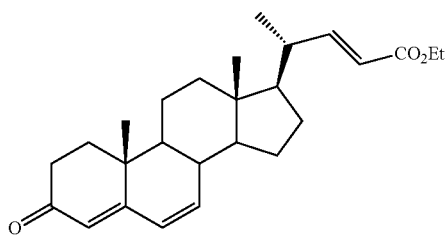

(IIA)

The starting material, (22E)-3-oxo-4,22-choladien-24-oic acid ethyl ester (compound (IIA)), was prepared from stigmasterol according to the method described by Uekawa et al in *Biosci, Biotechnol, Biochem.*, 2004, 68, 1332-1337.

Compound (IIA) (1.00 kg, 2.509 mol; 1 eq) was charged to a reaction vessel, followed by AcOH (3 vol, 3.0 L) and toluene (1 vol, 1.0 L) with stirring. Chloranil (0.68 kg, 2.766 mol; 1.1 eq) was then charged and the reaction mixture heated to 100° C. and maintained at this temperature for 1-2 h (IPC by TLC on silica, eluent 3:7 EtOAc:Heptane; Starting Material: $R_f$ 0.50, Product: $R_f$ 0.46; visualise with anisaldehyde stain). The mixture was then cooled in an ice/water bath to 10° C. and the resulting solid was filtered off. The filter-cake was washed with premixed 3:1 AcOH:Toluene (4×0.5 vol) at 5° C.±4° C. and the filtrate concentrated in vacuo at up to 70° C. The residue was dissolved in acetone (3 vol), then 3% w/w aq. NaOH (10 vol) was charged dropwise with stirring, maintaining the temperature below 30° C. (exothermic). The resulting suspension was cooled to 10-15° C. and stirred for 30 mins. The solids were collected by filtration and the filter cake was washed with premixed 1:1 acetone:water (1×2 vol then 3×1 vol). The filter cake (tan solid) was dried under vacuum at 70-75° C., resulting in 672 g of the title compound (68% yield). Characterisation of the compound agrees with the data published in the literature.

Examples 2-8—Synthesis of 3-oxo-4,6-choladien-24-oic acid ethyl ester (IIB) from deoxycholic acid Example 2—Synthesis of (3α, 5β)-3-acetoxy-12-oxo-cholan-24-oic acid methyl ester (VIIB)

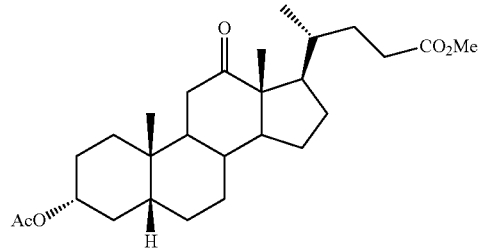

(VIIB)

To a solution of deoxycholic acid (referred to herein as compound (XB), 500 g, 1.27 mol) in MeOH (1.5 L) was charged $H_2SO_4$ (0.68 mL, 12.7 mmol) and the reaction heated to 64° C. until complete. The reaction was cooled to 55° C. and pyridine (2.06 mL, 25.4 mmol) was charged. MeOH (800 mL) was removed by distillation and the reaction cooled to 50° C. EtOAc (500 mL) was charged and the distillation continued. This co-evaporation was repeated until the MeOH content was <0.5%. The reaction was cooled to 40° C. and EtOAc (1.0 L) was charged followed by pyridine (134 mL, 1.65 mol) and DMAP (1.1 g, 8.89 mmol). Acetic anhydride (150 mL, 1.58 mmol) was added dropwise and the reaction vessel stirred at 40° C. until complete. The reaction was cooled to 22° C. and 2M aq. $H_2SO_4$ (1500 mL) added maintaining the temperature below 25° C. The aqueous phase was removed and the organic phase washed with water (1.2 L), sat. aq. $NaHCO_3$ solution (1.2 L×2) and water (1.2 L). AcOH (1.0 L) was charged to the organic layer, followed by NaBr (6.6 g, 63.5 mmol). Aq. 16.4% NaOCl solution (958 mL, 2.54 mol) was charged dropwise maintaining the reaction temperature below 25° C. The reaction was stirred until complete, then cooled to 10° C. and stirred for 90 mins. The resulting solids were collected by filtration, washed with water (3×500 mL) and the filter cake dried under vacuum at 40° C. The solids were crystallised from MeOH (10 vol) to give the title compound as an off white solid (268 g).

Example 3—Synthesis of (3α, 5β)-3-acetoxy-cholan-24-oic acid methyl ester

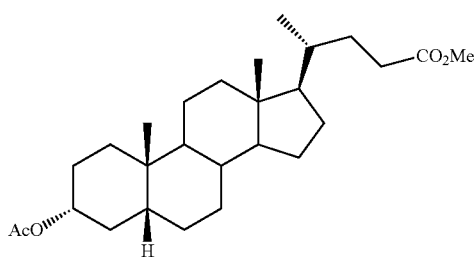 [SMILES: COC(=O)CC[C@@H](C)[C@H]1CCC2C3CC[C@@H]4C[C@H](OC(C)=O)CC[C@]4(C)C3CC[C@@]21C]

(3α, 5β)-3-acetoxy-12-oxo-cholan-24-oic acid methyl ester (compound (VIIB), 268 g, 0.6 mol) was charged to the reaction vessel under argon, followed by AcOH (1.8 L). Tosyl hydrazide (190 g, 1.02 mol) was then added maintaining the reaction temperature at 25° C. The reaction was stirred until complete and then NaBH$_4$ (113.5 g, 3.00 mol) was charged portion-wise maintaining the temperature below 25° C. The reaction mixture was stirred until complete and then quenched by the dropwise addition of water (1.34 L) maintaining the temperature below 25° C. The reaction mixture was stirred for 30 mins, the resulting solids collected by filtration, washed with water (3×270 mL) and the solid dried under vacuum at 40° C. The solids were crystallised from MeOH (3 vol) to give the title compound as an off white solid (214.5 g).

Example 4—Synthesis of (3α, 5β)-3-hydroxy-cholan-24-oic acid (Lithocholic Acid) (VIB)

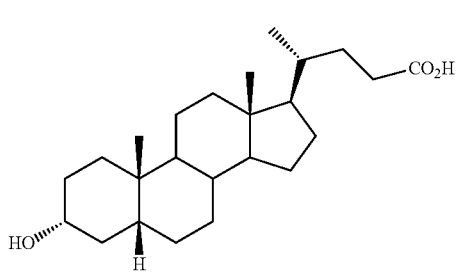

To a solution of (3α, 5β)-3-acetoxy-cholan-24-oic acid methyl ester (214.5 g, 0.50 mol) in IPA (536 mL) was charged water (536 mL) and 50% w/w NaOH (99 g, 1.24 mol). The reaction was heated to 50° C. and stirred until complete. 2M H$_2$SO$_4$ was charged slowly with vigorous stirring until pH 2-3 was obtained and then the reaction cooled to 20° C. The resulting solids were collected by filtration, washed with water (3×215 mL) and the resultant solid dried under vacuum at 40° C. to give the title compound (176.53 g)

Example 5—Synthesis of (5β)-3-oxocholan-24-oic acid ethyl ester (VB)

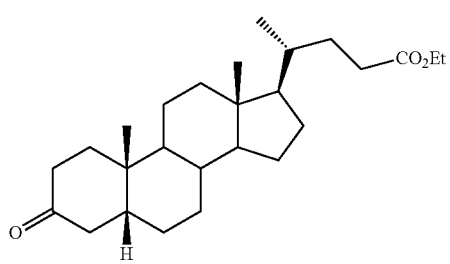

To a solution of (3α, 5β)-3-hydroxy-cholan-24-oic acid (compound (VIB), 10 g, 26.5 mmol) in EtOH (50 mL) was charged H$_2$SO$_4$ 96% (14 µL, 0.27 mmol) and the reaction mixture then heated to reflux for 16 h. Pyridine was then charged, the mixture stirred for 30 mins and concentrated in vacuo at 40° C. The residue was dissolved in EtOAc (30 mL) and AcOH (10 mL) and NaBr (136 mg, 1.33 mmol) was then charged. The solution was cooled to 5° C. and NaOCl 9% (27 mL, 39.8 mmol) was charged dropwise maintaining the temperature below 10° C. The resulting suspension was warmed to ambient temperature and stirred for 1 h. The reaction mixture was cooled to 0° C. for 10 mins, the solids collected by filtration and washed with water (3×3 vol). The resultant solid was dried under vacuum at 40° C. to give the title compound (7.83 g).

Example 6—Synthesis of (5β)-3-oxo-4-bromo-cholan-24-oic acid ethyl ester (IVB)

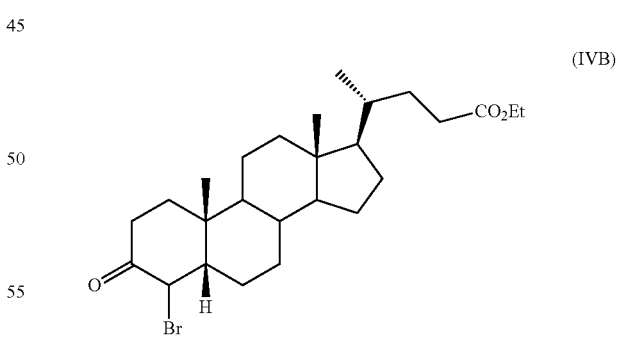

To a solution of (5β)-3-oxocholan-24-oic acid ethyl ester (compound (VB), 8.0 g, 19.9 mmol) in AcOH (84 mL) was added Br$_2$ in AcOH (16 mL, 21.9 mmol) dropwise over 15 mins. The reaction mixture was stirred for 10 mins, then diluted with EtOAc (250 mL), washed with water (2×200 mL) and concentrated in vacuo at 40° C. The crude material was purified by column chromatography (30% Heptane: EtOAc) and concentrated in vacuo at 40° C. to give the title compound a pale crystalline solid (7.49 g).

Example 7—Synthesis of (5β)-3-oxo-4-cholene-24-oic acid ethyl ester (IIIB)

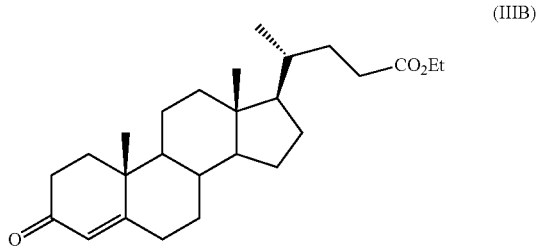 [SMILES: CCOC(=O)CC[C@@H](C)[C@H]1CCC2C3CCC4=CC(=O)CC[C@]4(C)C3CC[C@@]21C]

To a solution of (4α, 5β)-3-oxo-4-bromo-cholan-24-oic acid ethyl ester (compound (IVB), 4.0 g, 8.33 mmol) in DMF (40 mL) was charged $Li_2CO_3$ (4.0 g, 1 mass eq) and LiBr (2.0 g, 0.5 mass eq). The mixture was heated to 150° C. for 2 h then allowed to cool to ambient temperature and poured onto a mixture of water and ice (200 g, 50 volumes) and AcOH (8 mL). The resulting suspension was stirred for 15 mins, the solids collected by filtration and then purified by column chromatography (30% Heptane:EtOAc) to give the title compound as a pale crystalline solid (1.68 g).

Example 8—Synthesis of 3-oxo-4,6-choladien-24-oic acid ethyl ester (IIB)

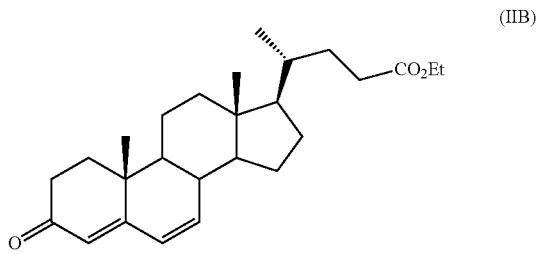 [SMILES: CCOC(=O)CC[C@@H](C)[C@H]1CCC2C3C=CC4=CC(=O)CC[C@]4(C)C3CC[C@@]21C]

3-oxo-4-cholene-24-oic acid ethyl ester (compound (IIIB), 2.23 g, 5.57 mmol) was charged to a reaction vessel, followed by AcOH (6.7 mL) and toluene (2.23 mL). Chloranil (1.5 g, 6.13 mmol) was charged and the reaction mixture heated to 100° C. for 2 h (IPC by TLC, 3:7 EtOAc:Heptane; visualized with Anisaldehyde stain). The reaction mixture was cooled to 10° C. for 10 mins and the resulting solid removed by filtration. The filter cake was washed with DCM (9 vol) and the resulting filtrate then concentrated in vacuo at 40° C. The residue was dissolved in acetone (9 vol) then 3% w/w aq. NaOH (27 vol) was added dropwise maintaining the temperature below 30° C. The resulting mixture was cooled in an ice bath for 10 mins and the solids collected by filtration. The filter cake was washed with water (2×9 vol) and acetone:water 2:1 (4 vol). Purification by column chromatography (0-30% Heptane:EtOAc) gave the title compound as a pale crystalline solid (1.45 g)

Examples 9-11—Epoxidation Reactions

Example 9—Various Epoxidation Reactions for (22E)-3-oxo-4,6,22-cholatrien-24-oic Acid Ethyl Ester (IIA)

A series of trials were carried out to evaluate alternative epoxidation conditions for the epoxidation of compound (IIA) to form compound (IA) to those described in Uekawa et al. in *Biosci. Biotechnol. Biochem.*, 2004, 68, 1332-1337 of magnesium monoperoxyphthalate hydrate (MMPP) in $Et_2O$ and $CHCl_3$ at ambient temperature, or meta-chloroperoxybenzoic acid (mCPBA) in $CHCl_3$ at reflux. The starting material used was compound (IIA) prepared according to Example 1, ultimately deriving from stigmasterol.

Firstly, the use of alternative reaction conditions using MMPP and mCPBA as oxidant were investigated.

A series of trials was performed using mCPBA in various solvents and temperatures. The temperatures ranged from 0 to 80° C. (or reflux for lower boiling solvents) and the solvents screened were $CH_2Cl_2$, $CHCl_3$, EtOAc, nBuOAc, $CH_3CN$ and PhMe. The reactions were performed with and without $H_2O$ as a co-solvent and with and without a catalytic amount of BHT (butylated hydroxytoluene). The equivalents of oxidant varied from 1-3 equivalents, often with further addition over the course of the reaction to drive completion. Compound (IA) yields of up to about 45% were observed, with moderate selectivity. There were also concerns about decomposition pathways and work-up conditions.

Trials using magnesium monoperoxyphthalate hexahydrate (MMPP) in range of solvents and temperatures were also carried out. MMPP epoxidations proved inconsistent, with crude yields (recovery of the product) ranging between 30% and 70%. However, isolated yields were seldom higher than 50%. It was established that the low and inconsistent yields obtained from the reaction were due to quick decomposition of the epoxide to further products, which are soluble in aqueous, especially in basic media.

Furthermore, when both the mCPBA and MMPP reactions were repeated on a larger scale (than used in the Uekawa reference), the yields were observed to decrease, and were inconsistent between batches.

Alternative oxidations systems were investigated. Experiments using various dioxiranes were performed. Initial experiments focussed on dimethyldioxirane (DMDO) and were performed in a range of solvents: $CH_2Cl_2$, $CH_3CN$, EtOAc and THF. In comparison to mCPBA and MMPP, DMDO gave a reduced selectivity towards the desired epoxide, with other by-products e.g. 4,5-epoxide forming in a higher proportion. Other substituted dioxiranes were also investigated, among them those formed from: trifluoroacetone, trifluoroacetophenone, cyclohexanone, menthone, 4'-methoxyacetophenone, methyl isobutyl ketone and 2,4-dimethylpentanone. None of these have proven to be more successful than mCPBA or MMPP.

The following oxidation systems were also investigated but were found to be inferior to mCPBA and MMPP: Jacobsen catalyst, oxo-vanadium, iron oxycatalysts and perborate.

Methyltrioxorhenium (VII) (MTO) was then evaluated as a potential catalyst for the epoxidation reaction. The reactions were screened in various solvents using $H_2O_2$ and urea hydrogen peroxide as oxidant, using various ligands. The reactions were conducted at 0 to 10° C. Good selectivity and yields were consistently observed, with HFIP as solvent, urea hydrogen peroxide as oxidant and 3-methyl pyrazole as ligand providing yields of up to 85% of compound (IA). The high yields and selectivity compared with the other oxidation conditions evaluated were surprising. Optimum quantities of MTO required for the reactions were established at about 1 mol % with 12 mol % of ligand and up to 2 equivalents of the oxidant. A full representative procedure is described in Example 10.

Moreover, as shown in Example 10a, this reaction using MTO could be scaled-up considerably without a reduction in the yield, unlike the prior art conditions. Thus, the process of the present invention is scalable.

Example 10—Epoxidation of (22E)-3-oxo-4,6,22-cholatrien-24-oic acid ethyl ester (IIA) using methyltrioxorhenium to form (6α, 7α, 22E)-6,7-epoxy-3-oxo-4,22-choladien-24-oic acid ethyl ester (IA)

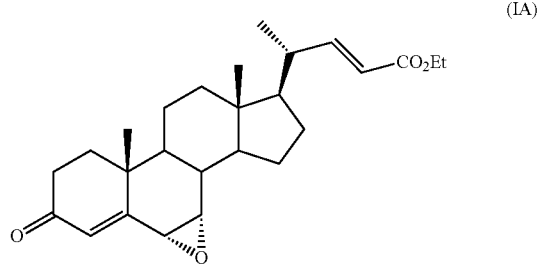 [SMILES: CCOC(=O)/C=C/[C@@H](C)[C@H]1CCC2C3C(CC[C@@]21C)[C@@]1(C)CCC(=O)C=C1[C@H]1O[C@@H]31]
(IA)

To a solution of (22E)-3-oxo-4,6,22-cholatrien-24-oic acid ethyl ester (compound (IIA) prepared according to Example 1, ultimately derived from stigmasterol, 5.00 g, 12.6 mmol) in HFIP (20 mL, 4 volumes) and EtOAc (10 mL, 2 volumes) was added MTO (37 mg, 0.126 mmol) and 3-methylpyrazole (122 μl, 1.51 mmol) and the mixture was cooled to 5° C. Urea hydrogen peroxide (UHP, 1.30 g, 13.9 mmol) was added portion-wise and the mixture was stirred at 5° C. for 24 h. After 24 h, a second addition of MTO (37 mg, 0.126 mmol) and UHP (1.30 g, 13.9 mmol) was conducted and the reaction was stirred at 5° C. for 18 h. The reaction was then quenched with the addition of 12% aqueous $NaHSO_3$ (15 mL, 3 volumes) which was added portion-wise to keep internal temperature <25° C. The chiller was then set to ambient and the mixture stirred for 0.5 h to ensure all peroxide was quenched (tested with peroxide paper). Water (12.5 mL, 2.5 volumes) and EtOAc (5 mL, 1 volume) were added and the layers were separated. The organic was washed with 5% aqueous $NaHCO_3$ (20 mL, 4 volumes) and water (20 mL, 4 volumes) and was concentrated under reduced pressure. The crude material (5.72 g) was crystallised from EtOAc (15 mL, 3 volumes) to give the desired product (3.1 g, 60% yield) as an off white crystalline solid.

The conversion from starting material to desired alpha epoxide and other undesired products (e.g. the beta-epoxide) can be assessed using HPLC, (see chromatographic conditions in General Procedures), with the following retention times.

| Compound | Approximate Retention Time (min) | RRT |
|---|---|---|
| α epoxide (Compound (IA)) | 7.2 | 1.0 |
| Starting material (Compound (IIA)) | 13.7 | 1.9 |
| β epoxide | 8.6 | 1.2 |

Crystal Data and Experimental

The single crystal structure of the title compound is shown in FIG. 2 (Thermal ellipsoids drawn at the 50% probability level).

Experimental. Single clear colourless fragment-shaped crystals of (2015sot0055-S-100K) were recrystallised from EtOAc by slow evaporation. A suitable crystal (0.60×0.32×0.12) was selected and mounted on a MITIGEN holder in perfluoroether oil on a Rigaku R-AXIS SPIDER IP diffractometer. The crystal was kept at T=100(2) K during data collection. Using Olex2 (Dolomanov et al., 2009), the structure was solved with the olex2.solve (Bourhis et al., 2015) structure solution program, using the Charge Flipping solution method. The model was refined with version of SheIXL (Sheldrick, 2008) using Least Squares minimisation.

Crystal Data. $C_{26}H_{36}O_4$, $M_r$=412.55, orthorhombic, $P2_12_12_1$ (No. 19), a=10.3271(7) Å, δ=10.6793(10) Å, c=20.3570(18) Å, α=β=γ=90°, V=2245.1(3) Å³, T=100(2) K, Z=4, Z'=1, μ(CuK$_α$)=0.637, 17551 reflections measured, 4187 unique ($R_{int}$=0.0982) which were used in all calculations. The final $wR_2$ was 0.0852 (all data) and $R_1$ was 0.0473 (I>2(I)).

TABLE 1

Fractional Atomic Coordinates (×10⁴) and Equivalent Isotropic Displacement Parameters (Å² × 10³) for 2015sot0055_S_100K.

$U_{eq}$ is defined as ⅓ of the trace of the orthogonalised $U_{ij}$.

| Atom | x | Y | z | $U_{eq}$ |
|---|---|---|---|---|
| O1 | 3852 (2) | 6518.8 (19) | −1709.3 (10) | 43.1 (6) |
| O2 | 5224 (2) | 5457 (2) | 930.5 (10) | 43.3 (6) |
| O3 | 4093 (2) | 7837 (2) | 5524 (1) | 46.8 (6) |
| O4 | 2179.8 (19) | 8068 (2) | 6028.6 (9) | 41.8 (6) |
| C1 | 1343 (3) | 5740 (3) | 233.1 (15) | 44.8 (9) |
| C2 | 2583 (3) | 6537 (3) | 253.3 (14) | 34.0 (8) |
| C3 | 2431 (3) | 7694 (3) | −189.5 (13) | 39.5 (8) |
| C4 | 2381 (3) | 7372 (3) | −921.3 (14) | 43.8 (9) |
| C5 | 3477 (3) | 6539 (3) | −1139.7 (15) | 36.7 (8) |
| C6 | 4052 (3) | 5728 (3) | −635.9 (14) | 37.0 (8) |
| C7 | 3689 (3) | 5733 (3) | −6.2 (15) | 34.2 (8) |
| C8 | 4340 (3) | 4864 (3) | 458.5 (15) | 38.2 (9) |
| C9 | 4047 (3) | 4910 (3) | 1162.8 (14) | 35.9 (8) |
| C10 | 3062 (3) | 5801 (3) | 1427.4 (13) | 33.4 (8) |
| C11 | 2914 (3) | 6947 (3) | 970.0 (13) | 33.6 (8) |
| C12 | 1987 (3) | 7917 (3) | 1248.6 (13) | 37.9 (8) |
| C13 | 2283 (3) | 8279 (3) | 1962.3 (14) | 37.2 (8) |
| C14 | 2348 (3) | 7128 (3) | 2412.6 (14) | 32.8 (8) |
| C15 | 3381 (3) | 6254 (3) | 2125.5 (14) | 33.6 (8) |
| C16 | 3593 (3) | 5272 (3) | 2661.3 (13) | 34.8 (8) |
| C17 | 3453 (3) | 6032 (3) | 3303.5 (14) | 36.1 (8) |
| C18 | 2908 (3) | 7336 (3) | 3112.6 (13) | 35.1 (8) |
| C19 | 1019 (3) | 6503 (3) | 2463.5 (14) | 36.3 (8) |
| C20 | 1525 (4) | 9199 (3) | 3500.4 (15) | 49.9 (10) |
| C21 | 2020 (3) | 7875 (3) | 3651.8 (13) | 36.5 (8) |
| C22 | 2711 (3) | 7885 (3) | 4298.3 (14) | 38.3 (8) |
| C23 | 2162 (3) | 7926 (3) | 4887.4 (14) | 37.4 (8) |
| C24 | 2930 (3) | 7940 (3) | 5491.6 (15) | 33.9 (8) |
| C25 | 2864 (3) | 8060 (3) | 6651.0 (13) | 39.6 (8) |
| C26 | 1902 (3) | 8245 (3) | 7187.8 (13) | 41.7 (9) |

Example 10a—Large Scale Epoxidation of (22E)-3-oxo-4,6,22-cholatrien-24-oic acid ethyl ester (IIA) using methyltrioxorhenium to form (6α, 7α, 22E)-6,7-epoxy-3-oxo-4,22-choladien-24-oic Acid Ethyl Ester (IA)

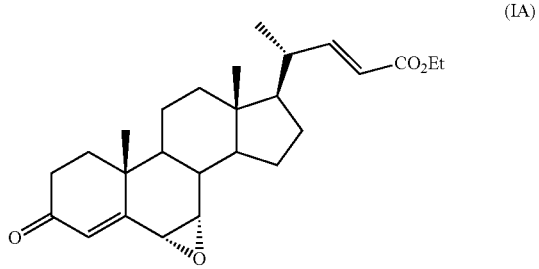 [SMILES: CCOC(=O)/C=C/[C@@H](C)[C@H]1CCC2C3C(CC[C@@]21C)[C@@]1(C)CCC(=O)C=C1[C@H]1O[C@@H]31]

(IA)

To a stirred mixture of hexafluoroisopropanol (20 L, 4 vol) and EtOAc (10 L, 2 vol) at 10° C. (±2° C.) was charged solid (22E)-3-oxo-4,6,22-cholatrien-24-oic acid ethyl ester (compound (IIA) (4.9 kg)) followed by MTO (15.0 g) and 3-methylpyrazole (31 mL). Solid urea hydrogen peroxide (1.3 kg) was then charged in three equal portions at 20 min intervals and the mixture was stirred at 10° C. (±2° C.). After 7 h a further portion of MTO (15.0 g) and 3-methylpyrazole (31 mL) was added. The mixture was maintained for 15 h at 10° C. (±2° C.) and a further portion of MTO (15.0 g), 3-methylpyrazole (31 mL) and urea hydrogen peroxide (0.47 kg) were charged. After 24 h at 10° C. (±2° C.) HPLC analysis indicated completion of the reaction and the reaction was quench by the addition of 5% aq. $NaHSO_3$ (20 L, 4 vol), maintaining the temperature between 5.5 and 9.5° C. After complete quench the phases were separated and the organic phase (bottom) was returned to the reaction vessel and washed with 5% aq. $NaHCO_3$ (20 L, 4 vol) and then $H_2O$ (20 L, 4 vol). The volume of the organic phase was concentrated to 1.8 vol (9 L) under reduces pressure at 47 (±2° C.). Two EtOAc (10 L, 2 vol) co-evaporations were then performed under reduced pressure with the total reaction volume reduced to 2 vol (10 L) each time. EtOAc (10 L, bringing the total volume of the reaction to 20 L=4 vol) was charged to the vessel and the mixture was heated at 80° C. until complete dissolution of the product. The solution was then cooled gradually to 0° C. over 4 h and then held at this temperature for further 16 h. The precipitated solid was filtered and rinsed with cold EtOAc (2 L, 0.4 vol, at 5° C.) to give (6α, 7α, 22E)-6,7-epoxy-3-oxo-4,22-choladien-24-oic acid ethyl ester (Compound (IA), 3.17 kg, 62% yield) after drying. The second crop of crystals was obtained by further reducing the solvent volume to give 527 g to give a total yield of compound (IA) of 3.7 kg (72%).

Example 11—Epoxidation of 3-oxo-4,6-choladien-24-oic acid ethyl ester (IIB) using mCPBA to form (6α, 7α)-6,7-epoxy-3-oxo-4-chola-ene-24-oic Acid Ethyl Ester (IB)

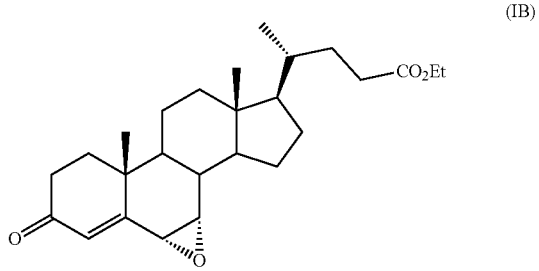 [SMILES: CCOC(=O)CC[C@@H](C)[C@H]1CCC2C3C(CC[C@@]21C)[C@@]1(C)CCC(=O)C=C1[C@H]1O[C@@H]31]

(IB)

3-oxo-4,6-choladien-24-oic acid ethyl ester (Compound (IIB), 1.37 g, 4.27 mmol) was charged to a reaction vessel, followed by BHT (23 mg, 0.13 mmol), EtOAc (11 mL) and water (3.4 mL) with stirring. The solution was heated to 80° C. and then a solution of mCPBA 70% (1.5 g, 7.51 mmol) in EtOAc (7.5 mL) was added dropwise over 15 mins. The reaction mixture was stirred at 70° C. for 2 h (IPC by TLC, 3:7 EtOAc:Heptane; visualized with Anisaldehyde stain), cooled to ambient temperature and then washed with 1M aq.NaOH (2×20 mL) followed by 10% aq. $NaS_2O_3$: 2% $NaHCO_3$ (3×20 mL). The organic phases were dried over $Na_2SO_4$ and concentrated in vacuo at 40° C. The crude solids were crystallized from EtOAc (3 vol) at 60° C. to give an off white solid which was dried under vacuum at 40° C. to give the title compound (0.90 g).

Examples 12-18—Subsequent Reactions of Compounds (IA) and (IB)

Example 12—Synthesis of (6β, 7α, 22E)-6-ethyl-7-hydroxy-3-oxo-4,22-choladien-24-oic Acid Ethyl Ester (XIXA)

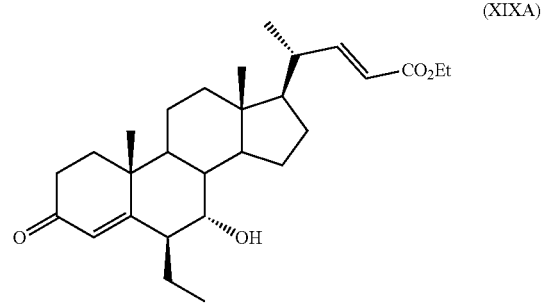 [SMILES: CCOC(=O)/C=C/[C@@H](C)[C@H]1CCC2C3C(CC[C@@]21C)[C@@]1(C)CCC(=O)C=C1[C@H](CC)[C@H]3O]

(XIXA)

Method 1:

To a suspension of CuI (1.40 g, 7.35 mmol) in diethyl ether (10 mL), cooled to −78° C. under an argon blanket was charged EtLi (28.8 mL, 14.4 mmol, 0.5 M solution in benzene/cyclohexane). The thick white suspension formed was allowed to warm to 0° C., stirred for 5 mins (forming a dark solution) and cooled to −78° C. A solution of (6α, 7α, 22E)-6,7-epoxy-3-oxo-4,22-choladien-24-oic acid ethyl ester (compound (IA) prepared according to Example 1, ultimately deriving from stigmasterol, 1.00 g, 2.42 mmol) in diethyl ether/THF (24 mL, 3:1) was prepared and charged to the vessel containing the organocuprate. THF (1 mL) was used to rinse the vessel that contained the solution of the epoxide and this was also charged to the organocuprate. The reaction mixture was allowed to warm to −4° C. over 30 mins after which time the reaction was complete by TLC (silica, 1:1 EtOAc:heptane). After a further 30 mins of stirring at c.a. −4° C. a solution of aq. sat. $NH_4Cl$ was charged and the mixture was stirred over 30 mins. The mixture was transferred to a separating funnel and the aqueous phase was removed, along with solid material present at the interface. The organic phase was washed with 5 wt % aq $NaHCO_3$(2×50 mL.) and water (1×50 mL). TBME (50 mL) was used to extract the original aqueous phase from the reaction and the combined washes. The combined organic phases were concentrated and the residue was purified by chromatography using silica (25 g) as the stationary phase (gradient elution with 0-30% EtOAc in heptane) to give the title compound (0.63 g, 59%) (FIG. 3).

¹H NMR (400 MHz, CDCl₃): δ=6.82 (1H, dd, J=15.6, 8.9, C22H), 5.75 (1H, s, C4H), 5.74 (1H, d, J=15.6, C23H), 4.17 (2H, q, J=7.1, OCH₂CH₃), 3.72 (1H, br s, C7H), 2.52-2.25 (5H, m), 2.05-1.98 (2H, m), 1.82-1.10 (23H, m), 0.91 (3H, t, J=7.4, CH₃), 0.77 (3H, s, CH₃). ¹³C NMR (100 MHz, CDCl₃): δ=199.2, 171.2, 167.1, 154.5, 128.4, 119.0, 71.9, 60.1, 55.3, 54.9, 49.9, 44.3, 42.7, 39.6, 39.1, 38.3, 37.4, 35.6, 34.0, 28.0, 26.3, 23.6, 20.8, 19.7, 19.2, 14.2, 12.8, 12.0; (IR) $v_{max}$(cm⁻¹): 3467, 2939, 2870, 1716, 1651, 1457, 1268, 1229, 1034; HRMS (ESI-TOF) m/z: (M+H)⁺ calcd for C₂₈H₄₃O₄ 443.3161; found: 443.3156. mp=59.4-62.9° C.

Method 2

ZnCl₂ (32.84 g, 240.9 mmol) was dried under vacuum with slow stirring at 180° C. for 2 h. The flask was cooled to room temperature under an argon atmosphere and the residue was dissolved in THF (520 mL) and transferred via cannula into a three neck reaction flask equipped with mechanical stirrer and temperature probe. The solution was cooled in an ice bath to 0-3° C. and a 3M solution of EtMgBr in Et₂O (80 mL, 240.0 mmol) was added dropwise over 20 mins, maintaining the internal temperature below 10° C. Formation of a white precipitate (active zincate species) was observed after addition of ca. ⅓ of the Grignard solution. The mixture was stirred for 1.2 h at 0° C. before a solution of the epoxide (IA) prepared according to Example 1, ultimately deriving from stigmasterol (43.0 g, 104.2 mmol) in THF (300 mL) was added dropwise, maintaining the internal temperature below 10° C. Solid CuCl (1.03 g, 0.104 mmol) was then added in two equal portions with vigorous stirring. After 10 mins the cooling bath was removed and stirring continued at ambient temperature for an additional 1.2 h. The reaction was quenched by dropwise addition of sat. aq. NH₄Cl (800 mL) at <15° C. and stirred for 0.5 h. The mixture was filtered and the solid rinsed with TBME (150 mL). The phases were separated and the aqueous phase extracted with TBME 2×250 mL. The combined organic extracts were washed with 10% aq. NaCl (2×200 mL), dried over Na₂SO₄, filtered and concentrated in vacuo to give 43.7 g of the crude title compound as a yellow foam.

Method 3

To a solution of ZnCl₂ in THF (0.5 M, 8.7 mL, 4.85 mmol, 0.9 eq) was charged anhydrous THF (8.0 mL) and the contents then cooled to −25° C. A solution of EtMgBr in TBME (1.0 M, 8.7 mL, 8.70 mmol, 1.8 eq) was added over 30 mins and the mixture stirred for 45 mins at −25° C. Solid CuCl (24 mg, 0.49 mmol, 0.05 eq) was added in one portion and a solution of compound (IA) prepared according to Example 1, ultimately deriving from stigmasterol (2.0 g, 4.85 mmol) in THF (8.0 mL) was added dropwise over 30 mins. The remaining solid CuCl (24 mg, 0.49 mmol, 0.05 eq) was added half way through the addition of compound (IA). The reaction was stirred for 1 h at −25° C., (TLC 1:1 Heptane:EtOAc, visualised by UV and developed using Ceric Ammonium Molybdate stain) and then additional of EtMgBr in TBME (1.0 M, 2.9 mL, 2.91 mmol, 0.6 eq) was added over 10 mins. The reaction was stirred for 0.5 h at −25° C. and then quenched by the addition of sat. aq. NH₄Cl (5 mL), maintaining the temperature below −5° C. The inorganic salts were filtered off, rinsed with TBME and filtrate phases were separated. The aqueous layer extracted with TBME and then the combined organic extracts were washed with sat. aq. NH₄Cl (3×5 mL) and 10% brine (3×6 mL). The organic phase was concentrated in vacuo at 40° C. to give crude title compound as a yellow foam (1.91 g).

Method 4

To a solution of ZnCl₂ in THF (0.5 M, 8.7 mL, 4.85 mmol, 0.9 eq) was charged anhydrous THF (8.0 mL) and the contents then heated to 40° C. A solution of EtMgBr in TBME (1.0 M, 8.7 mL, 8.70 mmol, 1.8 eq) was added over 30 mins and the mixture stirred for 45 mins at 40° C. Solid CuCl (24 mg, 0.49 mmol, 0.05 eq) was added in one portion and a solution of compound (IA) prepared according to Example 1, ultimately deriving from stigmasterol (2.0 g, 4.85 mmol) in THF (8.0 mL) was added dropwise over 30 mins. The remaining solid CuCl (24 mg, 0.49 mmol, 0.05 eq) was added half way through the addition of compound (IA). The reaction was stirred for 1 h at 40° C., (TLC 1:1 Heptane:EtOAc, visualised by UV and developed using Ceric Ammonium Molybdate stain) and then quenched by the dropwise addition of sat. aq. NH₄Cl (5 mL). The inorganic salts were filtered off, rinsed with TBME and the filtrate phases were separated. The aqueous layer was extracted with TBME and then the combined organic extracts were washed with sat. aq. NH₄Cl (3×5 mL) and 10% brine (3×6 mL). The organic phase was concentrated in vacuo at 40° C. to give crude title compound as a yellow foam (2.08 g).

Method 5

To a solution of ZnCl₂ in THF (0.5 M, 8.7 mL, 4.85 mmol, 0.9 eq) was charged anhydrous THF (8.0 mL) and the contents then cooled to −15° C. A solution of EtMgBr in THF (1.0 M, 8.7 mL, 8.70 mmol, 1.8 eq) was added over 30 mins and the mixture stirred for 45 mins at −15° C. Solid CuCl (24 mg, 0.49 mmol, 0.05 eq) was added in one portion and a solution of compound (IA) prepared according to Example 1, ultimately deriving from stigmasterol in THF (8.0 mL) was added dropwise over 30 mins. The remaining solid CuCl (24 mg, 0.49 mmol, 0.05 eq) was added half way through the addition of compound (IA). The reaction stirred for 1 h at −15° C., (TLC 1:1 Heptane:EtOAc, visualised by UV and developed using Ceric Ammonium Molybdate stain) and then additional EtMgBr in THF (1.0 M, 4.35 mL, 4.36 mmol, 0.9 eq) was added over 15 mins and then quenched by the dropwise addition of sat. aq. NH₄Cl (5 mL). The inorganic salts were filtered off, rinsed with TBME and the filtrate phases were separated. The aqueous phase was extracted with TBME and then the combined organic extracts were washed with sat. aq. NH₄Cl (3×5 mL) and 10% brine (3×6 mL). The organic phase was concentrated in vacuo at 40° C. to give crude title compound as a yellow foam (1.94 g).

Example 13—Synthesis of (5β, 6β, 7α)-6-ethyl-7-hydroxy-3-oxo-cholan-24-oic Acid Ethyl Ester (XXA)

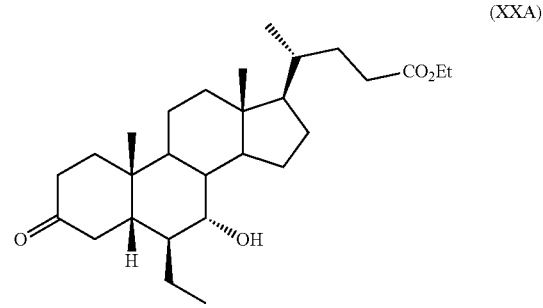 [SMILES: CCOC(=O)CC[C@@H](C)[C@H]1CCC2C3C(CC[C@@]21C)[C@@]1(C)CCC(=O)C[C@H]1[C@H](CC)[C@H]3O]

Method 1

To a suspension of 10 wt. % Pd/C (50% wet, 20 mg, 8.6 mol %) in DMF (2 mL) was added a solution of (6β, 7α, 22E)-6-ethyl-7-hydroxy-3-oxo-4,22-choladien-24-oic acid ethyl ester (compound (XIXA), prepared according to Example 12, ultimately deriving from stigmasterol, 50 mg, 0.11 mmol) in DMF (3 mL) and the reaction mixture was cooled to 0° C. The flask was evacuated then filled with hydrogen three times with vigorous stirring. After 3 h the flask was evacuated then filled with argon and the mixture filtered via syringe filter. The mixture was partitioned between TBME (30 mL) and H$_2$O (20 mL). The organic phase was dried (Na$_2$SO$_4$) and concentrated in vacuo. The crude product (50 mg) was a 14:1 mixture of 5β to 5α isomers (analysed by $^1$H NMR) of title compound, yield 92%. $^1$H NMR (700 MHz, CDCl$_3$): δ=4.12 (2H, q, J=7.1, OCH$_2$CH$_3$), 3.71 (1H, br s, C7H), 3.34 (1H, dd, J=15.5, 13.6, C4H), 2.39-2.32 (2H, m), 2.24-2.20 (1H, m), 2.14-2.09 (2H, m), 2.03-1.91 (4H, m), 1.83-1.79 (2H, m), 1.68-1.63 (2H, m), 1.58 (1H, s), 1.55-1.12 (19H, m), 1.04 (3H, s), 0.95-0.93 (6H, m), 0.88 (1H, J=7.0), 0.71 (3H, s). $^{13}$C NMR (100 MHz, CDCl$_3$): δ=213.5, 174.2, 72.1, 60.2, 55.9, 50.2, 49.8, 47.0, 46.7, 42.7, 39.5, 37.7, 36.3, 36.0, 35.7, 35.3, 34.2, 31.3, 31.0, 28.1, 27.7, 24.4, 23.8, 20.8, 18.3, 14.2, 13.9, 11.8. (IR) ν$_{max}$(cm$^{-1}$): 3514, 2939, 2870, 1710, 1462, 1377, 1159, 1099, 1032; HRMS (ESI-TOF) m/z: (M−H$_2$O+H)$^+$ calcd for C$_{28}$H$_{45}$O$_3$ 429.3369; found: 429.3363.

Method 2

Compound (XIXA) prepared according to Example 12, ultimately deriving from stigmasterol (20.0 g) was dissolved in DMF (400 mL) and added under argon to solid 10 wt. % Pd/C (50% wet, 10.0 g). The mixture was cooled in an ice-salt bath to approximately −15° C. and the flask was evacuated then filled with hydrogen three times with vigorous stirring. The mixture was stirred under an atmosphere of hydrogen for 6 h then the flask was evacuated, filled with argon and filtered through a pad of celite. The catalyst was rinsed with 400 mL of TBME. The filtrate was washed with 10% aq. NaCl (400 mL) and the aqueous phase extracted with TBME (400 mL). The combined organic phases were washed with 10% aq. NaCl (3×200 mL), dried over Na$_2$SO$_4$, filtered and concentrated in vacuo to give crude title compound (20.0 g, ca. 28:15Hβ:5Hα ratio) as pale yellow oil.

Method 3

10% Pd/C was charged to a stainless steel jacketed reaction vessel under an argon atmosphere; DMF was added (20 mL), followed by a solution of crude compound (XIXA) prepared according to Example 12, ultimately deriving from stigmasterol from Example 3 (approximately 72.6 mmol) in DMF (130 mL). The reaction mixture was cooled to −25° C. (over approximately 40 mins) with vigorous stirring (1200 rpm). The reaction vessel was evacuated and charged with hydrogen (10-12 bar) three times. The mixture was stirred for 16 h under an atmosphere of hydrogen (10-12 bar). The vessel was evacuated, purged with argon and warmed to 20° C. with stirring. TLC of the reaction mixture (1:1 Heptane:EtOAc, developed using Ceric Ammonium Molybdate or vanillin dip, Rf values: starting material=0.42, product=0.67) indicated complete consumption of the starting material. The suspension was diluted with CH$_3$CN (120 mL) and H$_2$O (30 mL) and the suspension filtered via a double GFA filter paper and the filter cake rinsed with CH$_3$CN (60 mL). The mixture was telescoped to the next step without further purification. The mixture contained approximately 5% of the 5H-α isomer.

Optimisation

The hydrogenation reaction of this example proceeds via the intermediate shown below and produces both the required 5Hβ compound and its 5Hα isomer. A solvent and catalyst screen was carried out to determine reaction conditions which led to the highest yield and the highest ratios of 5Hβ isomer to 5Hα isomer.

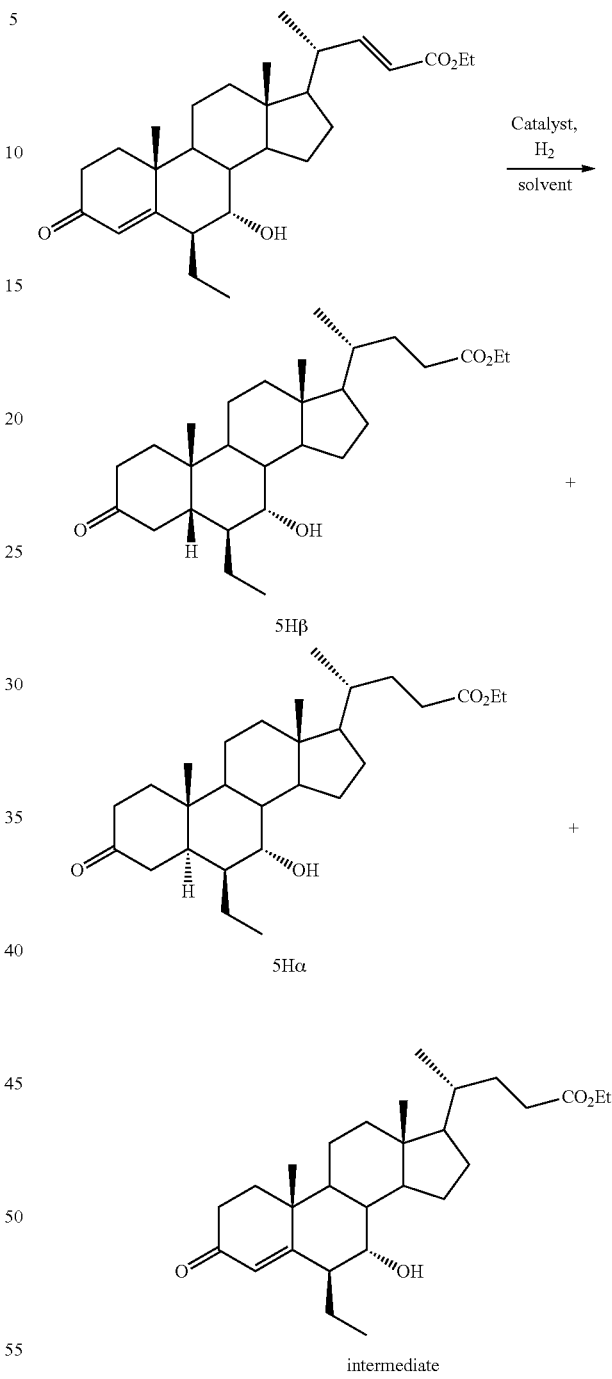

The solvent screen was performed using 10 wt. % Pd/C catalyst and the reactions were run at room temperature under atmospheric pressure of hydrogen. The reaction run in MeOH in the presence of NEt$_3$ was more selective than the one run in neat MeOH, whilst the addition of 10% of H$_2$O decreased the 5βH selectivity. The reaction in DMF provided the best β:α ratio. The reaction in pyridine gave poor conversion to the required product with mainly starting material and intermediate present in the mixture.

|   | Solvent | 5H β:α ratio |
| --- | --- | --- |
| A | MeOH | 4:1 |
| B | MeOH:H₂O | 2:1 |
| C | MeOH:NEt₃ | 7:1 |
| D | EtOH | 3:1 |
| E | IPA | 2:1 |
| F | EtOAc | 2:1 |
| G | Pyridine | 2:1 |
| H | AcOH | 1:1 |
| I | CPME | 1:1 |
| J | DMF | 9:1 |

Reactions in DMF and MeOH were tested at a range of temperatures. For reactions run in DMF temperature has substantial impact on selectivity (the selectivity decreases with increasing temperature), while little difference was observed for reactions in MeOH. Reactions in DMF and MeOH were tested at a range of commercially available 5 and 10 wt. % Pd catalysts, on carbon, calcium carbonate, barium sulfate and aluminium oxide support.

The reactions were run in 10 volumes of solvent at −15° C. under atmospheric pressure of hydrogen gas. For reactions run in DMF pressure has lower impact on the selectivity than the temperature. The effect of dilution on the selectivity is negligible.

Example 14—Synthesis of (6β,7α)-6-ethyl-7-hydroxy-3-oxo-4-cholen-24-oic Acid Ethyl Ester (XIXB)

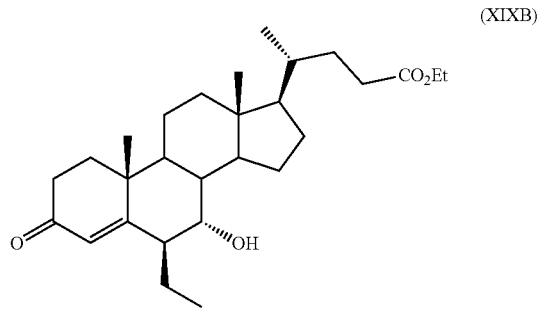 [SMILES: CCOC(=O)CC[C@@H](C)[C@H]1CCC2C3C(CC[C@@]21C)[C@@]1(C)CCC(=O)C=C1[C@H](CC)[C@H]3O]

(XIXB)

ZnCl₂ (600 mg, 4.25 mmol) was charged to a reaction vessel and dried under vacuum at 180° C. for 1 h. The reaction vessel was cooled to ambient temperature, THF (15 mL) charged and the contents of the reaction vessel cooled to 3° C. A solution of 3M EtMgBr in Et₂O (1.5 mL, 4.25 mmol) was charged to the reaction vessel over 40 mins maintaining the temperature below 5° C. The reaction mixture was then stirred for 1 h. (6α, 7α)-6,7-epoxy-3-oxo-4-chola-ene-24-oic acid ethyl ester (compound (IB), prepared according to Example 11, 0.80 g, 1.93 mmol) in THF (6 mL) was charged to the reaction vessel over 40 mins, maintaining the temperature below 5° C. CuCl (20 mg, 0.19 mmol) was charged in one portion and the reaction stirred at ambient temperature for 16 h (IPC by TLC, 3:7 EtOAc:Heptane; visualized with Anisaldehyde stain). The reaction mixture was cooled in an ice bath and sat. aq.NH₄Cl was added dropwise, maintaining the temperature below 10° C. The reaction mixture was filtered and the filter cake washed with TBME (12.5 vol). The organic phase of the filtrate was separated and the aqueous phase extracted with TBME (2×12.5 vol). The combined organic phases were washed with 5% NaCl (3×12.5 vol) and concentrated in vacuo at 40° C.

Example 15—Synthesis of (5β, 6β, 7α)-6-ethyl-7-hydroxy-3-oxo-cholan-24-oic acid ethyl ester (XXB)

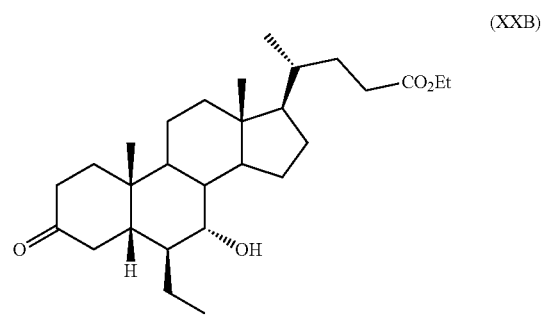 [SMILES: CCOC(=O)CC[C@@H](C)[C@H]1CCC2C3C(CC[C@@]21C)[C@@]1(C)CCC(=O)C[C@H]1[C@H](CC)[C@H]3O]

(XXB)

10% Pd/C (70 mg) was charged to a reaction vessel under an argon atmosphere followed by the crude material from Example 14 (compound (XIXB) ultimately deriving from deoxycholic acid) in DMF (14.6 mL). The mixture was cooled to −10° C. and the reaction vessel was evacuated then filled with hydrogen three times with vigorous stirring. The mixture was stirred under an atmosphere of hydrogen for 24 h while maintaining the temperature at −10° C. (IPC by TLC, eluent 1:1 EtOAc:Heptane; visualized with Anisaldehyde stain) then the flask was evacuated, filled with argon and filtered through a pad of celite and rinsed with DMF (7 mL). 10% Pd/C (70 mg) was recharged to the reaction vessel under an argon atmosphere followed by the DMF reaction mixture. The mixture was cooled to approximately −10° C. and the reaction vessel was evacuated then filled with hydrogen three times with vigorous stirring. The mixture was stirred under an atmosphere of hydrogen for 24 h at −10° C. (IPC by TLC, 1:1 EtOAc:Heptane; visualized with Anisaldehyde stain) then the flask was evacuated, filled with argon and filtered through a pad of celite and washed with TBME (62.5 vol, 50 mL). The filtrate was washed with 10% aq. NaCl (4×25 vol), dried over Na₂SO₄, filtered and concentrated in vacuo at 40° C. Purification by column chromatography (SiO₂, 0-30% Heptane:EtOAc) gave the title compound (0.17 g). The product was identical to the material (compound (XXA), see Example 13) obtained from (6β, 7α, 22E)-6-ethyl-7-hydroxy-3-oxo-4,22-choladien-24-oic acid ethyl ester (derived from stigmasterol i.e. of plant origin)

Example 16—Synthesis of (5β, 6β)-3,7-dioxo-6-ethyl-cholan-24-oic acid ethyl ester (XXIA)

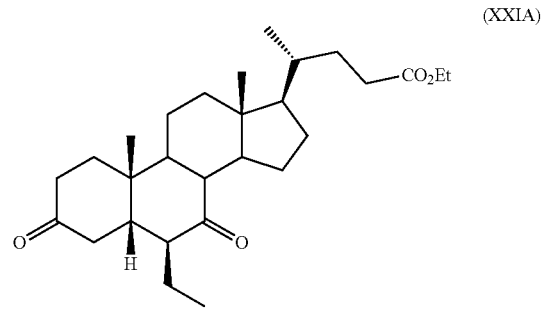 [SMILES: CCOC(=O)CC[C@@H](C)[C@H]1CCC2C3C(=O)[C@@H](CC)[C@@H]4CC(=O)CC[C@]4(C)C3CC[C@@]21C]

(XXIA)

Method 1

A solution of Jones's reagent prepared from CrO$_3$ (1.10 g, 11 mmol) in H$_2$SO$_4$ (1.4 mL) and made to 5 mL with water was charged dropwise to a solution of (6β, 5β, 7α)-6-ethyl-7-hydroxy-3-oxo-cholan-24-oic acid ethyl ester (compound (XXA)) prepared according to Example 15, 0.18 g, 0.40 mmol) in acetone (10 mL) until an orange colour persisted. The reaction mixture was quenched with IPA (1 mL), filtered through a 0.45 μm nylon syringe filter and the filter was washed with acetone (10 mL). The combined filtrate and wash was concentrated, the residue was dissolved in EtOAc (20 mL) and washed with water (2×10 mL). The aqueous phase was extracted with EtOAc (20 mL), the combined EtOAc phases were concentrated and the residue was dissolved and concentrated from toluene (20 mL) then acetone (20 mL) to give a clear oil containing the title compound (185 mg). $^1$H NMR (700 MHz, CDCl$_3$): δ=4.12 (2H, q, J=7.1), 2.42 (1H, t, J=11.4), 2.38-2.17 (6H, m), 2.09-1.74 (9H, m), 1.68-1.11 (17H, m), 0.93 (3H, d, J=6.5), 0.85 (3H, t, J=7.4), 0.72 (3H, s). $^{13}$C NMR (100 MHz, CDCl$_3$): δ=214.5, 211.4, 174.0, 60.1, 57.1, 55.1, 50.3, 48.4, 47.3, 44.9, 43.6, 43.1, 39.2, 35.8, 35.2 (×2), 34.9, 31.3, 30.9, 28.1, 24.6, 23.7, 23.4, 21.7, 18.3, 14.2, 12.6, 12.2. (IR) ν$_{max}$(cm$^{-1}$): 2950, 2872, 1709, 1461, 1377, 1304, 1250, 1177, 1097, 1034; HRMS (ESI-TOF) m/z: (M+H)$^+$ calcd for C$_{28}$H$_{45}$O$_4$ 445.3318; found: 445.3312;

Method 2

To a solution of compound (XXA) prepared according to Example 15 (41.0 g crude mass) in anhydrous CH$_2$Cl$_2$ (600 mL) at 0° C. was added solid DMP (34.0 g, 80.2 mmol) portion-wise over 20 mins (exothermic). The mixture was stirred at 0-5° C. for 2 h, then a further portion of DMP (4.0 g, 9.4 mmol) was added and reaction stirred at 0-5° C. for 1 h. The mixture was filtered through a GFA filter and the solid rinsed with CH$_2$Cl$_2$ (50 mL), the filtrate was stirred vigorously with 10% aq. Na$_2$S$_2$O$_3$ and 2% aq. NaHCO$_3$ (100 mL) for 20 mins. The phases were separated and the aq. extracted with CH$_2$Cl$_2$ (2×100 mL). The combined organic extracts were washed with 1M NaOH (100 mL). The mixture was diluted with CH$_2$Cl$_2$ (300 mL) and phases separated. The organic layer was concentrated under reduced pressure and the residue (cloudy brown oil) was dissolved in TBME (600 mL) and washed with 1M NaOH (100 mL) and NaCl (3×100 mL). The organic phase was concentrated in vacuo to give a dark yellow runny oil, crude mass 38.1 g. The oil was dissolved in EtOH (400 mL) and stirred with activated charcoal (10 g) at 50° C., the mixture was then filtered, the charcoal rinsed with EtOH (200 mL) and the filtrate concentrated in vacuo to give the title compound as a yellow oil (35.9 g).

Method 3

A solution of compound (XXA) prepared according to Example 15 (218 mmol) in DMF (450 ml), CH$_3$CN (540 mL) and H$_2$O (90 mL) was charged into a 2 L vessel and cooled to 9° C., then AcOH (180 mL) was charged, followed by NaBr (4.1 g). A solution of sodium hypochlorite (~10.5% w/v, 450 mL) was added dropwise over 1.5 h, maintaining the internal temperature at 5-6° C., then the mixture was stirred for 5 h at 7° C. TLC of the reaction mixture indicated complete consumption of the starting material (IPC by TLC, eluent EtOAc/heptane 3:7, Rf for (5β, 6β, 7α)-6-ethyl-7-hydroxy-3-oxo-cholan-24-oic acid ethyl ester (compound (XXA)=0.34; (5β, 6β)-3,7-dioxo-6-ethyl-cholan-24-oic acid ethyl ester (compound (XXIA)=0.45). A solution of aq. 10% w/v Na$_2$SO$_3$ (360 mL) was charged dropwise with vigorous stirring, maintaining the internal temperature at 8-10° C., then H$_2$O (270 mL) was added dropwise and the mixture stirred at 5° C. for 16 h. The solid was filtered and washed with H$_2$O (720 mL). The solid was then dissolved in TBME (1.1 L) and subsequently washed with an aq. NaHCO$_3$ (300 mL) and 10% brine (300 mL). The organic phase was then stirred with activated charcoal (10 g) for 20 mins at 40° C., treated with anhydrous MgSO$_4$ (5 g) and filtered via GFA filter paper, the filter cake was rinsed with TBME (50 mL) and the filtrate concentrated in vacuo to give the title compound as light brown oil which solidifies on standing (82.7 g).

Example 17—Synthesis of (5β, 6α)-3,7-dioxo-6-ethyl-cholan-24-oic acid (XXIIA)

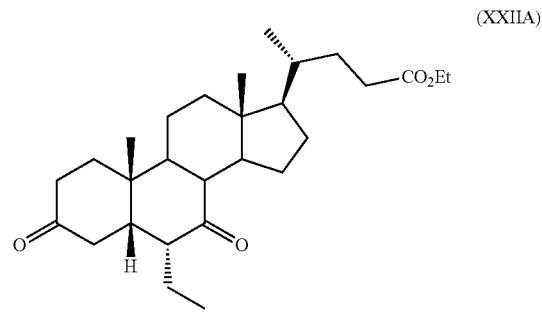 [SMILES: CCOC(=O)CC[C@@H](C)[C@H]1CCC2C3C(=O)[C@H](CC)[C@@H]4CC(=O)CC[C@]4(C)C3CC[C@@]21C]

(XXIIA)

Into a 500 mL flask was charged 0.5 vol of 0.5 M NaOH (9 mL) followed by (5β, 6β)-3,7-dioxo-6-ethyl-cholan-24-oic acid ethyl ester from Example 16 (compound (XXIA), 18.00 g, 1 eq) and then IPA (180 mL, 10 vol) The mixture was warmed to 60±2° C. and held until a solution was obtained (10-15 mins). The remaining 0.5 M NaOH solution (171 mL, 9.5 vol) was charged over 20 mins and then the reaction was stirred for a further 3.5 h at 60±2° C. The IPA was removed under vacuum at 60° C. and then 2M HCl (8 mL) charged to pH 9. EtOAc was charged (90 mL, 5 vol) followed by 2M HCl (54 mL) to pH 1. Vigorous mixing was followed by phase separation. The aqueous phase was back extracted with additional EtOAc (90 mL, 5 vol) and then the combined organic phases were washed with water (54 mL, 3 vol), followed by three portions of 10% aq. NaCl (3×54 mL, 3×3 vol). The organic phase was treated with activated charcoal (100 mesh powder, 3.37 g, ~0.20 mass eq) for 12 mins and then filtered through GF/B. Concentration at 50° C. in vacuo gave the title compound as a light yellow foam in quantitative yield (FIG. 4).

$^1$H NMR (700 MHz, CDCl$_3$): δ=2.74 (1H, dd, J=12.8, 5.4), 2.47 (1H, t, J=12.5), 2.43-0.90 (32H, m), 0.81 (3H, t, J=7.4), 0.70 (3H, s). $^{13}$C NMR (100 MHz, CDCl$_3$): δ=212.1, 210.6, 179.4, 54.9, 52.4, 52.3, 50.0, 48.9, 43.7, 42.7, 38.9, 38.3, 36.7, 36.0, 35.5, 35.2, 30.9, 30.7, 28.2, 24.6, 22.9, 22.3, 18.6, 18.3, 12.1, 11.8. (IR) ν$_{max}$(cm$^{-1}$): 2939, 2873, 1706, 1458, 1382, 1284.8. HRMS (ESI-TOF) m/z: (M+H)$^+$ calcd for C$_{26}$H$_{41}$O$_4$ 417.3005; found: 417.2997; mp=71.2-75.9° C.

Example 18—Synthesis of (3α, 5β, 6α, 7α)-6-ethyl-3,7-dihydroxy-cholan-24-oic Acid (Compound (XVIIIA), Obeticholic Acid)

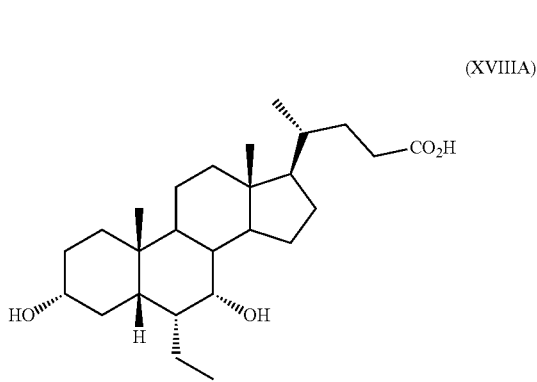 [SMILES: CC[C@H]1[C@@H](O)C2C3CC[C@H]([C@H](C)CCC(=O)O)[C@@]3(C)CCC2[C@@]2(C)CC[C@@H](O)C[C@@H]12]

(XVIIIA)

To a solution of crude (5β, 6α)-3,7-dioxo-6-ethyl-cholan-24-oic acid (compound (XXIIA) prepared according to Example 17, 21.7 g crude mass) in H₂O (260 mL) and 50% NaOH (15.2 mL) at 90° C. was added, dropwise, a solution of NaBH₄ (4.4 g, 116.3 mmol) in aq. NaOH (prepared from 25 mL of H₂O and 0.8 mL 50% NaOH). The mixture was heated to reflux and stirred for 3 h. The mixture was then cooled to 60° C. and a 2M solution of HCl (200 mL) added dropwise with vigorous stirring. nBuOAc (100 mL) was then charged to the reaction flask and the mixture stirred for a further 20 mins. The phases were separated and the aqueous phase (pH=½) extracted with nBuOAc (100 mL). The combined organic phases were washed with 2M HCl (50 mL) and 10% aq. NaCl (100 mL). The organic solvent was distilled off under reduced pressure at 70-80° C. The residue (dense oil) was dissolved in nBuOAc (60 mL) at 70° C. and allowed to gradually cool to room temperature, then stored at 6° C. for 2 h. The solid was collected via filtration, rinsed with cold nBuOAc (20 mL), then dried under vacuum at 70° C. for 5 h to give the title compound as a white solid (8.2 g).

Examples 19-36—Synthesis of Further Epoxidation Precursors

Example 19—Synthesis of (20S)-20-hydroxymethyl-pregna-4-en-3-one

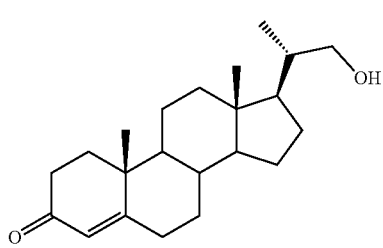 [SMILES: C[C@H](CO)[C@H]1CCC2C3CCC4=CC(=O)CC[C@]4(C)C3CC[C@@]21C]

(20S)-20-Hydroxymethyl-pregna-4-en-3-one (HMPO) can be prepared by chemoselective reduction of dinorcholenaldehyde ((20S)-20-formyl-pregn-4-en-3-one) with NaBH₄ in primary alcohol (Barry M. Trost, Alvin C. Lavoie *J. Am. Chem. Soc.*, 1983, 105 (15), 5075-5090, incorporated herein by reference).

Example 20—Synthesis of (20S)-20-acetoxymethyl-pregna-4,6-dien-3-one

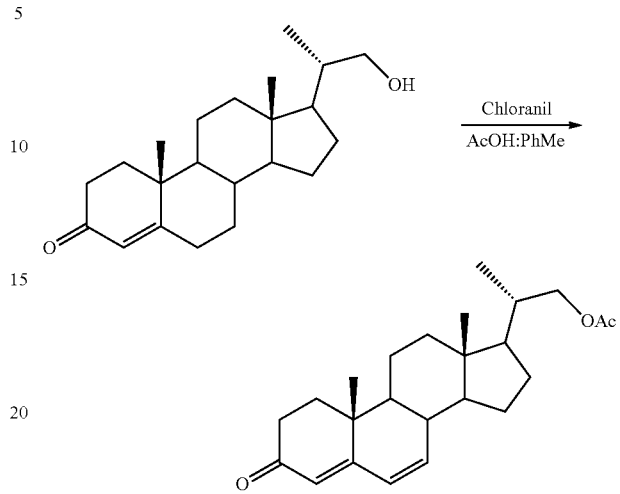

HMPO (300 g, 0.913 mol) was charged to a reaction vessel, followed by AcOH (0.9 L) and toluene (0.3 L) with stirring. p-Chloranil (245 g, 1.00 mol) was then charged and the reaction mixture heated to 110° C. and maintained at this temperature for 6 h. The mixture was then cooled to 5° C. and held at that temperature for 2 h. The resulting solid was filtered and the filter-cake washed with cold, premixed 3:1 AcOH:Toluene (4×150 mL) and the filtrate was concentrated in-vacuo. The residue was dissolved in acetone (900 mL), then 3.5% w/w aqueous NaOH (3.0 L) was charged dropwise with stirring, maintaining the temperature below 30° C. The resulting solids were collected by filtration and the filter cake was washed with premixed 1:1 acetone:water (1.5 L). The filter cake was then slurried in 1:1 acetone:water (600 mL) at 20° C., filtered and washed with premixed 1:1 acetone:water (1.0 L). The solid was dried under vacuum at 65-70° C. to give the desired product (224 g, 67%) as a tan solid. δH (400 MHz, CDCl₃); 6.17-6.12 (1H, m, C6-CH), 6.10 (1H, dd, J 9.9, 2.0, C7-CH), 5.68 (1H, s, C4-CH), 4.10 (1H, dd, J 10.7, 3.5, C22-CHaH$_b$), 3.79 (1H, dd, J 10.7, 7.4, C22-CH$_a$H$_b$), 2.58 (1H, ddd, J 17.9, 14.4, 5.4, C2-CH$_a$H$_b$), 2.49-2.39 (1H, m, C2-CH$_a$H$_b$), 2.20 (1H, brt, J 10.2, C8-CH), 2.10-1.97 (1H, m), 2.06 (3H, s, OC(O)CH₃), 1.96-1.66 (4H, m), 1.62-1.53 (1H, m), 1.52-1.16 (8H, m), 1.12 (3H, s, C19-CH₃), 1.04 (3H, d, J 6.6, C21-CH₃), 0.79 (3H, s, C18-CH₃); δC (100 MHz, CDCl₃); 199.6, 171.3, 163.8, 141.2, 127.9, 123.6, 69.4, 53.2, 52.6, 50.7, 43.6, 39.4, 37.7, 36.1, 35.8, 33.9, 33.9, 27.6, 23.8, 21.0, 20.7, 17.1, 16.3, 11.9.

Example 21—Synthesis of (20S)-20-hydroxymethyl-pregna-4,6-dien-3-one

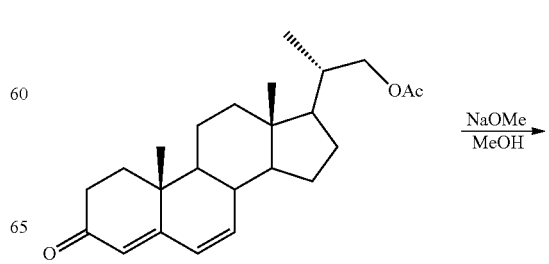

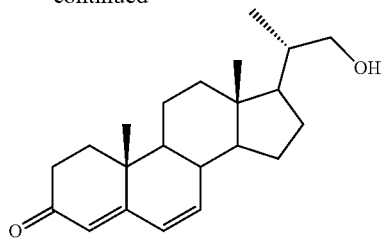

(20S)-20-Acetoxymethyl-pregna-4,6-dien-3-one (25 g, 67.5 mmol) was suspended in MeOH (250 mL) and sodium methoxide (25% w/v solution in MeOH) was added until pH 12 was achieved. The resulting mixture was stirred at room temperature for 4 h. The pH was adjusted to pH 4 by addition of Finex CS08GH+ resin. The mixture was filtered and the filtrate was concentrated under reduced pressure, co-evaporating with PhMe (2×250 mL). The residue was dried in a vacuum oven at 30° C. for 48 h to give the desired product (22.15 g, 99%) as a light brown solid. δH (400 MHz, CDCl$_3$); 6.16-6.11 (1H, m, C7-CH), 6.09 (1H, dd, J 9.9, 2.3, C6-CH), 5.67 (1H, s, C4-CH), 3.65 (1H, dd, J 10.5, 3.3, C22-CH$_a$H$_b$), 3.59 (1H, dd, J 10.5, 6.7, C22-CH$_a$H$_b$), 2.57 (1H, ddd, J 18.0, 14.4, 5.5, C2-CH$_a$H$_b$), 2.45-2.38 (1H, m, C2-CH$_a$H$_b$), 2.19 (1H, brt, J 10.4, C8-CH), 2.11-1.76 (5H, m), 1.71 (1H, td, J 13.9, 5.3, C1-CH$_a$H$_b$), 1.65-1.16 (9H, m), 1.11 (3H, s, C19-CH$_3$), 1.06 (3H, d, J 6.6, C21-CH$_3$), 0.78 (3H, s, C18-CH$_3$); δC (100 MHz, CDCl$_3$); 199.7, 164.0, 141.4, 127.9, 123.5, 67.8, 53.2, 52.3, 50.7, 43.5, 39.4, 38.7, 37.8, 36.1, 33.9, 33.9, 27.6, 23.8, 20.7, 16.7, 16.3, 12.0.

Example 22—Synthesis of (20S)-20-tertbutyldimethylsilyloxymethyl-pregna-4,6-dien-3-one

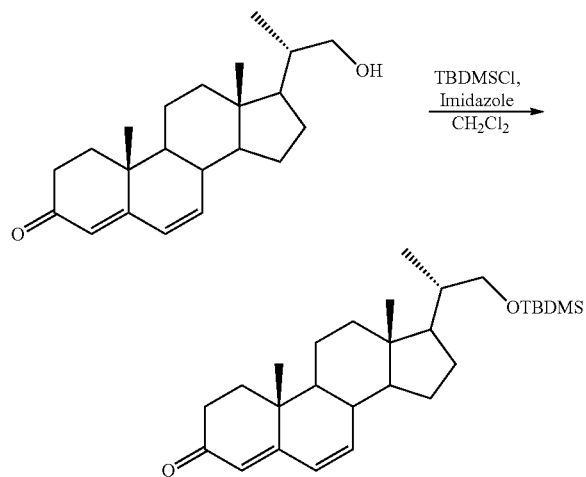

(20S)-20-Hydroxymethyl-pregna-4,6-dien-3-one (1.00 g, 3.04 mmol) was dissolved in anhydrous CH$_2$Cl$_2$ (10 mL) and the solution was cooled to 0° C. Imidazole (414 mg, 6.09 mmol) and TBDMSCl (551 mg, 3.65 mmol) were added and the reaction was stirred at 0° C. for 4 h. The reaction was warmed to room temperature and CH$_2$Cl$_2$ (10 mL) and water (20 mL) were added. The layers were separated and the organic phase was washed with water (20 mL), saturated aqueous sodium chloride (20 mL), dried over sodium sulfate and was concentrated under reduced pressure. The residue was purified by column chromatography on silica gel (0-25% EtOAc in heptane) to give the desired product (890 mg, 66%) as a light yellow solid. δH (400 MHz, CDCl$_3$); 6.14 (1H, dd, J 9.9, 1.3, C7-CH), 6.09 (1H, dd, J 9.8, 2.4, C6-CH), 5.66 (1H, s, C4-CH), 3.58 (1H, dd, J 9.7, 3.4, C22-CH$_a$H$_b$), 3.28 (1H, dd, J 9.7, 7.2, C22-CH$_a$H$_b$), 2.57 (1H, ddd, J 17.9, 14.4, 5.4, C2-CH$_a$H$_b$), 2.47-2.37 (1H, m, C2-CH$_a$H$_b$), 2.19 (1H, brt, J 10.3, C8-CH), 2.07 (1H, dt, J 12.9, 3.3), 2.00 (1H, dd, J 8.5, 2.1), 1.94-1.63 (3H, m), 1.60-1.15 (9H, m), 1.11 (3H, s, C19-CH$_3$), 1.00 (3H, d, J 6.7, C21-CH$_3$), 0.89 (9H, s, SiC(CH$_3$)$_3$), 0.77 (3H, s, C18-CH$_3$), 0.03 (6H, s, Si(CH$_3$)$_2$); δC (100 MHz, CDCl$_3$); 199.6, 163.9, 141.5, 127.8, 123.5, 67.7, 53.2, 52.5, 50.7, 43.5, 39.4, 39.0, 37.8, 36.1, 34.0, 33.9, 27.6, 25.9, 25.9, 25.9, 23.9, 20.7, 18.4, 16.9, 16.3, 12.0, −5.3, −5.4; (IR) ν$_{max}$(cm$^{-1}$): 3027, 2956, 2930, 2891, 2857, 1677, 1077, 753; HRMS (ESI-TOF) m/z: (M+H)+ calculated for C$_{28}$H$_{46}$O$_2$Si 442.3267, found 443.3338.

Example 23—Synthesis of (20S)-20-formyl-pregna-4,6-dien-3-one

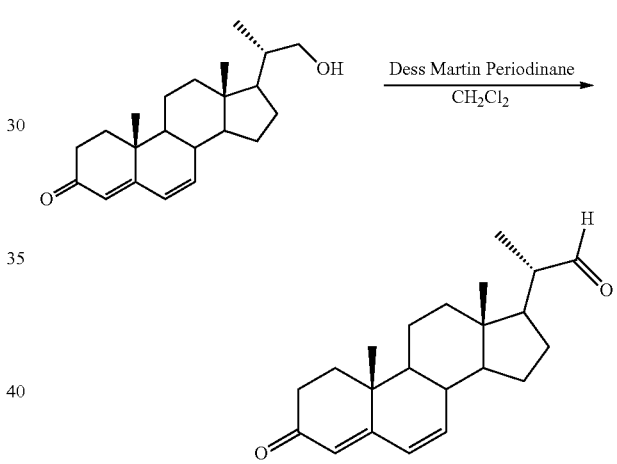

(20S)-20-Hydroxymethyl-pregna-4,6-dien-3-one (3.01 g, 9.16 mmol) was dissolved in anhydrous CH$_2$Cl$_2$ (60 ml) and the solution was cooled to 0° C. Dess-Martin periodinane (5.83 g, 13.7 mmol) was added portion-wise over 10 minutes and the reaction was allowed to slowly warm to room temperature and was stirred for 22 h. The mixture was cooled to 0° C. and a 1:1 mixture of 10% aq. Na$_2$S$_2$O$_3$ and 2% aq. NaHCO$_3$ (75 ml) was added portionwise. CH$_2$Cl$_2$ (50 mL) was added and the layers were separated. The aqueous phase was extracted with CH$_2$Cl$_2$ (2×50 mL) and the combined organics were dried over sodium sulfate and concentrated under reduced pressure. The residue was purified by column chromatography on silica gel (0-25% EtOAc in heptane) to give the desired product (1.23 g, 41%) as a pale yellow solid. δH (400 MHz, CDCl$_3$); 9.59 (1H, d, J 3.2, CHO), 6.12 (2H, s, C6-CH and C7-CH), 5.68 (1H, s, C4-CH), 2.58 (1H, ddd, J 17.9, 14.4, 5.4), 2.49-2.36 (2H, m), 2.22 (1H, t, J 10.6, C8-CH), 2.08-1.81 (4H, m), 1.73 (1H, td, J 13.8, 5.1, C1-CH$_a$H$_b$), 1.65-1.20 (8H, m), 1.15 (3H, d, J 6.9, C21-CH$_3$), 1.13 (3H, s, C19-CH$_3$), 0.82 (3H, d, C18-CH$_3$); δC (100 MHz, CDCl$_3$); 204.6, 199.5, 163.6, 140.8, 128.1, 123.7, 52.8, 50.8, 50.7, 49.4, 44.0, 39.2, 37.6, 36.0, 33.9, 33.9, 27.0, 24.1, 20.6, 16.3, 13.5, 12.3; (IR) $v_{max}$ (cm$^{-1}$): 3030, 2934, 2706, 1717, 1655, 1615, 15811; HRMS (ESI-TOF) m/z: (M+H)$^+$ calculated for $C_{22}H_{30}O_2$ 326.2246; found 327.2318.

Example 24—Synthesis of (20S)-20-(ethylenedioxymethyl)-pregna-4,6-dien-3-one

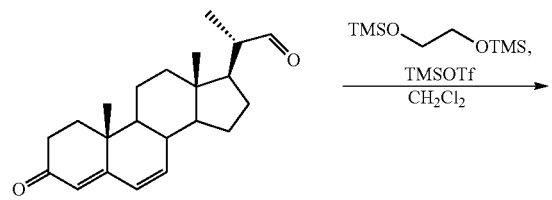

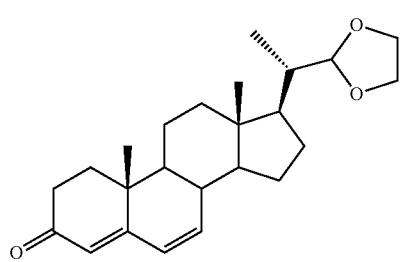

To a solution of (20S)-20-formyl-pregna-4,6-dien-3-one (3.89 g, 12 mmol) in CH$_2$Cl$_2$ (5 vol, 20 mL) under an argon atmosphere was added 1,2-bis (trimethylsilyloxy) ethane (2.94 mL, 12 mmol). The reaction mixture was cooled to −78° C. and TMSOTf (108 µL, 0.6 mmol) was added. After 2 h the reaction mixture was diluted with CH$_2$Cl$_2$ (100 mL) and washed with water (2×100 mL) and 5% aq. NaCl (100 mL). The organic phase was dried over Na$_2$SO$_4$ and was concentrated under reduced pressure. Purification by column chromatography on silica gel gave the desired product (2.42 g, 55%) as a colourless crystalline solid. δH (700 MHz, CDCl$_3$); 6.12 (2H, m), 5.67 (1H, m), 4.86 (1H, d, J 2.0), 3.94 (2H, m), 3.86 (2H, m), 2.56 (1H, m), 2.43 (1H, m), 2.19 (1H, t, J 10.6), 2.05-1.95 (3H, m), 1.85 to 1.20 (11H, m), 1.11 (3H, s), 0.95 (3H, d, J 6.7), 0.77 (3H, s). δC (176 MHz, CDCl$_3$); 199.7, 163.9, 141.4, 127.9, 123.6, 105.6, 65.3, 65.1, 52.9, 52.2, 50.6, 43.7, 39.3, 39.3, 37.8, 36.1, 34.0, 33.9, 27.3, 23.9, 20.67, 16.3, 11.7, 11.6.

Example 25—Synthesis of (20S)-20-(1-mesyloxymethyl)-pregna-4,6-dien-3-one

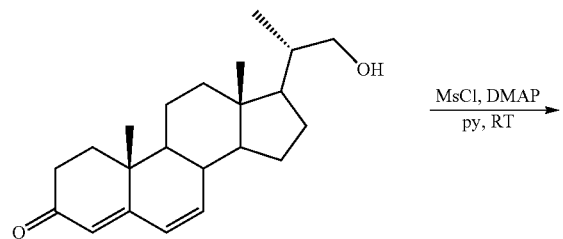

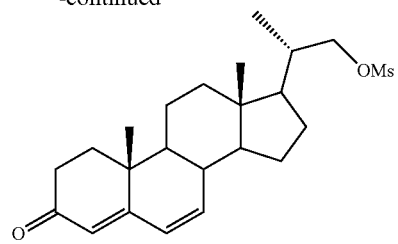

To a solution of (20S)-20-hydroxymethyl-pregna-4,6-dien-3-one (1.00 g, 3.05 mmol) in pyridine (10 mL) was added DMAP (19 mg, 0.15 mmol). MsCl (1.18 mL, 15.2 mmol) was added dropwise and the reaction was stirred at room temperature for 18 h. The reaction was cooled in an ice bath and water (10 mL) was added dropwise. EtOAc (20 mL) was added and the layers were separated. The aqueous layer was extracted with EtOAc (3×20 mL). The combined organic phases were washed with 2 M aq. HCl (20 mL), dried over sodium sulfate and were concentrated under reduced pressure. The residue was purified by column chromatography on silica gel (0-50% EtOAc in heptane) to give the desired product (1.01 g, 82%) as an orange solid. δH (400 MHz, CDCl$_3$); 6.12 (2H, brs, C6-CH and C7-CH), 5.68 (1H, s, C4-CH), 4.21 (1H, dd, J 9.4, 3.2, C22-CH$_a$H$_b$), 4.01 (1H, dd, J 9.4, 6.6, C22-CH$_a$H$_b$), 3.01 (3H, s, OS(O$_2$)CH$_3$), 2.58 (1H, ddd, J 18.0, 14.4, 5.5, C2-CH$_a$H$_b$), 2.49-2.39 (1H, m, C2-CH$_a$H$_b$), 2.21 (1H, brt, J 10.5, C8-CH), 2.09-1.80 (5H, m), 1.73 (1H, td, J 13.8, 5.2, C1-CH$_a$H$_b$), 1.63-1.53 (1H, m), 1.52-1.18 (7H, m), 1.13 (3H, s, C19-CH$_3$), 1.12 (3H, d, J 6.1, C21-CH$_3$), 0.80 (3H, s, C18-CH$_3$); δC (100 MHz, CDCl$_3$); 199.5, 163.6, 140.9, 128.0, 123.7, 74.8, 53.1, 51.8, 50.6, 43.6, 39.3, 37.7, 37.2, 36.3, 36.0, 33.9, 33.9, 27.5, 23.8, 20.6, 16.9, 16.3, 12.0.

Example 26—Synthesis of (20S)-20-(1-bromomethyl)-pregna-4,6-dien-3-one

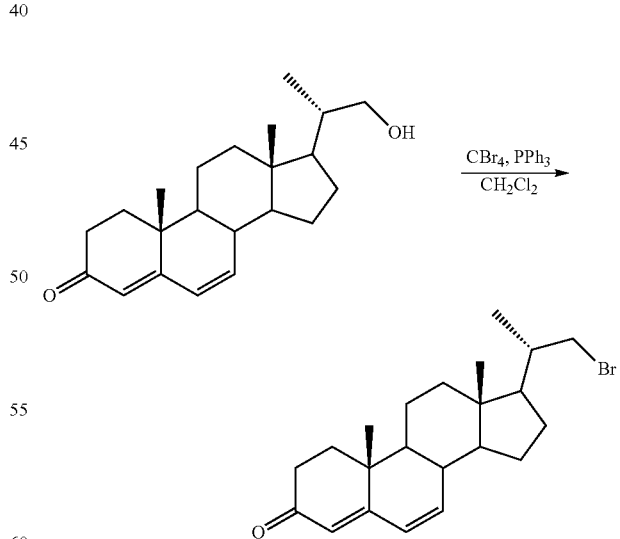

To a solution of (20S)-20-hydroxymethyl-pregna-4,6-dien-3-one (1.00 g, 3.05 mmol) in anhydrous CH$_2$Cl$_2$ (10 mL) was added carbon tetrabromide (1.52 g, 4.57 mmol). Triphenylphosphine (1.20 g, 4.57 mmol) was added and the mixture was heated at reflux for 2 h. The reaction was allowed to cool to room temperature and water (20 mL) was added. The layers were separated and the organic layer was washed with 5% aq. NaHCO$_3$ (20 mL), 10% aq NaCl (20 mL) and was concentrated under reduced pressure. The residue was purified by column chromatography on silica gel (0-25% acetone in heptane) to give the desired product (980 mg, 82%) as a light yellow crystalline solid. δH (400 MHz, CDCl$_3$); 6.09-6.00 (2H, m, C6-CH and C7 CH), 5.59 (1H, s, C4-CH), 3.43 (1H, dd, J 9.8, 2.7, C22-CH$_a$H$_b$), 3.29 (1H, dd, J 9.8, 5.8, C22-CH$_a$H$_b$), 2.50 (1H, ddd, J 17.9, 14.4, 5.4, C2-CH$_a$H$_b$), 2.40-2.30 (1H, m, C2-CH$_a$H$_b$), 2.13 (1H, brt, J 9.8, C8-CH), 2.01-1.57 (5H, m), 1.55-1.45 (1H, m), 1.44-1.10 (8H, m), 1.05 (3H, s, C19-CH$_3$), 1.03 (3H, d, J 6.5, C21-CH$_3$), 0.72 (3H, s, C18-CH$_3$); δC (100 MHz, CDCl$_3$); 199.2, 163.6, 141.0, 127.9, 123.6, 53.5, 53.1, 50.6, 43.4, 43.3, 39.2, 37.7, 37.6, 36.0, 33.9, 33.9, 27.4, 23.6, 20.6, 18.6, 16.3, 12.3.

Example 27—Synthesis of 23-carboxy-3-oxo-4,6-choldien-24-oic acid diethyl ester

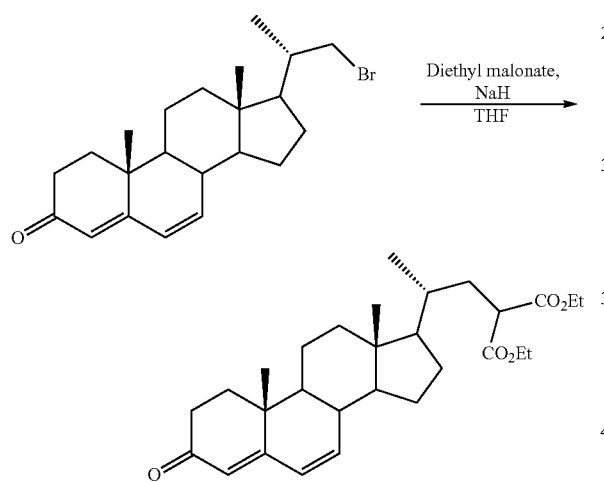

Sodium hydride (60% dispersion in mineral oil, 226 mg, 5.64 mmol) was suspended in anhydrous THF (10 mL) and the mixture was cooled to 0° C. Diethyl malonate (1.17 mL, 7.68 mmol) was added drop-wise and the mixture was stirred at 0° C. for 15 minutes. A solution of (20S)-20-(bromomethyl)-pregna-4,6-dien-3-one (1.00 g, 2.56 mmol) in anhydrous THF (10 mL) was added drop-wise and the reaction was heated at reflux for 18 h. The reaction was allowed to cool to room temperature and water (10 mL) was added. EtOAc (25 mL) was added and the layers were separated. The aqueous layer was extracted with EtOAc (3×50 mL) and the combined organics were washed with 10% aq. NaCl (50 mL), dried over sodium sulfate and were concentrated under reduced pressure. The residue was purified by column chromatography on silica gel (0-25% acetone in heptane) to give the desired product (1.00 g, 83%) as a clear oil. δH (400 MHz, CDCl$_3$); 6.17-6.07 (2H, m, C6-CH and C7-CH), 5.67 (1H, s, C4-CH), 4.29-4.14 (4H, m, 2×C(O)OCH$_2$), 3.44 (1H, dd, J 10.9, 3.7, EtO$_2$CCH), 2.57 (1H, ddd, J 17.9, 14.4, 5.4, C2-CH$_a$H$_b$), 2.43 (1H, dddd, J 17.8, 5.1, 2.0, 0.8, C2-CH$_a$H$_b$), 2.24-2.12 (2H, m), 2.10-1.93 (3H, m), 1.87-1.77 (1H, m), 1.71 (1H, td, J 16.2, 5.2, C1-CH$_a$H$_b$), 1.59-1.35 (4H, m), 1.34-1.14 (12H, m), 1.11 (3H, s, C18-CH$_3$), 0.96 (3H, d, J 6.2, C21-CH$_3$), 0.75 (3H, s, C19-CH$_3$); δC (100 MHz, CDCl$_3$); 199.5, 170.0, 169.6, 163.8, 141.3, 127.9, 123.6, 61.4, 61.2, 56.2, 53.4, 50.6, 49.8, 43.5, 39.5, 37.7, 36.1, 35.0, 34.3, 34.0, 33.9, 28.0, 23.7, 20.7, 18.2, 16.3, 14.2, 14.1, 11.9.

Example 28—Synthesis of 3-oxo-4,6-choladieno-24-nitrile

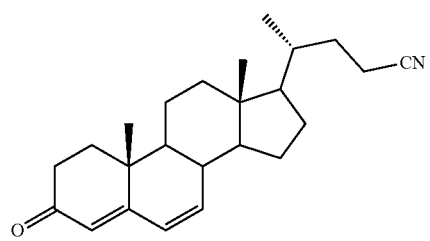 [SMILES: C[C@H](CCC#N)C1CCC2C3C=CC4=CC(=O)CC[C@]4(C)C3CC[C@@]21C]

Synthesis of (20S)-20-bromomethyl-3,3-ethylenedioxy-4-pregnene and (20S)-20-bromomethyl-3,3-ethylenedioxy-5-pregnene

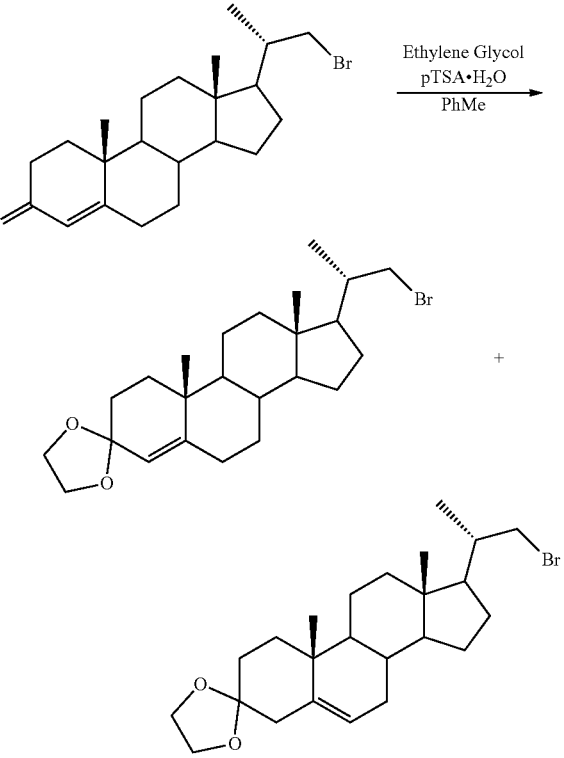

To a solution of (20S)-20-bromomethyl-4-pregnen-3-one (1.00 g, 2.59 mmol) and ethylene glycol (2.0 mL, 36.25 mmol) in toluene (30 mL) was added pTSA.H$_2$O (9.86 mg, 0.05 mmol) and the mixture was heated to reflux using a Dean Stark apparatus for 5 h. The reaction mixture was allowed to cool to room temperature before being poured onto 5% aq. NaHCO$_3$ (30 mL). The layers were separated and the aqueous layer was extracted with CH$_2$Cl$_2$ (2×30 mL). The combined organics were dried over sodium sulfate and were concentrated under reduced pressure. The residue was used in the next step without purification. A sample was purified by column chromatography (heptane/EtOAc) to give a mixture of (20S)-20-bromomethyl-3,3-ethylenedioxy-4-pregnene and (20S)-20-bromomethyl-3,3-ethylenedioxy-5-pregnene in 68% yield (the ratio of $\Delta^5:\Delta^4$ was approximately 3.6:1). δH (700 MHz, CDCl₃); 5.35 (0.8H, dt, J=4.4, 2.2), 5.23 (0.2H, s), 4.02-3.96 (4H, m, CH₂O), 3.51 (0.8H, dd, J 9.7, 2.7), 3.51-3.49 (0.2H, m), 3.34 (0.8H, dd, J 9.7, 6.0), 3.33 (0.2H, dd, J 9.7, 6.1), 2.56 (0.8H, dq, J 14.1, 2.9), 2.20 (0.2H, td, J 13.9, 4.9, 1.8), 2.12 (0.8H, dd, J 14.2, 2.9), 2.05 (0.2H, ddd, J 14.0, 4.2, 2.4), 1.99-1.93 (2H, m), 1.91-1.83 (1H, m), 1.81-1.75 (2H, m), 1.74-1.62 (4H, m), 1.60 (0.8H, s), 1.56-1.51 (1H, m), 1.50-1.41 (2H, m), 1.37-1.25 (3H, m), 1.21 (1H, td, J 6.5, 4.2), 1.17-1.04 (3H, m), 1.09 (3H, d, J 6.4), 1.03 (3H, s), 1.01-0.84 (0.8H, m), 0.71 (2.4H, s), 0.70 (0.6H, s); δC (176 MHz, CDCl₃); 151.6, 140.2, 122.1, 119.65, 109.5, 106.2, 64.6, 64.5, 64.2, 64.2, 56.4, 55.7, 53.8, 53.7, 53.7, 49.6, 43.6, 43.5, 42.5, 42.4, 41.8, 39.5, 39.5, 37.9, 37.8, 37.4, 36.6, 36.3, 35.8, 34.9, 32.4, 32.1, 31.9, 31.9, 31.7, 31.1, 30.0, 27.6, 27.4, 24.2, 24.1, 21.0, 18.9, 18.7, 18.6, 17.6, 12.3, 12.2.

Synthesis of 3,3-ethylenedioxy-4-choleno-24-nitrile and 3,3-Ethylenedioxy-5-choleno-24-nitrile

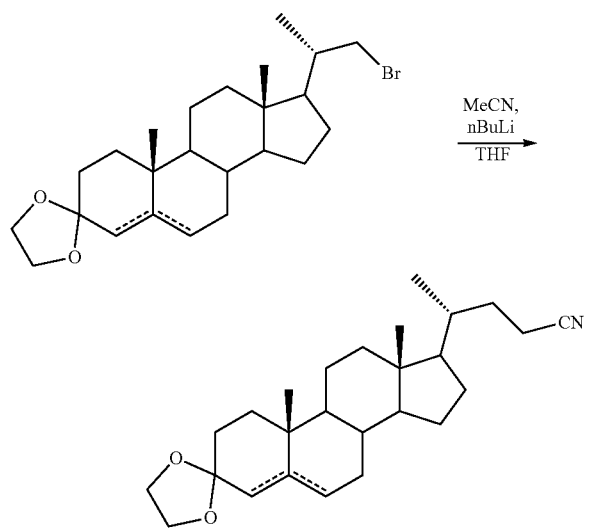

Procedure A

A solution containing MeCN (26.0 mg, 0.63 mmol) in THF (1.85 mL) was cooled to −78° C. under argon and nBuLi (0.32 mL, 2 M in cyclohexane, 0.63 mmol) was charged dropwise over 2 min. To this mixture, a solution containing (20S)-20-bromomethyl-3,3-ethylenedioxy-4-pregnene and (20S)-20-bromomethyl-3,3-ethylenedioxy-5-pregnene (185 mg, 0.423 mmol) in THF (2.15 mL) was charged dropwise over 30 min. The reaction mixture was allowed to warm to 0° C. over 4 h, cooled to −78° C. and quenched with 10% aq. NH₄Cl (3 mL). The reaction mixture was diluted with EtOAc (20 mL) and 10% aq. NH₄Cl (20 mL) and the organic phase was separated. The aqueous phase was extracted with EtOAc (20 mL), and the combined organic phases were washed with 5% aq. NaCl (20 mL), dried over sodium sulfate and concentrated under reduced pressure. The residue was purified by column chromatography on silica gel using heptane:EtOAc (5:1) as the eluent. A fraction containing 3,3-ethylenedioxy-4-choleno-24-nitrile and 3,3-ethylenedioxy-5-choleno-24-nitrile was obtained in 49% yield (the ratio of $\Delta^5:\Delta^4$ was approximately 7:1). δH (700 MHz, CDCl₃); 5.35 (0.9H, dt, J 4.5, 2.2), 5.2 (0.1H, br s), 4.02-3.86 (4H, m), 2.56 (0.9H, dq, J 14.2, 2.9), 2.39-2.34 (0.1H, m), 2.34 (0.9H, ddd, J 16.9, 8.6, 5.1), 2.27 (0.9H, dt, J 16.8, 8.4), 2.27 (0.1H, dt, J 16.8, 8.4), 2.20 (0.1H, td, J 13.9, 5.0, 1.8), 2.12 (0.9H, dd, J 14.2, 3.0), 2.05 (0.1H, ddd, J 13.8, 4.4, 2.2), 2.01-1.95 (2H, m), 1.87-1.75 (4H, m), 1.73-1.70 (0.3H, m), 1.69-1.59 (3.4H, m), 1.58-1.52 (2H, m), 1.50-1.43 (2H, m), 1.39-1.25 (4.6H, m), 1.18 (1H, td, J 6.5, 4.2), 1.14-0.99 (4H, m), 1.03 (3H, s), 0.96 (2.7H, d, J 6.6), 0.94 (0.3H, d, J 6.7), 0.88 (0.9H, t, J 14.3), 0.70 (2.7H, s), 0.70 (0.3H, s); δC (176 MHz, CDCl₃); 151.6, 140.1, 122.1, 120.2, 119.6, 109.5, 106.2, 64.6, 64.4, 64.2, 56.7, 56.0, 55.5, 55.5, 53.8, 49.6, 42.6, 42.5, 41.8, 39.8, 39.7, 37.4, 36.6, 36.3, 35.7, 35.2, 35.2, 34.9, 32.4, 32.1, 31.9, 31.7, 31.6, 31.5, 31.1, 30.0, 29.7, 28.1, 28.1, 24.2, 24.1, 21.0, 18.9, 17.9, 17.9, 17.6, 14.3, 14.2, 14.1, 12.0, 11.9.

Procedure B

A solution of MeCN (2.06 mL, 39.43 mmol) in THF (34 mL) was charged dropwise over 1.2 h to a solution of nBuLi (19.72 mL, 2 M in cyclohexane, 39.43 mmol) in THF (69 mL) at −60° C. under argon. To the resulting white suspension, a solution containing (20S)-20-bromomethyl-3, 3-ethylenedioxy-4-pregnene and (20S)-20-bromomethyl-3,3-ethylenedioxy-5-pregnene (6.9 g, 15.77 mmol) in THF (69 mL) was charged dropwise over 1.2 h. The thick suspension that formed was warmed to 0° C. over 15 min and water (69 mL) was charged dropwise. The layers were separated and the aqueous phase was extracted with EtOAc (2×100 mL). The combined organic phases were washed with 5% aq. NaCl (2×100 mL) and concentrated under reduced pressure. The residue was purified by column chromatography on silica gel using a gradient of EtOAc in heptane as the eluent. A fraction containing 3,3-ethylenedioxy-4-choleno-24-nitrile and 3,3-ethylenedioxy-5-choleno-24-nitrile was obtained which also contained the product from double-alkylation of MeCN (mass 3.88 g).

Synthesis of 3-oxo-4-choleno-24-nitrile

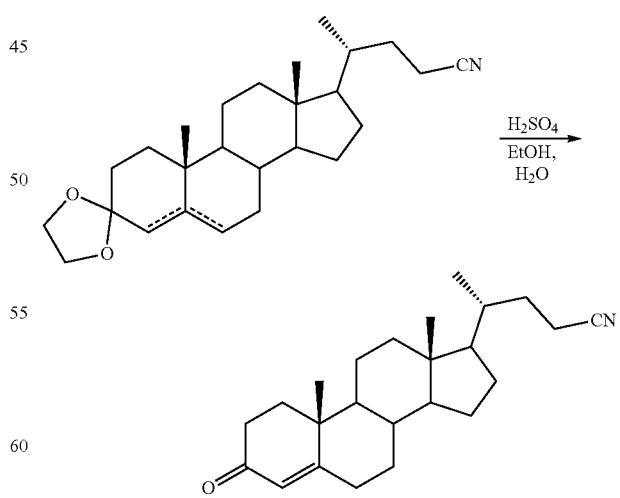

To a solution of 3,3-ethylenedioxy-4-choleno-24-nitrile and 3,3-ethylenedioxy-5-choleno-24-nitrile (3.75 g, 9.43 mmol) in EtOH (75 mL) was added a solution of H₂SO₄ (1 mL, conc, 18.86 mmol) in water (7.5 mL). The reaction mixture was heated at reflux for 30 min and cooled to room temperature. A white solid was removed by filtration and the filter-cake was washed with EtOH (2×20 mL). Pyridine (3 mL) was added to the combined wash and filtrate and the mixture was concentrated under reduced pressure. The residue was dissolved in EtOAc (100 mL), washed with 1 M aq. $H_2SO_4$ (100 mL), 5% aq. $NaHCO_3$ (100 mL), 5% aq. NaCl (2×100 mL), dried over sodium sulfate and was concentrated under reduced pressure to give the desired product (2.36 g). $^1$H NMR (700 MHz, $CDCl_3$): δ=5.72 (1H, s, C4-CH), 2.45-2.25 (6H, m), 2.04-2.00 (2H, m), 1.89-1.82 (3H, m), 1.69 (1H, td, J 7.0, 4.6), 1.67-1.62 (1H, m), 1.59-1.51 (3H, m), 1.44 (1H, qd, J 13.1, 4.0), 1.39-1.25 (2H, m), 1.20-1.10 (3H, m), 1.18 (3H, s), 1.05-0.99 (2H, m), 0.96 (3H, d, J 6.6), 0.95-0.91 (1H, m), 0.73 (3H, s); $^{13}$C NMR (176 MHz, $CDCl_3$): δ=199.6 (C=O), 171.4 (C≡CH), 123.8 (C≡CH), 120.2 (CN), 55.8, 55.5, 53.7, 42.6, 39.6, 38.6, 35.7, 35.6, 35.1, 34.0, 32.9, 32.0, 31.5, 28.1, 24.1, 21.0, 17.9, 17.4, 14.3, 12.0.

Synthesis of 3-oxo-4,6-choladieno-24-nitrile

δ=199.6, 163.8, 141.1, 127.9, 123.6, 120.1, 55.4, 53.4, 50.6, 43.6, 39.5, 37.7, 36.0, 35.2, 34.0, 33.9, 31.4, 28.1, 23.7, 20.6, 17.9, 16.3, 14.4, 11.9.

Example 29—Synthesis of (20S)-20-(1-aminomethyl)-pregna-4,6-dien-3-one

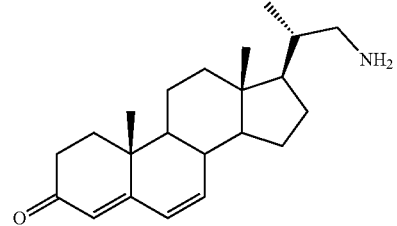 [SMILES: C[C@H](CN)[C@H]1CCC2C3C=CC4=CC(=O)CC[C@]4(C)C3CC[C@@]21C]

Synthesis of (20S)-tosyloxymethyl-pregna-4,6-dien-3-one

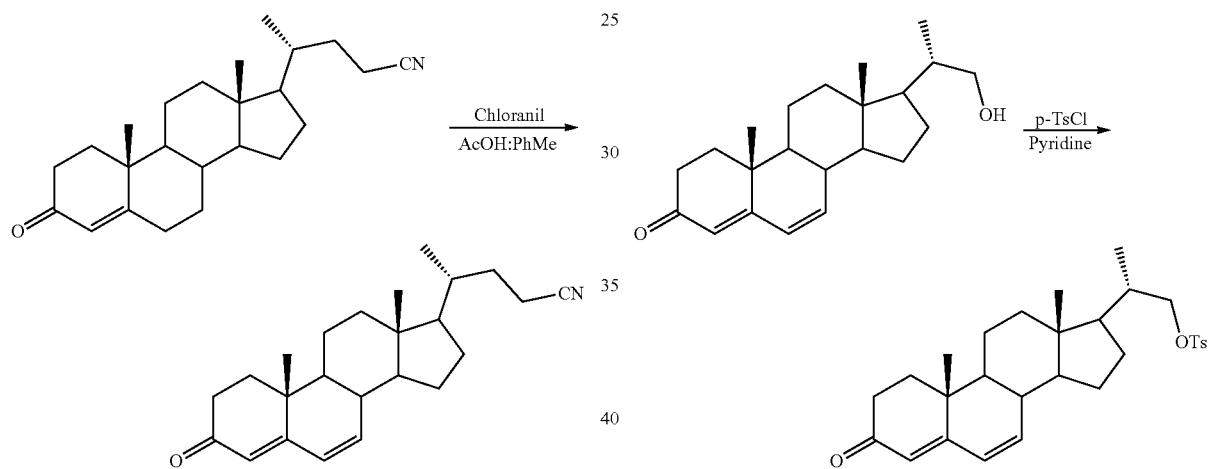

To a solution of 3-oxo-4-choleno-24-nitrile (2.25 g, 0.64 mmol) in toluene (2.25 mL) and AcOH (6.75 mL) was added chloranil (1.72 g, 0.70 mmol). The mixture was heated at 100° C. for 45 min and was then allow to cool to room temperature. The mixture was filtered, washing with AcOH:toluene (3:1, 20 mL) and the combined filtrates were concentrated under reduced pressure. The residue was concentrated from toluene (3×40 mL) and acetone (3×40 mL) and was then dissolved in acetone (6.75 mL). The solution was charged to an aqueous solution of NaOH (22.5 mL, 3% w/v) and the sticky solid that formed was collected by filtration and washed with water:acetone (2×20 mL, 2:1). The solid was purified by chromatography on silica gel using a gradient of EtOAc in heptane as the eluent to give the desired product as a yellow solid (1.33 g, 59% yield). $^1$H NMR (700 MHz, $CDCl_3$): δ=6.13 (1H, d, J 11.0), 6.10 (1H, dd, J 9.8, 2.3), 5.67 (1H, s), 2.57 (1H, ddd, J 17.9, 14.5, 5.4), 2.45-2.41 (1H, m), 2.39 (1H, ddd, J 17.0, 8.3, 5.1), 2.29 (1H, dt, J 16.8, 8.4), 2.20 (1H, t, J 10.6), 2.05 (1H, dt, J 12.9, 3.4), 2.00 (1H, ddd, J 13.2, 5.3, 2.0), 1.95-1.89 (1H, m), 1.88-1.80 (2H, m), 1.71 (1H, td, J 9.7, 1.3), 1.62-1.54 (2H, m), 1.44 (1H, qd, J 9.7, 1.3), 1.41-1.34 (2H, m), 1.30 (1H, ddd, J 24.0, 11.7, 5.8), 1.25-1.19 (3H, m), 1.17 (1H, q, J 9.5), 1.11 (3H, s), 0.97 (3H, d, J 6.7), 0.78 (3H, s); $^{13}$C NMR (176 MHz, $CDCl_3$):

To a solution of (20S)-hydroxymethyl-pregna-4,6-dien-3-one (1.50 g, 4.58 mmol) in pyridine (50 mL) at 0° C. was added p-toluenesulfonyl chloride (1.79 g, 9.39 mmol). The reaction was stirred at 0° C. for 1 h and ambient for 17 h. The reaction was quenched with 1 M aq. HCl (75 mL) and was diluted with ethyl acetate (150 mL). The organic phase was separated and washed with water (50 mL), 5% aq. sodium bicarbonate (75 mL), 5% aq. NaCl (50 mL) and was concentrated in vacuo. The residue was purified by column chromatography on silica gel (heptane-EtOAc) to give the desired product (1.59 g, 72%) as a yellow powder. $R_f$: 0.36 (3:2, heptane:ethyl acetate); $^1$H NMR (700 MHz, $CDCl_3$): δ=7.78 (2H, d, J 8.2, Ar—H), 7.35 (2H, d, J 8.2, Ar—H), 6.10 (2H, br. s, C6H and C7H), 5.67 (1H, s, C4H), 3.97 (1H, dd, J 9.3, 3.2, C22H), 3.80 (1H, dd, J 9.3, 6.4, C22H), 2.56 (1H, ddd, J 17.6, 14.6, 5.6, C2H), 2.45-2.41 (4H, m, C2H and Ts-$CH_3$), 2.17 (1H, t, J 10.5), 2.01-1.96 (2H, m), 1.80-1.67 (4H, m), 1.54 (1H, dq, J 13.5, 3.1), 1.41 (1H, qd, J 13.1, 3.9), 1.30-1.23 (3H, m), 1.23-1.17 (3H, m), 1.10 (3H, s, C19H), 1.00 (3H, d, J 6.7, C21H), 0.73 (3H, s, C18H). $^{13}$C NMR (176 MHz, $CDCl_3$): δ=197.9, 162.0, 142.9, 139.2, 131.3, 128.0, 126.2, 126.1, 121.9, 73.6, 51.3, 49.9, 48.8, 41.7, 37.4, 35.9, 34.4, 34.3, 32.2, 32.1, 25.6, 21.9, 20.0, 18.8, 15.1, 14.5, 10.1.

Synthesis of (20S)-azidomethyl-pregna-4,6-dien-3-one

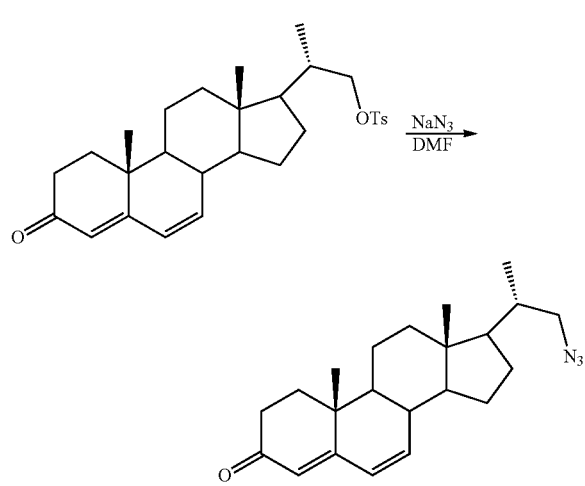

To a suspension of (20S)-tosyloxymethyl-pregna-4,6-dien-3-one (1.58 g, 3.27 mmol) in DMF (24 mL) and water (59 µL) was added sodium azide (273 mg, 4.20 mmol). The reaction was heated to 70° C. and stirred for 1 h. The reaction was quenched with 2% aq.sodium bicarbonate solution (50 mL) at 40° C., and was diluted with ethyl acetate (100 mL). The layers were separated and the organic layer was washed with 2% aq. sodium bicarbonate (50 mL), 5% aq. NaCl (50 mL) and was concentrated in vacuo. The residue was purified by column chromatography on silica gel (heptane-EtOAc) to give the desired product (1.01 g, 91% yield) as a colourless crystalline solid. R$_f$: 0.54 (3:2, heptane:ethyl acetate); $^1$H NMR (700 MHz, CDCl$_3$): δ=6.12 (1H, d, J 9.9, C6H), 6.10 (1H, dd, J 9.9, 2.1, C7H), 5.67 (1H, s, C4H), 3.38 (1H, dd, J 11.9, 3.3, C22H), 3.07 (1H, dd, J 11.9, 7.3, C22H), 2.57 (1H, ddd, J 17.8, 14.7, 5.4, C2H), 2.46-2.41 (1H, m, C2H), 2.17 (1H, t, J 10.6), 2.04 (1H, dt, J 12.8, 3.3), 2.00 (1H, ddd, J 13.2, 5.4, 2.1), 1.93-1.86 (1H, m), 1.86-1.81 (1H, m), 1.75-1.65 (2H, m), 1.56 (1H, dq, J 13.4, 3.7), 1.44 (1H, qd, J 13.0, 4.0), 1.40-1.28 (6H, m), 1.11 (3H, s, C19H), 1.06 (3H, d, J 6.7, C21H), 0.77 (3H, s, C18H). $^{13}$C NMR (176 MHz, CDCl$_3$): δ=199.9, 163.8, 141.1, 128.0, 123.6, 57.9, 53.2, 53.0, 50.6, 43.6, 39.3, 37.7, 36.9, 36.0, 34.0, 33.9, 27.8, 23.8, 20.6, 17.8, 16.3, 12.0.

(iii) Synthesis of (20S)-aminomethyl-pregna-4,6-dien-3-one

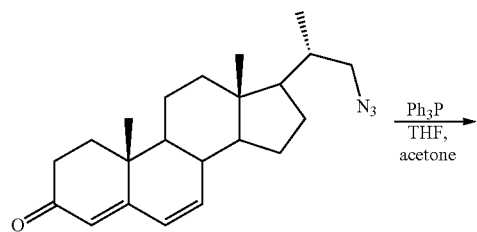

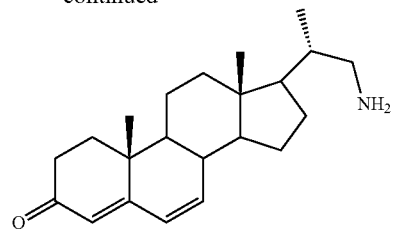

To a solution of (20S)-azidomethyl-pregna-4,6-dien-3-one (99 mg, 0.292 mmol) and triphenylphosphine (106 mg, 0.404 mmol) in THF (1.1 mL) under argon atmosphere was added acetone (300 µL). The reaction was stirred at room temperature for 64 h. The reaction was diluted with ethyl acetate (10 mL) and 2 M aq. hydrochloric acid solution (10 mL). The layers were separated and the aqueous phase was basified with 2 M aq. sodium hydroxide (6.5 mL) to pH 11, and was then extracted with ethyl acetate (10 mL). The organic phase was separated and concentrated in vacuo. The residue was purified by column chromatography on silica gel (DCM-MeOH) to give the desired product (28 mg, 30% yield) as an off-white powder. R$_f$ 0.23 (4:1, CH$_2$Cl$_2$:MeOH); $^1$H NMR (700 MHz, CDCl$_3$): δ=6.12-6.07 (2H, m, C6H and C7H), 5.67 (1H, s, C4H), 3.05 (1H, dd, J 12.7, 3.1, C22H$_a$H$_b$), 2.74 (1H, dd, J 12.7, 8.3, C22H$_a$H$_b$), 2.58 (1H, ddd, J 17.9, 14.5, 5.4, C2H$_a$H$_b$), 2.46-2.41 (1H, m, C2H$_a$H$_b$), 2.18 (1H, t, J 10.5), 2.05-1.94 (3H, m), 1.90-1.81 (2H, m), 1.68 (1H, td, J 13.9, 5.6), 1.55 (1H, dq, J 13.4, 3.4), 1.45-1.17 (9H, m), 1.20 (3H, obscured d, J 6.7, C21H), 1.11 (3H, s, C18H), 0.78 (3H, s, C19H). $^{13}$C NMR (140 MHz, CDCl$_3$): δ=199.5, 163.6, 140.8, 128.0, 123.7, 53.2, 52.8, 50.6, 45.3, 43.6, 39.3, 37.6, 36.0, 36.0, 35.1, 34.0, 33.9, 27.8, 23.7, 20.7, 17.3, 16.3.

Example 30—Synthesis of (20R)-20-(1-cyanomethyl)-pregna-4,6-dien-3-one

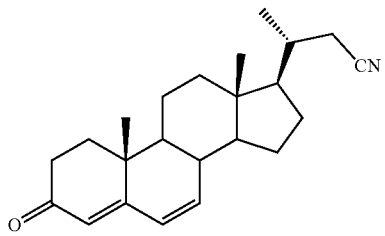 [SMILES: C[C@H](CC#N)[C@H]1CCC2C3C=CC4=CC(=O)CC[C@]4(C)C3CC[C@@]21C]

Synthesis of (20S)-20-bromomethyl-4-pregnen-3-one

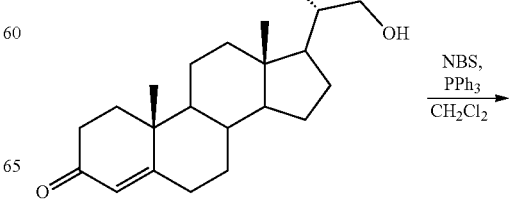

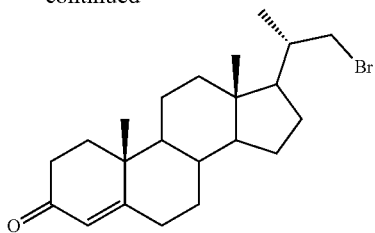

To a solution of (20S)-hydroxymethyl-4-pregnen-3-one (50 g, 0.15 mol) in CH$_2$Cl$_2$ (350 mL) at 0° C. was added triphenylphosphine (43.6 g, 0.17 mol). N-bromosuccinimide (29.6 g, 0.17 mol) was added portionwise and the reaction mixture was stirred at 18° C. After 18 h, the reaction mixture was cooled to 0° C. and triphenylphosphine (19.8 g, 0.08 mol) was added, followed by N-bromosuccinimide (13.5 g, 0.08 mol) portionwise. The mixture was warmed to 18° C. After 2 h the reaction mixture was washed with water (350 mL) and the aqueous phase extracted with CH$_2$Cl$_2$ (350 mL). The combined organic phases were washed with 5% aq. sodium bicarbonate (350 mL), and the aqueous phase extracted with CH$_2$Cl$_2$ (100 mL). The combined organic phases were washed with 5% aq. sodium chloride (150 mL), dried over sodium sulfate and were concentrated in vacuo. The residue was purified by column chromatography on silica gel (heptane-EtOAc) to give the desired product (47.1 g, 79%) as a yellow solid. $^1$H NMR (700 MHz, CDCl$_3$): δ=5.72 (1H, s), 3.50 (1H, dd, J=9.8, 2.7, C22-CH$_a$H$_b$), 3.35 (1H, dd, J=9.8, 5.9, C22-CH$_a$H$_b$), 2.45-2.32 (3H, m), 2.27 (1H, ddd, J=14.6, 4.1, 2.5), 2.04-1.98 (2H, m), 1.91-1.82 (2H, m), 1.72-1.64 (3H, m), 1.56-1.50 (2H, m), 1.43 (1H, qd, J=13.1, 4.1), 1.33-1.27 (2H, m), 1.22 (1H, dd, J=13.0, 4.2), 1.20-1.13 (1H, m), 1.18 (3H, s), 1.09 (3H, d, J=6.4), 1.09-1.00 (2H, m), 0.94 (1H, ddd, J=12.3, 10.9, 4.1), 0.74 (3H, s); $^{13}$C NMR (176 MHz, CDCl$_3$): δ=197.5, 169.3, 121.8, 53.5, 51.6, 51.6, 41.4, 40.4, 37.3, 36.5, 35.7, 33.6, 33.6, 31.9, 30.8, 29.9, 25.5, 22.0, 18.9, 16.6, 15.3, 10.3.

Synthesis of (20R)-cyanomethyl-4-pregnen-3-one

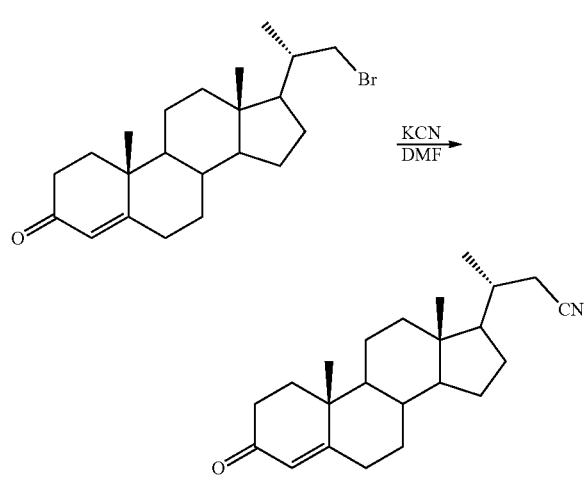

To a suspension of (20S)-20-bromomethyl-4-pregnen-3-one (15 g, 38.1 mmol) in DMF (225 mL) was added potassium cyanide (7.5 g, 114 mmol). The suspension was stirred at 80° C. for 41 h before cooling to room temperature. EtOAc (250 mL) and water (500 mL) were added and the layers were separated. The aqueous layer was extracted with EtOAc (2×250 mL) and the combined organic phases were washed with 5% aq. NaCl (250 mL) and were concentrated under reduced pressure. The residue was purified by column chromatography on silica gel (heptane/EtOAc) to afford the desired product (9.7 g, 75%) as a white solid. δH (700 MHz, CDCl$_3$); 5.73 (1H, s, C4-CH), 2.45-2.32 (4H, m), 2.27 (1H, ddd, J=14.6, 4.2, 2.7), 2.24 (1H, dd, J=16.8, 7.1), 2.04-1.99 (2H, m), 1.89-1.78 (3H, m), 1.72-1.65 (2H, m), 1.57-1.51 (2H, m), 1.43 (1H, qd, J=13.2, 4.0), 1.31-1.16 (4H, m), 1.18 (3H, s), 1.17 (3H, d, J=6.7), 1.11-1.01 (2H, m), 0.94 (1H, ddd, J=12.3, 10.7, 4.1), 0.74 (3H, s); δC (176 MHz, CDCl$_3$); 199.5, 171.2, 123.9, 118.9, 55.7, 54.7, 53.6, 42.5, 39.2, 38.5, 35.7, 35.6, 34.0, 33.6, 32.8, 31.9, 28.0, 24.8, 24.1, 20.9, 19.3, 17.4, 12.1.

Synthesis of (20R)-cyanomethyl-4,6-pregnadien-3-one

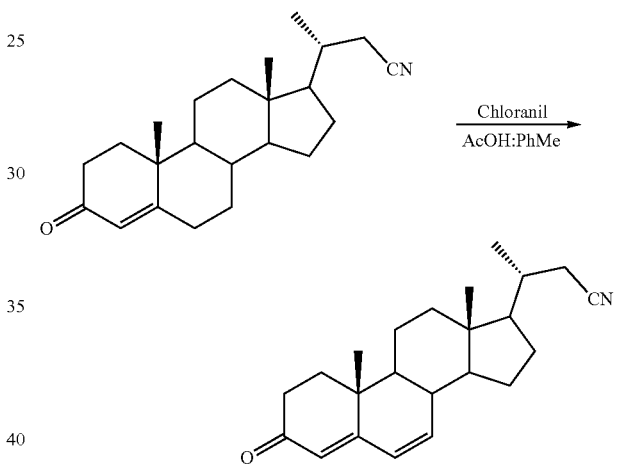

To a suspension of (20R)-cyanomethyl-4-pregnen-3-one (9.1 g, 26.8 mmol) in toluene (36 mL) and acetic acid (0.15 mL) was added p-chloranil (7.2 g, 29.5 mmol). The mixture was heated at reflux for 90 minutes before allowing to cool to room temperature. The suspension was filtered, washing with toluene (25 mL). The filtrate was concentrated under reduced pressure and the residue was purified by column chromatography on silica gel (heptane/EtOAc). The material was then dissolved in acetone (35 mL) and methanol (23 mL) and 0.5 M aq. NaOH (200 mL) was added dropwise. Water (100 mL) was added and the resulting solid was filtered, washing with water (2×50 mL) and 2:1 acetone: water (2×20 mL). The solid was dried in vacuo to afford the desired product (5.4 g, 60%) as a pale brown solid. δH (700 MHz, CDCl$_3$); 6.11 (2H, s), 5.67 (1H, s), 2.57 (1H, ddd, J=18.0, 14.4, 5.4), 2.45-2.42 (1H, m), 2.37 (1H, dd, J=16.7, 3.7), 2.25 (1H, dd, J=16.7, 7.2), 2.01 (1H, t, J=10.4), 2.03 (1H, dt, J=12.8, 3.3), 2.00 (1H, ddd, J=13.2, 5.4, 2.1), 1.96-1.91 (1H, m), 1.88-1.81 (1H, m), 1.74-1.70 (1H, m), 1.58 (1H, dq, J=13.4, 3.6), 1.44 (1H, qd, J=4.4, 3.9), 1.36-1.20 (7H, m), 1.18 (3H, d, J=6.7), 1.11 (3H, s), 0.79 (3H, s); δC (176 MHz, CDCl$_3$); 199.6, 163.67, 140.8, 128.1, 123.7, 118.8, 54.6, 53.2, 50.5, 43.5, 39.1, 37.6, 36.0, 33.9, 33.9, 33.5, 28.0, 24.8, 23.6, 20.6, 19.3, 16.3, 12.0.

93

Example 31—Synthesis of 23-carboxy-3-oxo-4,6-choladien-24-oic acid dimethyl ester

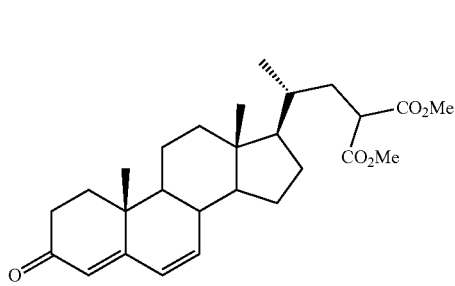 [SMILES: COC(=O)C(C[C@@H](C)[C@H]1CCC2C3C=CC4=CC(=O)CC[C@]4(C)C3CC[C@@]21C)C(=O)OC]

Synthesis of 23-carboxy-3-oxo-4-cholen-24-oic acid dimethyl ester

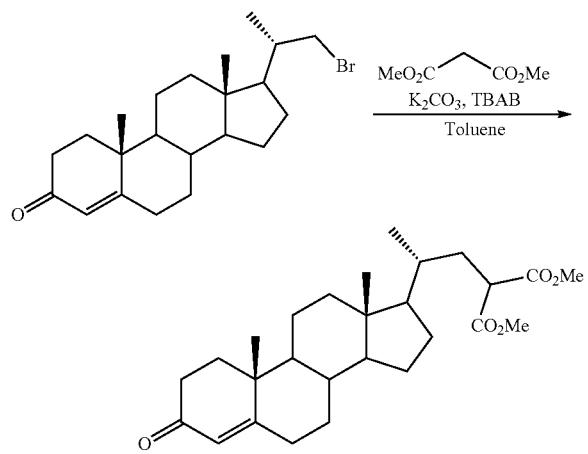

To a suspension of (20S)-20-bromomethyl-4-pregnen-3-one (15 g, 38.1 mmol), tetrabutylammonium bromide (1.2 g, 3.8 mmol) and potassium carbonate (26.3 g, 191 mmol) in toluene (150 mL) was added dimethylmalonate (13.1 mL, 114 mmol) and the reaction mixture was stirred at 80° C. for 91 h. The reaction mixture was then cooled to room temperature and was poured onto water (150 mL). The layers were separated and the aqueous phase was extracted with EtOAc (2×100 mL). The combined organic phases were washed with 5% aq. sodium chloride (100 mL) and were concentrated under reduced pressure. The residue was purified by column chromatography on silica gel (heptane-EtOAc) to give the desired product (14.8 g, 87%) as a yellow solid. $^1$H NMR (700 MHz, CDCl$_3$): δ=5.72 (1H, s), 3.75 (3H, s), 3.72 (3H, s), 3.48 (1H, dd, J=11.0, 4.0), 2.44-2.36 (2H, m), 2.33 (1H, dt, J=17.0, 3.6), 2.27 (1H, ddd, J=14.6, 4.1, 2.4), 2.18 (1H, ddd, J=13.7, 11.1, 2.5), 2.03-2.00 (2H, m), 1.95-1.89 (1H, m), 1.85-1.82 (1H, m), 1.71-1.67 (1H, m), 1.64-1.60 (1H, m), 1.54-1.39 (4H, m), 1.37-1.30 (2H, m), 1.19-1.09 (3H, m), 1.18 (3H, s), 1.05-0.99 (2H, m), 0.94-0.90 (1H, m), 0.93 (3H, d, J=6.5), 0.70 (3H, s); $^{13}$C NMR (176 MHz, CDCl$_3$): δ=199.6, 171.5, 170.4, 170.0, 123.8, 56.3, 55.8, 53.7, 52.6, 52.4, 49.4, 42.5, 39.6, 38.6, 35.7, 35.6, 35.1, 34.3, 34.0, 32.9, 32.0, 28.0, 24.1, 21.0, 18.1, 17.4, 11.9.

94

Synthesis of 23-carboxy-3-oxo-4,6-choladien-24-oic acid dimethyl ester

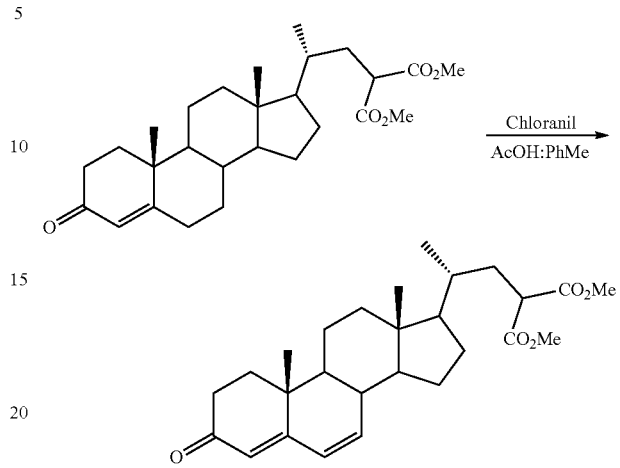

23-Carboxy-3-oxo-4-cholen-24-oic acid dimethyl ester (14.5 g, 32.7 mmol) was suspended in toluene (60 mL) and acetic acid (0.19 mL, 3.3 mmol). p-Chloranil (8.8 g, 35.9 mmol) was added and the mixture stirred at reflux for 65 min. The reaction mixture was cooled to room temperature and filtered. The filter cake was washed with toluene (45 mL) and the filtrate concentrated under reduced pressure. The residue (21.6 g) was used without further purification. A small portion was purified by column chromatography on silica gel (heptane-EtOAc) to give the product. $^1$H NMR (700 MHz, CDCl$_3$): δ=6.12 (1H, d, J=10.8), 6.08 (1H, dd, J=9.8, 2.2), 5.65 (1H, s), 3.74 (3H, s), 3.71 (3H, s), 3.47 (1H, dd, J=11.0, 3.9), 2.58 (1H, dd, J=14.3, 5.3), 2.53 (1H, dd, J=14.3, 5.3), 2.44-2.38 (1H, m), 2.21-2.15 (2H, m), 2.05-1.92 (3H, m), 1.83-1.77 (1H, m), 1.69 (1H, td, J=13.9, 5.2), 1.55-1.34 (5H, m), 1.31-1.11 (5H, m), 1.10 (3H, s), 0.93 (3H, d, J=6.3), 0.73 (3H, s); $^{13}$C NMR (176 MHz, CDCl$_3$): δ=199.6, 170.4, 170.0, 163.9, 141.4, 127.8, 123.5, 56.1, 53.4, 52.6, 52.4, 50.6, 49.4, 43.5, 39.5, 37.7, 36.0, 35.1, 34.3, 33.9, 33.9, 28.0, 23.7, 20.6, 18.1, 16.3, 11.9.

Example 32—Synthesis of (22E)-3-oxo-4,6,22-cholatrien-24-oic acid

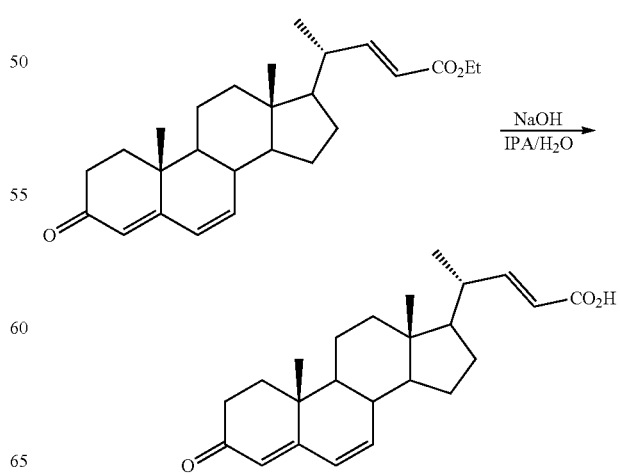

(22E)-3-Oxo-4,6,22-cholatrien-24-oic acid ethyl ester (10 g, 25.2 mmol) was suspended in IPA (100 mL) and the mixture was heated to 60° C. 0.5 M aq. NaOH (60 mL, 30 mmol) was added and the mixture was stirred at 60° C. for 3 h. The volatiles were removed under reduced pressure and EtOAc (250 mL) was added. The mixture was acidified to pH 1 using 2 M aq. HCl, and further EtOAc (100 mL) was added. The layers were separated and the organic layer was washed with water (3×100 mL) and concentrated under reduced pressure. The residue was dissolved in EtOAc (200 mL) with heating and was then cooled to −20° C. for 18 h. The solid formed was filtered, washing with EtOAc (20 mL). The solid was then dried under reduced pressure to give the desired product (4.55 g, 49%) as a tan solid. δH (400 MHz, CDCl$_3$); 6.94 (1H, dd, J 15.6, 9.0, C23-CH), 6.11 (2H, brs, C6-CH and C7-CH), 5.77 (1H, dd, J 15.6, 0.6, C22-CH), 5.68 (1H, s, C4-CH), 2.58 (1H, ddd, J 18.0, 14.4, 5.4, C2-CH$_a$H$_b$), 2.51-2.40 (1H, m, C2-CH$_a$H$_b$), 2.40-2.28 (1H, m), 2.21 (1H, appt, J 10.1), 2.10-1.95 (2H, m), 1.89-1.65 (3H, m), 1.64-1.53 (1H, m), 1.53-1.39 (1H, m), 1.38-1.18 (7H, m), 1.12 (3H, s, C19-CH$_3$), 1.12 (3H, d, J 6.6, C21-CH$_3$), 0.81 (3H, s, C18-CH$_3$); δC (100 MHz, CDCl$_3$); 199.7, 171.8, 163.9, 156.9, 141.1, 128.0, 123.6, 118.6, 54.7, 53.2, 50.7, 43.7, 39.7, 39.3, 37.7, 36.1, 33.9, 33.9, 27.8, 23.7, 20.6, 19.1, 16.3, 12.1.

Example 33—Synthesis of N-((22E)-3,24-dioxo-4,6,22-cholatrien-24-yl)cyclopropylsulfonamide

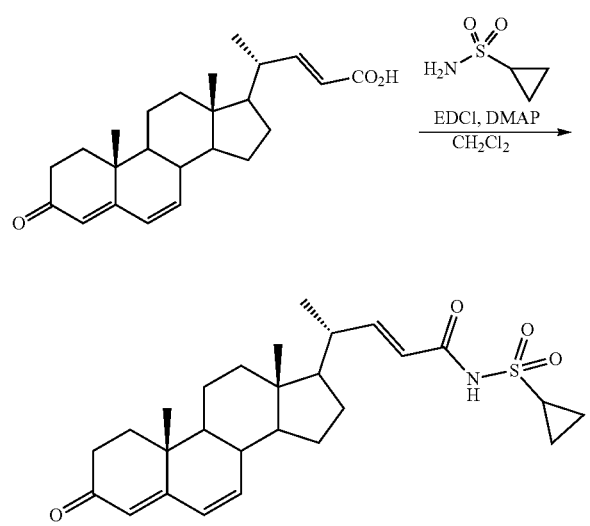

To a solution of (22E)-3-oxo-4,6,22-cholatrien-24-oic acid (2.00 g, 5.43 mmol) in CH$_2$Cl$_2$ (40 mL) was added EDCI (1.69 g, 10.9 mmol) and DMAP (1.33 g, 10.9 mmol). Cyclopropane sulfonamide (1.97 g, 16.3 mmol) was added and the reaction was stirred at room temperature for 22 h. Water (25 mL) was added and the layers were separated. The aqueous layer was extracted with CH$_2$Cl$_2$ (2×25 mL) and the combined organics were washed with 2 M aq HCl (20 mL), 10% aq. NaCl (10 mL), dried over sodium sulfate and concentrated under reduced pressure. The residue was purified by column chromatography on silica gel (0-10% acetone in toluene) to give the desired product (1.68 g, 66%) as an off-white solid. δH (400 MHz, CDCl$_3$); 8.90 (1H, s, NH), 6.95 (1H, dd, J 15.5, 9.0, C23-CH), 6.11 (2H, brs, C6-CH and C7-CH), 5.86 (1H, dd, J 15.5, 0.5, C22-CH), 5.68 (1H, s, C4-CH), 3.00 (1H, dddd, J 12.8, 9.5, 8.1, 4.8, SO$_2$CH), 2.64 (1H, ddd, J 18.1, 14.4, 5.4, C2-CH$_a$H$_b$), 2.51-2.41 (1H, m, C2-CH$_a$H$_b$), 2.40-2.28 (1H, m), 2.25-2.15 (1H, m), 2.09-1.96 (2H, m), 1.85-1.64 (3H, m), 1.63-1.52 (1H, m), 1.51-1.17 (9H, m), 1.17-1.07 (5H, m), 1.12 (3H, s, C19-CH$_3$), 0.80 (3H, s, C18-CH$_3$); δC (100 MHz, CDCl$_3$); 200.0, 164.2, 164.1, 155.5, 141.3, 127.9, 123.6, 119.4, 54.7, 53.2, 50.6, 43.8, 39.8, 39.3, 37.8, 36.1, 33.9, 33.9, 31.5, 28.1, 23.7, 20.6, 19.1, 16.3, 12.2, 6.3, 6.3.

Example 34—Synthesis of N-((22E)-3,24-dioxo-4,6,22-cholatrien-24-yl)-4-(trifluoromethoxy)benzenesulfonamide

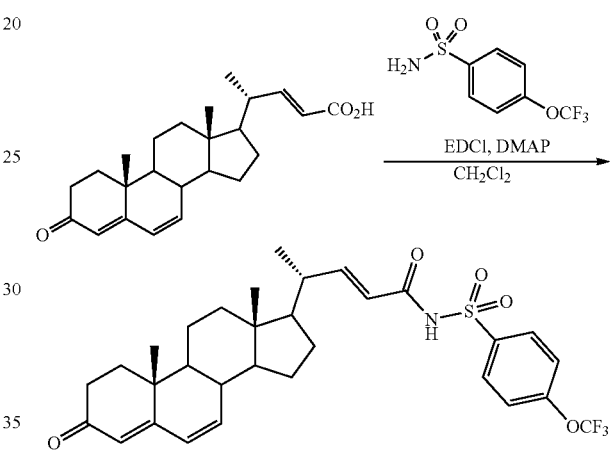

To a solution of (22E)-3-oxo-4,6,22-cholatrien-24-oic acid (2.00 g, 5.43 mmol) in CH$_2$Cl$_2$ (40 mL) was added EDCI (1.69 g, 10.9 mmol) and DMAP (1.33 g, 10.9 mmol). 4-(Trifluoromethoxy)benzene sulfonamide (3.93 g, 16.3 mmol) was added and the reaction was stirred at room temperature for 22 h. Water (25 mL) was added and the layers were separated. The aqueous layer was extracted with CH$_2$Cl$_2$ (2×25 mL) and the combined organics were washed with 2 M aq HCl (20 mL), 10% aq. NaCl (10 mL), dried over sodium sulfate and concentrated under reduced pressure. The residue was used in the next step without purification. A portion was purified by column chromatography on silica gel (0-50% EtOAc in heptane) to give the desired product as an off-white solid. δH (400 MHz, MeOD); 8.16-8.11 (2H, m, ArH), 7.52-7.46 (2H, m, ArH), 6.82 (1H, dd, J 15.4, 9.0, C23-CH), 6.20 (1H, brdd, J 9.8, 1.4, C6-CH), 6.15 (1H, dd, J 9.9, 1.4, C7-CH), 5.82 (1H, dd, J 15.4, 0.7, C22-CH), 5.64 (1H, s, C4-CH), 2.62 (1H, ddd, J 18.2, 14.5, 5.4, C2-CH$_a$H$_b$), 2.42-2.20 (3H, m), 2.12-1.98 (2H, m), 1.88-1.63 (3H, m), 1.63-1.55 (1H, m), 1.49 (1H, dd, J 12.6, 3.8), 1.40-1.18 (7H, m), 1.14 (3H, s, C19-CH$_3$), 1.08 (3H, d, J 6.6, C21-CH$_3$), 0.81 (3H, s, C18-CH$_3$); δC (100 MHz, MeOD); 202.3, 167.2, 165.9, 156.7, 154.0, 143.3, 139.7, 131.8, 128.8, 123.9, 123.0 (q, J 254), 121.9, 120.6, 56.0, 54.6, 52.2, 44.9, 40.9, 40.6, 39.1, 37.4, 35.0, 34.7, 30.2, 29.0, 24.7, 21.7, 19.5, 16.6, 12.5.

Example 35—Synthesis of (20S)-20-(5-tosyltetrazol-1-yl)methyl-pregna-4,6-dien-3-one

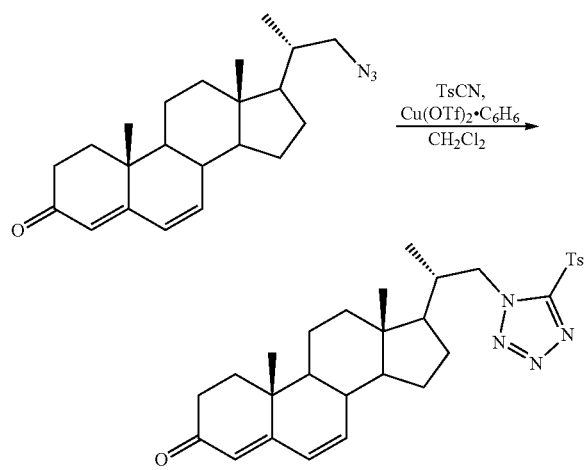

To a solution of (20S)-azidomethyl-pregna-4,6-dien-3-one (500 mg, 1.41 mmol) in CH$_2$Cl$_2$ (5 mL) was added p-toluenesulfonyl cyanide (282 mg, 1.55 mmol). Copper(I) trifluoromethanesulfonate benzene complex (71 mg, 0.141 mmol) was added and the mixture was stirred at room temperature for 18 h. Toluene (5 mL), added p-toluenesulfonyl cyanide (128 mg, 0.708 mmol) and copper(I) trifluoromethanesulfonate benzene complex (71 mg, 0.141 mmol) were added and the mixture was heated to 60° C. for 24 h. Water (10 mL) and CH$_2$Cl$_2$ (30 mL) were added and the layers were separated. The organic layer was washed with 10% aq. Na$_2$S$_2$O$_3$/2% aq. NaHCO$_3$ (2×20 mL), 10% aq. NaCl (20 mL), was dried over sodium sulfate and was concentrated under reduced pressure. The residue was purified by column chromatography on silica gel (0-50% EtOAc in heptane) to give the desired product (381 mg, 50%) as a light yellow solid. δH (400 MHz, CDCl$_3$); 8.03-7.97 (2H, m, ArH), 7.46 (2H, m, ArH), 6.14 (2H, brs, C6-CH and C7-CH), 5.69 (1H, s, C4-CH), 4.80 (1H, dd, J 13.4, 3.9, C22-CH$_a$H$_b$), 4.45 (1H, dd, J 13.4, 10.5, C22-CH$_a$H$_b$), 2.26-2.53 (1H, m), 2.51 (3H, s, ArCH$_3$), 2.49-2.28 (2H, m), 2.24 (1H, appt, J, 10.5), 2.13-1.97 (2H, m), 1.96-1.87 (1H, m), 1.79-1.63 (2H, m), 1.53-1.18 (8H, m), 1.13 (3H, s, C19-CH$_3$), 0.89 (3H, d, J 6.6, C21-CH$_3$), 0.86 (3H, s, C18-CH$_3$); δC (100 MHz, CDCl$_3$); 199.5, 163.6, 147.5, 140.8, 134.3, 130.4, 129.3, 128.1, 123.7, 55.1, 53.9, 53.2, 50.7, 44.0, 39.4, 37.8, 37.6, 36.0, 33.9, 33.9, 31.9, 27.5, 23.8, 22.7, 21.9, 20.6, 16.5, 16.3, 12.0.

Example 36—Synthesis of (20S)—(N-phthalimidomethyl)-pregna-4,6-dien-3-one

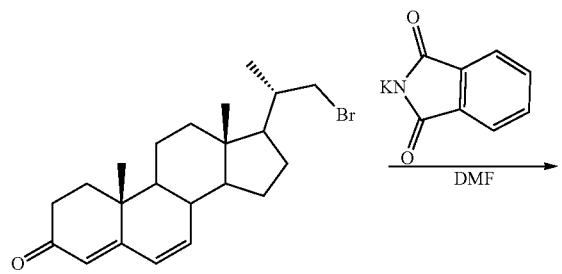

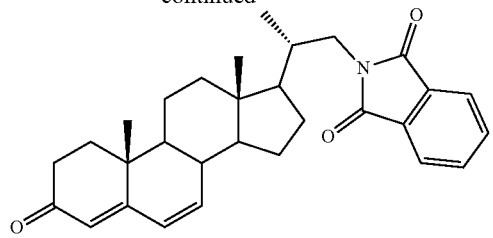

(20S)-Bromomethyl-pregna-4,6-dien-3-one (1.25 g, 3.2 mmol) was dissolved in DMF (25 mL, 20 vol) and potassium phthalimide (0.65 g, 1.1 eq) was added. The mixture was stirred at 50° C. under argon for 65 h and cooled to 25° C. TBME (80 mL, 64 vol) was added and the reaction mixture was washed with water (80 mL, 64 vol). The aqueous phase was separated, extracted with TBME (80 mL) and the organic phases were combined, washed with aqueous NaOH (0.2 M, 80 mL), aqueous 5% w/v NaCl (80 mL) and concentrated to give (20S)—(N-phthalimidomethyl)-pregna-4,6-dien-3-one (0.97 g, 66%). R$_f$: 0.30 (3:7, EtOAc: Heptane); $^1$H NMR (700 MHz, CDCl$_3$): 7.84 (2H, m), 7.72 (2H, m), 6.15 (1H, dd, J 9.7, 1.4), 6.11 (1H, dd, J 9.8, 2.7), 5.67 (1H, s), 3.65 (1H, dd, J 13.3, 3.8), 3.44 (1H, dd, J 13.6, 10.5), 2.57 (1H, ddd, J 17.8, 14.4, 5.4), 2.43 (1H, m), 2.21 (1H, t, J 10.6), 2.11-2.03 (2H, m), 2.02-1.96 (2H, m), 1.87 (1H, m), 1.72 (1H, td, J 13.9, 5.1), 1.66, (1H, m), 1.55 (1H, m), 1.43 (1H, qd, J 13.1, 4.0), 1.36 (1H, m), 1.29-1.20 (4H, m) 1.11 (3H, s), 0.91 (3H, d, J 6.63), 0.80, (3H, s); $^{13}$C NMR (175 MHz, CDCl$_3$): 199.7, 168.8, 163.9, 141.3, 133.9, 132.1, 127.9, 123.6, 123.2, 54.5, 53.2, 50.6, 43.8, 43.7, 39.4, 37.7, 36.2, 36.1, 34.0, 33.9, 27.8, 23.9, 20.6, 17.0, 16.3, 12.0.

Examples 37-50—Further Epoxidation Reactions of Compounds of Formula (II)

General Procedure A: MTO Catalyzed Epoxidation

To a solution of dienone of general formula (II) (1 eq.) and MTO (1 mol %) in EtOAc (2 vol) and HFIP (4 vol) was added 3-methylpyrazole (0.12 eq.) and the mixture was cooled to 5° C. UHP (1.1 eq) was added and the mixture was stirred for 18-50 h until deemed complete by TLC analysis. The reaction mixture was then quenched with the addition of 12% aq. NaHSO$_3$ (3 vol) then partitioned between water (2.5 vol) and EtOAc (1 vol). Phases were separated and the organic washed with 5% aq NaHCO$_3$ (4 vol) and water (4 vol). After concentration under reduced pressure the crude residue was purified by column chromatography (SiO$_2$, eluting with heptane:EtOAc gradient).

Example 37—Epoxidation of (20S)-20-hydroxymethyl-pregna-4,6-dien-3-one to form (6α, 7α, 20S)-6,7-epoxy-20-hydroxymethyl-pregn-4-en-3-one

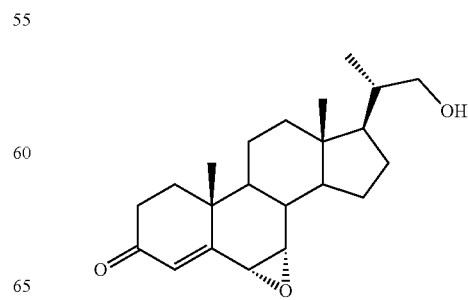

The product was prepared according to the general procedure for MTO catalysed epoxidation on 500 mg scale, isolated in 40% yield (210 mg) as a light yellow solid. δH (400 MHz, CDCl$_3$); 6.11 (1H, s, C4-CH), 3.66 (1H, dd, J 10.4, 3.3, C22-CH$_a$H$_b$), 3.45 (1H, d, J 3.7, C6-CH), 3.42-3.32 (2H, m, C7-CH and C22-CH$_a$H$_b$), 2.56 (1H, ddd, J 18.2, 14.1, 5.5, C2-CH$_a$H$_b$), 2.45 (1H, dddd, J 18.0, 5.3, 2.0, 0.8, C2-CH$_a$H$_b$), 2.02 (1H, dt, J 12.8, 2.7, C12-CH$_a$H$_b$), 1.98-1.83 (4H, m), 1.71 (1H, td, J 13.6, 5.5, C1-CH$_a$H$_b$), 1.65-1.16 (10H, m), 1.10 (3H, s, C19-CH$_3$), 1.06 (3H, d, J 6.6, C21-CH$_3$), 0.77 (3H, s, C18-CH$_3$); δC (100 MHz, CDCl$_3$); 198.3, 162.7, 131.1, 67.8, 54.6, 52.5, 52.5, 51.1, 43.2, 40.6, 39.2, 38.8, 35.6, 34.7, 34.1, 33.9, 27.8, 23.8, 19.9, 17.2, 16.7, 11.9.

Example 38—Epoxidation of (20S)-20-(1-bromomethyl)-pregna-4,6-dien-3-one to form (6α, 7α, 20S)-20-(1-bromomethyl)-6,7-epoxy-pregn-4-en-3-one

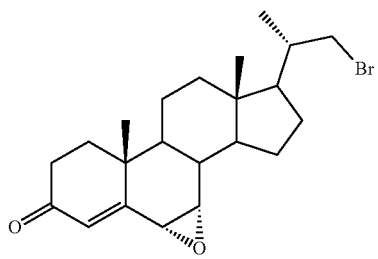 [SMILES: C[C@H](CBr)C1CCC2C3C(CC[C@@]21C)[C@@]1(C)CCC(=O)C=C1[C@H]1O[C@@H]31]

The product was prepared according to the general procedure for MTO catalysed epoxidation on 500 mg scale, isolated in 56% yield (290 mg) as a light brown solid. δH (400 MHz, CDCl$_3$); 6.12 (1H, s, C4-CH), 3.52 (1H, dd, J 9.8, 2.6, C22-CH$_a$H$_b$), 3.46 (1H, d, J 3.7, C6-CH), 3.39-3.17 (2H, m, C7-CH and C22-CH$_a$H$_b$), 2.56 (1H, ddd, J 18.1, 14.0, 5.4, C2-CH$_a$H$_b$), 2.47 (1H, dddd, J 18.0, 5.5, 2.2, 0.9, C2-CH$_a$H$_b$), 2.05-1.84 (5H, m), 1.79-1.66 (2H, m), 1.58-1.46 (1H, m), 1.44-1.19 (7H, m), 1.11 (3H, d, J 6.3, C21-CH$_3$), 1.10 (3H, s, C19-CH$_3$), 0.78 (3H, s, C18-CH$_3$); δC (100 MHz, CDCl$_3$); 198.2, 162.6, 131.2, 54.5, 53.5, 52.5, 51.2, 43.1, 43.0, 40.6, 39.0, 37.8, 35.6, 34.7, 34.1, 33.9, 27.6, 34.6, 19.9, 18.6, 17.2, 12.2.

Example 39—Epoxidation of (20S)-20-(1-mesyloxymethyl)-pregna-4,6-dien-3-one to form (6α, 7α, 20S)-20-(1-mesyloxymethyl)-6,7-epoxy-pregn-4-en-3-one

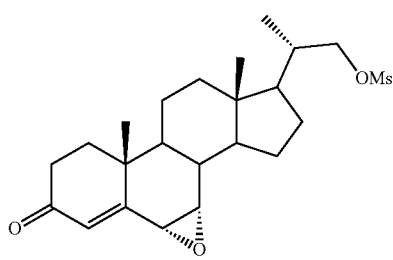 [SMILES: C[C@H](COS(C)(=O)=O)C1CCC2C3C(CC[C@@]21C)[C@@]1(C)CCC(=O)C=C1[C@H]1O[C@@H]31]

The product was prepared according to the general procedure for MTO catalysed epoxidation on 500 mg scale, isolated in 88% yield (460 mg) as a light yellow solid. δH (400 MHz, CDCl$_3$); 6.12 (1H, s, C4-CH), 4.22 (1H, dd, J 9.4, 3.2, C22-CH$_a$H$_b$), 3.99 (1H, dd, J 9.4, 6.9, C22-CH$_a$H$_b$), 3.46 (1H, brd, J 3.7, C6-CH), 3.34 (1H, brd, J 3.6, C7-CH), 3.01 (3H, s, OS(O$_2$)CH$_3$), 2.56 (1H, ddd, J 18.2, 14.1, 5.5, C2-CH$_a$H$_b$), 2.50-2.41 (1H, m), 2.05-1.80 (6H, m), 1.72 (1H, td, J 13.6, 5.6, C1-CH$_a$H$_b$), 1.65-1.17 (8H, m), 1.11 (3H, d, J 6.5, C21-CH$_3$), 1.10 (3H, C19-CH$_3$), 0.76 (3H, s, C18-CH$_3$); δC (100 MHz, CDCl$_3$); 198.2, 162.5, 131.2.

Example 40—Epoxidation of (20S)-20-(1-tertbutyldimethylsilyloxymethyl)-pregna-4,6-dien-3-one to form (6α, 7α, 20S)-20-(1-tertbutyldimethylsilyloxymethyl)-6,7-epoxy-pregn-4-en-3-one

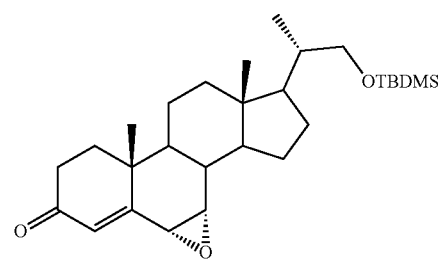 [SMILES: C[C@H](CO[Si](C)(C)C(C)(C)C)C1CCC2C3C(CC[C@@]21C)[C@@]1(C)CCC(=O)C=C1[C@H]1O[C@@H]31]

The product was prepared according to the general procedure for MTO catalysed epoxidation on 500 mg scale, isolated in 19% yield (100 mg) as a light brown solid. δH (400 MHz, CDCl$_3$); 6.11 (1H, s, C4-CH), 3.58 (1H, dd, J 9.6, 3.3, C22-CH$_a$H$_b$), 3.45 (1H, d, J 3.7, C6-CH), 3.42 (1H, brd, J 3.5, C7-CH), 3.28 (1H, dd, J 9.6, 7.2, C22-CH$_a$H$_b$), 2.55 (1H, ddd, J 18.2, 14.1, 5.5, C2-CH$_a$H$_b$), 2.49-2.40 (1H, m, C2-CH$_a$H$_b$), 2.02 (1H, td, J 12.8, 3.0, C12-CH$_a$H$_b$), 1.98-1.82 (4H, m), 1.71 (1H, td, J 13.6, 5.5, C1-CH$_a$H$_b$), 1.61-1.14 (9H, m), 1.10 (3H, s, C19-CH$_3$), 1.00 (3H, d, J 6.6, C21-CH$_3$), 0.89 (9H, s, SiC(CH$_3$)$_3$), 0.75 (3H, s, C18-CH$_3$), 0.06 (6H, d, J 0.6, 2×SiCH$_3$); δC (100 MHz, CDCl$_3$); 198.3, 162.8, 131.1, 67.7, 54.7, 52.6, 52.3, 51.1, 43.1, 40.7, 39.2, 39.0, 35.6, 34.7, 34.1, 33.9, 27.8, 26.0, 26.0, 26.0, 23.8, 19.9, 18.4, 17.2, 16.9, 11.9, −5.3, −5.4.

Example 41—Epoxidation of (20S)-20-acetoxymethyl-pregna-4,6-dien-3-one to form (6α, 7α, 20S)-20-acetoxymethyl-6,7-epoxy-pregn-4-en-3-one

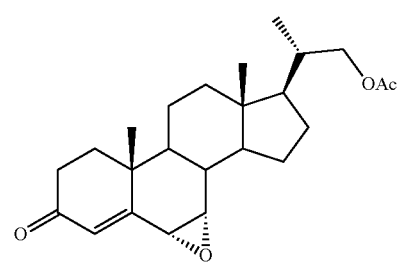 [SMILES: CC(=O)OC[C@@H](C)[C@H]1CCC2C3C(CC[C@@]21C)[C@@]1(C)CCC(=O)C=C1[C@H]1O[C@@H]31]

The product was prepared according to the general procedure for MTO catalysed epoxidation on 200 g scale, isolated in 50% yield (105 g) as a tan solid. $^1$H NMR (700 MHz, CDCl$_3$): δ=6.11 (1H, s), 4.09 (1H, dd, J 10.7, 3.4), 3.79 (1H, dd, J 10.7, 7.4), 3.45 (1H, d, J 3.7), 3.34 (1H, d, J 3.5), 2.55 (1H, m), 2.46 (1H, m), 2.05 (3H, s), 2.02-1.85 (5H, m), 1.78-1.68 (2H, m), 1.55-1.20 (8H, m), 1.10 (3H, s), 1.02 (3H, d, J 6.6), 0.76 (3H, s); $^{13}$C NMR (175 MHz, CDCl$_3$): δ=198.3, 171.3, 162.7, 131.1, 69.3, 54.6, 52.5, 52.4, 51.1, 43.2, 40.6, 39.1, 35.8, 35.6, 34.6, 34.1, 33.9, 27.7, 23.7, 21.0, 19.9, 17.2, 17.1, 11.8.

Example 42—Epoxidation of (20S)-20-(ethylenedioxymethyl)-pregna-4,6-dien-3-one (Example 1F) to form (6α, 7α, 20S)-6,7-epoxy-20-(ethylenedioxymethyl)-pregn-4-en-3-one

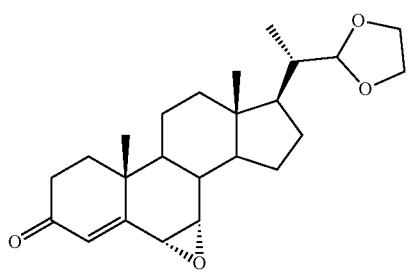 [SMILES: C[C@H](C1OCCO1)[C@H]1CCC2C3C(CC[C@@]21C)[C@@]1(C)CCC(=O)C=C1[C@H]1O[C@@H]31]

The product was prepared according to the general procedure for MTO catalysed epoxidation and was obtained as a crude colourless solid in a 7.6:1 ratio of α:β epoxides.

$^1$H NMR (700 MHz, CDCl$_3$): δ=6.31 (1H, s), 4.85 (1H, d, J=2.0), 4.0-3.8 (2H, m), 3.45 (1H, d, J=3.7), 3.35 (1H, d, J=3.6), 2.59-2.43 (2H, m), 2.05-1.68 (8H, m), 1.55-1.20 (9H, m), 1.10 (3H, s), 0.93 (3H, d, J=6.6), 0.75 (3H, s). $^{13}$C NMR (176 MHz, CDCl$_3$): δ=198.6, 163.0, 131.0, 105.9, 65.2, 65.0, 54.7, 52.5, 51.9, 50.8, 43.4, 40.6, 39.3, 39.0, 35.6, 34.6, 34.1, 33.8, 27.4, 23.8, 19.9, 17.2, 11.6, 11.6.

Example 43—Epoxidation of 23-carboxy-3-oxo-4,6-choladien-24-oic acid dimethyl ester to form (6α,7α)-23-carboxy-6,7-epoxy-3-oxo-4-cholen-24-oic acid dimethyl ester

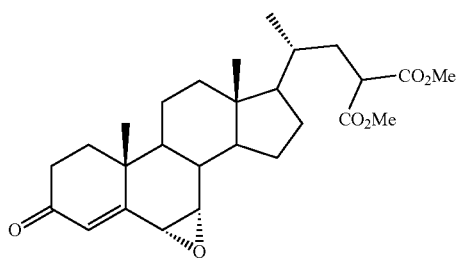 [SMILES: COC(=O)C(C[C@@H](C)C1CCC2C3C(CC[C@@]21C)[C@@]1(C)CCC(=O)C=C1[C@H]1O[C@@H]31)C(=O)OC]

23-Carboxy-3-oxo-4,6-choladien-24-oic acid dimethyl ester (8.94 g, 19.5 mmol) was dissolved in HFIP (35.8 mL) and EtOAc (17.9 mL) and the solution was cooled to 10° C. MTO (51 mg, 0.195 mmol) and 3-methylpyrazole (97 μL, 1.17 mmol) were charged to the solution followed by UHP (2.08 g, 21.4 mmol) in 2 portions over 5 minutes. After 2 h further MTO (51 mg, 0.195 mmol) and 3-methylpyrazole (97 μL, 1.17 mmol) were charged and the solution stirred for 16 h. Further MTO (51 mg, 0.195 mmol), 3 methylpyrazole (97 μL, 1.17 mmol) and UHP (0.38 g, 3.90 mmol) were charged and the solution stirred for 2 h. The reaction was quenched by addition of 5% aq. NaHSO$_3$ (36 mL) over 5 minutes. The phases were separated and the organic phase washed with 5% aq. NaHSO$_3$ until a negative test for peroxides was observed. The organic phase was washed with 5% aq. NaHCO$_3$ (40 mL) and water (40 mL), then dried over sodium sulfate and was concentrated in vacuo. The residue was purified by column chromatography on silica gel to give the desired product (7.07 g, 76%) as a white crystalline solid. $^1$H NMR (700 MHz, CDCl$_3$): δ=6.10 (1H, s), 5.31 (2H, s), 3.75 (3H, s), 3.73 (3H, s), 3.48 (1H, dd, J=11.1, 4.0), 3.45 (1H, d, J=4.0 Hz), 3.34 (1H, d, J=3.6 Hz), 2.55 (1H, ddd, J=18.1, 14.4, 5.6), 2.45 (1H, m), 2.19 (1H, ddd, J=13.6, 11.1, 2.4), 2.05-1.85 (5H, m), 1.70 (1H, td, J=13.9, 5.2), 1.53-1.25 (6H, m), 1.22-1.17 (2H, m), 1.09 (3H, s), 0.49 (3H, d, J=6.5), 0.72 (3H, s); $^{13}$C NMR (176 MHz, CDCl$_3$): δ=198.4, 170.3, 170.0, 162.8, 131.1, 56.0, 54.6, 53.4, 52.6, 52.5, 52.4, 51.3, 49.3, 43.1, 40.6, 39.2, 35.5, 35.1, 34.5, 34.3, 34.1, 33.8, 28.1, 23.6, 19.9, 18.1, 17.2, 11.8.

Example 44—Epoxidation of 3-oxo-4,6-choladieno-24-nitrile to form (6α,7α)-6,7-epoxy-3-oxo-4-choleno-24-nitrile

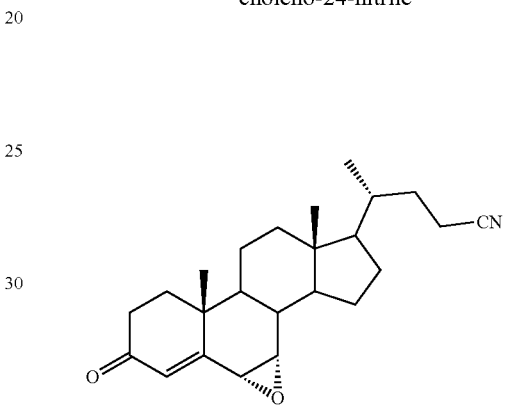

A solution of 3-oxo-4,6-choladieno-24-nitrile (1.25 g, 3.56 mmol) in EtOAc (2.5 mL) and HFIP (5 mL) under argon was cooled to 10° C. MTO (8.9 mg, 0.036 mmol), 3-methylpyrazole (0.017 mL, 0.213 mmol) and UHP (0.37 g, 3.91 mmol) were charged and the mixture was stirred for 2 h. Further portions of MTO (8.9 mg, 0.036 mmol), 3-methylpyrazole (0.017 mL, 0.213 mmol) and UHP (67 mg, 0.71 mmol) were charged and the mixture was stirred overnight at 10° C. The reaction was quenched by addition of 5% aq. NaHSO$_3$ (15 mL) was charged and the mixture was extracted with EtOAc (20 mL). The aqueous phase was separated and extracted with EtOAc (20 mL). The combined organic phases were washed with 5% aq. NaCl (20 mL) and were concentrated under reduced pressure. The residue was purified by column chromatography on silica gel using a gradient of EtOAc in heptane as the eluent to give the desired product (0.92 g, 70%). $^1$H NMR (700 MHz, CDCl$_3$): δ=6.11 (1H, s), 3.46 (1H, d, J 3.7), 3.34 (1H, d, J 3.6), 2.55 (1H, ddd, J 18.1, 14.3, 5.5), 2.47-2.44 (1H, m), 2.41-2.37 (1H, ddd, J 16.9, 8.3, 5.0), 2.30 (1H, dt, J 16.8, 8.4), 2.01 (1H, dt, J 12.9, 3.3), 1.98-1.83 (5H, m), 1.71 (1H, td, J 6.9, 5.2), 1.61-1.56 (1H, m), 1.52 (1H, dq, J 12.7, 3.6), 1.46 (1H, ddd, J 12.4, 11.4, 7.0), 1.41-1.26 (5H, m), 1.22-1.17 (2H, m), 1.10 (3H, s), 0.97 (3H, d, J 6.6), 0.76 (3H, s); $^{13}$C NMR (176 MHz, CDCl$_3$): δ=198.3, 162.6, 131.1, 120.1, 55.3, 54.6, 52.6, 51.3, 43.2, 50.6, 39.3, 35.6, 35.1, 34.6, 34.1, 33.9, 31.4, 28.2, 23.6, 19.9, 17.8, 17.2, 14.4, 11.8.

Example 45—Epoxidation of (20R)-20-(1-cyanomethyl)-pregna-4,6-dien-3-one to form (6α, 7α, 20R)-20-(1-cyanomethyl)-6,7-epoxy-pregn-4-en-3-one

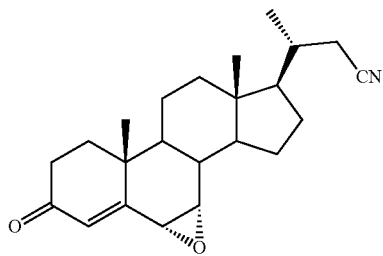 [SMILES: C[C@H](CC#N)[C@H]1CCC2C3C(CC[C@@]21C)[C@@]1(C)CCC(=O)C=C1[C@H]1O[C@@H]31]

(20R)-Cyanomethyl-4,6-pregnadien-3-one (5.1 g, 15.1 mmol) was dissolved in HFIP (20 mL) and EtOAc (10 mL) and was cooled to 10° C. MTO (38 mg, 1 mol %), 3-methylpyrazole (73 µL, 6 mol %) and UHP (1.6 g, 16.6 mmol) were added and the mixture stirred at 10° C. After 4 h, MTO (38 mg, 1 mol %), 3-methylpyrazole (73 µL, 6 mol %) and UHP (0.28 g, 3.0 mmol) were added and the mixture stirred at 10° C. After a further 17 h, MTO (38 mg, 1 mol %), 3-methylpyrazole (73 µL, 6 mol %) and UHP (0.28 g, 3.0 mmol) were added and the mixture stirred at 10° C. After a further 72 h the mixture was quenched with 5% aq. sodium bisulfite (20 mL). The mixture was diluted with EtOAc (80 mL), 5% aq. sodium bisulfite (50 mL) and 5% aq. sodium chloride (50 mL). The aqueous phase was extracted with EtOAc (80 mL), and the combined organics washed with 5% aq. sodium chloride (50 mL), dried over sodium sulfate and concentrated in vacuo. The residue was purified by column chromatography on silica gel (heptane-EtOAc) to give the desired product (3.9 g, 73%) as an off-white solid. $^1$H NMR (700 MHz, CDCl$_3$): δ=6.11 (1H, s, C4-CH), 3.46 (1H, d, J=3.9, C6-CH), 3.33 (1H, d, J=3.8, C7-CH), 2.55 (1H, ddd, J=5.6, 14.2, 18.1, C2-CH$_a$H$_b$), 2.48-2.45 (1H, m, C2-CH$_a$H$_b$), 2.39 (1H, dd, J=3.8, 16.7, C22-CH$_a$H$_b$), 2.23 (1H, dd, J=7.6, 16.8, C22-CH$_a$H$_b$), 2.01-1.91 (4H, m, C1-CH$_a$H$_b$, C12-CH$_a$H$_b$, C15-CH$_a$H$_b$, C16-CH$_a$H$_b$), 1.88 (1H, td, J=10.9, 1.3, C8-CH), 1.84-1.80 (1H, m, C20-CH), 1.72 (1H, td, J=5.2, 13.9, C1-CH$_a$H$_b$), 1.56-1.49 (2H, m, C11-CH$_a$H$_b$, C14-CH), 1.38-1.21 (6H, m, C9-CH, C11-CH$_a$H$_b$, C12-CH$_a$H$_b$, C15-CH$_a$H$_b$, C16-CH$_a$H$_b$, C17-CH), 1.18 (3H, d, J=6.8, C21-CH$_3$), 1.10 (3H, s, C19-CH$_3$), 0.77 (3H, s, C18-CH$_3$); $^{13}$C NMR (176 MHz, CDCl$_3$): δ=198.3, 162.5, 131.2, 118.9, 54.6, 54.5, 52.5, 51.2, 43.2, 40.5, 38.9, 35.5, 34.6, 34.1, 33.8, 33.7, 28.2, 24.8, 23.6, 19.8, 19.3, 17.2, 11.9.

Example 46—Epoxidation of (20S)-azidomethyl-pregna-4,6-dien-3-one to form (6α, 7α, 20S)-6,7-epoxy-20-azidomethyl-pregna-4-en-3-one

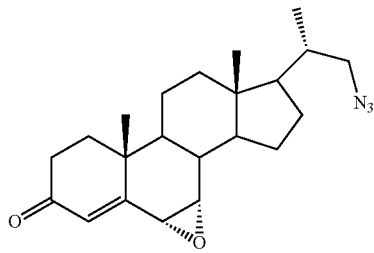 [SMILES: C[C@H](CN=[N+]=[N-])C1CCC2C3C(CC[C@@]21C)[C@@]1(C)CCC(=O)C=C1[C@H]1O[C@@H]31]

To a solution of (20S)-azidomethyl-pregna-4,6-dien-3-one (203 mg, 0.598 mmol) and 3-methylpyrazole (3 µL, 0.04 mmol) in HFIP (0.8 mL) under argon atmosphere at 10° C., MTO (3.2 mg, 0.013 mmol) and UHP (64 mg, 0.68 mmol) were added. The reaction was stirred at 10° C. for 2 h, and quenched with 5% aq. sodium bisulfite solution (1.0 mL). The reaction was diluted with ethyl acetate (10 mL) and washed with water (10 mL) and 10% aq. sodium bicarbonate solution (10 mL). The organic phase was separated and concentrated in vacuo. The residue was purified by column chromatography on silica gel (heptane-EtOAc, R$_f$ in 3:2 heptane:EtOAc=0.42) to the desired product (99 mg, 47%) as a white powder. $^1$H NMR (700 MHz, CDCl$_3$): δ=6.11 (1H, s, C4-CH), 3.46 (1H, d, J=3.7, C6-CH), 3.39 (1H, dd, J=11.9, 3.3, C22-CH$_a$H$_b$), 3.34 (1H, d, J=3.7, C7-CH), 3.06 (1H, dd, J=11.9, 7.5, C22-CH$_a$H$_b$), 2.55 (1H, ddd, J=18.0, 14.3, 5.5, C2-CH$_a$H$_b$), 2.48-2.44 (1H, m, C2-CH$_a$H$_b$), 2.00 (1H, dt, J=11.9, 3.3), 1.97-1.90 (3H, m), 1.87 (1H, td, J=10.8, 1.4, C8-CH), 1.74-1.63 (2H, m), 1.53 (1H, dq, J=12.7, 3.5), 1.49-1.45 (1H, m), 1.41-1.23 (5H, m), 1.22 (1H, td, J=12.7, 3.5), 1.10 (3H, s, C18-CH$_3$), 1.06 (3H, d, J=6.6, C21-CH$_3$), 0.78 (3H, s, C19-CH$_3$). $^{13}$C NMR (140 MHz, CDCl$_3$): δ=198.3, 162.6, 131.1, 57.9, 54.6, 52.9, 52.5, 51.2, 43.2, 40.6, 39.1, 36.9, 35.6, 34.6, 34.1, 33.9, 28.0, 23.7, 19.9, 17.7, 17.2 11.9.

Example 47—Epoxidation of N-((22E)-3,24-dioxo-4,6,22-cholatrien-24-yl)cyclopropylsulfonamide to form N-((6α, 7α, 22E)-3,24-dioxo-6,7-epoxy-4,22-choladien-24-yl)cyclopropylsulfonamide

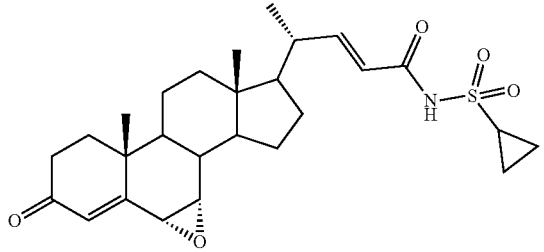 [SMILES: C[C@H](/C=C/C(=O)NS(=O)(=O)C1CC1)C1CCC2C3C(CC[C@@]21C)[C@@]1(C)CCC(=O)C=C1[C@H]1O[C@@H]31]

The product was prepared according to the general procedure for MTO catalysed epoxidation on 1 g scale, isolated in 68% yield (697 mg) as an off white solid. δH (400 MHz, CDCl$_3$); 8.69 (1H, brs, NH), 6.93 (1H, dd, J 15.4, 9.6, C23-CH), 6.12 (1H, s, C4-CH), 5.83 (1H, m, C22-CH), 3.47 (1H, d, J 14.7, C6-CH), 3.36-3.32 (1H, m, C7-CH), 3.00 (1H, dddd, J 12.8, 9.5, 8.1, 4.8, SO$_2$CH), 2.67-2.40 (2H, m), 2.39-2.27 (1H, m), 2.09-1.64 (7H, m), 1.62-1.18 (11H, m), 1.11 (3H, d, J 6.1, C21-CH$_3$), 1.10 (3H, s, C19-CH$_3$), 0.78 (3H, s, C18-CH$_3$); δC (100 MHz, CDCl$_3$); 198.6, 164.0, 162.8, 156.6, 131.1, 119.3, 54.6, 54.5, 52.6, 51.2, 43.4, 40.6, 39.8, 39.1, 35.6, 34.6, 34.1, 33.9, 31.5, 28.2, 23.7, 19.9, 19.1, 17.2, 12.1, 6.3, 6.3.

Example 48—Epoxidation of N-((22E)-3,24-dioxo-4,6,22-cholatrien-24-yl)-4-(trifluoromethoxy)benzenesulfonamide to form N-((6α, 7α, 22E)-3,24-dioxo-6,7-epoxy-4,22-choladien-24-yl)-4-(trifluoromethoxy)benzenesulfonamide

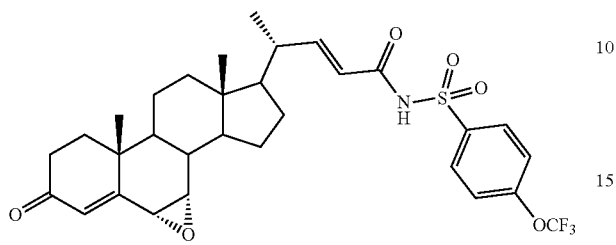

The product was prepared according to the general procedure for MTO catalysed epoxidation on 1 g scale, isolated in 5% yield (50 mg) as a colourless solid. δH (400 MHz, MeOD); 8.17-8.09 (2H, m, ArH), 7.52-7.46 (2H, m, ArH), 6.82 (1H, dd, J 15.4, 8.9, 3.7, C23-CH), 6.07 (1H, s, C4-CH), 5.84 (1H, dd, J 15.4, 0.7, C22-CH), 3.49 (1H, d, J 3.8, C6-CH), 3.37-3.33 (1H, m, C7-CH), 2.62 (1H, ddd, J 18.2, 14.6, 5.6, C2-CH$_a$H$_b$), 2.44-2.27 (2H, m), 2.08-1.88 (3H, m), 1.85-1.60 (2H, m), 1.60-1.49 (1H, m), 1.48-1.17 (9H, m), 1.12 (3H, s, C19-CH$_3$), 1.07 (3H, d, J 6.6, C21-CH$_3$), 0.80 (3H, s, C18-CH$_3$); δC (100 MHz, MeOD); 201.0, 166.2, 166.1, 156.5, 153.9, 139.8, 131.8, 131.4, 122.0, 121.7 (q, J 256), 120.8, 55.9, 55.7, 53.6, 52.8, 44.6, 42.3, 41.0, 40.5, 36.9, 35.9, 35.2, 35.0, 29.2, 24.6, 21.0, 19.5, 17.3, 12.4.

Example 49—Epoxidation of (20S)—(N-phthalimidomethyl)-pregna-4,6-dien-3-one to form (6α,7α, 20S)-6,7-epoxy-20-(N-phthalimidomethyl)-pregna-4,6-dien-3-one

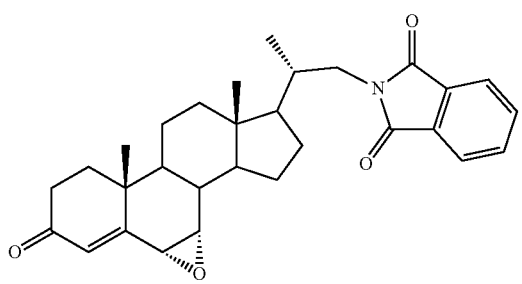 [SMILES: C[C@H](CN1C(=O)c2ccccc2C1=O)C1CCC2C3C(CC[C@@]21C)[C@@]1(C)CCC(=O)C=C1[C@H]1O[C@@H]31]

To a solution of (20S)—(N-phthalimidomethyl)-pregna-4,6-dien-3-one (100 mg, 0.22 mmol) in EtOAc (200 μL, 2 vol) and HFIP (400 μL, 4 vol) under argon was added 3-methylpyrazole (2.1 μL, 0.12 eq) and MTO (5 mg, 10 mol %) and the reaction mixture cooled to 5° C. UHP (23 mg, 1.2 eq) was added. After 20 hours the reaction mixture was quenched with the addition of aqueous 10% NaHSO$_3$ (300 uL, 3 vol) then partitioned between H$_2$O (10 mL) and EtOAc (10 mL). The organic phase was washed with aqueous 5% w/v NaHCO$_3$ (10 mL) and H$_2$O (10 mL). The organic phase was dried over Na$_2$SO$_4$ and concentrated in vacuo. Purification by column chromatography on silica gel gave (6α, 7α,20S)-6,7-epoxy-20-(N-phthalimidomethyl)-pregna-4,6-dien-3-one (62 mg, 60%) as a mixture with the 3-epoxide (7.4:1 α:β), R$_f$ 0.37 (1:1, EtOAc:Heptane); $^1$H NMR (700 MHz, CDCl$_3$): 7.84 (2H, dd, J 5.4, 3.0), 7.72 (2H, dd, J 5.5, 3.0), 6.12 (1H, s), 3.65 (1H, dd, J 13.5, 3.7), 3.48-3.36 (3H, m), 2.60-2.51 (1H, m), 2.50-2.43 (1H, m), 2.16-1.87 (6H, m), 1.76-1.62 (2H, m), 1.55-1.20 (7H, m), 1.10 (3H, s), 0.90 (3H, d, J 6.6), 0.78 (3H, s); $^{13}$C NMR (175 MHz, CDCl$_3$): 198.6, 168.8, 163.0, 133.9, 132.0, 131.0, 123.2, 54.7, 54.3, 52.5, 51.1, 43.6, 43.5, 40.5, 39.1, 36.2, 35.6, 34.6, 34.0, 33.8, 27.9, 23.8, 19.8, 17.2, 17.0, 11.8.

Example 50—Epoxidation of (20S)-20-(5-tosyltetrazol-1-yl)methyl-pregna-4,6-dien-3-one to form (6α, 7α, 20S)-20-(5-tosyltetrazol-1-yl)methyl-6,7-epoxy-pregna-4-en-3-one

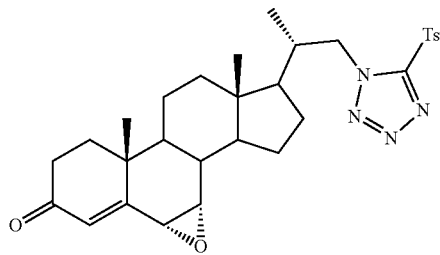 [SMILES: Cc1ccc(S(=O)(=O)c2nnnn2C[C@@H](C)C2CCC3C4C(CC[C@@]32C)[C@@]2(C)CCC(=O)C=C2[C@H]2O[C@@H]42)cc1]

The product was prepared according to the general procedure for MTO catalysed epoxidation on 300 mg scale, isolated in 33% yield (103 mg) as a colourless solid. δH (400 MHz, CDCl$_3$); 8.00-7.94 (2H, m, ArH), 7.47-7.41 (2H, m, ArH), 6.10 (1H, s, C4-CH), 4.77 (1H, dd, J 13.4, 3.9, C22-CH$_a$H$_b$), 4.42 (1H, dd, J 13.4, 3.9, C22-CH$_a$H$_b$), 3.46 (1H, d, J 3.7, C6-CH), 3.37-3.33 (1H, m, C7-CH), 2.61-2.37 (3H, m), 2.48 (3H, s, ArCH$_3$), 2.37-2.24 (1H, m), 2.11-1.80 (3H, m), 1.76-1.61 (2H, m), 1.58-1.17 (8H, m), 1.09 (3H, s, C19-CH$_3$), 0.85 (3H, d, J 7.0, C21-CH$_3$), 0.81 (3H, s, C18-CH$_3$); δC (100 MHz, CDCl$_3$); 198.2, 162.5, 153.3, 147.5, 134.4, 131.1, 130.4, 129.3, 55.1, 54.5, 53.8, 52.5, 51.2, 43.6, 40.6, 39.1, 37.7, 35.5, 34.6, 34.1, 33.9, 27.6, 23.8, 21.9, 19.9, 17.2, 16.4, 11.9.

The invention claimed is:
1. A process for preparing a compound of general formula (Ia):

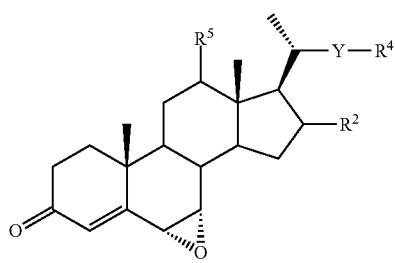

(Ia)

and salts and isotopic variants thereof
wherein:
R$^2$ is selected from the group consisting of H, halo, OH and a protected OH group;
Y is selected from the group consisting of a bond, and a C$_{1-20}$ alkylene, C$_{2-20}$ alkenylene or C$_{2-20}$ alkynylene linker group any of which is optionally substituted with one or more R$^3$;

wherein each $R^3$ is independently selected from H, halo, OH, a protected OH group and $NR^8R^9$;
  wherein each of $R^8$ and $R^9$ is independently selected from H, $C_{1-6}$ alkyl, C(O)Ph, benzyl, phthalimide, tert-butyloxycarbonyl and carboxybenzyl;
$R^4$ is selected from the group consisting of $C(O)OR^{10}$, $OC(O)R^{10}$, $C(O)NR^{10}R^{11}$, $OR^{10}$, $OSi(R^{13})_3$, $S(O)R^{10}$, $SO_2R^{10}$, $OSO_2R^{10}$, $SO_3R^{10}$, $OSO_3R^{10}$, halo, CN, $C(O)R^{10}$, $NR^{10}R^{11}$, $BR^{10}R^{11}$, $C(O)CH_2N_2$, —CH=CH$_2$, —C≡CH, $CH[C(O)OR^{10}]_2$, $CH(BR^{10}R^{11})_2$, azide, $NO_2$, $NR^{10}C(O)NR^{10}SO_2R^{11}$, $NR^{10}C(O)NR^{10}SO_2NR^{10}R^{11}$, $NR^{10}SO_2R^{11}$, $C(O)NR^{10}SO_2R^{11}$, $CH(XR^{10})(XR^{11})$, $CH(R^{10})(XR^{11})$, phthalimide and a carboxylic acid mimetic group;
  wherein each X is independently selected from O, S and $NR^8$;
  wherein each $R^{10}$ and $R^{11}$ is independently selected from:
  a. hydrogen;
    and
  b. $C_{1-20}$ alkyl, $C_{3-7}$ cycloalkyl, $C_{2-20}$ alkenyl or $C_{2-20}$ alkynyl, any of which is optionally substituted with one or more substituents selected from:
    $C_{1-4}$ alkyl, $C_{1-4}$ haloalkyl, halo, $NO_2$, CN, $OR^{19}$, $SR^{19}$, $C(O)OR^{19}$, $C(O)N(R^{19})_2$, $SO_2R^{19}$, $OSO_2R^{19}$, $SO_3R^{19}$, $OSO_3R^{19}$, $N(R^{19})_2$ and a 6- to 14-membered aryl or 5- to 14-membered heteroaryl group, either of which is optionally substituted with one or more substituents selected from $C_{1-6}$ alkyl, $C_{1-6}$ haloalkyl, halo, $NO_2$, CN, $OR^{19}$, $SR^{19}$, $C(O)OR^{19}$, $C(O)N(R^{19})_2$, $SO_2R^{19}$, $SO_3R^{19}$ and $N(R^{19})_2$;
    and
  c. a 6- to 14-membered aryl, 5- to 14-membered heteroaryl group or 3- to 10-membered heterocyclic ring, any of which is optionally substituted with one or more substituents selected from:
    $C_{1-6}$ alkyl, $C_{3-7}$ cycloalkyl, $C_{1-6}$ haloalkyl, halo, $NO_2$, CN, $OR^{19}$, C=O, $C(O)C_{1-4}$alkyl, $SR^{19}$, $C(O)OR^{19}$, $C(O)N(R^{19})_2$, $SO_2R^{19}$, $SO_3R^{19}$, $N(R^{19})_2$, phenyl, 5- to 14-membered heteroaryl, 3- to 10-membered heterocyclic ring, methylenedioxy and ethylenedioxy;
    and
  d. a polyethylene glycol residue;
    or
  e. when $R^4$ is selected from $C(O)NR^{10}R^{11}$, $CH(XR^{10})(XR^{11})$, $CH(R^{10})(XR^{11})$, $NR^{10}R^{11}$, $BR^{10}R^{11}$, $CH[C(O)OR^{10}]_2$ and $CH(BR^{10}R^{11})_2$, an $R^{10}$ and an $R^{11}$ group, together with the atom or atoms to which they are attached, may combine to form a 3- to 10-membered heterocyclic ring;
    wherein each $R^{19}$ is independently selected from:
      H, $C_{1-6}$ alkyl, $C_{1-6}$ haloalkyl, and a 6- to 14-membered aryl or 5- to 14-membered heteroaryl group either of which is optionally substituted with one or more substituents selected from halo, $C_{1-6}$ alkyl and $C_{1-6}$ haloalkyl;
  and wherein each $R^{13}$ is independently selected from:
  a. $C_{1-20}$ alkyl, $C_{2-20}$ alkenyl or $C_{2-20}$ alkynyl, any of which is optionally substituted with one or more substituents selected from:
    halo, $NO_2$, CN, $OR^{19}$, $SR^{19}$, $C(O)OR^{19}$, $C(O)N(R^{19})_2$, $SO_2R^{19}$, $SO_3R^{19}$, $OSO_3R^{19}$, $N(R^{19})_2$ and a 6- to 14-membered aryl or 5- to 14-membered heteroaryl group, either of which is optionally substituted with one or more substituents selected from $C_{1-6}$ alkyl, $C_{1-6}$ haloalkyl, halo, $NO_2$, CN, $OR^{19}$, $SO_2R^{19}$, $SO_3R^{19}$ and $N(R^{19})_2$;

and
  b. a 6- to 14-membered aryl or 5- to 14-membered heteroaryl group either of which is optionally substituted with one or more substituents selected from:
    $C_{1-6}$ alkyl, $C_{1-6}$ haloalkyl, halo, $NO_2$, CN, $OR^{19}$, $SR^{19}$, $C(O)OR^{19}$, $C(O)N(R^{19})_2$, $SO_2R^{19}$, $SO_3R^{19}$ and $N(R^{19})_2$;
    wherein each $R^{19}$ is independently selected from:
      H, $C_{1-6}$ alkyl and $C_{1-6}$ haloalkyl; or
Y and $R^4$ together form a=CH$_2$ group; and
$R^5$ is selected from H, OH or a protected OH group;
comprising:
oxidation of a compound of general formula (IIa) or a salt or isotopic variant thereof
using an oxidant and methyltrioxorhenium as catalyst:

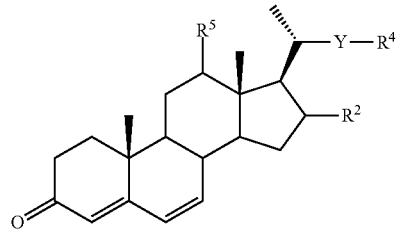

(IIa)

wherein $R^2$, $R^4$, $R^5$ and Y are as defined for compounds of general formula (Ia).

2. The process according to claim 1 for preparing a compound of general formula (I):

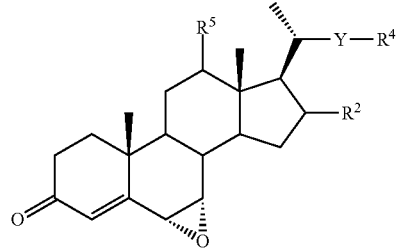

(I)

and salts and isotopic variants thereof
wherein:
$R^2$ is selected from the group consisting of H, halo, OH and a protected OH group;
Y is selected from the group consisting of a bond, and a $C_{1-20}$ alkylene, $C_{2-20}$ alkenylene or $C_{2-20}$ alkynylene linker group any of which is optionally substituted with one or more $R^3$;
  wherein each $R^3$ is independently selected from halo, $OR^8$ and $NR^8R^9$;
    wherein each of $R^8$ and $R^9$ is independently selected from H or $C_{1-4}$ alkyl;
$R^4$ is selected from the group consisting of $C(O)OR^{10}$, $OC(O)R^{10}$, $C(O)NR^{10}R^{11}$, $OR^{10}$, $OSi(R^{13})_3$, $S(O)R^{10}$, $SO_2R^{10}$, $OSO_2R^{10}$, $SO_3R^{10}$, $OSO_3R^{10}$, halo, CN, $C(O)R^{10}$, $CH(OR^{10})(OR^{11})$, $CH(SR^{10})(SR^{11})$, $NR^{10}R^{11}$, $BR^{10}R^{11}$, $C(O)CH_2N_2$, —CH=CH$_2$, —C≡CH, $CH[C(O)OR^{10}]_2$, $CH(BR^{10}R^{11})_2$, azide and a carboxylic acid mimetic group;

wherein each R¹⁰ and R¹¹ is independently selected from:

a. hydrogen; and b. $C_{1-20}$ alkyl, $C_{2-20}$ alkenyl or $C_{2-20}$ alkynyl, any of which is optionally substituted with one or more substituents selected from:

halo, $NO_2$, CN, $OR^{19}$, $SR^{19}$, $C(O)OR^{19}$, $C(O)N(R^{19})_2$, $SO_2R^{19}$, $SO_3R^{19}$, $OSO_3R^{19}$, $N(R^{19})_2$ and a 6- to 14-membered aryl or 5- to 14-membered heteroaryl group, either of which is optionally substituted with one or more substituents selected from $C_{1-6}$ alkyl, $C_{1-6}$ haloalkyl, halo, $NO_2$, CN, $OR^{19}$, $SR^{19}$, $C(O)OR^{19}$, $C(O)N(R^{19})_2$, $SO_2R^{19}$, $SO_3R^{19}$ and $N(R^{19})_2$; and c. a 6- to 14-membered aryl or 5- to 14-membered heteroaryl group either of which is optionally substituted with one or more substituents selected from:

$C_{1-6}$ alkyl, $C_{1-6}$ haloalkyl, halo, $NO_2$, CN, $OR^{19}$, $SR^{19}$, $C(O)OR^{19}$, $C(O)N(R^{19})_2$, $SO_2R^{19}$, $SO_3R^{19}$ and $N(R^{19})_2$; and d. a polyethylene glycol residue; or e. when $R^4$ is selected from $C(O)NR^{10}R^{11}$, $CH(OR^{10})(OR^{11})$, $CH(SR^{10})(SR^{11})$, $NR^{10}R^{11}$, $BR^{10}R^{11}$, $CH[C(O)OR^{10}]_2$ and $CH(BR^{10}R^{11})_2$, an $R^{10}$ and an $R^{11}$ group, together with the atom or atoms to which they are attached, may combine to form a 3- to 10-membered heterocyclic ring;

wherein each $R^{19}$ is independently selected from:

H, $C_{1-6}$ alkyl, $C_{1-6}$ haloalkyl, and a 6- to 14-membered aryl or 5- to 14-membered heteroaryl group either of which is optionally substituted with one or more substituents selected from halo, $C_{1-6}$ alkyl and $C_{1-6}$ haloalkyl;

and wherein each $R^{13}$ is independently selected from:

a. $C_{1-20}$ alkyl, $C_{2-20}$ alkenyl or $C_{2-20}$ alkynyl, any of which is optionally substituted with one or more substituents selected from:

halo, $NO_2$, CN, $OR^{19}$, $SR^{19}$, $C(O)OR^{19}$, $C(O)N(R^{19})_2$, $SO_2R^{19}$, $SO_3R^{19}$, $OSO_3R^{19}$, $N(R^{19})_2$ and a 6- to 14-membered aryl or 5- to 14-membered heteroaryl group, either of which is optionally substituted with one or more substituents selected from $C_{1-6}$ alkyl, $C_{1-6}$ haloalkyl, halo, $NO_2$, CN, $OR^{19}$, $SO_2R^{19}$, $SO_3R^{19}$ and $N(R^{19})_2$; and b. a 6- to 14-membered aryl or 5- to 14-membered heteroaryl group either of which is optionally substituted with one or more substituents selected from:

$C_{1-6}$ alkyl, $C_{1-6}$ haloalkyl, halo, $NO_2$, CN, $OR^{19}$, SR', $C(O)OR^{19}$, $C(O)N(R^{19})_2$, $SO_2R^{19}$, $SO_3R^{19}$ and $N(R^{19})_2$;

wherein each $R^{19}$ is independently selected from:

H, $C_{1-6}$ alkyl and $C_{1-6}$ haloalkyl; or

Y and $R^4$ together form a=$CH_2$ group; and $R^5$ is H, OH or a protected OH group;

comprising:
oxidation of a compound of general formula (II) or a salt or isotopic variant thereof
using an oxidant and methyltrioxorhenium as catalyst:

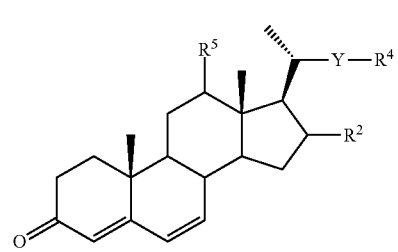

(II)

wherein $R^2$, $R^4$, $R^5$ and Y are as defined for compounds of general formula (I).

3. The process according to claim 1, wherein the methyltrioxorhenium is present in the reaction at 0.1-10 mol %.

4. The process according to claim 1, wherein the oxidant is selected from the group consisting of hydrogen peroxide, urea-hydrogen peroxide, and sodium percarbonate.

5. The process according to claim 1, wherein up to 3 equivalents of oxidant are used per mole of compound of general formula (II).

6. The process according to claim 1, wherein the reaction is carried out in the presence of a ligand.

7. The process according to claim 6, wherein the ligand is a Lewis base.

8. The process according to claim 6, wherein the ligand is a moiety which is bound to the rhenium via 1 to 3 atoms of at least one element selected from oxygen and nitrogen, such that the 5- to 7-valency of rhenium is fulfilled.

9. The process according to claim 6, wherein the ligand is selected from the group consisting of 3-cyanopyridine, 4-cyanopyridine, 2-hydroxypyridine, 3-methyl pyridine, and 3-methyl pyrazole.

10. The process according to claim 1, wherein the reaction solvent is selected from the group consisting of $CH_2Cl_2$, $CHCl_3$, toluene, $CH_3CN$, EtOAc, IPA, MIBK, nBuOAc, fluorinated solvents, and mixtures thereof.

11. The process according to claim 10, wherein the reaction solvent comprises fluorinated solvent.

12. The process according to claim 10, wherein the fluorinated solvent is selected from the group consisting of HFIP (hexafluoroisoproanol), TFE (2,2,2-trifluoroethanol), hexafluorobutanol, trifluorotoluene, and hexafluorobenzene.

13. The process according to claim 10, wherein the reaction solvent is a mixture of a fluorinated solvent and a non-fluorinated solvent.

14. The process according to claim 1, wherein the reaction is carried out in the temperature range of about −10° C. to about 50° C.

15. The process according to claim 1, wherein $R^2$ is H.

16. The process according to claim 1, wherein Y is selected from a bond or a $C_{1-3}$ alkylene or $C_{2-3}$ alkenylene linker group, either of which is optionally substituted with one or two $R^3$ groups, wherein $R^3$ is as defined in claim 1 or claim 2.

17. The process according to claim 16, wherein Y is selected from —$CH_2CH_2$— and —CH=CH—.

18. The process according to claim 1, wherein $R^3$ is selected from the group consisting of H, halo, OH, OC(O)$R^{14}$, OSi$(R^{16})_3$, and $NR^8R^9$; wherein $R^H$ is selected from $C_{1-6}$ alkyl and phenyl; each $R^{16}$ is independently selected from C$_{1-6}$ alkyl and phenyl; and each R$^8$ and R$^9$ is independently selected from H, methyl, ethyl and tert-butoxycarbonyl.

19. The process according to claim 1, wherein R$^4$ is selected from the group consisting of C(O)OR$^{10}$, OC(O)R$^{10}$, OR$^{10}$, C(O)NR$^{10}$R$^{11}$, OSi(R$^{13}$)$_3$, OSO$_2$R$^{10}$, SO$_3$R$^{10}$, OSO$_3$R$^{10}$, halo, CN, C(O)R$^{10}$, NR$^{10}$R$^{11}$, CH(XR$^{10}$)(XR$^{11}$), CH=CH$_2$, CH[C(O)OR$^{10}$]$_2$, azide, C(O)NR$^{10}$SO$_2$R$^{11}$, phthalimide, tetrazole, substituted tetrazole and BR$^{10}$R$^{11}$ or wherein Y and R$^4$ together form a =CH$_2$ group.

20. The process according to claim 1, wherein each R$^{10}$ and R$^{11}$ is independently selected from:
   a. hydrogen; and
   b. C$_{1-10}$ alkyl, C$_{2-10}$ alkenyl or C$_{2-10}$ alkynyl, any of which is optionally substituted with one or more substituents selected from C$_{1-4}$ alkyl, C$_{1-4}$ haloalkyl, halo, NO$_2$, CN, OR$^{19}$, SR$^{19}$, C(O)OR$^{19}$, C(O)N(R$^{19}$)$_2$, SO$_2$R$^{19}$, OSO$_2$R$^{19}$, SO$_3$R$^{19}$, OSO$_3$R$^{19}$, N(R$^{19}$)$_2$ and a 6- to 14-membered aryl or 5- to 14-membered heteroaryl group, either of which is optionally substituted with one or more substituents selected from C$_{1-6}$ alkyl, C$_{1-6}$ haloalkyl, halo, NO$_2$, CN, OR$^{19}$, SR$^{19}$, C(O)OR$^{19}$, C(O)N(R$^{19}$)$_2$, SO$_2$R$^{19}$, SO$_3$R$^{19}$ and N(R$^{19}$)$_2$; and
   c. a 6- to 10-membered aryl, 5- to 10-membered heteroaryl group or 3- to 10 membered heterocyclic ring, any of which is optionally substituted with one or more substituents selected from C$_{1-6}$ alkyl, C$_{3-7}$ cycloalkyl, C$_{1-6}$ haloalkyl, halo, NO$_2$, CN, OR$^{19}$, C=O, C(O)C$_{1-4}$ alkyl, SR$^{19}$, C(O)OR$^{19}$, C(O)N(R$^{19}$)$_2$, SO$_2$R$^{19}$, SO$_3$R$^{19}$ and N(R$^{19}$)$_2$, phenyl, 5- to 14-membered heteroaryl, 3- to 10-membered heterocyclic ring, methylenedioxy and ethylenedioxy; and
   d. a polyethylene glycol residue; or
   e. when R$^4$ is C(O)NR$^{10}$R$^{11}$, CH(XR$^{10}$)(XR$^{11}$), CH(R$^{10}$)(XR$^{11}$), NR$^{10}$R$^{11}$ or BR$^{10}$R$^{11}$, an R$^{10}$ and an R$^{11}$ group, together with the atom or atoms to which they are attached, may combine to form a 3- to 10-membered heterocylic ring.

21. The process according to claim 1, wherein R$^{10}$ is selected from hydrogen; and C$_{1-6}$ alkyl or C$_{2-6}$ alkenyl, either of which is optionally substituted with 6- to 14-membered aryl.

22. The process according to claim 1, wherein R$^5$ is H.

23. The process according to claim 1, wherein:
the compound of general formula (I) is compound (IA): (6α, 7α, 22E)-6,7-epoxy-3-oxo-4,22-choladien-24-oic acid ethyl ester and the compound of general formula (II) is compound (IIA): (22E)-3-oxo-4,6,22-cholatrien-24-oic acid ethyl ester; or the compound of general formula (I) is compound (IB): (6α, 7α)-6,7-epoxy-3-oxo-4-cholen-24-oic acid ethyl ester and the compound of general formula (II) is compound (IIB): 3-oxo-4,6-choladien-24-oic acid ethyl ester.

24. A process for the preparation of a compound of general formula (XVIIIa):

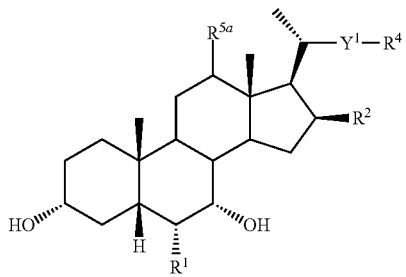

(XVIIIa)

wherein R$^1$ is selected from the group consisting of C$_{1-4}$ alkyl, C$_{2-4}$ alkenyl and C$_{2-4}$ alkynyl optionally substituted with one or more substituents selected from halo, OR$^6$ and NR$^6$R$^7$;
   wherein each of R$^6$ and R$^7$ is independently selected from H and C$_{1-4}$ alkyl;
R$^2$ is selected from the group consisting of H, halo and OH;
R$^{5a}$ is selected from the group consisting of H and OH; and
Y$^1$ is selected from the group consisting of a bond, and a C$_{1-20}$ alkylene linker group which is optionally substituted with one or more R$^3$;
   wherein each R$^3$ is independently selected from H, halo, OH, a protected OH group and NR$^8$R$^9$;
      wherein each of R$^8$ and R$^9$ is independently selected from H, C$_{1-6}$ alkyl, C(O)Ph, benzyl, phthalimide, tert-butyloxycarbonyl and carboxybenzyl;
R$^4$ is selected from the group consisting of C(O)OR$^{10}$, OC(O)R$^{10}$, C(O)NR$^{10}$R$^{11}$, OR$^{10}$, OSi(R$^{13}$)$_3$, S(O)R$^{10}$, SO$_2$R$^{10}$, OSO$_2$R$^{10}$, SO$_3$R$^{10}$, OSO$_3$R$^{10}$, halo, CN, C(O)R$^{10}$, NR$^{10}$R$^{11}$, BR$^{10}$R$^{11}$, C(O)CH$_2$N$_2$, —CH=CH$_2$, —C≡CH, CH[C(O)OR$^{10}$]$_2$, CH(BR$^{10}$R$^{11}$)$_2$, azide, NO$_2$, NR$^{10}$C(O) NR$^{10}$SO$_2$R$^{11}$, NR$^{10}$C(O)NR$^{10}$SO$_2$N R$^{10}$R$^{11}$, NR$^{10}$SO$_2$R$^{11}$, C(O)NR$^{10}$SO$_2$R$^{11}$, CH(XR$^{10}$)(XR$^{11}$), CH(R$^{10}$)(XR$^{11}$), phthalimide and a carboxylic acid mimetic group;
   wherein each X is independently selected from O, S and NR$^8$;
   wherein each R$^{19}$ and R$^{11}$ is independently selected from:
      a hydrogen;
      and
      b. C$_{1-20}$ alkyl, C$_{3-7}$ cycloalkyl, C$_{2-20}$ alkenyl or C$_{2-20}$ alkynyl, any of which is optionally substituted with one or more substituents selected from:
         C$_{1-4}$ alkyl, C$_{1-4}$ haloalkyl, halo, NO$_2$, CN, OR$^{19}$, SR$^{19}$, C(O)OR$^{19}$, C(O)N(R$^{19}$)$_2$, SO$_2$R$^{19}$, OSO$_2$R$^{19}$, SO$_3$R$^{19}$, OSO$_3$R$^{19}$, N(R$^{19}$)$_2$ and a 6- to 14-membered aryl or 5- to 14-membered heteroaryl group, either of which is optionally substituted with one or more substituents selected from C$_{1-6}$ alkyl, C$_{1-6}$ haloalkyl, halo, NO$_2$, CN, OR$^{19}$, SR$^{19}$, C(O)OR$^{19}$, C(O)N(R$^{19}$)$_2$, SO$_2$R$^{19}$, SO$_3$R$^{19}$ and N(R$^{19}$)$_2$;
         and
      c. a 6- to 14-membered aryl, 5- to 14-membered heteroaryl group or 3- to 10-membered heterocyclic ring, any of which is optionally substituted with one or more substituents selected from:
         C$_{1-6}$ alkyl, C$_{3-7}$ cycloalkyl, C$_{1-6}$ haloalkyl, halo, NO$_2$, CN, OR$^{19}$, C=O, C(O)C$_{1-4}$alkyl, SR$^{19}$, C(O)OR$^{19}$, C(O)N(R$^{19}$)$_2$, SO$_2$R$^{19}$, SO$_3$R$^{19}$, N(R$^{19}$)$_2$, phenyl, 5- to 14-membered heteroaryl, 3- to 10-membered heterocyclic ring, methylenedioxy and ethylenedioxy;
         and
      d. a polyethylene glycol residue;
         or
      e. when R$^4$ is selected from C(O)NR$^{10}$R$^{11}$, CH(XR$^{10}$)(XR$^{11}$), CH(R$^{10}$)(XR$^{11}$), NR$^{10}$R$^{11}$, BR$^{10}$R$^{11}$, CH[C(O)OR$^{10}$]$_2$ and CH(BR$^{10}$R$^{11}$)$_2$, an R$^{10}$ and an R$^{11}$ group, together with the atom or atoms to which they are attached, may combine to form a 3- to 10-membered heterocyclic ring;
         wherein each R$^{19}$ is independently selected from:
            H, C$_{1-6}$ alkyl, C$_{1-6}$ haloalkyl, and a 6- to 14-membered aryl or 5- to 14-membered heteroaryl group either of which is optionally substituted with one or more substituents selected from halo, C$_{1-6}$ alkyl and C$_{1-6}$ haloalkyl;

and wherein each $R^{13}$ is independently selected from:
a $C_{1-20}$ alkyl, $C_{2-20}$ alkenyl or $C_{2-20}$ alkynyl, any of which is optionally substituted with one or more substituents selected from:
halo, $NO_2$, CN, $OR^{19}$, $SR^{19}$, $C(O)OR^{19}$, $C(O)N(R^{19})_2$, $SO_2R^{19}$, $SO_3R^{19}$, $OSO_3R^{19}$, $N(R^{19})_2$ and a 6- to 14-membered aryl or 5- to 14-membered heteroaryl group, either of which is optionally substituted with one or more substituents selected from $C_{1-6}$ alkyl, $C_{1-6}$ haloalkyl, halo, $NO_2$, CN, $OR^{19}$, $SO_2R^{19}$, $SO_3R^{19}$ and $N(R^{19})_2$,
and
b. a 6- to 14-membered aryl or 5- to 14-membered heteroaryl group either of which is optionally substituted with one or more substituents selected from:
$C_{1-6}$ alkyl, $C_{1-6}$ haloalkyl, halo, $NO_2$, CN, $OR^{19}$, $SR^{19}$, $C(O)OR^{19}$, $C(O)N(R^{19})_2$, $SO_2R^{19}$, $SO_3R^{19}$ and $N(R^{19})_2$,
wherein each $R^{19}$ is independently selected from: H, $C_{1-6}$ alkyl and $C_{1-6}$ haloalkyl; or
$Y^1$ and $R^4$ together form a=$CH_2$ group;
comprising:
i. preparing a compound of general formula (Ia):

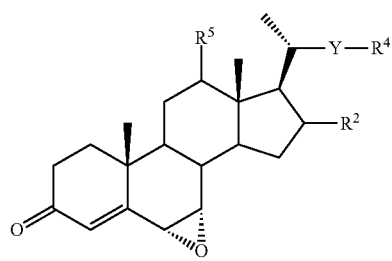

(Ia)

wherein:
$R^2$ is selected from the group consisting of H, halo, OH and a protected OH group;
Y is selected from the group consisting of a bond, and a $C_{1-20}$ alkylene, $C_{2-20}$ alkenylene or $C_{2-20}$ alkynylene linker group any of which is optionally substituted with one or more $R^3$;
wherein each $R^3$ is independently as defined for general formula (XVIIIa);
$R^4$ is as defined for general formula (XVIIIa); or
Y and $R^4$ together form a=$CH_2$ group; and
$R^5$ is selected from H, OH or a protected OH group;
by oxidation of a compound of general formula (IIa) using an oxidant and methyltrioxorhenium as catalyst:

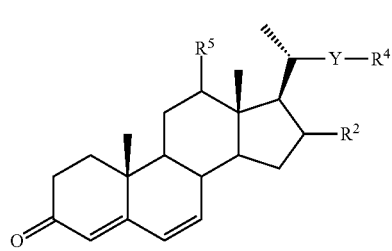

(IIa)

wherein Y, R2, R4 and R5 are as defined for compounds of general formula (Ia) and optionally converting the compound of general formula (Ia) to a second compound of general formula (Ia) by modifying the side chain $Y^1$—$R^4$;
ii. selective alkylation of a compound of general formula (Ia) with an organometallic reagent to give a compound of general formula (XIXa):

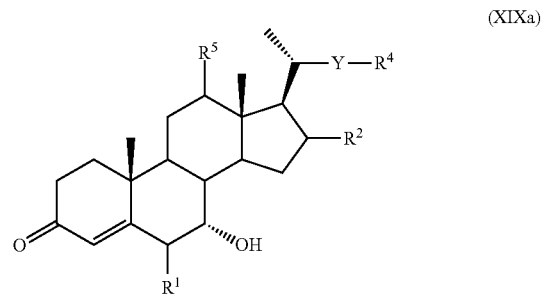

(XIXa)

wherein $R^1$ is as defined for compounds of general formula (XVIIIa) and Y, $R^2$, $R^4$ and $R^5$ are as defined for compounds of general formula (Ia); and optionally converting the compound of general formula (XIXa) to a second compound of general formula (XIXa) by modifying the side chain $Y^1$—$R^4$;
iii. reducing a compound of formula (XIXa) using a suitable reducing agent to give a compound of general formula (XXa):

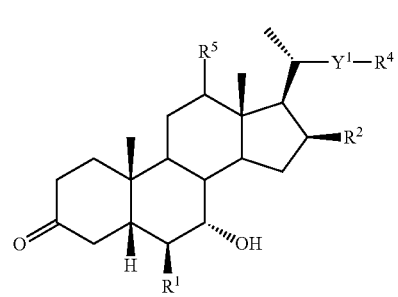

(XXa)

wherein $R^1$ and $Y^1$ are as defined for compounds of general formula (XVIIIa) and $R^2$, $R^4$ and $R^5$ are as defined for compounds of general formula (Ia) and optionally converting the compound of general formula (XXa) to a second compound of general formula (XXa) by modifying the side chain $Y^1$—$R^4$;
iv. oxidising a compound of general formula (XXa) using a suitable oxidizing agent to give a compound of general formula (XXIa):

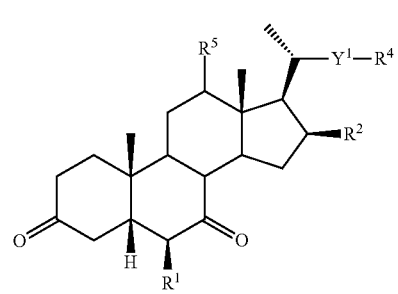

(XXIa)

wherein $R^1$ and $Y^1$ are as defined for compounds of general formula (XVIIIa) and $R^2$, $R^4$ and $R^5$ are as defined for compounds of general formula (Ia) and optionally converting the compound of general formula (XXIa) to a second compound of general formula (XXIa) by modifying the side chain $Y^1$—$R^4$;

v. epimerisation of a compound of general formula (XXIa) to give a compound of general formula (XXIIa):

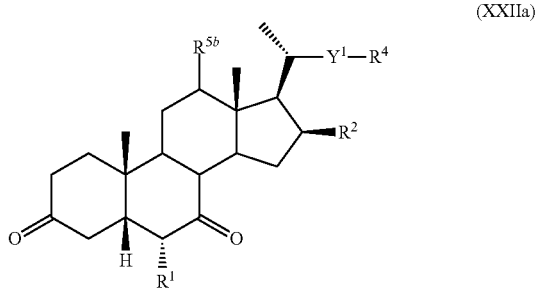

(XXIIa)

wherein $R^1$ and $Y^1$ are as defined for compounds of general formula (XVIIIa) and $R^4$ is as defined for compounds of general formula (Ia);
$R^2$ is selected from H, OH and a protected OH group which is stable under basic conditions; and
$R^{5b}$ is selected from H, OH and a protected OH group which is stable under basic conditions and optionally converting the compound of general formula (XXIIa) to a second compound of general formula (XXIIa) by modifying the side chain $Y^1$—$R^4$; and vi. reduction of the compound of general formula (XXIIa) using a suitable reducing agent and, where $R^2$ and/or $R^{5b}$ is a protected OH, removal of the protecting group(s), to give a compound of general formula (XVIIIa), wherein removal of the protecting group can take place before or after the reduction; and optionally converting the compound of general formula (XVIIIa) to a second compound of general formula (XVIIIa) by modifying the side chain $Y^1$—$R^4$.

25. The process according to claim 24 for the preparation of a compound of general formula (XVIII):

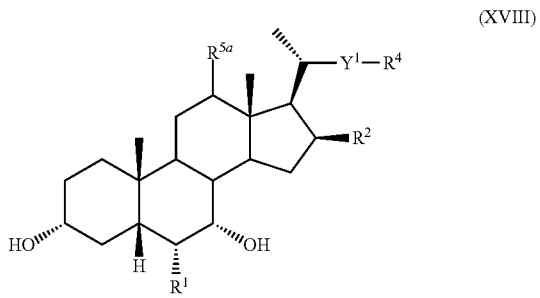

(XVIII)

wherein $R^1$ is $C_{1-4}$ alkyl optionally substituted with one or more substituents selected from halo, $OR^6$ and $NR^6R^7$;
wherein each of $R^6$ and $R^7$ is independently selected from H and $C_{1-4}$ alkyl;
$R^2$ is selected from the group consisting of H, halo and OH;
$R^{5a}$ is selected from the group consisting of H and OH; and
$Y^1$ is selected from the group consisting of a bond, and a $C_{1-20}$ alkylene linker group which is optionally substituted with one or more $R^3$;

wherein each $R^3$ is independently selected from halo, $OR^8$ and $NR^8R^9$; wherein each of $R^8$ and $R^9$ is independently selected from H or $C_{1-4}$ alkyl;
$R^4$ is selected from the group consisting of $C(O)OR^{10}$, $OC(O)R^{10}$, $C(O)NR^{10}R^{11}$, $OR^{10}$, $OSi(R^{13})_3$, $S(O)R^{10}$, $SO_2R^{10}$, $OSO_2R^{10}$, $SO_3R^{10}$, $OSO_3R^{10}$, halo, CN, $C(O)R^{10}$, $CH(OR^{10})(OR^{11})$, $CH(SR^{10})(SR^{11})$, $NR^{10}R^{11}$, $BR^{10}R^{11}$, $C(O)CH_2N_2$, —$CH$=$CH_2$, —C≡CH, $CH[C(O)OR^{10}]_2$, $CH(BR^{10}R^{11})_2$, azide and a carboxylic acid mimetic group;
wherein each $R^{10}$ and $R^{11}$ is independently selected from:
a. hydrogen;
and
b. $C_{1-20}$ alkyl, $C_{2-20}$ alkenyl or $C_{2-20}$ alkynyl, any of which is optionally substituted with one or more substituents selected from:
halo, $NO_2$, CN, $OR^{19}$, $SR^{19}$, $C(O)OR^{19}$, $C(O)N(R^{19})_2$, $SO_2R^{19}$, $SO_3R^{19}$, $OSO_3R^{19}$, $N(R^{19})_2$ and a 6- to 14-membered aryl or 5- to 14-membered heteroaryl group, either of which is optionally substituted with one or more substituents selected from $C_{1-6}$ alkyl, $C_{1-6}$ haloalkyl, halo, $NO_2$, CN, $OR^{19}$, $SR^{19}$, $C(O)OR^{19}$, $C(O)N(R^{19})_2$, $SO_2R^{19}$, $SO_3R^{19}$ and $N(R^{19})_2$;
and
c. a 6- to 14-membered aryl or 5- to 14-membered heteroaryl group either of which is optionally substituted with one or more substituents selected from:
$C_{1-6}$ alkyl, $C_{1-6}$ haloalkyl, halo, $NO_2$, CN, $OR^{19}$, $SR^{19}$, $C(O)OR^{19}$, $C(O)N(R^{19})_2$, $SO_2R^{19}$, $SO_3R^{19}$ and $N(R^{19})_2$;
and
d. a polyethylene glycol residue;
or
e. when $R^4$ is selected from $C(O)NR^{10}R^{11}$, $CH(OR^{10})(OR^{11})$, $CH(SR^{10})(SR^{11})$, $NR^{10}R^{11}$, $BR^{10}R^{11}$, $CH[C(O)OR^{10}]_2$ and $CH(BR^{10}R^{11})_2$, an $R^{10}$ and an $R^{11}$ group, together with the atom or atoms to which they are attached, may combine to form a 3- to 10-membered heterocyclic ring;
wherein each $R^{19}$ is independently selected from:
H, $C_{1-6}$ alkyl, $C_{1-6}$ haloalkyl, and a 6- to 14-membered aryl or 5- to 14-membered heteroaryl group either of which is optionally substituted with one or more substituents selected from halo, $C_{1-6}$ alkyl and $C_{1-6}$ haloalkyl;
and wherein each $R^{13}$ is independently selected from:
a. $C_{1-20}$ alkyl, $C_{2-20}$ alkenyl or $C_{2-20}$ alkynyl, any of which is optionally substituted with one or more substituents selected from:
halo, $NO_2$, CN, $OR^{19}$, $SR^{19}$, $C(O)OR^{19}$, $C(O)N(R^{19})_2$, $SO_2R^{19}$, $SO_3R^{19}$, $OSO_3R^{19}$, $N(R^{19})_2$ and a 6- to 14-membered aryl or 5- to 14-membered heteroaryl group, either of which is optionally substituted with one or more substituents selected from $C_{1-6}$ alkyl, $C_{1-6}$ haloalkyl, halo, $NO_2$, CN, $OR^{19}$, $SO_2R^{19}$, $SO_3R^{19}$ and $N(R^{19})_2$;
and
b. a 6- to 14-membered aryl or 5- to 14-membered heteroaryl group either of which is optionally substituted with one or more substituents selected from:
$C_{1-6}$ alkyl, $C_{1-6}$ haloalkyl, halo, $NO_2$, CN, $OR^{19}$, $SR^{19}$, $C(O)OR^{19}$, $C(O)N(R^{19})_2$, $SO_2R^{19}$, $SO_3R^{19}$ and $N(R^{19})_2$;
wherein each $R^{19}$ is independently selected from:
H, $C_{1-6}$ alkyl and $C_{1-6}$ haloalkyl; or
$Y^1$ and $R^4$ together form a=$CH_2$ group;

comprising:
i. preparing a compound of general formula (I):

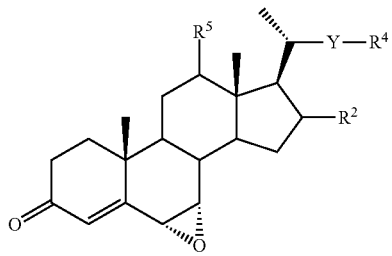

wherein:
$R^2$ is selected from the group consisting of H, halo, OH and a protected OH group;
Y is selected from the group consisting of a bond, and a $C_{1-20}$ alkylene, $C_{2-20}$ alkenylene or $C_2$-20 alkynylene linker group any of which is optionally substituted with one or more $R^3$;
  wherein each $R^3$ is independently selected from halo, $OR^8$ and $NR^8R^9$;
  wherein each of $R^8$ and $R^9$ is independently selected from H or $C_{1-4}$ alkyl;
$R^4$ is selected from the group consisting of $C(O)OR^{10}$, $OC(O)R^{10}$, $C(O)NR^{10}R^{11}$, $OR^{10}$, $OSi(R^{13})_3$, $S(O)R^{10}$, $SO_2R^{10}$, $OSO_2R^{10}$, $SO_3R^{10}$, $OSO_3R^{10}$, halo, CN, $C(O)R^{10}$, $CH(OR^{10})(OR^{11})$, $CH(SR^{10})(SR^{11})$, $NR^{10}R^{11}$, $BR^{10}R^{11}$, $C(O)CH_2N_2$, —CH=CH$_2$, —C≡CH, $CH[C(O)OR^{10}]_2$, $CH(BR^{10}R^{11})_2$, azide and a carboxylic acid mimetic group;
  wherein each $R^{10}$ and $R^{11}$ is independently selected from:
  a. hydrogen;
  and
  b. $C_{1-20}$ alkyl, $C_{2-20}$ alkenyl or $C_{2-20}$ alkynyl, any of which is optionally substituted with one or more substituents selected from:
    halo, $NO_2$, CN, $OR^{19}$, $SR^{19}$, $C(O)OR^{19}$, $C(O)N(R^{19})_2$, $SO_2R^{19}$, $SO_3R^{19}$, $OSO_3R^{19}$, $N(R^{19})_2$ and a 6- to 14-membered aryl or 5- to 14-membered heteroaryl group, either of which is optionally substituted with one or more substituents selected from $C_{1-6}$ alkyl, $C_{1-6}$ haloalkyl, halo, $NO_2$, CN, $OR^{19}$, $SR^{19}$, $C(O)OR^{19}$, $C(O)N(R^{19})_2$, $SO_2R^{19}$, $SO_3R^{19}$ and $N(R^{19})_2$;
  and
  c. a 6- to 14-membered aryl or 5- to 14-membered heteroaryl group either of which is optionally substituted with one or more substituents selected from:
    $C_{1-6}$ alkyl, $C_{1-6}$ haloalkyl, halo, $NO_2$, CN, $OR^{19}$, $SR^{19}$, $C(O)OR^{19}$, $C(O)N(R^{19})_2$, $SO_2R^{19}$, $SO_3R^{19}$ and $N(R^{19})_2$,
  and
  d. a polyethylene glycol residue;
  or
  e. when $R^4$ is selected from $C(O)NR^{10}R^{11}$, $CH(OR^{10})(OR^{11})$, $CH(SR^{10})(SR^{11})$, $NR^{10}R^{11}$, $BR^{10}R^{11}$, $CH[C(O)OR^{10}]_2$ and $CH(BR^{10}R^{11})_2$, an $R^{10}$ and an $R^{11}$ group, together with the atom or atoms to which they are attached, may combine to form a 3- to 10-membered heterocyclic ring;
  wherein each $R^{19}$ is independently selected from:
    H, $C_{1-6}$ alkyl, $C_{1-6}$ haloalkyl, and a 6- to 14-membered aryl or 5- to 14-membered heteroaryl group either of which is optionally substituted with one or more substituents selected from halo, $C_{1-6}$ alkyl and $C_{1-6}$ haloalkyl;
and wherein each $R^{13}$ is independently selected from:
a. $C_{1-20}$ alkyl, $C_{2-20}$ alkenyl or $C_{2-20}$ alkynyl, any of which is optionally substituted with one or more substituents selected from:
    halo, $NO_2$, CN, $OR^{19}$, $SR^{19}$, $C(O)OR^{19}$, $C(O)N(R^{19})_2$, $SO_2R^{19}$, $SO_3R^{19}$, $OSO_3R^{19}$, $N(R^{19})_2$ and a 6- to 14-membered aryl or 5- to 14-membered heteroaryl group, either of which is optionally substituted with one or more substituents selected from $C_{1-6}$ alkyl, $C_{1-6}$ haloalkyl, halo, $NO_2$, CN, $OR^{19}$, $SO_2R^{19}$, $SO_3R^{19}$ and $N(R^{19})_2$; and
b. a 6- to 14-membered aryl or 5- to 14-membered heteroaryl group either of which is optionally substituted with one or more substituents selected from:
    $C_{1-6}$ alkyl, $C_{1-6}$ haloalkyl, halo, $NO_2$, CN, $OR^{19}$, $SR^{19}$, $C(O)OR^{19}$, $C(O)N(R^{19})_2$, $SO_2R^{19}$, $SO_3R^{19}$ and $N(R^{19})_2$;
  wherein each $R^{19}$ is independently selected from:
    H, $C_{1-6}$ alkyl and $C_{1-6}$ haloalkyl; or Y and $R^4$ together form a=$CH_2$ group; and $R^5$ is H, OH or a protected OH group;
by oxidation of a compound of general formula (II) using an oxidant and methyltrioxorhenium as catalyst:

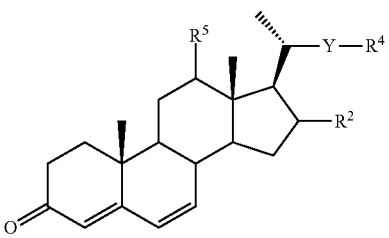

wherein Y, $R^2$, $R^4$ and IV are as defined for compounds of general formula (I) and optionally converting the compound of general formula (II) to a second compound of general formula (II) by modifying the side chain $Y^1$—$R^4$;
ii. selective alkylation of a compound of general formula (I) with an organometallic reagent to give a compound of general formula (XIX):

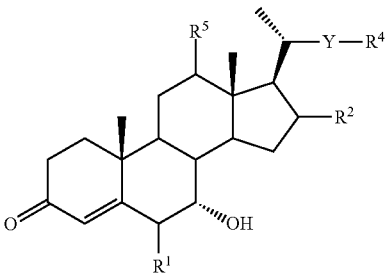

wherein $R^1$ is as defined for compounds of general formula (XVIII) and Y, $R^2$, $R^4$ and $R^5$ are as defined for compounds of general formula (I) and optionally converting the compound of general formula (XIX) to a second compound of general formula (XIX) by modifying the side chain $Y^1—R^4$;

iii. reducing a compound of formula (XIX) using a suitable reducing agent to give a compound of general formula (XX):

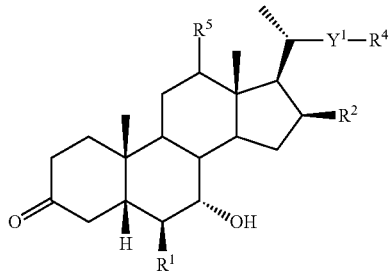

(XX)

wherein $R^1$ and $Y^1$ are as defined for compounds of general formula (XVIII) and $R^2$, $R^4$ and IV are as defined for compounds of general formula (I) and optionally converting the compound of general formula (XX) to a second compound of general formula (XX) by modifying the side chain $Y^1—R^4$;

iv. oxidising a compound of general formula (XX) using a suitable oxidizing agent to give a compound of general formula (XXI):

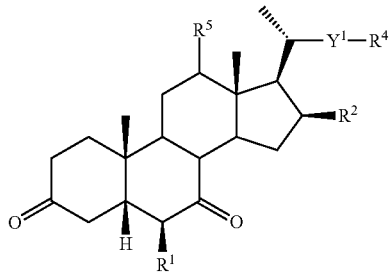

(XXI)

wherein $R^1$ and $Y^1$ are as defined for compounds of general formula (XVIII) and $R^2$, $R^4$ and $R^5$ are as defined for compounds of general formula (I) and optionally converting the compound of general formula (XXI) to a second compound of general formula (XXI) by modifying the side chain $Y^1—R^4$;

v. epimerisation of a compound of general formula (XXI) to give a compound of general formula (XXII):

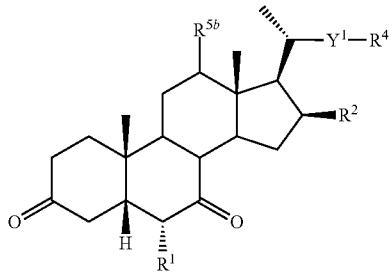

(XXII)

wherein $R^1$ and $Y^1$ are as defined for compounds of general formula (XVIII) and $R^4$ is as defined for compounds of general formula (I);

$R^2$ is H or OH or a protected OH group which is stable under basic conditions; and $R^{5b}$ is H or OH or a protected OH group which is stable under basic conditions and optionally converting the compound of general formula (XXII) to a second compound of general formula (XXII) by modifying the side chain $Y^1—R^4$; and vi. reduction of a compound of general formula (XXII) using a suitable reducing agent and, where $R^2$ and/or $R^{5b}$ is a protected OH, removal of the protecting group(s), to give a compound of general formula (XVIII), wherein removal of the protecting group can take place before or after the reduction; and optionally converting the compound of general formula (XVIII) to a second compound of general formula (XVIII) by modifying the side chain $Y^1—R^4$.

\* \* \* \* \*